(12) United States Patent
Bone et al.

(10) Patent No.: US 9,725,757 B2
(45) Date of Patent: Aug. 8, 2017

(54) TARGET DETECTION AND SIGNAL AMPLIFICATION

(71) Applicant: SpeeDx Pty Ltd, Eveleigh, New South Wales (AU)

(72) Inventors: Simon Mark Bone, Summer Hill (AU); Alison Velyian Todd, Glebe (AU); Timothy Daniel Meehan, Austin, TX (US)

(73) Assignee: SPEEDX PTY LTD, Eveleigh, NSW (AU)

( * ) Notice: Subject to any disclaimer, the term of this patent is extended or adjusted under 35 U.S.C. 154(b) by 88 days.

(21) Appl. No.: 14/409,375

(22) PCT Filed: Jun. 18, 2013

(86) PCT No.: PCT/AU2013/000651
§ 371 (c)(1),
(2) Date: Dec. 18, 2014

(87) PCT Pub. No.: WO2013/188912
PCT Pub. Date: Dec. 27, 2013

(65) Prior Publication Data
US 2016/0083785 A1 Mar. 24, 2016

(30) Foreign Application Priority Data

Jun. 18, 2012 (AU) .............................. 2012902551
Aug. 10, 2012 (AU) .............................. 2012903462
Apr. 3, 2013 (AU) .............................. 2013202354

(51) Int. Cl.
| | | |
|---|---|---|
| C12Q 1/68 | (2006.01) |
| C12N 15/113 | (2010.01) |
| C07H 21/00 | (2006.01) |
| C12P 19/34 | (2006.01) |
| C12N 9/22 | (2006.01) |

(52) U.S. Cl.
CPC ............. *C12Q 1/6823* (2013.01); *C12N 9/22* (2013.01); *C12Q 1/682* (2013.01); *G01N 2333/9005* (2013.01)

(58) Field of Classification Search
CPC ...... C12Q 1/68; C12N 15/113; C12N 15/115; C07H 21/00; C12P 19/34
See application file for complete search history.

(56) References Cited

U.S. PATENT DOCUMENTS

| 6,140,055 A * | 10/2000 | Todd ..................... C12Q 1/6816 435/6.16 |
| 2004/0106109 A1* | 6/2004 | Belly ...................... C07H 21/04 435/6.11 |
| 2006/0240462 A1* | 10/2006 | Todd ..................... C12Q 1/6816 435/6.16 |
| 2007/0231810 A1* | 10/2007 | Todd ..................... C12N 15/111 435/6.18 |
| 2008/0268516 A1* | 10/2008 | Perreault ............... C12N 15/111 435/184 |
| 2010/0035229 A1* | 2/2010 | Rimsky ................... C12Q 1/703 435/5 |
| 2010/0041049 A1* | 2/2010 | Smith ..................... C12Q 1/682 435/6.12 |
| 2010/0136536 A1* | 6/2010 | Todd ..................... C12Q 1/6818 435/6.1 |
| 2010/0221711 A1* | 9/2010 | Nauwelaers ....... C12N 15/1003 435/6.16 |
| 2011/0143338 A1* | 6/2011 | Todd ..................... C12N 15/111 435/6.1 |
| 2012/0101267 A1* | 4/2012 | Todd ..................... C12Q 1/6811 536/23.1 |
| 2014/0017669 A1* | 1/2014 | Todd ..................... C12Q 1/682 435/5 |
| 2014/0349276 A1* | 11/2014 | Brown, III ........... C12Q 1/6816 435/5 |
| 2015/0050656 A1* | 2/2015 | Todd ..................... C12Q 1/6818 435/6.12 |
| 2016/0348161 A1* | 12/2016 | Todd ..................... C12Q 1/6818 |

FOREIGN PATENT DOCUMENTS

| EP | 0552931 | * | 7/1993 |
| WO | WO 01/98541 A2 | | 12/2001 |
| WO | WO 2007/041774 | * | 4/2007 |
| WO | WO 2008/122084 A1 | | 10/2008 |
| WO | WO 2009/022125 | * | 2/2009 |
| WO | WO 2010/017246 | * | 2/2010 |

(Continued)

OTHER PUBLICATIONS

Elbaz et al.,Cooperative Multicomponent Self-Assembly of Nucleic Acid Structures for the Activation of DNAzyme Cascades: A Paradigm for DNA Sensors and Aptasensors. Chem. Eur. J. 15 3411 (2009).*
Mokany et al.,MNAzymes, a Versatile New Class of Nucleic Acid EnzymesThat Can Function as Biosensors and Molecular Switches. JACS 132 : 1051 (2010).*
Pavlov et al., Fluorescence Detection of DNA by the Catalytic Activation of an Aptamer/Thrombin Complex. JACS 127 :6522 (2005).*

(Continued)

*Primary Examiner* — Ethan C Whisenant
(74) *Attorney, Agent, or Firm* — Alston & Bird LLP

(57) ABSTRACT

The present invention relates to compositions and methods for the detection of target molecules, and the amplification of detectable signals generated by detection assays. More specifically, the present invention relates to methods utilizing catalytic nucleic acid enzymes to generate and/or amplify a signal indicative of the presence of target molecules (e.g. nucleic acids and proteins), and compositions for use in the methods.

14 Claims, 34 Drawing Sheets

(56) References Cited

FOREIGN PATENT DOCUMENTS

| WO | WO 2012/065231 | * | 5/2012 |
| WO | WO 2012/070863 A2 | | 5/2012 |

OTHER PUBLICATIONS

Tian et al., Cascade Signal Amplification for DNA Detection. ChemBioChem 7 :1862 (2006).*

Wang et al.DNA Switches: From Principles to Applications Angewante Reviews 54 :1098 (2015).*

Willner et al., DNAzymes for sensing, nanobiotechnology and logic gate applications. Chem Soc. Rev., 37 :1153 (2008).*

Chen et al., "Design Principles for Ligand-Sensing, Conformation-Switching Ribozymes," PLoS Comput. Biol, 5(12):e1000620, 15 pages, (2009).

EPO Application No. EP2013807047, European Search Report and Supplementary European Search Opinion mailed Nov. 25, 2015.

Fu et al., "DNAzyme Molecular Beacon Probes for Target-Induced Signal-Amplifying Colorimetric Detection of Nucleic Acids," Anal. Chem., 83(2):494-500, (2011).

Li et al., "Amplified Analysis of Low-Molecular-Weight Substrates or Proteins by the Self-Assembly of DNAzyme-Aptamer Conjugates," J. Am. Chem. Soc., 129(18):5804-5805, (2007).

Song et al., "Label-free Catalytic and Molecular Beacon Containing an Abasic Site for Sensitive Fluorescent Detection of Small Inorganic and Organic Molecules," Anal. Chem., 84(6): 2916-2922, (2012).

Sun et al., "An aptazyme-based electrochemical biosensor for the detection of adenosine," Anal Chim Acta, 669:87-93, (2010).

WIPO Application No. PCT/AU2013/000651, PCT International Search Report mailed Sep. 2, 2013.

WIPO Application No. PCT/AU2013/000651, PCT Written Opinion of the International Searching Authority mailed Sep. 2, 2013.

WIPO Application No. PCT/AU2013/000651, PCT International Preliminary Report on Patentability issued Apr. 29, 2014.

* cited by examiner

TARGET DETECTION AND SIGNAL AMPLIFICATION

CROSS-REFERENCE TO RELATED APPLICATIONS

The present application is a U.S. national stage of PCT/AU2013/000651 filed Jun. 18, 2013, which claims the benefit of AU 2012902551 filed Jun. 18, 2012, AU 2012903462 filed Aug. 10, 2012 and AU 2013202354 filed Apr. 3, 2013, the entire contents of each of which are incorporated herein by cross-reference.

REFERENCE TO A SEQUENCE LISTING

This application includes an electronic sequence listing in a file named 456301_SEQLST.TXT, created on Dec. 1, 2015 and containing 32,266 bytes, which is hereby incorporated by reference.

TECHNICAL FIELD

The present invention relates to compositions and methods for the detection of target molecules, and the amplification of detectable signals generated by detection assays. More specifically, the present invention relates to methods utilizing catalytic nucleic acid enzymes to generate and/or amplify a signal indicative of the presence of target molecules (e.g. nucleic acids and proteins), and compositions for use in the methods.

BACKGROUND

A number of assays are currently available for the detection of target molecules in a sample. Some rely on the use of enzymes, and in particular enzymes that catalyse modifications to nucleic acids including the following discussed below.
Nucleases Nucleases are enzymes that cleave phosphodiester bonds between the nucleotide subunits of nucleic acids. Deoxyribonucleases act on DNA while ribonucleases act on RNA, however some nucleases utilize both DNA and RNA as substrates. Nucleases can be further categorized as endonucleases and exonucleases, although some enzymes may have multiple functions and exhibit both endonuclease and exonuclease activity. Endonucleases cleave phosphodiester bonds within a polynucleotide chain. In contrast, exonucleases cleave phosphodiester bonds at the end of a polynucleotide chain. Exonucleases may remove 'nucleotides from either the 5' end or the 3' end or from both ends of a DNA or RNA strand.

Non-limiting examples of protein exonucleases include Exonuclease I (E. coli), Exonuclease III (E. coli), Exonuclease VII and T7 Exonuclease. Exonuclease III (ExoIII) is an exonuclease that catalyzes the step-wise removal of mononucleotides from the 3' end of blunt or 3' recessed duplexed DNA. It is also capable of acting at nicks within duplexed DNA. ExoIII has minimal activity on single-stranded DNA or duplexed DNA that have single stranded protruding ends of at least 4 nt.
Catalytic Nucleic Acid Enzymes Catalytic nucleic acid enzymes are non-protein enzymes capable of modifying specific substrates. Catalytic nucleic acid enzymes include DNA molecules (also known in the art as a DNAzyme, deoxyribozyme, or DNA enzyme), RNA, molecules (also known in the art as a ribozyme), and multi-component nucleic acid enzymes composed of multiple DNA and/or RNA molecules (also known in the art as an MNAzyme). Catalytic nucleic acid enzymes can modify specific nucleic acid substrate sequences by, for example, cleavage or ligation. A unique class of catalytic nucleic acid enzyme (known in the art as a horseradish peroxidase-mimicking DNAzyme) can catalyse peroxidase reactions that convert specific chemical substrates into their oxidated products which can for example, produce a change in colour or emit a fluorescent or chemiluminescent signal.

DNAzymes and ribozymes capable of cleaving or ligating RNA substrates, DNA substrates and/or chimeric DNA/RNA substrates, can generally only modify a target nucleic acid substrate that meets minimum sequence requirements. For example, the substrate should exhibit sufficient base pair complementarity to the substrate binding arms of the enzyme, and also needs a specific sequence at the site of catalytic modification. Examples of such sequence requirements at the catalytic cleavage site include the requirement for a purine:pyrmidine sequence for DNAzyme cleavage (10-23 model) and the requirement for the sequence uridine:X where X can equal A, C or U but not G, for the hammerhead ribozymes. The 10-23 DNAzyme is a DNAzyme that is capable of cleaving nucleic acid substrates at specific RNA phosphodiester bonds. This DNAzyme has a catalytic domain of 15 deoxyribonucleotides flanked by two substrate-recognition domains (arms).

MNAzymes are another category of catalytic nucleic acid enzymes. These multi-component nucleic acid enzymes require an assembly facilitator (e.g. a target nucleic acid) for their assembly and catalytic activity. MNAzymes are composed of multiple part-enzymes, or partzymes, which self-assemble in the presence of one or more assembly facilitators and form catalytically active MNAzymes capable of catalytically modifying substrates. The partzymes have multiple domains including sensor arms which bind to the assembly facilitator (such as a target nucleic acid); substrate arms which bind the substrate, and partial catalytic core sequences which, upon assembly of multiple partzyme components, combine to provide a complete catalytic core. MNAzymes can be designed to recognize a broad range of assembly facilitators including, for example, different target nucleic acid sequences. In the presence of the assembly facilitator, a catalytically active MNAzyme can assemble from partzyme components, and then bind and catalytically modify a substrate to generate an output signal. The assembly facilitator may be a target nucleic acid present in a biological or environmental sample. In such cases, MNAyme catalytic activity is indicative of the presence of the target. Several MNAzymes capable of cleaving nucleic acid substrates have been reported and additional MNAzymes which can ligate nucleic acid substrates are also known in the art.

Aptazymes are specific types of catalytic nucleic acids (DNAzymes, ribozymes or MNAzymes) which have been linked with an aptamer domain to allosterically regulate the nucleic acid enzymes such that their activity is dependent on the presence of the target analyte/ligand capable of binding to the aptamer domain. Complementary regulator oligonucleotides have been used to inhibit the activities of aptazymes in the absence of target analytes by binding to both the aptamer and part of the catalytic nucleic acid domains within the aptazymes. The inhibition of catalytic activity of aptazymes was reversible by the binding of target ligands to the aptamer portions thus promoting removal of the regulator oligonucleotide. The present inventors are not aware of any previous disclosure of a method that employs oligonucleotides designed to reversibly inhibit the modification of nucleic acid substrates by the catalytic activity of catalytic nucleic acids which are not coupled with an aptamer (i.e. a catalytic nucleic acid which is not an aptazyme), whereby inhibition is mediated by an oligonucleotide which binds to the catalytic core, or a portion thereof, of the catalytic nucleic acid.

Strand Displacing Polymerases

DNA polymerases catalyze the polymerization of deoxyribonucleotides into a DNA strand. They are naturally occurring enzymes responsible for DNA replication, in which the polymerase "reads" an intact DNA strand as a template and uses it to synthesize a new strand. Some DNA polymerases contain 5'-3' proofreading exonuclease activity, whereby they will degrade any downstream strands encountered during synthesis (e.g. Taq DNA polymerase). In contrast, strand-displacing DNA polymerases have the ability to displace any downstream strands, encountered during synthesis. The downstream strands are not degraded and remain intact. Examples of strand-displacing DNA polymerases include Phi29, DNA polymerase I Klenow Fragment, $Vent_R$ and Bst polymerase large fragment.

Kinases and Phosphatases

Kinases can catalyse the transfer of a γ-phosphate from ATP to specific amino acids in proteins and also to nucleic acid termini. Phosphatases can catalyse the removal of phosphate groups via hydrolysis of esterified phosphoric acid, resulting in a phosphate ion and a molecule with a free hydroxyl group. Protein phosphorylation via kinases and de-phosphorylation via phosphatases are important for regulating signal transduction pathways within a cell, thus performing crucial functions in cellular process such as metabolism, cell cycle progression, cell movement, and apoptosis. In molecular biology, phosphorylation of the 3' termini of oligonucleotides can be used as a method to prevent their extension by polymerases. Alternatively, de-phosphorylation of the 3' termini of oligonucleotides can be used as a method to allow for their extension by polymerases.

Target and Signal Amplification Technologies

In order to increase the sensitivity of target detection, strategies for target amplification or signal amplification have been employed, many of which utilize DNA and/or RNA polymerase enzymes. Examples of existing methods which employ target amplification include the polymerase chain reaction (PCR), strand displacement amplification (SDA), loop-mediated isothermal amplification (LAMP), rolling circle amplification (RCA), transcript-mediated amplification (TMA); self-sustained sequence replication (3SR), or nucleic acid sequence based amplification (NASBA). Those methods which are dependent on strand displacement for amplification, for example SDA, RCA and LAMP, require the use of polymerases which possess strand displacing activity. Signal amplification cascades that utilize nucleases including nicking endonucleases have also been described (e.g. NESA).

Signal amplification cascades that utilize catalytic nucleic acids have also been described. One example involves the use of an oligonucleotide consisting of two adjacent peroxidase-mimicking DNAzymes joined by a ribonucleotide junction. The ends of this oligonucleotide are linked together via a short linker DNA which hybridizes to each end, so as to form a quasi-circular structure. The formation of this structure temporarily inhibits the catalytic activity of the DNAzymes. An MNAzyme that assembles in the presence of its target assembly facilitator molecule hybridizes directly to the DNAzymes and cleaves the ribonucleotide junction between them. Cleavage of the oligonucleotide containing the DNAzymes results in separation of the two DNAzymes from each other and from the short linker DNA resulting in activation of the DNAzymes. The limitations of this strategy are that amplification of signal is limited to only two DNAzymes activated for each MNAzyme cleavage event, and since these peroxidase-mimicking DNAzymes have no capacity to modify nucleic acid substrates, there is no mechanism for these DNAzymes to activate additional DNAzyme molecules. As such the strategy is unsuitable as a first step in a circular feedback cascade capable of exponential signal amplification. Further, the complementarity between the MNAzyme arms and the DNAzymes, which is necessary for the initial cleavage event to occur, may also result in the sequestering of DNAzyme molecules once they have been released from the quasi-circular structure, potentially limiting the sensitivity of the reaction.

Many limitations are evident in other existing signal amplification methods. For, example, in a number of techniques the speed of the reaction is limited by the number of target DNA molecules initially present in the sample. These and other methods thus often lack the speed and sensitivity required for clinical application. Others suffer from false positive signal generation in the absence of target due to inadequate inhibition of the catalytic nucleic acid molecules. A number of methods utilizing DNA strand displacement are slow and lack the sensitivity of target amplification methods. Assays relying predominantly on unique recognition sites can preclude detecting universal target sequences, or may require new probes for each new target sequence.

Thus, there is an ongoing need for methods for detecting and quantifying nucleic acid sequences and other targets which incorporate signal amplification.

SUMMARY OF INVENTION

The present invention addresses at least one of the disadvantages evident in existing target molecule detection and/or signal amplification methods by providing the compositions, kits and methods described herein.

The present invention relates at least in part to the following embodiments 1-174:

Embodiment 1: A composition comprising: (i) a first molecular complex comprising: a first catalytic nucleic acid enzyme; or a catalytic portion thereof; or a nucleotide sequence complementary to the enzyme or the catalytic portion thereof; hybridised to a first blocker oligonucleotide (BL) by complementary base pairing, wherein at least one: catalytic core nucleotide of the first enzyme or the catalytic portion thereof, or nucleotides of the sequence that is complementary to a catalytic core nucleotide, is hybridised to the first BL, and the first catalytic nucleic acid enzyme is not an aptazyme; and (ii) a nucleic acid substrate capable of catalytic modification by the first catalytic nucleic acid.

Embodiment 2: The composition according to embodiment 1, wherein at least two, at least three, at least four, or at least five: catalytic core nucleotides of the first enzyme or the catalytic portion thereof, or nucleotides of the sequence that are complementary to the catalytic core nucleotides; are hybridised to the first blocker oligonucleotide or portion thereof.

Embodiment 3: The composition according to embodiment 1 or embodiment 2, wherein only one: catalytic core nucleotide of the first enzyme or the catalytic portion thereof, or nucleotide of the sequence that is complementary to the catalytic core nucleotide; is not hybridised to the first blocker oligonucleotide.

Embodiment 4: The composition according to any one of embodiments 1 to 3, wherein at least two, at least three, at least four, or at least five: catalytic core nucleotides of the first enzyme or the catalytic portion thereof, or nucleotides of the sequence that are complementary to the catalytic core nucleotides; are not hybridised to the first blocker oligonucleotide.

Embodiment 5: The composition according to any one of embodiments 1 to 4 wherein: the blocker oligonucleotide comprises first and second segments, each hybridised to: a distinct hybridising arm of said first enzyme or said catalytic portion thereof; by complementary base pairing, and an intermediate segment between the first and second segments; and the intermediate segment comprises a substrate for a second catalytic nucleic acid enzyme, and at least a segment of the substrate is not hybridised to the first enzyme, or catalytic portion thereof.

Embodiment 6: The composition according to any one of embodiments 1 to 5, wherein the intermediate segment partially or completely spans: the catalytic core of the first catalytic nucleic acid enzyme or catalytic portion thereof; or nucleotides of the complementary nucleotide sequence that are complementary to the catalytic core.

Embodiment 7: The composition according to any one of embodiments 1 to 6, wherein the catalytic portion thereof is a partzyme.

Embodiment 8: The composition according to any one of embodiments 1 to 7, wherein the 5' terminus of the first blocker oligonucleotide opposes the 3' terminus of the first catalytic nucleic acid enzyme, catalytic portion thereof, or complementary nucleotide sequence.

Embodiment 9: The composition according to any one of embodiments 1 to 7, wherein the 5' terminus of the first blocker oligonucleotide opposes the 5' terminus of the first catalytic nucleic acid enzyme, catalytic portion thereof, or complementary nucleotide sequence.

Embodiment 10: The composition according to any one of embodiments 5 to 9, wherein the intermediate segment comprises first substrate and optionally a second substrate, and at least a segment of each said substrate is not hybridised to the first enzyme, catalytic portion thereof, or complementary nucleotide sequence.

Embodiment 11: The composition according to embodiment 10, wherein the first and second substrates comprise differing nucleotide sequences.

Embodiment 12: The composition according to embodiment 10 or embodiment 11, wherein the intermediate segment further comprises a third substrate comprising a different nucleotide sequence to the first and second substrates, and at least a segment of the third substrate is not hybridised to the first enzyme, catalytic portion thereof, or complementary nucleotide sequence.

Embodiment 13: The composition according to any one of embodiments 10 to 12, wherein at least a portion of each said substrate comprises the same nucleotide sequence.

Embodiment 14: The composition according to any one of embodiments 10 to 13, wherein any said substrate of the intermediate segment comprises a partial recognition site for a restriction enzyme.

Embodiment 15: The composition according to any one of embodiments 10 to 14, wherein any of the said first BL; said first enzyme or the catalytic portion thereof; said nucleotides of the sequence that is complementary to a catalytic core nucleotide; or said nucleic acid substrate is tethered to an insoluble support.

Embodiment 16: The composition according to embodiment 15, wherein the substrate is tethered by virtue of a streptavidin-biotin interaction.

Embodiment 17: The composition of embodiment 10, further comprising a second molecular complex comprising said second catalytic nucleic acid enzyme, hybridised to a second BL by complementary base pairing, wherein: the second BL comprises first and second segments, each hybridised to a distinct hybridising arm of said second enzyme by complementary base pairing, and an intermediate segment between the first and second segments; the intermediate segment optionally comprises a copy of said first substrate and a third substrate, and at least a segment of each said substrate is not hybridised to the second enzyme; and said first enzyme is capable of hybridising and cleaving the third substrate, and said second enzyme is capable of hybridising and cleaving said second substrate.

Embodiment 18: The composition according to any one of embodiments 5 to 9, wherein the first and second catalytic nucleic acid enzymes have different substrate specificity.

Embodiment 19: The composition according to any one of embodiments 5 to 9, wherein the first and second catalytic nucleic acid enzymes have the same substrate specificity.

Embodiment 20: The composition according to any one of embodiments 5 to 19, wherein the number of nucleotides in the intermediate segment of any said molecular complex exceeds the number of catalytic core nucleotides.

Embodiment 21: The composition according to any one of embodiments 5 to 19, wherein the number of nucleotides in the intermediate segment of any said complex equals the number of catalytic core nucleotides.

Embodiment 22: The composition according to any one of embodiments 5 to 21, further comprising a hairpin loop linking one terminus of the first blocker oligonucleotide to one terminus of the first catalytic nucleic acid enzyme, catalytic portion thereof, or complementary nucleotide sequence.

Embodiment 23: The composition according to any one of embodiments 1 to 4, comprising first and second blocker oligonucleotides and first and second catalytic nucleic acid enzymes, wherein: the first and second enzymes each comprise two separate hybridising arms; the first blocker oligonucleotide comprises first and second segments hybridised to a single hybridising arm of the first and second enzyme, respectively; the second blocker oligonucleotide comprises first and second segments which are hybridised to a single hybridising arm of the first and second enzyme, respectively; the first and second segments of the first and second blocker oligonucleotides are each hybridised to a different hybridising arm; the first and second blocker oligonucleotides each comprise an intermediate segment between the first and second segments, wherein each intermediate segment is not hybridised to either the first or the second enzyme; and either or both of the intermediate segments comprises a substrate for a catalytic nucleic acid enzyme.

Embodiment 24: The composition according to any one of embodiments 1 to 4, wherein each nucleotide of the first enzyme, the catalytic portion thereof, or the complementary nucleotide sequence, is hybridised to the first BL.

Embodiment 25: The composition according to any one of embodiments 1 to 4, wherein the hybridised blocker oligonucleotide provides a single-stranded 3' or 5' overhang segment extending from the first molecular complex.

Embodiment 26: The composition according to embodiment 25, wherein the overhang segment or a portion thereof is complementary to a releaser oligonucleotide (RL) capable of hybridising to the overhang portion and dissociating the first catalytic nucleic acid enzyme or a catalytic portion thereof from the BL.

Embodiment 27: The composition according to embodiment 26, wherein the releaser oligonucleotide does not comprise the same nucleotide sequence as the first catalytic nucleic acid enzyme or a catalytic portion thereof.

Embodiment 28: The composition according to any one of embodiments 25 to 27, wherein said first enzyme provides a single-stranded 3' overhang segment extending from the complex.

Embodiment 29: The composition according to any one of embodiments 1 to 4, further comprising a hairpin loop linking one end of the blocker oligonucleotide to one end of said first enzyme.

Embodiment 30: The composition according to any one of embodiments 1 to 4, further comprising a second BL hybridised to a second catalytic nucleic acid enzyme forming a second molecular complex, wherein: a first hairpin loop links the first BL to the first catalytic nucleic acid enzyme, and a second hairpin loop links the second BL to the second catalytic nucleic acid enzyme; the first and second blocker oligonucleotides provide a single-stranded overhang segment extending from the first and second molecular complex, respectively; a portion of the overhang segment of the first molecular complex is hybridised to a portion of the overhang segment of the second molecular complex by complementary base pairing; and unhybridised portions of each overhang segment combine to form a segment comprising base pair complementarity to an intermediate segment of a releaser oligonucleotide (RL).

Embodiment 31: The composition according to any one of embodiments 25 to 29, wherein the blocker oligonucleotide comprises first and second segments, each hybridised to said first enzyme by complementary base pairing, and an intermediate segment between the first and second segments comprising a single-strand component of a restriction endonuclease recognition site.

Embodiment 32: The composition according to embodiment 31, wherein the nucleotides of said blocker oligonucleotide containing the single-strand component of a restriction endonuclease recognition site are not hybridised to the first enzyme.

Embodiment 33: The composition according to embodiment 31 or embodiment 32, wherein the restriction endonuclease recognition site is a nicking endonuclease recognition site.

Embodiment 34: The composition according to embodiment 29 wherein the hairpin loop comprises a stem in which one strand provides a binding site for a primer that is extendable by a strand displacing polymerase, and/or the blocker oligonucleotide and/or first enzyme are each 3' phosphorylated.

Embodiment 35: The composition according to embodiment 34, wherein the strand displacing polymerase is selected, from the group consisting of Klenow fragment, Bst, Sequenase 2.0, Vent, Phi29, Pyrophage 3137 or any variants thereof.

Embodiment 36: The composition according to any one of embodiments 1 to 35, wherein the first catalytic nucleic acid enzyme or portion thereof is a DNAzyme, a ribozyme, or a component of an MNAzyme.

Embodiment 37: The composition according to any one of embodiments 5 to 22, wherein the second catalytic nucleic acid enzyme is a DNAzyme, a ribozyme or an MNAzyme.

Embodiment 38: The composition according to embodiment 36, wherein the DNAzyme, ribozyme, or MNAzyme is capable of cleaving a substrate.

Embodiment 39: The composition according to embodiment 37, wherein the DNAzyme, ribozyme or MNAzyme is capable of cleaving a substrate.

Embodiment 40: The composition according to any one of embodiments 36 to 39, wherein the first catalytic nucleic acid enzyme is a DNAzyme.

Embodiment 41: A kit comprising the composition according to any one of embodiments 1 to 40.

Embodiment 42: A kit comprising the composition according to any one of embodiments 5 to 23, and either or both of the following components: a reporter substrate capable of providing a detectable signal upon catalytic modification by the first and/or second catalytic nucleic acid enzyme; an initiator catalytic nucleic acid enzyme, or catalytic component thereof, specific for the substrate of the intermediate segment.

Embodiment 43: The kit according to embodiment 42, wherein the initiator catalytic enzyme is a DNAzyme, a ribozyme, an aptazyme, an aptaMNAzyme, or an MNAzyme.

Embodiment 44: The kit according to embodiment 42 or embodiment 43, wherein any said BL comprises a partial recognition site for a restriction enzyme and the kit further comprises said restriction enzyme.

Embodiment 45: A kit comprising the composition of any one of embodiments 25 to 30, and any one or more of the following components: a releaser oligonucleotide comprising a sequence complementary to the blocker oligonucleotide and having binding affinity for the blocker oligonucleotide in a region complementary to the first catalytic nucleic acid enzyme; a reporter substrate capable of providing a detectable signal upon catalytic modification by the first catalytic nucleic acid enzyme; an exonuclease; a nuclease recognition fragment comprising a sequence complementary to a segment of the blocker oligonucleotide, and which is capable of recruiting exonuclease activity when hybridised to the blocker oligonucleotide.

Embodiment 46: The kit, according to embodiment 45, wherein the exonuclease is selected from the group consisting of Exonuclease III and T7 exonuclease.

Embodiment 47: The kit according to embodiment 45 or embodiment 46, wherein the second catalytic nucleic acid enzyme is a ribozyme, a DNAzyme, or an MNAzyme.

Embodiment 48: A kit comprising the composition of any one of embodiments 31 to 33, and any one or more of the following components: a releaser oligonucleotide comprising a sequence complementary to the blocker oligonucleotide and having binding affinity for the blocker oligonucleotide in a region complementary to the first catalytic nucleic acid enzyme; a reporter substrate capable of providing a detectable signal upon catalytic modification by the first catalytic nucleic acid enzyme; a restriction endonuclease specific for a recognition sequence formed upon hybridisation of the releaser oligonucleotide and the blocker oligonucleotide.

Embodiment 49: The kit according to embodiment 48, wherein a component of the recognition sequence provided by the releaser oligonucleotide comprises a phosphorothioate linkage preventing cleavage of the releaser oligonucleotide by the restriction endonuclease.

Embodiment 50: The kit according to embodiment 48, wherein the recognition sequence is for a nicking endonuclease, and the restriction endonuclease is a nicking endonuclease.

Embodiment 51: A kit comprising the composition of embodiment 34 or embodiment 35, and any one or more of the following components: a primer specific for said binding site; a strand displacing polymerase or a component thereof; a reporter substrate capable of providing a detectable signal upon catalytic modification by the first catalytic nucleic acid enzyme.

Embodiment 52: A kit comprising: a first catalytic nucleic acid enzyme hybridised to a blocker oligonucleotide by complementary base pairing and a hairpin loop linking one terminus of the blocker oligonucleotide to one terminus of the catalytic nucleic acid first enzyme; a reporter substrate capable of providing a detectable signal upon catalytic modification by the first catalytic nucleic acid enzyme; an initiator catalytic nucleic acid enzyme specific for a target molecule; a primer oligonucleotide specific for a segment of the hairpin loop; a strand displacing polymerase or component thereof; a restriction endonuclease specific for a recognition sequence formed upon hybridisation of the primer to said segment of the hairpin loop and optionally subsequent extension of the primer by said strand displacing polymerase using the blocker oligonucleotide as a template.

Embodiment 53: The kit according to embodiment 52, wherein a component of the recognition sequence provided by the segment of the hairpin loop comprises a phosphorothioate linkage preventing cleavage of the segment by the restriction endonuclease.

Embodiment 54: The kit according to embodiment 52, wherein the recognition sequence is for a nicking endonuclease, and the restriction endonuclease is a nicking endonuclease.

Embodiment 55: The kit according to any one of embodiments 52 to 54, wherein each nucleotide of the first enzyme is hybridised to the BL.

Embodiment 56: The kit according to any one of embodiments 52 to 55, wherein strand displacing polymerase is selected from the group consisting of a Klenow fragment, Bst, Sequenase 2.0, Vent, Phi29, Pyrophage 3137 or any variants thereof.

Embodiment 57: The kit according to any one of embodiments 41 to 56, wherein the first catalytic nucleic acid enzyme is a DNAzyme, a ribozyme, or an MNAzyme.

Embodiment 58: A method for detecting the presence or absence of a first target molecule in a sample, the method comprising: (a) contacting the sample with at least one molecular complex comprising a BL and a first catalytic nucleic acid enzyme, the BL comprising first and second segments hybridised to the first enzyme by complementary base pairing, and an intermediate segment between the first and second segments comprising a first substrate for a catalytic nucleic acid enzyme, wherein at least a segment of the first substrate is not hybridised to the first enzyme; a first initiator enzyme, and a reporter substrate; wherein, the first initiator enzyme has binding specificity for the first target and the first substrate of said intermediate, segment and hybridisation of the target to the first initiator enzyme induces catalytic activity of the first initiator enzyme thereby facilitating cleavage of the first substrate when hybridised to the first initiator enzyme; the cleavage of the first substrate causes dissociation of hybridised strands of the blocker oligonucleotide and the first catalytic nucleic acid enzyme of said molecular complex; and the first enzyme of said molecular complex has binding specificity for the reporter substrate and, after said dissociation, is capable of hybridising to the reporter substrate and cleaving it to thereby provide a detectable signal indicative of the presence of the first target in the sample; and (b) determining whether a detectable signal is generated by said contacting, wherein detection of the signal indicates the first target molecule is present, and failure to detect the signal indicates the first target molecule is absent.

Embodiment 59: The method according to embodiment 58, wherein said molecular complex contacted with the sample is provided with a 5' terminus of the blocker oligonucleotide opposing a 5' terminus of the catalytic nucleic acid enzyme.

Embodiment 60: The method according to embodiment 58, wherein said molecular complex contacted with the sample is provided with a 5' terminus of the blocker oligonucleotide opposing a 3' terminus of the catalytic nucleic acid enzyme.

Embodiment 61: The method according to embodiment 58 or embodiment 59, comprising contacting the sample with first and second molecular complexes, wherein the first molecular complex comprises said BL and said first catalytic nucleic acid enzyme, and the intermediate segment between said first and second segments comprises the first substrate and a second substrate; the second molecular complex comprises a second BL and a second catalytic nucleic acid enzyme, the second BL comprising first and second segments hybridised to the second enzyme by complementary base pairing, and an intermediate segment between the first and second segments comprising a copy of said first substrate and a third substrate; said initiator enzyme has binding specificity for the target and the first substrate of each said intermediate segment, and hybridisation of the target to the initiator enzyme induces catalytic activity of the initiator enzyme thereby facilitating cleavage of the first substrate of each said intermediate segment when hybridised to the initiator enzyme; the cleavage of the first substrate of each said intermediate segment causes dissociation of hybridised strands of the blocker oligonucleotide and the catalytic nucleic acid enzyme of each said molecular complex; the first enzyme has binding specificity for said third substrate, and the second enzyme has binding specificity for said second substrate; and after the dissociation of each said molecular complex, the first enzyme is capable of hybridising and cleaving the third substrate of another second molecular complex, and the second enzyme is capable of hybridising and cleaving the second substrate of another first molecular complex, thereby amplifying said detectable signal.

Embodiment 62: The method according to embodiment 61, wherein said first, second or third substrate is identical to said reporter substrate.

Embodiment 63: The method according to embodiment 61, wherein the substrate of the intermediate segment of said molecular complex is identical to the reporter substrate, and upon said dissociation from the blocker oligonucleotide, the first catalytic nucleic acid enzyme of a first said molecular complex can hybridise and cleave the substrate of the intermediate segment of a second said molecular complex, thereby facilitating amplification of the detectable signal.

Embodiment 64: The method according to embodiment 60, wherein the intermediate segment between the first and second segments forms a hairpin loop structure comprising said at least a segment of the first substrate.

Embodiment 65: The method according to embodiment 59, wherein the intermediate segment comprises a second substrate for a second initiator catalytic nucleic enzyme, and the method further comprises contacting the sample with the second initiator catalytic nucleic acid enzyme; wherein the second initiator enzyme has binding specificity for a target and the second substrate of said intermediate segment, and hybridisation of the target to the second initiator enzyme induces catalytic activity of the second initiator enzyme thereby facilitating cleavage of the second substrate when hybridised to the second initiator enzyme; wherein the cleavage of the second substrate causes dissociation of hybridised strands of the blocker oligonucleotide and the first catalytic nucleic acid enzyme of said molecular complex, thereby allowing the first catalytic nucleic acid enzyme to hybridise to the reporter substrate and cleave it to thereby provide a detectable signal.

Embodiment 66: The method according to embodiment 65, wherein the second initiator enzyme has binding specificity for a second target that is distinct from said first target.

Embodiment 67: The method according to embodiment 66, wherein the second initiator enzyme has binding specificity for said first target.

Embodiment 68: The method according to any one of embodiments 65 to 67, wherein the intermediate segment comprises a third substrate for a third initiator catalytic nucleic enzyme, and the method further comprises contacting the sample with the third initiator catalytic nucleic acid enzyme; wherein the third initiator enzyme has binding specificity for a target and the third substrate of said intermediate segment, and hybridisation of the target to the third initiator enzyme induces catalytic activity of the third initiator enzyme thereby facilitating cleavage of the third substrate when hybridised to the third initiator enzyme; wherein the cleavage of the third substrate causes dissociation of hybridised strands of the blocker oligonucleotide and the first catalytic nucleic acid enzyme of said molecular complex, thereby allowing the first catalytic nucleic acid enzyme to hybridise to the reporter substrate and cleave it to thereby provide a detectable signal.

Embodiment 69: The method according to embodiment 68, wherein the third initiator enzyme has binding specificity for a third target that is distinct from the first and second targets.

Embodiment 70: The method according to embodiment 68, wherein the third initiator enzyme has binding specificity for the first target.

Embodiment 71: The method according to any one of embodiments 65 to 70, wherein said first and second substrates of the intermediate segment share a common segment of nucleotides that comprises the 5' terminus of the first substrate and the 3' terminus of the second substrate or vice versa.

Embodiment 72: The method according to embodiment 71, wherein the common segment of nucleotides commences in a 3' portion of the first substrate and terminates in a 5' portion of the second substrate.

Embodiment 73: The method according to any one of embodiment 59, wherein the reporter substrate is identical to the second substrate, and said first catalytic nucleic acid enzyme of said molecular complex is capable of hybridising to and cleaving the second substrate.

Embodiment 74: The method according to any one of embodiments 65 to 72, wherein the reporter substrate is distinct from any said substrate of the intermediate segment, and said first catalytic nucleic acid enzyme is not capable of hybridising to and cleaving any said substrate of the intermediate segment.

Embodiment 75: The method according to any one of embodiments 58 to 74, wherein any one or more of the first catalytic nucleic acid, the first substrate, the first initiator, enzyme, and the reporter substrate is tethered to an insoluble support.

Embodiment 76: The method according to embodiment 75, wherein the substrate of the intermediate segment is tethered to the support by virtue of a streptavidin-biotin interaction.

Embodiment 77: The method according to any one of embodiments 59 to 76, wherein the method comprises detecting an additional target by: (a) further contacting the sample with an additional molecular complex comprising an additional BL and an additional catalytic nucleic acid enzyme, the additional BL comprising two end segments each hybridised to the additional enzyme by complementary base pairing, and a middle segment between the two end segments comprising at least one additional substrate for an additional catalytic nucleic acid enzyme, wherein at least a portion of the additional substrate is not hybridised to the additional enzyme; an additional initiator catalytic nucleic acid enzyme; and an additional reporter substrate; wherein, the additional target is distinct from the first target, the at least one additional substrate of the intermediate segment is distinct from said first substrate, the additional reporter substrate is distinct from said first reporter substrate, the additional initiator catalytic nucleic acid enzyme is distinct from the first initiator catalytic nucleic acid enzyme, the additional initiator enzyme has binding specificity for the additional target and the additional substrate of said intermediate segment, and hybridisation of the additional target to the additional initiator enzyme induces catalytic activity of the additional initiator enzyme thereby facilitating cleavage of the additional substrate when hybridised to the additional initiator enzyme; the cleavage of the additional substrate causes dissociation of hybridised strands of the additional blocker oligonucleotide and the additional catalytic nucleic acid enzyme of said additional molecular complex; and the additional enzyme of said additional molecular complex has binding specificity for the additional reporter substrate and, after said dissociation, is capable of hybridising to the additional reporter substrate and cleaving it to thereby provide an additional detectable signal indicative of the presence of the additional target in the sample; and (b) determining whether an additional detectable signal is generated by said further contacting, wherein detection of the signal indicates the additional target molecule is present, and failure to detect the additional signal indicates the additional target molecule is absent.

Embodiment 78: The method according to embodiment 77, wherein the additional reporter substrate is identical to the at least one additional substrate, and said additional catalytic nucleic acid enzyme of said additional molecular complex is capable of hybridising to and cleaving the at least one additional substrate.

Embodiment 79: The method according to embodiment 77, wherein the additional reporter substrate is distinct to the at least one additional substrate, and said additional catalytic nucleic acid enzyme of said additional molecular complex is not capable of hybridising to and cleaving the at least one additional substrate.

Embodiment 80: The method according to embodiment 59, wherein any said substrate of any said molecular complex comprises a partial restriction enzyme recognition site, and any said target comprises a complementary portion of said partial restriction enzyme recognition site; said method further comprises contacting the sample with a restriction enzyme capable of recognising and cleaving the restriction enzyme recognition site; said target is capable of hybridising to said BL comprising the partial recognition site by complementary base pairing to thereby complete the restriction enzyme recognition site, thereby allowing said restriction enzyme to cleave the BL comprising the partial recognition site causing dissociation of hybridised strands of the blocker oligonucleotide and the catalytic nucleic acid enzyme of said molecular complex; and the catalytic nucleic acid enzyme of said molecular complex has binding specificity for the reporter substrate and, after said dissociation, is capable of hybridising to the reporter substrate and cleaving it to thereby provide a detectable signal indicative of the presence of said target in the sample.

Embodiment 81: The method according to embodiment 80, wherein the reporter substrate is identical to the substrate cleaved by said catalytic nucleic acid enzyme of said molecular complex.

Embodiment 82: The method according to embodiment 80, wherein the reporter substrate is distinct to the substrate comprising the partial recognition site, and said catalytic nucleic acid enzyme of said molecular complex.

Embodiment 83: The method according to any one of embodiments 58 to 79, wherein any said initiator enzyme comprises an aptamer; the absence of the target the aptamer adopts a conformation that prevents catalytic activity of the initiator enzyme; and in the presence of the target the aptamer binds to the target and adopts a conformation that allows catalytic activity of the initiator enzyme, to thereby cleave the substrate of the molecular complex.

Embodiment 84: A method for detecting the presence or absence of a target molecule in a sample, the method comprising: (a) contacting the sample with a reporter substrate; and at least one molecular complex comprising a BL and a first catalytic nucleic acid enzyme, the BL comprising first and second segments hybridised to the first enzyme by complementary base pairing, and an intermediate segment between the first and second segments comprising an aptamer, wherein at least a segment of the aptamer is not hybridised to the first enzyme; wherein, said molecular complex contacted with the sample is provided with a 5' terminus of the blocker oligonucleotide opposing a 5' terminus of the catalytic nucleic acid enzyme, and the intermediate segment between the first and second segments comprising said aptamer, the target has binding affinity for the aptamer and hybridisation of the target to the aptamer induces catalytic activity of the first enzyme thereby facilitating cleavage of the first substrate; the binding of the target to the aptamer portion of the BL causes dissociation of hybridised strands of the blocker oligonucleotide and the first catalytic nucleic acid enzyme of said molecular complex; and the first enzyme of said molecular complex has binding specificity for the reporter substrate and, after said dissociation, is capable of hybridising to the reporter substrate and cleaving it to thereby provide a detectable signal indicative of the presence of the first target in the sample; and (b) determining whether a detectable signal is generated by said contacting, wherein detection of the signal indicates the first target molecule is present, and failure to detect the signal indicates the first target molecule is absent.

Embodiment 85: A method according to embodiment 58 for detecting the presence or absence of a target molecule in a sample, the method comprising: (a) contacting the sample with first and second molecular complexes, wherein said first complex comprising a first BL and a first catalytic nucleic acid enzyme, wherein said second complex comprising a second BL and a second catalytic nucleic acid enzyme, the first and second BL each comprising first and second segments hybridised to the enzyme by complementary base pairing, and an intermediate segment between the first and second segments comprising a substrate for a catalytic nucleic acid enzyme, wherein at least a segment of the substrate is not hybridised to the first or second enzyme; and an initiator enzyme, wherein the initiator enzyme has binding specificity for the target and the substrate of said first molecular complex and hybridisation of the target to the initiator enzyme induces catalytic activity of the initiator enzyme thereby facilitating cleavage of the substrate when hybridised to the initiator enzyme; the cleavage of the substrate of the first molecular complex causes dissociation of hybridised strands of the blocker oligonucleotide and the catalytic nucleic acid enzyme of said first molecular complex; the catalytic nucleic acid enzyme of said first molecular complex, after said dissociation, is capable of hybridising to and cleaving the substrate of the second molecular complex causing dissociation of hybridised strands of the blocker oligonucleotide and the catalytic nucleic acid enzyme of the second molecular complex; the catalytic nucleic acid enzyme of said second molecular complex, after said dissociation, is capable of hybridising to and cleaving the substrate of a further said first molecular complex causing dissociation of the blocker oligonucleotide and the catalytic nucleic acid enzyme of the further said first molecular complex; and either or both substrates of the first and second molecular complexes is a reporter substrate capable of providing a detectable signal when cleaved; and (b) determining whether a detectable signal is generated by said contacting, wherein detection of the signal indicates the target molecule is present, and failure to detect the signal indicates the target molecule is absent.

Embodiment 86: The method according to embodiment 63 or embodiment 85, wherein either or both of the first and second molecular complexes comprises a hairpin loop linking one terminus of the blocker oligonucleotide to one terminus of the catalytic nucleic acid enzyme.

Embodiment 87:

A method for detecting the presence or absence of a plurality of target molecules in a sample, the method comprising: (a) contacting the sample with a molecular complex comprising first and second blocker oligonucleotides and first and second catalytic nucleic acid enzymes, wherein the first and second enzymes each comprise two separate hybridising arms; the first blocker oligonucleotide comprises first and second segments hybridised to a single hybridising arm of the first and second enzyme, respectively; the second blocker oligonucleotide comprises first and second segments which are hybridised to a single hybridising arm of the first and second enzyme, respectively; the first and second segments of the first and second blocker oligonucleotides are each hybridised to a different hybridising arm; the first and second blocker oligonucleotides each comprise an intermediate segment between the first and second segments, wherein each intermediate segment is not hybridised to either the first or the second enzyme; and either or both of the intermediate segments comprises a substrate for a catalytic nucleic acid enzyme; and a plurality of initiator catalytic nucleic acid enzymes; and a plurality of reporter substrates, wherein a first initiator catalytic nucleic acid enzyme has binding specificity for a first target molecule, and a second initiator catalytic nucleic acid enzyme has binding specificity for a second target molecule; the first and second initiator enzymes have binding specificity for the substrate of the intermediate segment of either or both of the first and second blocker oligonucleotides of said molecular complex; hybridisation of each said target to each said initiator enzyme induces catalytic activity of each said initiator enzyme, thereby facilitating cleavage of the substrate of each said blocker oligonucleotide when hybridised to the initiator enzyme; the cleavage of each said substrate causes dissociation of hybridised strands of the first and second blocker oligonucleotides from the hybridising arms of the first and second catalytic nucleic acid enzymes of said molecular complex; and each said catalytic nucleic acid enzyme has binding specificity for at least one reporter substrate and, after said dissociation, is capable of hybridising to at least one of said reporter substrates and cleaving it to thereby provide a detectable signal indicative of the presence of the target molecules in the sample; and (b) determining whether a detectable signal is generated by said contacting, wherein detection of the signal indicates the target molecules are present, and failure to detect the signal indicates the target molecule are absent.

Embodiment 88: The method according to embodiment 87, wherein the intermediate segments of said first and second blocker oligonucleotides of the molecular complex comprise identical substrates.

Embodiment 89: The method according to embodiment 88, wherein the intermediate segments of said first and second blocker oligonucleotides of the molecular complex comprise unidentical substrates.

Embodiment 90: The method according to any one of embodiments 87 to 89, wherein the plurality of target molecules comprises unidentical target molecules that are hybridised by different initiator enzymes.

Embodiment 91: The method according to any one of embodiments 87 to 90, wherein the plurality of reporter substrates comprises unidentical reporter substrates.

Embodiment 92: The method according to any one of embodiments 87 to 91, wherein the first and second catalytic nucleic acid enzymes of said molecular complex have different substrate specificity, and each said enzyme hybridises and cleaves a different reporter substrate.

Embodiment 93: The method according to any one of embodiments 58 to 93, wherein any said molecular complex comprises a blocker oligonucleotide (BL) hybridised to a catalytic nucleic acid by complementary base pairing and at least one but not all catalytic core nucleotides of the enzyme are hybridised to the BL.

Embodiment 94: The method according to any one of embodiments 58 to 63, 85 or 86, wherein said contacting comprises contacting the sample with a composition according to any one of embodiments 1 to 10 or 17 to 21.

Embodiment 95: The method according to any one of embodiments 87 to 92, wherein said contacting comprises contacting the sample with a composition according to embodiment 23.

Embodiment 96: A method for detecting the presence or absence of a target molecule in a sample, the method comprising: (a) contacting the sample with at least one molecular complex comprising a blocker oligonucleotide and a first catalytic nucleic acid enzyme, the blocker oligonucleotide comprising first and second segments hybridised to the first enzyme by complementary base pairing and an intermediate segment between the first and second segments that is not hybridised to the first enzyme, wherein the blocker oligonucleotide provides a single-stranded 3' or 5' overhang segment extending from the molecular complex; and an initiator catalytic nucleic acid enzyme, a precursor substrate, and a reporter substrate, wherein the initiator enzyme has binding specificity for the target, and hybridisation of the target to the initiator enzyme induces catalytic activity of the initiator enzyme facilitating catalytic modification of the precursor substrate when hybridised to the initiator enzyme, to thereby provide a releaser oligonucleotide; the releaser oligonucleotide comprises a sequence having base pair complementarity to: at least a portion of the overhang segment provided by the blocker oligonucleotide of said molecular complex; and at least a portion of the blocker oligonucleotide hybridised by complementary base pairing to the first catalytic nucleic acid enzyme of said molecular complex; the nucleotide sequence of the releaser oligonucleotide is not the same as the nucleotide sequence of the catalytic nucleic acid enzyme; the releaser oligonucleotide when present can hybridise with the blocker oligonucleotide forming a duplex and thereby causing dissociation of hybridised strands of the first catalytic nucleic acid enzyme and the blocker oligonucleotide of said molecular complex; and the first catalytic nucleic acid enzyme of said molecular complex, after said dissociation, is capable of hybridising to and cleaving the reporter substrate to thereby provide a detectable signal; and (b) determining whether a detectable signal is generated by said contacting, wherein detection of the signal indicates the target molecule is present, and failure to detect the signal indicates the target molecule is absent.

Embodiment 97: The method according to embodiment 96, wherein said molecular complex comprises a hairpin loop linking one end of the blocker oligonucleotide to one end of the first catalytic nucleic acid enzyme.

Embodiment 98: The method according to embodiment 97, wherein said contacting comprises contacting a plurality of said molecular complexes with the sample, wherein; a portion of the overhang segment of a first said molecular complex is hybridised to a portion of the overhang segment of a second said molecular complex by complementary base pairing; the releaser oligonucleotide comprises a first segment having base pair complementarity to a portion of the said overhang segment of said first molecular complex, and, a portion of the blocker oligonucleotide hybridised to the first catalytic nucleic acid enzyme of said first molecular complex; a second segment having base pair complementarity to a portion of the overhang segment of said second molecular complex, and, a portion of the blocker oligonucleotide hybridised to the first catalytic nucleic acid enzyme of said second molecular complex; and an intermediate segment between the first and third segments having base pair complementarity to at least a portion of the overhang segment of each said blocker oligonucleotide; the first segment of the releaser oligonucleotide has binding affinity for a portion of the blocker oligonucleotide of said first molecular complex hybridised by complementary base pairing to the first catalytic nucleic acid enzyme of said first molecular complex; the second segment of the releaser oligonucleotide has binding affinity for the blocker oligonucleotide of said second molecular complex hybridised by complementary base pairing to the first catalytic nucleic acid enzyme of said second molecular complex; the releaser oligonucleotide when present can hybridise with each said blocker oligonucleotide causing dissociation of hybridised strands of the catalytic nucleic acid and the blocker oligonucleotide of each said molecular complex; and the first catalytic nucleic acid enzyme of each said molecular complex, after said dissociation, is capable of hybridising to and cleaving a reporter substrate to thereby provide a detectable signal; and (b) determining whether a detectable signal is generated by said contacting, wherein detection of the signal indicates the target molecule is present, and failure to detect the signal indicates the target molecule is absent.

Embodiment 99: The method according to any one of embodiments 96 to 98, wherein the precursor substrate is or comprises the target.

Embodiment 100: The method according to embodiment 96, further comprising amplifying the detectable signal by contacting the sample with an exonuclease capable of digesting the blocker oligonucleotide when hybridised to the releaser oligonucleotide, wherein said digesting liberates the releaser oligonucleotide which can then bind to a second said molecular complex and initiate generation of further detectable signal.

Embodiment 101: The method according to embodiment 100, wherein the duplex formed by hybridisation of the releaser oligonucleotide to the blocker oligonucleotide comprises a 3' overhang segment of at least four nucleotides and an opposing blunt end.

Embodiment 102: The method according to embodiment 100 or embodiment 101, wherein the exonuclease is selected from ExoIII and T7 exonuclease.

Embodiment 103: The method according to embodiment 96, further comprising amplifying the detectable signal by contacting the sample with a nicking endonuclease capable of cleaving the blocker oligonucleotide when hybridised to the releaser oligonucleotide, thereby liberating the releaser oligonucleotide from said duplex and allowing it to hybridise with the blocker oligonucleotide of a second said molecular complex and initiate generation of further detectable signal.

Embodiment 104: The method according to embodiment 96, further comprising amplifying the detectable signal by contacting the sample with a restriction endonuclease capable of cleaving the blocker oligonucleotide when hybridised to the releaser oligonucleotide, thereby liberating the releaser oligonucleotide from said duplex and allowing it to hybridise with the blocker oligonucleotide of a second said molecular complex and initiate generation of further detectable signal.

Embodiment 105: The method according to embodiment 104, wherein the restriction endonuclease cleaves the blocker oligonucleotide after binding a recognition site formed by segments of the releaser oligonucleotide and the blocker oligonucleotide, each said segment comprising a partial recognition site; the partial recognition sequence provided by the releaser oligonucleotide segment comprises a phosphorothioate linkage preventing cleavage of the releaser oligonucleotide by the restriction endonuclease; and the partial recognition site of the blocker oligonucleotide is not hybridised to the first catalytic nucleic acid enzyme of said molecular complex.

Embodiment 106:

The method according to embodiment 104, wherein the restriction endonuclease is a nicking endonuclease; the nicking endonuclease cleaves the blocker oligonucleotide after binding a recognition site formed by segments of the releaser oligonucleotide and the blocker oligonucleotide, each said segment comprising a partial recognition site; and the partial recognition site of the blocker oligonucleotide is not hybridised to the first catalytic nucleic acid enzyme of said molecular complex.

Embodiment 107: The method according to embodiment 96, further comprising amplifying the detectable signal by contacting the sample with a primer oligonucleotide and a strand displacing polymerase or component thereof, wherein said molecular complex further comprises a hairpin loop extending from one terminus of the blocker oligonucleotide wherein the first catalytic nucleic acid enzyme is hybridised to the blocker oligonucleotide adjacent to the hairpin loop terminus; the hairpin loop comprises a stem in which one strand provides a binding site for the primer; the blocker oligonucleotide, first catalytic nucleic acid enzyme and releaser oligonucleotide when present, are each 3' phosphorylated; the releaser oligonucleotide when present can hybridise with the blocker oligonucleotide forming a duplex, thereby causing dissociation of hybridised strands of the first catalytic nucleic acid enzyme and the blocker oligonucleotide of said molecular complex and forming a 3' overhang segment comprising the primer binding site; the primer is capable of hybridising with the binding site, thereby providing a free 3' hydroxyl group for the strand displacing polymerase or component thereof to initiate synthesis of a new polynucleotide having base pair complementarity with the blocker oligonucleotide; and said synthesis liberates the releaser oligonucleotide from the duplex allowing it to hybridise with the blocker oligonucleotide of a second said molecular complex and initiate generation of further detectable signal.

Embodiment 108: The method according to embodiment 107, wherein the hairpin loop is linked to the blocker oligonucleotide.

Embodiment 109: The method according to any one of embodiments 96 to 98 and embodiment 108, wherein, the precursor substrate is a component of a precursor complex comprising a releaser oligonucleotide hybridised to a blocker oligonucleotide comprising the precursor substrate, and a hairpin loop links one terminus of the blocker oligonucleotide to one terminus of the releaser oligonucleotide; the releaser oligonucleotide comprises first and second segments each hybridised to a separate segment of the blocker oligonucleotide of said precursor complex by complementary base pairing, and an intermediate segment between the first and third segments that is not hybridised to at least a portion of the precursor substrate; and cleavage of the precursor substrate by said initiator catalytic nucleic acid enzyme causes dissociation of hybridised strands of the blocker oligonucleotide and the releaser oligonucleotide.

Embodiment 110: The method of embodiment 96, wherein the precursor substrate is the reporter substrate; the precursor substrate is a component of a precursor complex comprising a releaser oligonucleotide hybridised by complementary base pairing to a blocker oligonucleotide comprising the precursor substrate; the releaser oligonucleotide comprises first and second segments each hybridised to a separate segment of the blocker oligonucleotide of the precursor complex by complementary base pairing, and an intermediate segment between the first and second segments that is not hybridised to at least a portion of the precursor substrate; and the first catalytic nucleic acid enzyme of said molecular complex, after said dissociation, is capable of hybridising to and cleaving the precursor substrate to thereby provide a detectable signal.

Embodiment 111: The method according to embodiment 110, wherein said precursor complex comprises a hairpin loop linking one terminus of the blocker oligonucleotide to one terminus of the releaser oligonucleotide.

Embodiment 112: A method for detecting the presence or absence of a target molecule in a sample, the method comprising: (a) contacting the sample with at least one molecular complex comprising a blocker oligonucleotide and a first catalytic nucleic acid enzyme, the blocker oligonucleotide comprising first and second segments hybridised to the first enzyme by complementary base pairing and an intermediate segment between the first and second segments that is not hybridised to the first enzyme, wherein the blocker oligonucleotide provides a single-stranded 3' or 5' overhang segment extending from the molecular complex; and an initiator catalytic nucleic acid enzyme, an exonuclease, a precursor substrate, and a reporter substrate, wherein: the initiator enzyme has binding specificity for the target and hybridisation of the target to the initiator enzyme induces catalytic activity of the initiator enzyme, the catalytic activity of the initiator enzyme facilitates the catalytic modification of the precursor substrate when hybridised to the initiator enzyme, to thereby provide a nuclease recognition fragment; the nuclease recognition fragment comprises a first segment having base pair complementarity to at least a portion of the 3' or 5' overhang segment of the blocker oligonucleotide of said molecular complex, and a second segment of at least four nucleotides in length that does not share base pair complementarity with the blocker oligonucleotide of said molecular complex; the nuclease recognition fragment when present can hybridise with the blocker oligonucleotide of said molecular complex forming a duplex capable of initiating degradation of the blocker nucleotide by the exonuclease; the degradation of the duplex by the exonuclease digests the blocker nucleotide liberating the nuclease recognition fragment and first catalytic nucleic acid of said molecular complex as separate entities; the first catalytic nucleic acid enzyme, after said degradation, is capable of hybridising to and cleaving the reporter substrate to thereby provide a detectable signal; and the nuclease recognition fragment can bind to at least a portion of the 3' or 5' overhang segment of the blocker oligonucleotide of a second said molecular complex; and (b) determining whether a detectable signal is generated by said contacting, wherein detection of the signal indicates the target molecule is present, and failure to detect the signal indicates the target molecule is absent.

Embodiment 113: The method of embodiment 112, wherein the precursor substrate is the reporter substrate; the precursor substrate is a component of a precursor complex comprising a nuclease recognition fragment hybridised to a blocker oligonucleotide comprising the precursor substrate, and a hairpin loop links one terminus of the blocker oligonucleotide to one terminus of the releaser oligonucleotide; the nuclease recognition fragment of said precursor complex comprises first and second segments each hybridised to a separate segment of the blocker oligonucleotide of the precursor complex by complementary base pairing, and an intermediate segment between the first and third segments that is not hybridised to at least a portion of the precursor substrate; and the first catalytic nucleic acid enzyme of said molecular complex, after said degradation of the duplex by the exonuclease, is capable of hybridising to and cleaving the precursor substrate to thereby provide a detectable signal.

Embodiment 114: A method for detecting the presence or absence of a target molecule in a sample, the method comprising: (a) contacting the sample with: a molecular complex comprising a first catalytic nucleic acid enzyme, or component thereof, hybridised to a blocker oligonucleotide by complementary base pairing; an initiator catalytic nucleic acid enzyme; a precursor substrate, a reporter substrate; a first restriction endonuclease; and a strand displacing polymerase or component thereof; wherein the initiator enzyme has binding specificity for the target, and hybridisation of the target to the initiator enzyme induces catalytic activity of the initiator enzyme facilitating catalytic modification of the precursor substrate when hybridised to the initiator enzyme, to thereby provide a primer oligonucleotide; the blocker oligonucleotide provides a single-stranded overhang segment extending from the molecular complex which comprises a first partial recognition site for the first restriction endonuclease; the overhang segment comprises nucleotides which form a binding site for the primer; the primer is capable of hybridising with the binding site, thereby providing a free 3' hydroxyl group for the strand displacing polymerase or component thereof to initiate synthesis of a second catalytic nucleic acid enzyme having base pair complementarity with the blocker oligonucleotide; said synthesis of the second catalytic nucleic acid enzyme causes disassociation of hybridised segments of the first catalytic nucleic enzyme and the blocker oligonucleotide, and the first catalytic nucleic enzyme, after said disassociation, is capable of hybridising to and cleaving the reporter substrate to thereby provide a detectable signal; said hybridising of the primer and/or said synthesis completes the first partial recognition site, and the first restriction endonuclease is capable of introducing a single-strand nick at a junction between the primer and the second catalytic nucleic acid enzyme, thereby providing a free 3' hydroxyl group for the strand displacing polymerase or component thereof to initiate synthesis of a third catalytic nucleic acid enzyme having base pair complementarity with the blocker oligonucleotide; and said synthesis of the third catalytic nucleic acid enzyme causes disassociation of hybridised segments of the second catalytic nucleic enzyme and the blocker oligonucleotide, and the second catalytic nucleic enzyme, after said disassociation, is capable of hybridising to and cleaving the reporter substrate to thereby provide a detectable signal; and (b) determining whether a detectable signal is generated by said contacting, wherein detection of the signal indicates the target molecule is present, and failure to detect the signal indicates the target molecule is absent.

Embodiment 115: The method according to embodiment 114, wherein the partial recognition site provided by the overhang segment comprises a phosphorothioate linkage preventing its cleavage by the restriction endonuclease.

Embodiment 116: The method according to embodiment 114, wherein the first restriction endonuclease is a nicking endonuclease and the overhang segment comprises a partial recognition site for the nicking endonuclease.

Embodiment 117: The method according to any one of embodiments 114 to 116, wherein the overhang segment is modified to form a hairpin loop linking one terminus of the blocker oligonucleotide to one terminus of the enzyme, opposing nucleotides of at least a segment of the hairpin loop do not share base pair complementarity, the segment of the hairpin loop comprises nucleotides which form a partial recognition site for the restriction endonuclease and a binding site for the primer.

Embodiment 118: The method of any one of embodiments 114 to 117, wherein the precursor substrate is the reporter substrate; the precursor substrate is a component of a precursor complex comprising the primer hybridised to a blocker oligonucleotide comprising the precursor substrate, and a hairpin loop links one terminus of the blocker oligonucleotide to one terminus of the primer; the primer of said precursor complex comprises first and second segments each hybridised to a separate segment of the blocker oligonucleotide of the precursor complex by complementary base pairing, and an intermediate segment between the first and third segments that is not hybridised to at least a portion of the precursor substrate; and any one or more of the first, second or third catalytic nucleic acid enzymes, after said disassociation, is capable of hybridising to and cleaving said precursor substrate to thereby provide a detectable signal.

Embodiment 119: The method according to any one of embodiments 114 to 117, wherein the primer oligonucleotide is a component of a precursor complex comprising the primer oligonucleotide hybridised by complementary base pairing to a blocker oligonucleotide comprising the precursor substrate; the primer oligonucleotide comprises first and second segments each hybridised to a separate segment of the blocker oligonucleotide of the precursor complex by complementary base pairing, and an intermediate segment between the first and third segments that is not hybridised to at least a portion of the precursor substrate; the initiator catalytic nucleic acid enzyme is an MNAzyme capable of hybridising to the precursor substrate in the presence of a target; and recognition of the target in the sample by the MNAzyme facilitates cleavage of the precursor substrate by the MNAzyme thereby releasing the primer oligonucleotide.

Embodiment 120: The method according to embodiment 119, wherein a hairpin loop links one terminus of the blocker oligonucleotide to one terminus of the primer oligonucleotide in said precursor complex.

Embodiment 121: The method according to any one of embodiments 114 to 117, further comprising amplifying the detectable signal by: providing a template oligonucleotide comprising a first 5' segment and a second 3' segment each comprising a nucleotide sequence complementary to the primer, and an intermediate segment between the first and second segments comprising a single-stranded component of a restriction endonuclease recognition site; and contacting the template with the primer oligonucleotide, a further restriction enzyme, and a strand displacing polymerase or component thereof; wherein, the primer hybridises to the first segment of the template thereby providing a free 3' hydroxyl group for the strand displacing polymerase or component thereof to initiate synthesis of a new strand complementary to the template; said hybridising of the primer and/or said synthesis completes the partial recognition site and provides a first copy of the primer that is complementary to said second segment; and the completed partial recognition site is located adjacent and 5' to the first copy of the primer forming a junction, and the further restriction endonuclease introduces a single-strand nick at the junction thereby providing a free 3' hydroxyl group for the strand displacing polymerase or component thereof to initiate synthesis of a second copy of the primer that is complementary to said second segment and displace said first copy of the primer, to thereby initiate generation of further detectable signal.

Embodiment 122: The method according to embodiment 121, wherein the template oligonucleotide is provided as a component of a hairpin structure comprising a second strand that is hybridised by complementary base pairing to a least a portion of said second and intermediate segments of the template; at least a portion of said first segment exists in a hairpin loop formed at one end of said template linking termini of the first and second strands; and the nucleotide sequence of said first segment complementary to the primer is not hybridised to the template or second strand.

Embodiment 123: The method according to any one of embodiments 114 to 117, further comprising producing a plurality of said primer oligonucleotides by: providing a template oligonucleotide comprising a first 5' segment comprising a nucleotide sequence complementary to a initiator primer; a second 3' segment comprising a nucleotide sequence complementary to the primer; and an intermediate segment between the first and second segments comprising a single-stranded component of a restriction endonuclease recognition site; and contacting the template with the initiator primer, a further restriction enzyme, and a strand displacing polymerase or component thereof, wherein the initiator primer hybridises to the first segment of the template thereby providing a free 3' hydroxyl group for the strand displacing polymerase or component thereof to initiate synthesis of a new strand complementary to the template; said hybridising of the initiator primer and/or said synthesis completes the partial recognition site and provides a first copy of said primer oligonucleotide that is complementary to said second segment; and the completed partial recognition site is located adjacent and 5' to the first copy of said primer oligonucleotide forming a junction, and the further restriction endonuclease introduces a single-strand nick at a junction thereby providing a free 3' hydroxyl group for the strand displacing polymerase or component thereof to initiate synthesis of a second copy of said primer oligonucleotide that is complementary to said second segment and displace the first copy of said primer oligonucleotide.

Embodiment 124: The method according to any one of embodiments 121 to 123, wherein the component of the restriction endonuclease recognition site in said intermediate segment comprises a phosphorothioate linkage preventing its cleavage by the further restriction endonuclease.

Embodiment 125: The method according to any one of embodiments 121 to 123, wherein the further restriction endonuclease is a nicking endonuclease.

Embodiment 126: The method according to any one of embodiments 114 to 118, wherein the blocker oligonucleotide of said molecular complex further comprises a second segment comprising a nucleotide sequence complementary to the primer oligonucleotide; and said synthesis of the second catalytic nucleic acid enzyme having base pair complementarity with the blocker oligonucleotide provides a first copy of the primer oligonucleotide.

Embodiment 127: The method according to embodiment 126, wherein said second segment of the blocker oligonucleotide comprising a nucleotide sequence complementary to the primer is located 3' of a first segment of said blocker oligonucleotide comprising a nucleotide sequence complementary to the first catalytic nucleic acid enzyme.

Embodiment 128: The method according to embodiment 126 or embodiment 127, wherein the blocker oligonucleotide comprises an intermediate segment between said first and second segments, said intermediate segment comprising a second partial recognition site for a restriction endonuclease; and said synthesis of the second catalytic nucleic acid enzyme having base pair complementarity with the blocker oligonucleotide provides a first copy of the primer oligonucleotide and completes the second partial recognition site, which is then capable of recognition and cleavage by a further restriction endonuclease.

Embodiment 129: The method according to any one of embodiments 121 to 125 or 128, wherein the further restriction endonuclease is the same as said first restriction endonuclease.

Embodiment 130: The method according to any one of embodiments 121 to 125 or 128, wherein the further restriction endonuclease is different to said first restriction endonuclease.

Embodiment 131: The method according to embodiment 130, wherein said method further comprises contacting said sample with said further restriction endonuclease.

Embodiment 132: The method according to any one of embodiments 126 to 131, wherein the further restriction endonuclease is capable of introducing a single-strand nick at a junction between the second catalytic nucleic acid enzyme and the first copy of the primer, thereby providing a free 3' hydroxyl group for the strand displacing polymerase or component thereof to initiate synthesis of a second copy of the primer, and cause dissociation of the first copy of the primer from the BL.

Embodiment 133: The method according to any one of embodiments 128 to 132, wherein the second partial recognition site for a restriction endonuclease comprises a phosphorothioate linkage preventing its cleavage by the restriction endonuclease.

Embodiment 134: The method according to any one of embodiments 128 to 133, wherein the further restriction endonuclease is a nicking endonuclease.

Embodiment 135: A method for detecting the presence or absence of a target molecule in a sample, the method comprising: (a) contacting the sample with: a molecular complex comprising a first catalytic nucleic acid enzyme, or component thereof, hybridised to a blocker oligonucleotide by complementary base pairing; an initiator catalytic nucleic acid enzyme; a precursor substrate, a reporter substrate; an enzyme having phosphatase activity; and a strand displacing polymerase or component thereof; wherein the initiator enzyme has binding specificity for the target, and hybridisation of the target to the initiator enzyme induces catalytic activity of the initiator enzyme facilitating catalytic modification of the precursor substrate when hybridised to the initiator enzyme, to thereby provide an inactive form of a primer oligonucleotide comprising a 2'3'cylic phosphate group at its 3' end; the enzyme having phosphatase activity is capable of removing the 2'3'cylic phosphate group from said inactive form of the primer oligonucleotide, to thereby provide an active form of the primer oligonucleotide; a portion of the blocker oligonucleotide of said molecular complex is single-stranded and comprises nucleotides which form all or a portion of a binding site for the active form of the primer oligonucleotide; the active form of the primer oligonucleotide is capable of hybridising with the binding site by complementary base pairing, thereby providing a free 3' hydroxyl group for the strand displacing polymerase or component thereof to initiate synthesis of a second catalytic nucleic acid enzyme having base pair complementarity with the blocker oligonucleotide; said synthesis of the second catalytic nucleic acid enzyme causes disassociation of hybridised segments of the first catalytic nucleic acid enzyme and the blocker oligonucleotide, and the first catalytic nucleic enzyme, after said disassociation, is capable of hybridising to and cleaving the reporter substrate to thereby provide a detectable signal; and (b) determining whether a detectable signal is generated by said contacting, wherein detection of the signal indicates the target molecule is present in the sample, and failure to detect the signal indicates the target molecule is absent in the sample.

Embodiment 136: The method according to embodiment 135, further comprising contacting the sample with a restriction endonuclease, wherein said single-stranded segment of the blocker oligonucleotide comprising all or a portion of the binding site for the active form of the primer oligonucleotide further comprises a partial, recognition site for said restriction endonuclease; said hybridising of the active from of the primer and/or said synthesis completes the partial recognition site; and the restriction endonuclease is capable of introducing a single-strand nick at a junction between the primer and the second catalytic nucleic acid enzyme, thereby providing a free 3' hydroxyl group for the strand displacing polymerase or component thereof to initiate synthesis of a third catalytic nucleic acid enzyme having base pair complementarity with the blocker oligonucleotide; and said synthesis of the third catalytic nucleic acid enzyme causes disassociation of hybridised segments of the second catalytic nucleic enzyme and the blocker oligonucleotide, and the second catalytic nucleic enzyme, after said disassociation, is capable of hybridising to and cleaving the reporter substrate to thereby provide a detectable signal.

Embodiment 137: A method for detecting the presence or absence of a target molecule in a sample, the method comprising: (a) contacting the sample with: a molecular complex comprising a first template (ASDz) for a catalytic nucleic acid enzyme, or a component thereof, hybridised to a blocker oligonucleotide by complementary base pairing; an initiator catalytic nucleic acid enzyme; a precursor substrate, a reporter substrate; an enzyme having phosphatase activity; a restriction endonuclease; and a strand displacing polymerase or component thereof; the initiator enzyme has binding specificity for the target, and hybridisation of the target to the initiator enzyme induces catalytic activity of the initiator enzyme facilitating catalytic modification of the precursor substrate when hybridised to the initiator enzyme, to thereby provide an inactive form of a primer oligonucleotide comprising a 2'3'cyclic phosphate group at its 3' end; the enzyme having phosphatase activity is capable of removing the 2'3'cylic phosphate group from said inactive form of the primer oligonucleotide, to thereby provide an active form of the primer oligonucleotide; a portion of the blocker oligonucleotide of said molecular complex is single-stranded and comprises nucleotides which form all or a portion of a binding site for the active form of the primer oligonucleotide, wherein said binding site comprises a partial recognition site for said restriction endonuclease; the active form of the primer oligonucleotide is capable of hybridising with the binding site by complementary base pairing, completing the partial recognition site, and providing a free 3' hydroxyl group for the strand displacing polymerase or component thereof to initiate synthesis of a catalytic nucleic acid enzyme having base pair complementarity with the ASDz template, and thereby causing disassociation of hybridised segments of (i) the BL; and (ii) the ASDz template; the restriction endonuclease is capable of introducing a single-strand nick at a junction between the primer and the second catalytic nucleic acid enzyme, thereby providing a free 3' hydroxyl group for the strand displacing polymerase or component thereof to initiate synthesis of a second catalytic nucleic acid enzyme having base pair complementarity with the ASDz template; said synthesis of the second catalytic nucleic acid enzyme causes disassociation of hybridised segments of the first catalytic nucleic enzyme and ASDz template, and the first catalytic nucleic enzyme, after said disassociation, is capable of hybridising to and cleaving the reporter substrate to thereby provide a detectable signal; and (b) determining whether a detectable signal is generated by said contacting, wherein detection of the signal indicates the target molecule is present in the sample, and failure to detect the signal indicates the target molecule is absent in the sample.

Embodiment 138: The method according to any one of embodiments 135 to 107, wherein said single-stranded portion of the blocker oligonucleotide is in the form of a hairpin loop linking one terminus of the blocker oligonucleotide to one terminus of the first nucleic acid enzyme; opposing nucleotides of at least a segment of the hairpin loop do not share base pair complementarity; and said at least a segment of the hairpin loop is the binding site for said active form of the primer.

Embodiment 139 : The method according to any one of embodiments 135 to 138, wherein said catalytic modification of the precursor substrate by the initiator catalytic nucleic acid enzyme forms said a 2'3'cyclic phosphate group at the 3' end of the inactive form of the primer oligonucleotide.

Embodiment 140: The method according to any one of embodiments 135 to 139, wherein said enzyme having phosphatase activity is an enzyme having polynucleotide phosphatase activity.

Embodiment 141: The method according to any one of embodiments 135 to 140, wherein said enzyme having phosphatase activity is a T4 polynucleotide kinase enzyme.

Embodiment 142: The method according to any one of embodiments 135 to 141, wherein the precursor substrate is also the reporter substrate.

Embodiment 143: A method for detecting the presence or absence of a target molecule in a sample, the method comprising: contacting the sample with: a hairpined primer template comprising a blocker oligonucleotide (BL) strand hybridised by complementary base pairing to a primer template strand, wherein: the primer template strand comprises a first segment of nucleotides complementary to a first primer oligonucleotide and a second segment of nucleotides complementary to a second primer oligonucleotide and a partial restriction enzyme recognition site intermediate to the first and second segments, the BL and primer template strand comprise at least one internally mismatched nucleotide when optimally hybridised together by complementary base pairing, and the BL strand and primer template strand are linked together by a hairpin portion comprising unhybridised nucleotides that provide a binding site for the second primer oligonucleotide; a strand displacing polymerase or component thereof; a first restriction endonuclease; and an initiator enzyme having binding specificity for the target and a precursor substrate, wherein hybridisation of the target to the initiator enzyme induces catalytic activity of the initiator enzyme facilitating catalytic modification of the precursor substrate when hybridised to the initiator enzyme, to thereby produce the second primer oligonucleotide; wherein: the second primer oligonucleotide produced by the initiator enzyme hybridises by complementary base pairing to the binding site of the hairpin loop portion thereby providing a free 3' hydroxyl group for the strand displacing polymerase or component thereof to initiate synthesis of a first new oligonucleotide strand having base pair complementarity with the primer template strand while disassociating hybridised portions of the BL from the primer template strand, the new oligonucleotide strand comprises initial first and second primer oligonucleotides and a partial restriction enzyme recognition site situated intermediate to the first and second primer oligonucleotides that is the complement of the partial restriction enzyme recognition site of the primer template strand, generation of the new oligonucleotide strand completes the partial recognition site of the primer template strand providing a cleavage site for the first restriction endonuclease, the first restriction endonuclease is capable of introducing a single-strand nick in the new oligonucleotide strand thereby providing a free 3' hydroxyl group for the strand displacing polymerase or component thereof to initiate synthesis of an additional first primer having base pair complementarity with the first segment of nucleotides of the primer template strand, and said synthesis of the additional first primer oligonucleotide causes disassociation of the initial first primer oligonucleotide hybridised to the primer template strand; and additionally contacting the sample with: a molecular complex comprising a first strand comprising a template for a first catalytic nucleic acid enzyme or component thereof, hybridised to a second strand comprising a blocker oligonucleotide by complementary base pairing, wherein the BL comprises a partial nucleotide sequence of the first catalytic nucleic enzyme with at least one substituted catalytic core nucleotide that does not share base pair complementarity with said template for the first catalytic nucleic acid enzyme or component thereof, and wherein the first catalytic nucleic acid enzyme or component thereof provides a single-stranded overhang segment at one terminus of the molecular complex a polymerase capable of using the overhang as a template to extend the BL sequence along the full length of the first catalytic nucleic acid enzyme or component thereof, a second restriction endonuclease and a reporter substrate; wherein the first and second strands of the molecular complex are linked by a hairpin portion comprising an additional primer oligonucleotide binding site and an additional partial recognition site for a second restriction endonuclease; the additional primer oligonucleotide is capable of hybridising to the additional primer oligonucleotide binding site, thereby providing a free 3' hydroxyl group for the strand displacing polymerase or component thereof to initiate synthesis of a first catalytic nucleic acid enzyme or component thereof having base pair complementarity with the first strand template; said hybridising of the additional primer oligonucleotide and/or said synthesis completes the additional partial recognition site, and the second restriction endonuclease is capable of introducing a single-strand nick at a junction between the additional primer oligonucleotide and the second catalytic nucleic acid enzyme, thereby providing a free 3' hydroxyl group for the strand displacing polymerase or component thereof to initiate synthesis of an additional catalytic nucleic acid enzyme or component thereof having base pair complementarity with the first strand template; and said synthesis of the additional catalytic nucleic acid enzyme causes disassociation of hybridised segments of the first catalytic nucleic enzyme and the first strand template, and the first catalytic nucleic enzyme, after said disassociation, is capable of hybridising to and cleaving the reporter substrate to thereby provide a detectable signal; and (b) determining whether a detectable signal is generated by said contacting and additionally contacting, wherein detection of the signal indicates the target molecule is present, and failure to detect the signal indicates the target molecule is absent.

Embodiment 144: The method according to embodiment 143, wherein the first and second restriction endonucleases are identical.

Embodiment 145: The method according to embodiment 144, wherein the first and second restriction endonucleases are distinct.

Embodiment 146: The method according to any one of embodiments 143 to 145, wherein the first primer and the additional primer are identical.

Embodiment 147: The method according to any one of embodiments 143 to 145, wherein the first primer and the additional primer are distinct.

Embodiment 148: A method for detecting the presence or absence of a target molecule in a sample, the method comprising: (a) contacting the sample with: a partial hairpined primer complex comprising a primer and a first blocker oligonucleotide (BL) having first and second segments hybridised to the primer by complementary base pairing, and an intermediate segment between the first and second segments comprising a first substrate for a catalytic nucleic acid enzyme, wherein at least a segment of the first substrate is not hybridised to the primer, and the first BL provides a first single-stranded overhang segment at one terminus of the partial hairpined primer complex; a partial hairpined molecular complex comprising a template strand for a first catalytic nucleic acid enzyme or component thereof, hybridised to a second BL, wherein the second BL comprises a partial nucleotide sequence of the first catalytic nucleic enzyme or component thereof with at least one substituted catalytic core nucleotide that does not share base pair complementarity with said template strand, the partial hairpined molecular complex comprises a hairpin loop portion comprising unhybridised nucleotides that provide a binding site for the primer of the primer complex and a partial recognition site for a restriction endonuclease, and the template provides a second single-stranded overhang segment at one terminus of the molecular complex; a first polymerase, wherein the first polymerase facilitates extension of the primer strand along the full length of the first BL in the partial hairpined primer complex, using the first overhang segment as a template, to form a complete hairpined primer complex; a second polymerase, wherein the second polymerase facilitates extension of the second BL along the full length of the template strand in the partial hairpined molecular complex using the second overhang segment as a template, to form a complete hairpined molecular complex; a second catalytic nucleic acid enzyme capable of hybridising specifically to and cleaving the intermediate segment of the first BL causing disassociation of hybridised segments of the first BL and the primer, and the primer, after said disassociation, is capable of hybridising by complementary base pairing to a hairpin loop portion of the complete hairpined molecular complex to thereby provide a free 3' hydroxyl group; a strand displacing polymerase or component thereof capable of using the free 3' hydroxyl group to initiate synthesis of the first catalytic nucleic acid enzyme or component thereof having base pair complementarity with the template strand of the molecular complex, wherein said hybridising of the primer oligonucleotide and/ or said synthesis completes the partial recognition site; a second restriction endonuclease capable of introducing a single-strand nick at a junction between the primer and the first catalytic nucleic acid enzyme, thereby providing a free 3' hydroxyl group for the strand displacing polymerase or component thereof to initiate synthesis of an additional first catalytic nucleic acid enzyme or component thereof having base pair complementarity with the template strand of the molecular complex, and said synthesis of the additional first catalytic nucleic acid enzyme causes disassociation of hybridised segments of the first catalytic nucleic enzyme and the template strand of the molecular complex, and the first catalytic nucleic enzyme, after said disassociation, is capable of hybridising to and cleaving the reporter substrate to thereby provide a detectable signal; and (b) determining whether a detectable signal is generated by said contacting, wherein detection of the signal indicates the target molecule is present, and failure to detect the signal indicates the target molecule is absent.

Embodiment 149: The method according to any one of embodiments 96 to 148, wherein any said molecular complex comprises a blocker oligonucleotide (BL) hybridised to a catalytic nucleic acid by complementary base pairing and at least one but not all catalytic core nucleotides of the enzyme are hybridised to the BL.

Embodiment 150: The method according to any one of embodiments 96, 97 or 99 to 111, comprising contacting the sample with the composition of any one of embodiments 23 to 29.

Embodiment 151: The method according to embodiment 98 or 99, comprising contacting the sample with the composition of embodiment 30.

Embodiment 152: The method according to any one of embodiments 103 to 106 or 109, comprising contacting the sample with the composition of any one of embodiments 33 to 35.

Embodiment 153: The method according to any one of embodiments 107 to 109, comprising contacting the sample with the composition of embodiment 36 or embodiment 37.

Embodiment 154: The method according to any one of embodiments 58 to 153, wherein the target is an ionic compound required as a cofactor for catalytic activity of said initiator catalytic nucleic acid, enzyme.

Embodiment 155: The method according to embodiment 154, wherein the target is a monovalent or divalent metal ion.

Embodiment 156: The method according to embodiment 154 or embodiment 155, wherein the target is selected from any one or more of $Ba^{2+}$, $Sr^{2+}$, $Mg^{2+}$, $Ca^{2+}$, $Co^{2+}$, $Mn^{2+}$, $Zn^{2+}$, and $Pb^{2+}$.

Embodiment 157: The method according to any one of embodiments 100 to 109, 112, or 114 to 117 wherein the precursor substrate is or comprises the target molecule.

Embodiment 158: The method according to any one of embodiments 58 to 157, wherein the first catalytic nucleic enzyme is a ribozyme, a DNAzyme, an aptazyme, an MNAzyme or an apta-MNAzyme.

Embodiment 159: The method according to any one of embodiments 58 to 158, wherein the initiator catalytic nucleic enzyme is a ribozyme, a DNAzyme, an aptazyme, an MNAzyme or an apta-MNAzyme.

Embodiment 160: The method according to any one of embodiments 87 to 93, 95 or 114 to 142, wherein the second catalytic nucleic enzyme is a ribozyme, a DNAzyme, an aptazyme, an MNAzyme or an apta-MNAzyme.

Embodiment 161: The method according to any one of embodiments 114 to 134, 136 or 137, wherein the third catalytic nucleic enzyme is a ribozyme, a DNAzyme, an aptazyme, an MNAzyme or an apta-MNAzyme.

Embodiment 162: The method according to any one of embodiments 58 to 153, wherein the target molecule is a nucleic acid comprising DNA, RNA, ligand or a combination thereof.

Embodiment 163: The method according to any one of embodiments 107 to 109, 111, or 114 to 142, wherein the strand displacing polymerase or component thereof is selected from the group consisting of a klenow fragment, Bst, Sequenase 2.0, Vent, Phi29, Pyrophage 3137 strand displacing polymerase or any variants thereof.

Embodiment 164: The method according to any one of embodiments 103, 106, 116, 125, 136 or 137 wherein the nicking endonuclease is selected from the group consisting of Nt.AlwI, Nb.BsmAI, Nt.BbvCI, Nb.BbvCI, Nt.BhaIII, Nt.BsmAI, Nb.BsmI, Nt.CviPII, Nb.Mva1269I, Nt.BspQI, Nb.BtsI, Nb.BsrDI, Nt.BstNBI.

Embodiment 165: The composition according to any one of embodiments 1 to 4 wherein the blocker oligonucleotide comprises first and second segments, each hybridised to a distinct hybridising arm of said first enzyme, or said catalytic portion thereof, by complementary base pairing, and an intermediate segment between the first and second segments; the 5' terminus of the first blocker oligonucleotide opposes the 3' terminus of the first catalytic nucleic acid enzyme or catalytic portion thereof and the intermediate segment comprises an aptamer and at least a segment of the aptamer is not hybridised to the first enzyme or catalytic portion thereof.

Embodiment 166: The composition according to embodiments 1 to 4 where one end of the blocker oligonucleotide further comprises a hairpin loop comprising at least a portion of self-complementarity.

Embodiment 167: The composition according to any one of embodiments 5 to 35, further comprising an initiator catalytic nucleic acid enzyme, or catalytic component thereof, selected from the group consisting of a DNAzyme, a ribozyme, an aptazyme, an MNAzyme, or an apta-MNAzyme; wherein the initiator catalytic nucleic acid enzyme, or catalytic component thereof, is capable of catalytically modifying the substrate of the intermediate segment.

Embodiment 168: The composition according to embodiment 10, wherein the first enzyme is capable of catalytically modifying the first substrate and/or the second substrate.

Embodiment 169: The composition according to embodiment 5, wherein the first or second segment of the BL is joined to a hybridising arm of said first enzyme or said catalytic portion thereof via a hairpin loop segment.

Embodiment 170: In one embodiment of the invention, the blocker oligonucleotide cannot hybridise to a target molecule of the catalytic nucleic acid enzyme.

Embodiment 171: In one embodiment of the method is performed: in vitro or ex vivo.

Embodiment 172: In one embodiment of the invention, the sample is a biological sample or an environmental sample.

Embodiment 173: In one embodiment of the invention, the method is performed on a biological sample for diagnosing a disease or infection in an animal, a human, a mammal, a non-human animal, or a non-human mammal.

Embodiment 174: In one embodiment of the invention, the method is not performed for diagnosing a disease or infection.

Figure 1:
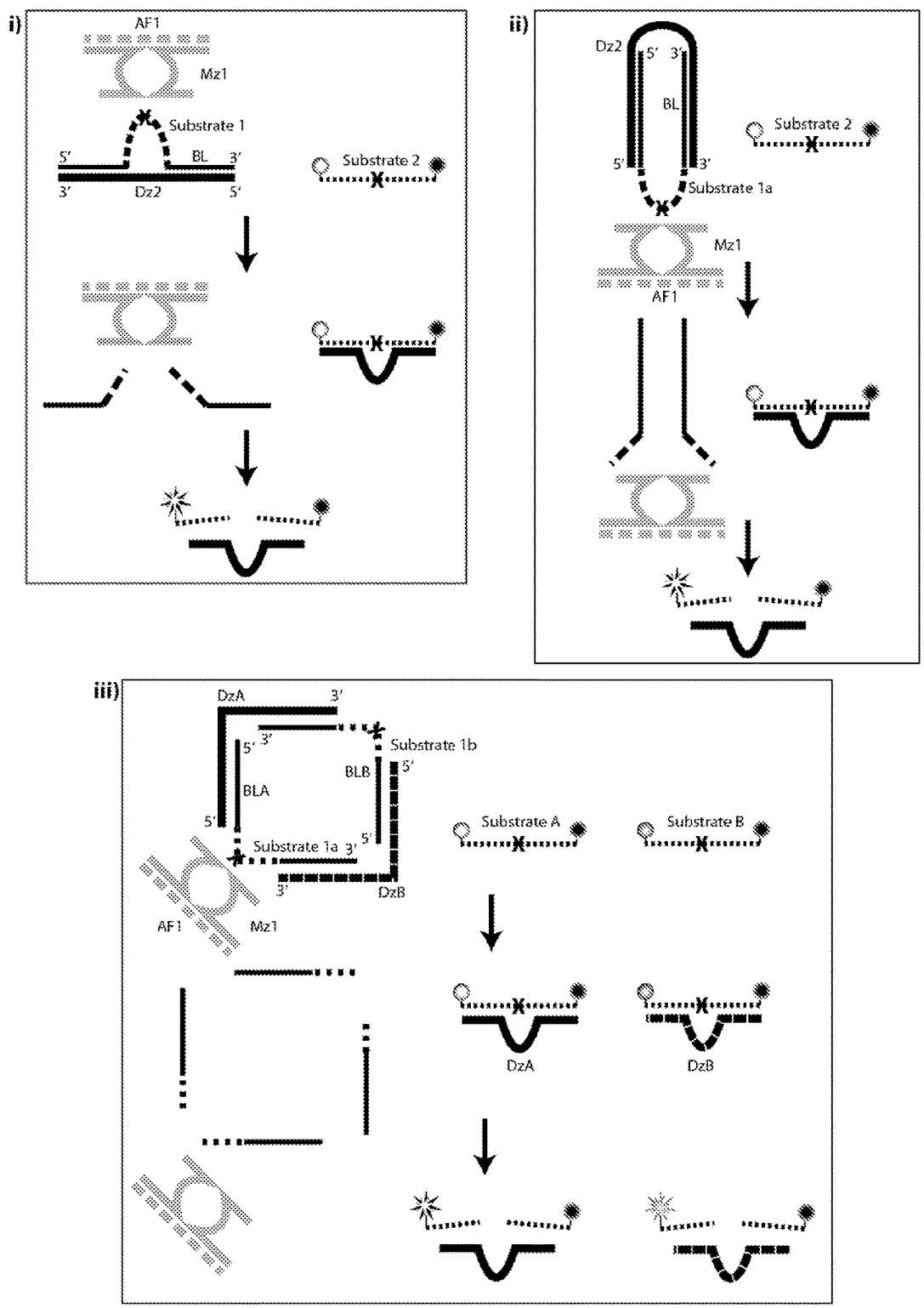
FIG. 1 depicts the reversible inactivation of a DNAzyme molecule by hybridisation to a Blocker Oligonucleotide (BL). The BL contains a substrate sequence (Substrate 1) that can be cleaved by a first MNAzyme (Mz1) resulting in the separation of the DNAzyme (Dz) from the BL thus activating/re-instating the catalytic activity of the DNAzyme. The DNAzyme can then cleave a substrate between a fluorophore (light circle) and quencher (dark circle) and this cleavage can result in an increase in fluorescent signal. Three non-limiting examples of this strategy are demonstrated (panels i)-iii)). In all of the illustrations of exemplary strategies the initiating event is cleavage by Mz1, however, in all cases the initiating event can be facilitated by another different catalytic nucleic acid (e.g. a DNAzyme or aptazyme) capable of cleaving the same substrate (substrate 1). When an MNAzyme is used, for example, the initiation can be made to be dependent on the presence of any specific target which can function as an assembly facilitator (AF1) for any MNAzyme capable of cleaving substrate 1.

Panel ii) depicts an exemplary strategy involving the inclusion of an Aptamer directly within a BL of a molecular switch. In panel ii) a DNAzyme (Dz) is hybridized with a BL, resulting in its temporary inactivation. The BL consists of 5' and 3' ends which hybridize to the Dz, connected by a central portion which is not complementary to the Dz, but is comprised of an Aptamer sequence. In the presence of the target analyte (ligand), the Aptamer may bind to the analyte which may result in a conformational change of the BL resulting in the separation of the BL from the Dz, restoring the catalytic activity of the Dz. The active Dz may then function to cleave its substrate (Substrate) which may be labeled with a fluorophore and quencher moiety and cleavage may result in an increase, in fluorescent signal.

Panel iii) demonstrates the fluorescent signal achieved from the strategy depicted in panel i).

DEFINITIONS

Certain terms and phrases are used herein which shall have the meanings set forth as follows.

As used in this application, the singular form "a", "an" and "the" include plural references unless the context clearly dictates otherwise. For example, the term "an MNAzyme" also includes a plurality of MNAzymes. Unless the context requires otherwise or specifically stated to the contrary, integers, steps, or elements of the invention recited herein as singular integers, steps or elements clearly encompass both singular and plural forms of the recited integers, steps or elements.

Unless indicated differently, the terms "comprising" and "having" mean "including principally, but not necessarily solely". Furthermore, variations of the word "comprising", such as "comprise" and "comprises", have correspondingly varied meanings. Thus, for example, a sample "comprising" target molecule A may consist exclusively of target molecule A or may include one or more different type/s of target molecules (e.g. target molecule B and/or target molecule C). Similarly, an enzyme "having" phosphatase activity may have only phosphatase activity, or may also have other additional activity (e.g. kinase activity).

The terms "blocking oligonucleotide", "blocker", "blocker molecule" and "BL" are used interchangeably herein and have the same meaning. A BL is an oligonucleotide capable of hybridising to a second oligonucleotide by complementary base pairing, thereby preventing the second oligonucleotide from performing a function which it is capable of doing in the absence of the BL. For example, a BL when hybridised to a second oligonucleotide may prevent the second oligonucleotide from functioning by inhibiting its capacity to hybridise with other oligonucleotide(s) and/or by inhibiting its capacity to form an active conformation. The specific function of the second oligonucleotide which is inhibited by hybridisation with the BL may include, for example, the ability to: catalytically modify a substrate; provide a component partzyme for an active MNAzyme; function as a "releaser oligonucleotide" capable of replacing one strand of a nucleic acid duplex; serve as a primer capable of polymerase mediated elongation; serve as a template for polymerase mediated synthesis of a complementary strand; and/or to form a duplex capable of recognition and digestion by an endonuclease or exonuclease. The specific function of the second oligonucleotide which is inhibited in the presence of the BL may not include the ability to block binding of a ligand to an aptazyme. A BL may comprise one or more segments that do not hybridise to the second oligonucleotide by complementary base pairing. Alternatively, all nucleotides of a BL may be capable of hybridising to the second oligonucleotide. A BL may be dissociated from a second oligonucleotide to which it is hybridised by the addition of another entity having binding affinity for the BL in a region complementary to the second oligonucleotide (e.g. a "releaser oligonucleotide" (RL) as defined below). For example, an RL may hybridise by complementary base pairing to an overhang segment ("toehold") provided by a BL in a duplex formed between hybridised strands of the BL and functionally inactive the second oligonucleotide. The RL may have stronger, equal, or reduced binding affinity for the BL or a segment thereof compared to the binding affinity of the second oligonucleotide for the same BL or segment thereof. A BL may be a discrete entity, a segment of a larger oligonucleotide, or linked to another oligonucleotide (e.g. the second oligonucleotide), for example, by a linking nucleic acid sequence (e.g. a hairpin loop linker sequence) or by any other means (e.g. non-nucleic acid chemistry including spacer modifications such as the C3 phosphoramide spacer and ethelenglycol spacers such as Spacer 9 and Spacer 18, each of which can be used to form the loop of a hairpin structure). A BL may comprise one or more substrates for catalytic nucleic acid enzymes. A BL may also comprise one or more aptamer sequences for recognition by one or more target analytes, but in such cases the BL may not be capable or is not capable of inhibiting the function of an aptazyme by complementary binding. A BL may be dissociated from a second oligonucleotide to which it is hybridised via the interaction between the aptamer sequence(s) and target analyte(s).

The terms "releaser oligonucleotide", "releaser", "releaser molecule" and "RL" are used interchangeably herein and have the same meaning. An RL is an oligonucleotide capable of hybridising by complementary base pairing with a first strand of a given nucleic acid duplex to thereby replace the second strand of the duplex and substantially or completely prevent the second strand from re-hybridising with the first strand. The RL, affects disassociation of hybridised stands of the duplex by virtue of having binding affinity for the first strand of the duplex in a region complementary to the second strand and following binding the RL replaces the second oligonucleotide. The RL may comprise one or more segments that do not hybridise with the first strand by complementary base pairing. An RL may initially hybridise by complementary base pairing to an overhang segment ("toehold") provided by the first strand of a given nucleic acid duplex. The RL may have stronger, equal, or reduced binding affinity for the first strand or a segment thereof, compared to the binding affinity that the second strand has for the same first strand or segment thereof. By way of non-limiting example an RL may hybridise by complementary base pairing to a BL that is a component of a "molecular switch" as defined below. Hybridisation of the RL and the BL may sequester the BL from another component of the molecular switch to which the BL was previously hybridised (e.g. a catalytic nucleic acid enzyme), thereby releasing the enzyme in a catalytically active state. In this scenario, the BL may be provided as an independent oligonucleotide, a component of an oligonucleotide comprising the RL, or may be linked to the RL (e.g. by a linking nucleic acid or non-nucleic acid spacer sequence).

The term "molecular switch" as used herein refers to a complex containing any one or more of an RL, NRF, primer, catalytic nucleic acid enzyme, and/or a catalytic nucleic acid enzyme component, which may be rendered functionally inactive or active by various methods including, but not limited to, inactivation by hybridisation to a BL, or activation by removal of a BL hybridised to the switch by complementary base pairing (e.g. by cleavage of the BL or replacement by a RL).

The terms "template", "polymerase template", "template for a polymerase", "nucleic acid template for polymerase", and "nucleic acid polymerase template" are used interchangeably herein and have the same meaning, referring to a single-stranded sequence of nucleic acid (e.g. DNA and/or RNA) that serves as a template for a polymerase to produce a new sequence of nucleic acids that has base pair complementarity with the template sequence (i.e. the new sequence of nucleic acids is the antisense of the template). Various types of templates are useful in the current invention. Non-limiting examples of templates include a "DNAzyme template", "Dz template" or "Dz-template" which comprises the antisense nucleic acid sequence of a DNAzyme, which can be used by a polymerase to synthesise an active DNAzyme. Other examples of templates include a "primer template" or "template for primer synthesis" which comprises the antisense nucleic acid sequence of a primer, which can be used by a polymerase to synthesise an active primer to initiate synthesis of another molecule. A further example of a template includes an "RE template" which comprises one strand of a duplex RE recognition site, which can be copied by a polymerase to synthesise the second strand of duplex RE recognition site thus creating a functional sequence cleavable by a RE.

The terms "target" and "target molecule" as used herein refer to any molecule capable of detection by the molecular complexes described herein including, but not limited to, nucleic acids, proteins, prions, small organic compounds, catalytic nucleic acid enzyme cofactors (e.g. a divalent or monovalent ion) and entire organisms. For example, a target may be a nucleic acid which serves as an assembly facilitator to direct the assembly of an MNAzyme, any molecule capable of binding to an aptamer whereby binding to the aptamer results in the activation of an Apta-MNAzyme or other aptazyme, or any molecule capable of facilitating the release of a catalytic nucleic acid, RL, primer or NRF from a BL molecule.

The terms "nuclease recognition fragment" and "NRF" as used herein refer to an oligonucleotide that can hybridise by complementary base pairing to a second oligonucleotide, and thereby create a recognition site for a nuclease enzyme. Creation of the recognition site initiates activity of the enzyme on a component of a duplex formed by hybridisation of the NRF and the second oligonucleotide (e.g. digestion of the second oligonucleotide by an exonuclease). The NRF may be complementary to the second oligonucleotide along its entire length. Alternatively, one or more segments of the NRF may be complementary to the second oligonucleotide, whilst one or more other segments may not be.

The terms "primer", "primer sequence" and "primer oligonucleotide" are used interchangeably herein and have the same meaning. A primer refers to a short oligonucleotide (e.g. less than: 50, 40, 35, 30, 25, 20, 15, or 10 nucleotides in length) that can hybridise by complementary base pairing to a single-stranded segment of another nucleic acid, and thereby facilitate synthesis of a new strand of nucleic acid having base pair complementarity to the single-stranded segment by a polymerase enzyme.

The terms "catalytic nucleic acid molecule", "catalytic nucleic acid", "catalytic nucleic acid enzyme", "nucleic acid enzyme" and "catalytic nucleic acid sequence" are used interchangeably herein and have the same meaning. These terms encompass any nucleic acid capable of the specific recognition and catalytic modification of one or more substrates. For example, the substrate or substrates may be nucleic acids, and the catalytic modification may be ligation or cleavage. Catalytic nucleic acid enzymes as used herein include. DNA molecules or DNA-containing molecules, RNA or RNA-containing molecules, and DNA-RNA or DNA-RNA-containing molecules. Non-limiting examples of catalytic nucleic acid enzymes include DNAzymes (also known as DNA enzymes and deoxyribozymes), ribozymes (also known as RNA enzymes and RNAzymes) and multi-component nucleic acid enzymes (MNAzymes). A catalytic nucleic acid enzyme may be referred to herein as an "initiator catalytic nucleic acid enzyme" or an "initiator enzyme" which refers to a catalytic nucleic acid enzyme responsible for initiating the first step of a cascade according to the present invention. "Initiator catalytic nucleic acid enzyme" or an "initiator enzyme" may also include an aptazyme whereby a DNAzyme or ribozyme is linked to an aptamer or an apta-MNAzyme, where an MNAzyme component is linked to an aptamer.

As used herein, the terms "polynucleotide" and "nucleic acid" are used interchangeably and have the same meaning, referring to a single-stranded or double-stranded polymer of deoxyribonucleotide and/or ribonucleotide bases, or analogues, derivatives, variants, fragments or combinations thereof including, but not limited to, DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof. By way of non-limiting example, the source of a nucleic acid may be selected from the group comprising synthetic, mammalian, human, animal, plant, fungal, bacterial, viral, archael or any combination thereof.

As used herein, the terms "oligonucleotide" and "oligo" are used interchangeably and have the same meaning, referring to a DNA or a DNA-containing nucleic acid molecule, an RNA or RNA-containing molecule, or a DNA-RNA or DNA-RNA-containing molecule. Non-limiting examples of oligonucleotides include nucleic acid targets, BL; RL; NRF; catalytic nucleic acid enzymes (e.g. DNAzymes, ribozymes, MNAzymes); substrates, for example, those which can be modified by an MNAzyme, DNAzyme and/or ribozyme; primers such as those used in cascades as described herein; and components of MNAzymes. Oligonucleotides may comprise at least one addition or substitution, including but not limited to any one or more of those set out in Table 1 below. An oligonucleotide may, for example, function asa PCR primer, DNAzyme, partzyme or aptamer. An oligonucleotide as referred to herein may be synthesised by any method including, for example, by chemical synthesis (e.g. from component nucleotides, or the addition of nucleotide(s) to a pre-existing fragment of the oligonucleotide). An oligonucleotide can also be constructed by ligating or otherwise joining multiple fragments of the oligonucleotide. A "ligation product" as referred to herein is a nucleic acid comprising an oligonucleotide composed of two or more oligonucleotides that have been joined (ligated) together by a ligase enzyme.

The terms "nucleotide" and "nucleotide residue" and "bases" as used herein have the same meaning and encompass nucleotides comprising the bases A, C, G, T, or U, as well as derivatives or analogues thereof (non-limiting examples of which are listed in Table 1).

The term "derivative" as used herein in relation to a nucleic acid or nucleotide includes any functionally equivalent nucleic acid or nucleotide, including any fusion molecule produced integrally (e.g. by recombinant means) or added post-synthesis (e.g. by chemical means). Such fusions may comprise oligonucleotides of the invention with RNA or DNA added thereto or conjugated to a polypeptide (e.g. puromycin or other polypeptide), a small molecule (e.g., psoralen), or an antibody.

The term "analogue" as used herein in relation to a nucleic acid or nucleotide includes a compound having a physical structure that is related to a DNA or RNA molecule or residue, and may be capable of forming a hydrogen bond with a DNA or RNA residue or an analogue thereof (i.e. it is able to anneal with a DNA or RNA residue or an analogue thereof to form a base-pair), but such bonding is not so required for said compound to be encompassed within the term "analogue". Such analogues may possess different chemical and biological properties to the ribonucleotide or deoxyribonucleotide residue to which they are structurally related. Methylated, iodinated, brominated or biotinylated residues are examples of analogues. Active DNAzymes have been described which contain nucleotide analogues, including deoxyinosine, C-5-immidazole deoxyuridine, 3-(aminopropynyl)-7-deaza-dATP, 2'-O-methyl RNA, 2'O-methyl cap. Other analogues could also be compatible with catalytic activity of catalytic nucleic acid enzymes such as DNAzymes, ribozymes and MNAzymes. Alteration of a nucleic acid with catalytic activity, for example by substitution of one base for another, by substitution of an analogue for a base, or alteration of the sugar component or phosphodiester backbone, can be straight forward for the skilled artisan. For example, alterations can be made during synthesis or by modification of specific bases after synthesis. Empirical testing of catalytic nucleic acids incorporating alterations such as base changes or base analogues allows for assessment of the impact of the altered sequences, or specific analogues, on catalytic activity. Analogues of the bases A, C, G, T and U are known in the art, and a subset is listed in Table 1. Non-limiting examples of analogues which can inhibit nuclease digestion are also well known in the art. Such analogues can be strategically placed within oligonucleotides to prevent cleavage by an exonuclease and/or an endonuclease. By way of example, $S_p$ stereoisomer of the phosphorothioate linkage is known to greatly inhibit cleavage of many nucleases including, but not limited to, restriction endonucleases, Lambda Exonuclease, T7 Exonuclease, Exonuclease III (*E. coli*), Exonuclease I (*E. coli*), Exonuclease T and RecJ. Inclusion of multiple phosphorothioate linkages can be highly effective in blocking nuclease activity.

TABLE 1

Examples of Nucleotide Analogues

| Abbreviation | Name |
| --- | --- |
| ac4c | 4-acetylcytidine |
| chm5u | 5-(carboxyhydroxylmethyl)uridine |
| Cm | 2'-O-methylcytidine |
| Cmnm5s2u | 5-carboxymethylaminomethyl thiouridine |
| D | Dihydrouridine |
| Fm | 2'-O-methylpseudouridine |
| Galq | beta, D-galactosylqueosine |
| Gm | 2'-O-methylguanosine |
| I | Inosine |
| i6a | N6-isopentenyladenosine |
| m1a | 1-methyladenosine |
| m1f | 1-methylpseudouridine |
| m1g | 1-methylguanosine |
| m1I | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| Manq | beta, D-mannosylmethyluridine |
| mcm5s2u | 5-methoxycarbonylmethyluridine |
| mo5u | 5-methoxyuridine |
| ms2i6a | 2-methylthio-N6-isopentenyladenosine |
| ms2t6a | N-((9-beta-ribofuranosyl-2-methylthiopurine-6-yl)carbamoyl)threonine |
| mt6a | N-((9-beta-ribofuranosylpurine-6-yl)N-methyl-carbamoyl)threonine |
| Mv | Uridine-5-oxyacetic acid methylester |
| o5u | Uridine-5-oxyacetic acid (v) |

TABLE 1-continued

Examples of Nucleotide Analogues

| Abbreviation | Name |
| --- | --- |
| Osyw | Wybutoxosine |
| P | Pseudouridine |
| PS | phosphothioate |
| Q | Queosine |
| s2c | 2-thiocytidine |
| s2t | 5-methyl-2-thiouridine |
| s2u | 2-thiouridine |
| s4u | 4-thiouridine |
| T | 5-methyluridine |
| t6a | N-((9-beta-D-ribofuranosylpurine-6-yl)carbamoyl)threoninetm 2'-O-methyl-5-methyluridine |
| Um | 2'-O-methyluridine |
| Yw | Wybutosine |
| X | 3-(3-amino-3-carboxypropyl)uridine, (acp3)u |
| AraU | beta, D-arabinosyl |
| AraT | beta, D-arabinosyl |

The terms "MNAzyme" and multi-component nucleic acid enzyme" as used herein, refer to two or more oligonucleotide sequences (e.g. partzymes) which, only in the presence of MNAzyme assembly facilitator molecule (for example, a target analyte), assemble to form a catalytically active nucleic acid enzyme that is capable of catalytically modifying one or more substrates. For example, partzymes A and B may each bind to a target analyte (e.g. by complementary base pairing with a nucleic acid target). The MNAzyme only forms when the sensor arms of partzymes A and B hybridize adjacent to each other on the target. The substrate arms of the MNAzyme engage the substrate, the modification of which (e.g. cleavage or ligation) is catalyzed by the catalytic core of the MNAzyme, formed by the interaction of the partial catalytic domains on partzymes A and B. It will be understood that the terms "MNAzyme" and "multi-component nucleic acid enzyme" as used herein encompass all known MNAzymes and modified MNAzymes including those disclosed in any one or more of PCT patent publication numbers WO/2007/041774, WO/2008/040095, WO2008/122084, and related US patent publication numbers 2007-0231810, 2010-0136536, and 2011-0143338 (the contents of each of these documents are incorporated herein by reference in their entirety). Non-limiting examples of MNAzymes and modified MNAzymes encompassed by the terms "MNAzyme" and "multi-component nucleic acid enzyme" include MNAzymes with cleavage catalytic activity (as exemplified herein), disassembled or partially assembled MNAzymes comprising one or more assembly inhibitors, MNAzymes comprising one or more aptamers ("apta-MNAzymes"), MNAzymes comprising one or more truncated sensor arms and optionally one or more stabilizing oligonucleotides, MNAzymes comprising one or more activity inhibitors, multi-component nucleic acid inactive proenzymes (MNAi), and MNAzymes with ligase catalytic activity ("MNAzyme ligases"), each of which is described in detail in one or more of WO/2007/041774, WO/2008/040095, WO2008/122084, US 2007-0231810, US 2010-0136536, and/or US 2011-0143338.

The term "aptazyme" as used herein, refers to a catalytic nucleic acid (a DNAzyme or a ribozyme or an MNAzyme) which has been linked with an aptamer domain to allosterically regulate its activity such that it is dependent on the presence of the target analyte. Methods for incorporating an aptamer into a catalytic nucleic acid or catalytic nucleic acid component, include, but are not limited to, direct conjugation of the aptamer to one or more domains of the catalytic nucleic acid or catalytic nucleic acid component; incorporation of the aptamer into a non-functional region of the catalytic nucleic acid, or conjugation of the aptamer adjacent to a functional region of the catalytic nucleic acid, where both are partially hybridized to a regulator oligonucleotide to inhibit catalytic activity of the aptazyme in the absence of the analyte.

The terms "assembly facilitator molecule", "assembly facilitator", "MNAzyme assembly facilitator molecule", and "MNAzyme assembly facilitator" are used interchangeably herein and refer to entities (e.g. nucleic acids) that can hybridise with a sensor arm of one or more partzyme components, and thereby facilitate the assembly of a catalytically active MNAzyme. Assembly facilitators may facilitate the assembly of MNAzymes which have cleavage, ligase or other enzymatic activities. An assembly facilitator may be a single molecule or comprise multiple separate molecules; which hybridise to a sensor arm of one or more oligonucleotide "partzymes". The assembly facilitator may be a target to be detected or quantified (e.g. a nucleic acid selected from the group consisting of DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof).

As used herein, the terms "partzyme", "partzyme component" and partzyme oligonucleotide" are used interchangeably and have the same meaning, each referring to DNA-containing and/or RNA-containing oligonucleotide, two or more of which, only in the presence of an MNAzyme assembly facilitator molecule, can together form an "MNAzyme." A partzyme, comprises three domains: a "catalytic" domain, which forms part of the MNAzyme's catalytic core that catalyzes the chemical modification; a "sensor arm" domain, which associates with and/or binds to an assembly facilitator (e.g. a target analyte); and a "substrate arm" domain, which associates with and/or binds to a substrate.

The terms "substrate", and "substrate molecule", are used interchangeably herein and refer to any molecule capable of recognition and catalytic modification by a catalytic molecule (e.g. a catalytic nucleic acid enzyme or a protein enzyme). A substrate may comprise, for example, a single-stranded or double-stranded nucleic acid capable of specific recognition and catalytic modification by a catalytic nucleic acid enzyme. A substrate that is catalytically modified may be detected by indirect and/or direct means. For example, the catalytic modification of a substrate may be detected indirectly by virtue of one or more subsequent steps in a cascade that rely on the substrate being catalytically modified. Additionally or alternatively, the catalytic modification of a substrate may be detected, for example, by directly detecting one or more modified substrate products and/or any other signal directly generated by modification of the substrate (e.g. a fluorescent signal generated by cleaving the substrate and thereby spatially separating previously paired fluorophore and quencher molecules present on the unmodified substrate). A substrate that can be detected directly upon catalytic modification by a catalytic molecule is also referred to herein as a "reporter substrate" or a "reporter probe substrate".

As used herein the term "aptamer" encompasses a nucleic acid or peptide sequence that has the ability to recognize one or more ligands with high affinity and specificity due to their higher level structure, for example, a 3-D binding domain or pocket. Aptamers can bind nucleic acid, proteins, prions, small organic compounds, or entire organisms. Preferred aptamers herein are short single-strand DNA or RNA oligomers which can be isolated from complex libraries of synthetic nucleic acid by an iterative process of adsorption, recovery, and reamplification. Aptamers can be generated against almost any target, ranging from small molecules such as amino acids, or antibiotics to proteins, nucleic acid structures or whole cells.

The term "ligand" as used herein refers to any molecule capable of binding to an aptamer with high affinity and specificity, including but not limited to, proteins, prions, polypeptides, peptides or nucleic acids, glycoproteins, lipids, lipoproteins, viruses, bacteria, archaea, fungi, antibodies, metabolites, pathogens, toxins, contaminants, poisons, small molecules, polymers, metal ions, metal salts, small organic compounds, whole cells and entire organisms. A ligand may also be refereed to as a "target analyte" or "analyte".

Reference herein to "hybridisation" between two or more nucleic acids, or, to two or more nucleic acids that are "hybridised", will be understood to require complementary base pairing between all or a portion of the nucleic acids.

ABBREVIATIONS

The following abbreviations are used herein and throughout the specification:
AS: Anti-sense
ATP: Adenosine triphosphate
BL: blocking oligonucleotide
RL: releaser oligonucleotide
NRF: nuclease recognition fragment
ExoIII: exonuclease HI
NESA: nicking endonuclease signal amplification
SDA: strand displacement amplification
LAMP: loop-mediated isothermal amplification
RCA: rolling circle amplification
TMA: transcript-mediated amplification
3SR: self-sustained sequence replication
NASBA: nucleic acid sequence based amplification
MNAzyme or Mz: multi-component nucleic acid enzyme
DNAzyme or Dz: deoxyribonucleic acid enzyme;
PCR: polymerase chain reaction;
F: fluorophore dye molecule;
Q: quencher molecule;
dNTPα: α-thio-deoxynucleotide
JOE or 6-JOE: 6-carboxy-4',5'-dichloro-2',7'-dimethoxy-fluorescein;
FAM or 6-FAM: 6-Carboxyfluorescein.
TxR: texas red
Oligo: oligonucleotide
IB: Iowa Black
IDT: Integrated DNA Technologies
Pol: Polymerase
RE: Restriction Endonuclease
T4 PNK: T4 Polynucleotide Kinase

DETAILED DESCRIPTION

The following detailed description conveys exemplary embodiments of the present invention in sufficient detail to enable those of ordinary skill in the art to practice the present invention. Features or limitations of the various embodiments described do not necessarily limit other embodiments of the present invention or the present invention as a whole. Hence, the following detailed description does not limit the scope of the present invention, which is defined only by the claims.

As discussed above, numerous limitations are evident in currently available assays for target molecule detection and methods designed to amplify the signals generated by such assays. One or more of these limitations are addressed by the compositions, kits and methods of the present invention.

Compositions, methods and kits are provided for the detection, identification and/or quantification of a target.

Some aspects of the present invention relate to molecular complexes which have the capability of functioning as molecular switches. These complexes may comprise, for example, any one or more of an RL, NRF, primer, catalytic nucleic acid enzyme, catalytic nucleic acid enzyme component, or polymerase template, which may be rendered functionally inactive by hybridization to a BL. Removal of the BL from the complex may render the remaining component/s functionally active. Alternatively, the compositions may comprise, for example, any one or more of a functionally active RL, NRF, primer, catalytic nucleic acid enzyme, catalytic nucleic acid enzyme component, or a polymerase template that is not hybridised to a BL, and which may be rendered functionally inactive by hybridization to a BL.

Other aspects of the present invention relate to methods for detecting target molecules and/or signal amplification utilising molecular complexes of the present invention. The methods generally comprise the use of compositions comprising components for molecular switches which may be formed by hybridisation between a catalytic nucleic acid, a polymerase template, primer, NRF or RL molecules and a BL molecule. This hybridisation may result in the functional inactivation of the catalytic nucleic acid, primer, NRF, RL or polymerase template until such time as the BL is dissociated from it. The provision of these molecular switches has facilitated the development of detection and signal amplification cascades.

For example, the BL may contain one or more substrate sequences for one or more different catalytic nucleic acid molecules, such that cleavage of one or more of the substrates may separate the BL from one or more other molecules, for example a different catalytic nucleic acid, a primer, an NRF, an RL and/or a polymerase template previously hybridized by complementary base pairing to the BL. The BL may comprise one or more aptamers capable of being bound by one or more target analytes. Binding of the target analyte(s) to the aptamer(s) may result in the separation of the BL or more other molecules, for example, a different catalytic nucleic acid, a primer, an NRF, a RL, and/or a polymerase template previously hybridised by complementary base pairing to the BL. Separation from the BL may restore the ability of these molecules to perform their respective functions, namely, catalyze substrate modification, prime the synthesis of new nucleic acids, initiate nuclease activity, release an oligonucleotide in a duplex, or serve as a template for a polymerase to synthesise a sequence of nucleotides that is the complement of the template.

In another example, a catalytic nucleic acid molecule rendered functionally inactive by hybridisation to a BL may be separated from the BL by an RL molecule, thereby restoring its catalytic activity. Although the RL is hybridised to the BL following release of the enzyme, the process may be repeated autonomously via the activity of enzymes such as DNAzymes, MNAzymes or other catalytic nucleic acid enzymes, restriction enzymes including but not limited to nicking enzymes, other endonucleases, exonucleases and/or strand displacing polymerase enzymes, which may function either alone or in combination to liberate the RL from the RL/BL complex formed. This in turn allows the RL to participate in further rounds of BL sequestration, thereby releasing further catalytic enzymes from BL/enzyme complexes.

In a further example, catalytic nucleic acids rendered functionally inactive by hybridisation to a BL may be activated directly by the activity of a nuclease (e.g. an RE or an exonuclease), or a strand displacing polymerase, the activities of which may be initiated by providing either a NRF or primer. An RE may be used together with a strand displacing polymerase to continuously synthesize new catalytic nucleic acids through cycles of RE cleavage (including single strand nicking), primer extension and strand displacement activity.

The molecular switches described herein may be used to construct circular cascades whereby the cleavage of a BL by an initial active catalytic nucleic acid (such as an MNAzyme in the presence of its target assembly facilitator), and/or removal of a BL via a target analyte binding to an aptamer within a BL, may trigger the activation of a functional molecule (e.g. another catalytic nucleic acid, a primer, an NRF, an RL or a polymerase template). The functional molecule may directly or indirectly (via the recruitment of protein enzymes such as nucleases or polymerases) activate another catalytic nucleic acid, which may then function to cleave the BL causing activation of additional functional molecules. The circular feedback cascades may be used for the amplification of signal following the detection of a target.

Other aspects of the present invention relate to kits comprising the molecular complexes described herein and optionally other component(s) necessary to perform the methods of the invention (e.g. any one or more of catalytic nucleic acids such as MNAzymes and components thereof, DNAzymes, and/or ribozymes, exonucleases, endonucleases, RL, BL, NRF, primers, polymerase templates, substrates and the like).

Compositions and Kits

Provided herein are compositions and kits for carrying out the methods of the invention. By way of non-limiting example only, the compositions and kits may comprise any one or more of catalytic nucleic acid enzymes (e.g. MNAzymes and/or a partzyme component thereof, DNAzymes, and/or ribozymes), exonucleases, endonucleases, RL, BL, NRF, primers, polymerase templates, and substrates (e.g. substrates for catalytic nucleic acid enzymes, exonucleases, endonucleases).

Various components of the compositions and kits may be provided in a functionally inactivated form. For example, the components may be provided in a molecular complex comprising a BL, wherein the BL is hybridised to the component thereby preventing it from functioning as it would in the absence of the BL. The inclusion of other components in the compositions and kits (e.g. RL, exonucleases, endonucleases, polymerases, NRF, primers, and/or other catalytic nucleic acid enzymes) may provide a means of disassociating the component from the BL, thereby restoring the functional capacity of the component.

Additionally or alternatively, various components of the compositions and kits may be provided in a functionally active form. The inclusion of a BL capable of hybridising to the component may provide a means of inactivating the component.

Accordingly, various components of the compositions and kits can be provided in the form of a molecular switch, wherein the components may subsequently be rendered functionally inactive or active by various methods including, but not limited to, inactivation by hybridization to a BL, or activation by removal of BL hybridised to the component (e.g. by cleavage of the BL, displacement by an RL or target analyte binding to an aptamer within a BL).

Non-limiting examples of components suitable for inclusion in the compositions and kits are provided below.

Catalytic Nucleic Acid Enzymes

Compositions and kits of the present invention may comprise one or more different types of catalytic nucleic acid enzymes and/or one or more components thereof (e.g. one or more partzymes and/or assembly facilitators) and/or the complement of catalytic nucleic acid enzymes or components thereof.

The catalytic nucleic acid enzymes and/or components thereof may be provided in molecular complexes in which the enzyme or component thereof is rendered catalytically inactive due to hybridization with another element (e.g. a BL). In such cases, dissociation of a catalytic nucleic acid enzyme or component thereof from other element(s) of the complex may render the enzyme capable of catalytic activity, thereby providing a molecular switch.

Additionally or alternatively, the catalytic nucleic acid enzymes and/or components thereof may be provided as discrete entities that are not components of a molecular complex and capable of catalytic activity in the presence of a substrate and/or target. In such cases, the enzyme or component thereof may be capable of modifying a substrate. Without imposing any particular limitation, the substrate may be a component of a BL, a primer oligonucleotide or a reporter substrate. When provided in this form, the catalytic nucleic acid enzyme or component thereof may have specificity for a substrate that is a component of another constituent of the composition or kit and/or a reporter substrate constituent. The substrate may be capable of providing a detectable signal upon catalytic modification. For example, the substrate may comprise one or more detectable labels (e.g. a fluorophore and quencher).

The compositions and kits may comprise any suitable catalytic nucleic acid enzyme(s) (non-limiting examples of which include DNAzymes, MNAzymes, ribozymes and/or aptazymes) and/or components thereof (e.g. partzyme(s) and/or assembly facilitator(s)).

For example, compositions and kits of the present invention may comprise DNAzymes. Any suitable DNAzyme may be utilised. The DNAzymes may be known/existing DNAzymes or newly generated by in vitro selection. The DNAzymes may be capable of cleaving or ligating either RNA or DNA molecules. Divalent metal ions such as, for example, $Ba^{2+}$, $Sr^{2+}$, $Mg^{2+}$, $Ca^{2+}$, $Ni^{2+}$, $Co^{2+}$, $Mn^{2+}$, $Zn^{2+}$, and/or $Pb^{2+}$ may be provided as co-factors for the DNAzymes. The DNAzymes may comprise a catalytic domain (catalytic core) flanked by two non-conserved substrate binding domains ("hybridizing arms"), which are regions of sequence that specifically bind to a target substrate. Non-limiting examples of suitable DNAzymes include 10:23 DNAzymes which comprise a catalytic domain of 15 deoxyribonucleotides flanked by two substrate-recognition arms, and 8:17 DNAzymes.

Additionally or alternatively, the compositions and kits may comprise ribozymes. Any suitable ribozyme may be utilised. The ribozymes may be natural ribozymes or artificially generated ribozymes. The ribozymes may be capable of cleaving or ligating either RNA or DNA molecules. Divalent metal ions such as, for example, $Ba^{2+}$, $Sr^{2+}$, $Mg^{2+}$, $Ca^{2+}$, $Ni^{2+}$, $Co^{2+}$, $Mn^{2+}$, $Zn^{2+}$, and/or $Pb^{2+}$ and/or monovalent cations may be provided as co-factors for the ribozymes. The ribozymes may comprise a catalytic domain (catalytic core) flanked by two non-conserved substrate binding domains ("hybridizing arms"), which are regions of sequence that specifically bind to a target substrate. Alternatively, other ribozyme structures are contemplated wherein the structures may comprise separate target and substrate binding arms and a catalytic core. Non-limiting examples of suitable ribozymes include hammerhead ribozymes, hairpin ribozymes, branching ribozymes, maxizymes, Group I ribozymes, Group II intron ribozymes, HDV ribozyme, RNase P, CPEB3 ribozyme, glmS ribozyme, peptidyl transferase 23S rRNA, VS ribozyme, CoTC ribozyme and GIR1 leadzyme.

Additionally or alternatively, compositions and kits of the present invention may comprise any one or more of MNAzymes, partzyme components capable of forming catalytically active MNAzymes, MNAzyme assembly facilitators, and/or MNAzyme substrates. As well known to those in the field, MNAzymes are catalytically active nucleic acid enzymes which self-assemble from two or more partzymes upon hybridisation to an appropriate assembly facilitator (e.g. a target). Each partzyme component comprises a partial catalytic core, which upon assembly of the MNAzyme combine to form a single catalytic core capable of modifying a substrate.

Non-limiting examples of suitable MNAzymes and methods for their generation are disclosed, for example in any one or more of PCT patent publication numbers WO/2007/041774, WO/2008/040095, WO2008/122084, and related US patent publication numbers 2007-0231810, 2010-0136536, and 2011-0143338 (the contents of each of these documents are incorporated herein by reference in their entirety). Suitable MNAzymes include those with cleavage catalytic activity, those with ligation activity, disassembled or partially assembled MNAzymes comprising one or more assembly inhibitors, MNAzymes comprising one or more aptamers ("apta-MNAzymes"), MNAzymes comprising one or more truncated sensor arms and optionally one or more stabilizing oligonucleotides, MNAzymes comprising one or more activity inhibitors, multi-component nucleic acid inactive proenzymes (MNAi), and MNAzymes with ligase catalytic activity ("MNAzyme ligases"), each of which is described in detail in one or more of WO/2007/041774, WO/2008/040095, WO2008/122084, US 2007-0231810, US 2010-0136536, and/or US 2011-0143338. The partzyme oligonucleotides self-assemble in the presence of an MNAzyme assembly facilitator to form an MNAzyme. In some embodiments, the presence of an MNAzyme can be detected, and is indicative of the presence of a target, because the MNAzyme forms only in the presence of the target, wherein the target comprises the assembly facilitator. MNAzymes are described in more detail in PCT/AU2006/001473 (published as WO 2007/041774) and in PCT/AU2007/001517 (published as WO 2008/040095) which are incorporated herein by reference in their entirety.

As known to those skilled in the field, MNAzyme structures are based on one or more DNAzymes (e.g. 10:23 and 8:17 DNAzymes) and/or ribozymes. The MNAzymes may comprise ribonucleotide bases and/or deoxyribonucleotide bases and/or analogues thereof. For example, one or more of a sensor arm, a substrate arm, or the catalytic core of the MNAzyme, may comprise one or more ribonucleotide bases and/or one or more deoxyribonucleotide bases and/or one or more analogues thereof. In some embodiments the MNAzyme comprises at least one deoxyribonucleotide base, or its analogue, within the catalytic core of the MNAzyme. The deoxyribonucleotide base, or its analogue, may be required for catalytic activity.

MNAzymes of the compositions and kits may contain one or more substitutions such as analogues, derivatives, modified or altered bases, ribonucleotides, alterations of the sugar or phosphate backbone, various deletions, insertions, substitutions, duplications or other modifications, or any combination of these, well known to those skilled in the art. Such modifications, substitutions, deletions, insertions, etc may be made in the sensor and/or substrate arms and/or in the catalytic core portions such that the molecule retains catalytic activity. Substitutions and modifications to arms that bind the substrate or assembly facilitator may be well tolerated and allow tailoring of the molecules to different substrates/assembly facilitators. For example, modification of the sensor arms allows tailoring to different assembly facilitators, while modification of the substrate arms allows tailoring to different substrates.

Additionally or alternatively, compositions and kits of the present invention may comprise one or more components of a catalytic nucleic acid enzyme. For example, the compositions and kits may comprise individual component(s) of an MNAzyme (e.g. one or more partzymes, and/or one or more assembly facilitators).

By way of non-limiting example, the compositions and kits may comprise individual partzyme(s) which, upon recognition of a target molecule, are capable of self-assembly to form a catalytically active MNAzyme capable of modifying one or more substrates. The MNAzyme so formed may be designed to assemble only upon hybridisation of partzyme sensor arms to certain assembly facilitators (which may be specific target molecule(s)) and/or to only catalytically modify certain specific substrate(s) capable of hybridisation to substrate arm(s) of the MNAzyme. Accordingly, MNAzymes included in the compositions and kits may be designed for use as "initiator enzymes" capable of initiating a detection and/or signal amplification cascade according to the present invention.

For example, by altering only the sensor arms of the partzymes, but by leaving the substrate arms unchanged, a large variety of MNAzymes specific for various targets can be designed all of which may utilize a universal MNAzyme substrate for detection. The skilled artisan will appreciate the advantages that this offers in terms of eliminating the need for customized or unique substrates for each target. Each new target requires only one or more changes in one or more of the sensor arm portions; the substrate arm portion and the catalytic core portion can remain constant. Thus, a single MNAzyme substrate can be used for a single target using an MNAzyme, and multiple targets in a series of assays using altered MNAzymes. A plurality of MNAzyme substrates allows multiplexing to detect multiple targets in a single assay using multiple MNAzymes, one for each target. Such multiplexed methods of using MNAzymes are readily accomplished in solution or with attachment to a support system. It is contemplated herein that multiplexed assays can thus be accomplished in systems involving attaching one or more of the substrate, or the MNAzyme partzymes or assembly facilitator, or additional enzyme activities, to a support as described herein.

Similarly, the MNAzymes may be engineered to specifically hybridise to and catalytically modify certain target substrates. For example, by altering only the substrate arms of the partzymes, but by leaving the sensor arms unchanged, a large variety of MNAzymes specific for a given target can be designed which recognise and catalytically modify a series of different MNAzyme substrates. Without imposing any particular limitation, the substrate may be an oligonucleotide that comprises a component of, or is a component of, an RL, NRF, primer oligonucleotide, BL, catalytic nucleic acid enzyme or component thereof (e.g. DNAzyme, ribozyme, partzyme, assembly facilitator). The substrate may be a reporter substrate capable of providing a detectable signal upon catalytic modification by the MNAzyme.

In certain embodiments, MNAzymes of the compositions and kits may be engineered to specifically hybridise to and catalytically modify a universal or generic substrate. Universal MNAzyme substrates may be used to allow rapid assay development by allowing facile design changes to create new MNAzymes which recognize different targets. The substrate arm portion and the catalytic core portion of the partzymes may remain unchanged, with changes only to the sensor arm portion of one or more partzymes required for new targets. Universal substrate sequences are provided and thus the same substrate can be incorporated in assays for many different targets. Further, the same substrate can be incorporated into the methods in various embodiments herein, including assays where the substrate is free in solution or is tethered or attached to a support. A series of universal substrates can be used in a multiplex reaction allowing simultaneous detection of multiple targets. MNAzyme strategies using universal substrates offer a major advantage over detection technologies such as TaqMan® or Beacons or Hybridization probes which require the design and use of probes specific for each new target. Since the MNAzyme substrate is universal and useful for any target, cleavage of this universal MNAzyme substrate allows for the generation and amplification of a signal in the presence of any target.

DNAzymes, ribozymes, partzymes, assembly facilitators and/or MNAzyme substrates included in compositions and kits of the present invention may comprise an aptamer which is capable of binding to a target. Preferred aptamers may comprise short single-stranded DNA or RNA oligomers or peptides that can be isolated from complex libraries of synthetic nucleic acids or peptides by an iterative process of adsorption, recovery, and re-amplification. Aptamers may therefore be generated against almost any target, ranging from small molecules such as amino acids or antibiotics, to protein and nucleic acid structures. In preferred embodiments, aptamers include, for example, nucleic acid binding molecules which are preferably generated by evolution and selection techniques. The aptamers may comprise DNA molecules, RNA molecules or a combination of both including, but not limited to, the nucleotide analogues as per, for example, Table 1 above.

Strategies for combining the use of aptamers with ribozymes or DNAzymes are known in the art. Such molecules are generally chimeric and contain both the aptamer domain and DNAzyme or ribozyme domain, and are activated by the presence of the target ligand. The aptazyme functional activity may be switched on in response to the aptamer domain binding to its analyte. Strategies for generating aptazymes include, but are not limited to, the fusion of the ribozyme or DNAzyme and the aptamer domains together via a communication domain. The communication domain can be evolved via in vitro selection methods to improve its ability to allow for ribozyme or DNAzyme activity only in the presence of the target analyte. Another exemplary strategy involves the incorporation of the aptamer into a non-functional stem loop or hairpin that merely plays a structural role in the ribozyme or DNAzyme. Aptamers may also be linked to a DNAzyme or ribozyme and both the aptamer domain and enzyme domain may be partially hybridized to a regulator oligonucleotide, which is used to inhibit the catalytic activity of the enzyme domain in the absence of the analyte. In the presence of the analyte, the aptamer can bind to the analyte, releasing the regulator oligonucleotide from the enzyme domain and restoring its catalytic activity. In this case, the presence of the analyte may remove the aptamer from the DNAzyme or ribozyme and restore its catalytic activity. Aptamers can also be used to bridge two or more components of a DNAzyme or ribozyme together such that the enzyme is then capable of modifying its substrate. A unique class of DNAzymes also exists that contains an aptamer for hemin and in its presence can mimic the activities of peroxidase, catalysing various chemical substrates to generate fluorescent, chemiluminescent, and colorimetric signals. In preferred embodiments, aptazymes may be used for detecting nucleic acid analytes and/or non-nucleic acid analytes, and can be used to initiate the cascade reactions described herein by acting as a catalytic nucleic acid which can modify one or more substrates present within a BL molecule that is/are complementary to nucleic acids which do not comprise aptazymes or ligation products.

Strategies for combining the use of aptamers with MNAzymesre also known in the art. Aptazymes which contain MNAzyme components linked to aptamer may also be referred to as Apta-MNAzymes. For example at least one partzyme of an MNAzyme may incorporate an aptamer (an apta-partzyme) as well as a complementary sequence capable of forming a hairpin and therefore inhibiting MNAzyme assembly. An analyte or target to be detected may bind to the apta-partzyme, thus enabling assembly of an active MNAzyme. In the absence of a target analyte the apta-partzyme adopts a hairpin structure which inhibits assembly of an active MNAzyme. In the presence of target analyte, the target analyte binds to the aptamer domain of the apta-partzyme, thus disrupting the hairpin structure and allowing the apta-partzyme to participate in assembly of an active MNAzyme. The active MNAzyme may then be capable of modifying an MNAzyme substrate which may exist as part of a BL molecule, which can then restore the function of a DNAzyme or other catalytic nucleic acid, apolymerase template, or of a primer, NRF or RL molecule that had been previously inactive within a molecular switch complex.

In other embodiments the aptamer may be present as part of an assembly facilitator that incorporates an aptamer as well as complementary inhibitor sequence capable of forming a hairpin structure. In the absence of a target analyte, the assembly facilitator adopts a hairpin structure which inhibits the ability of this component to direct the assembly of active MNAzymes. In the presence of target analyte, the target analyte binds to the aptamer domain of the assembly facilitator, thus disrupting the hairpin structure and allowing the component to direct the assembly of an active MNAzyme. The active MNAzyme can then modify an MNAzyme substrate which may exist as part of a BL molecule, which can then restore the function of a catalytic nucleic acid, a polymerase template, a primer, NRF or a RL molecule, that had been previously inactive within a molecular switch complex.

One skilled in the art will appreciate that the aptamer may be incorporated into either end of the assembly facilitator molecule or molecules. Further it will be appreciated that multiple aptamers could be incorporated into one or more of the partzyme oligonucleotide components.

In preferred embodiments, catalytic nucleic acid enzymes including DNAzymes, ribozymes, MNAzymes, or components thereof, and/or their nucleic acid substrates, included in compositions and kits of the present invention may be fully or partially complementary to a first BL comprising an aptamer which is capable of binding to a target molecule. In the presence of a target molecule such as a target analyte, the target analyte may bind to the aptamer which may separate the first BL from the catalytic nucleic acid, the catalytic nucleic acid component, and/or their nucleic acid substrate and restore the capacity of the catalytic nucleic acid, or component, to hybridize with their substrates, and/or additional catalytic nucleic acid components, to form a functional catalytic nucleic acid enzyme/substrate complex. This may then be used to initiate the cascade reactions described herein by acting as the catalytic nucleic acid which may modify substrates present within a second BL molecule which inhibits functionality of complementary oligonucleotides hybridized to it; wherein the said complementary oligonucleotides is not an aptazyme.

In other preferred embodiments, one or more aptamer sequences or portions thereof may be present within a BL molecule. In the presence of a target analyte, the target analyte may bind to the aptamer, which may change the conformation of the aptamer and may result in the separation of the catalytic nucleic acid, RL, primer or NRF from the BL and the subsequent restoration of their catalytic, releasing, priming and nuclease initiation activities respectively wherein the said catalytic nucleic acid is not an aptazyme.

In further embodiments an aptamer sequence may be incorporated at the end of a partzyme (apta-partzyme) in a configuration whereby an active initiating Apta-MNAzyme is only formed in the presence of the target analyte. In this case the partzymes required for the detection strategy include; a standard partzyme; an apta-partzyme which is a partzyme with an aptamer incorporated into one of its ends; an assembly facilitator which binds to both the apta-partzyme and the partzyme enabling assembly of an active initiating Apta-MNAzyme (in the presence of target); a substrate; and an assembly inhibitor which hybridises to, the apta-partzyme in a region which spans at least part of the aptamer sequence and part of the substrate binding arm of the partzyme sequence. In the absence of a target the assembly inhibitor binds to the apta-partzyme preventing cleavage of the reporter probe substrate. In the presence of a target, the target binds to the aptamer sequence of the apta-partzyme, preventing the binding of the assembly inhibitor and allowing the binding and cleavage of the MNAzyme substrate by the initiating Apta-MNAzyme. As such, an active initiating Apta-MNAzyme can only form and modify an MNAzyme substrate in the presence of target.

Further, it will be appreciated by persons skilled in the art that the assembly inhibitor can be a separate molecule or can be incorporated, into one of the components that participate in the MNAzyme complex.

It will also be appreciated by persons skilled in the art that one or more aptamers may be incorporated into any of the oligonucleotide components, including the partzymes, the assembly facilitator or the MNAzyme substrate. Further the aptamer may be incorporated into either end of any one of these oligonucleotides. One or more aptamers may be incorporated into the BL. The aptamer may, for example, be incorporated at either end or internally.

Catalytic nucleic acid enzymes (e.g. DNAzymes, ribozymes, MNAzymes, partzymes, assembly facilitators, substrates, and/or aptazymes) in compositions and kits of the present invention may be provided as a component of a molecular complex hybridised with other molecule(s) by complementary base pairing.

In some embodiments, the compositions and kits may comprise a molecular complex comprising a catalytic nucleic acid enzyme (e.g. a DNAzyme, ribozyme or MNAzyme) hybridised to one or more blocker oligonucleotide(s) by complementary base pairing. Dissociation of the BL(s) from the catalytic nucleic acid enzyme may allow the enzyme to hybridise with and catalytically modify a substrate (e.g. a reporter substrate or a substrate present in a second molecular complex). In this manner, removal of the BL may function to activate a molecular switch.

In some embodiments, the compositions and kits may comprise a molecular complex comprising a DNAzyme and/or ribozyme hybridised to at least one other BL by complementary base pairing. The BL may be entirely or partially hybridised to the DNAzyme or ribozyme. The DNAzyme or ribozyme may be rendered functionally inactive due to hybridisation with the BL(s). Dissociation of the DNAzyme or ribozyme from the BL(s) may restore catalytic activity to the DNAzyme or ribozyme. A molecular complex comprising a DNAzyme or ribozyme hybridised to one or more BL(s) may thus provide a molecular switch.

In some embodiments, a BL hybridised to a catalytic nucleic acid in a molecular complex may comprise: two or more segments hybridised by complementary base pairing to the DNAzyme or ribozyme, and, at least one intermediate segment located between two hybridised segments, wherein the intermediate segment(s) are not hybridised by complementary base pairing to the DNAzyme or ribozyme. The BL may or may not comprise a substrate for a catalytic nucleic acid enzyme.

For example, the BL may comprise one or more substrates for the DNAzyme or ribozyme to which the BL is hybridised, and/or one or more substrates for a different catalytic nucleic acid enzyme. Without any particular limitation, one or more intermediate segment(s) of the BL may comprise a substrate for the DNAzyme or ribozyme to which the BL is hybridised, or, a substrate for a different catalytic nucleic acid enzyme. The nucleotide sequence of the substrate may be partially complementary, entirely complementary, or entirely non-complementary, to the nucleotide sequence of the catalytic core of the DNAzyme or ribozyme. Accordingly, a substrate in a BL of the complex may be partially but incompletely hybridised, entirely hybridised, or entirely unhybridised to the catalytic core of the DNAzyme or ribozyme.

By way of non-limiting example, the BL may comprise first and second segments, each hybridised to a distinct hybridising arm and a region of the catalytic core of the DNAzyme or ribozyme by complementary base pairing, and an intermediate segment located between the first and second segments. The intermediate segment may comprise a substrate for a catalytic nucleic acid enzyme. The intermediate segment may span, but not hybridise to, some or all of the catalytic core nucleotides of the DNAzyme or ribozyme. Alternatively, the intermediate segment of the BL may not span any catalytic core nucleotides of the DNAzyme or ribozyme. Accordingly, the intermediate segment may be partially but incompletely hybridised, or, entirely unhybridised, to the catalytic core of the DNAzyme or ribozyme. In some embodiments, a substrate of the intermediate segment may be partially but incompletely hybridised, or, entirely unhybridised, to the catalytic core of the DNAzyme or ribozyme. Hence, the intermediate segment of the BL including, but not limited to, a substrate within the intermediate segment may, in some embodiments, be hybridised to one or more catalytic core nucleotides of the DNAzyme or ribozyme, but not hybridised to all the catalytic core nucleotides. The intermediate segment of the BL including, but not limited to, a substrate within the intermediate segment, may be hybridised to all but 1, 2, 3, 4, 5, 6, 7, 8, 9, 10, 11, 12, 13, 14 or 15 nucleotides of the DNAzyme or ribozyme catalytic core.

In some embodiments, one or more substrate(s) within an intermediate segment of the BL may be a substrate for the DNAzyme or ribozyme to which the BL is not hybridised in the molecular complex (i.e. it is a substrate for a different catalytic nucleic acid). In such cases the DNAzyme or ribozyme hybridised to the BL is unable to cleave the substrate.

In other embodiments, one or more substrate(s) within an intermediate segment of the BL may be a substrate for the same DNAzyme or ribozyme to which the BL is hybridised in the molecular complex. In such cases, the DNAzyme or ribozyme may be prevented from cleaving the substrate due to a greater amount of hybridisation with the first and second segments of the BL than with the intermediate region of the BL.

In some embodiments, the number of nucleotides in the intermediate segment of the BL including, but not limited to, the number of nucleotides within a substrate of the intermediate segment, may exceed the number of catalytic core nucleotides of the DNAzyme or ribozyme to which the BL is hybridised in the molecular complex (e.g. by at least: 1, 2, 3, 4, 5, 6, 7, 8, 9, 10, 11, 12, 13, 14, 15 additional nucleotides). Without specific limitation, the substrate may be provided within a loop structure that remains unhybridised to the DNAzyme or ribozyme.

In other embodiments, the number of nucleotides in the intermediate segment of the BL including, but not limited to, the number of nucleotides within a substrate of the intermediate segment, may not exceed the number of catalytic core nucleotides of the DNAzyme or ribozyme to which the BL is hybridised in the molecular complex.

In some embodiments, at least one base-pair mismatch (e.g. at least: 1, 2, 3, 4, 5, 6, 7, 8, 9, 10, 11, 12, 13, 14, or 15 mismatches) may exist between the catalytic core of the DNAzyme or ribozyme and the intermediate segment of the BL.

In some embodiments, at least one base-pair mismatch (e.g. at least: 1, 2, 3, 4, 5, 6, 7, 8, 9, 10, 11, 12, 13, 14, 15 mismatches) may exist between the catalytic core of the DNAzyme or ribozyme and a substrate sequence within the intermediate segment of the BL.

In some embodiments, at least one base-pair mismatch (e.g. at least: 1, 2, 3, 4, 5, 6, 7, 8, 9, 10, 11, 12, 13, 14, or 15 mismatches) may exist between the antisense catalytic core of the DNAzyme or ribozyme and the intermediate segment of the BL.

In some embodiments, at least one base-pair mismatch (e.g. at least: 1, 2, 3, 4, 5, 6, 7, 8, 9, 10, 11, 12, 13, 14, 15 mismatches) may exist between the antisense catalytic core of the DNAzyme or ribozyme and a substrate sequence within the intermediate segment of the BL.

The compositions and kits may comprise molecular complexes comprising a BL and a catalytic nucleic acid (e.g. DNAzyme, MNAzyme, or ribozyme), wherein the entire BL may be hybridised with the catalytic nucleic acid, and/or with a segment of the catalytic nucleic acid comprising the catalytic core residues. For example, the sequences of the catalytic core of a DNAzyme or ribozyme and a BL may be entirely complementary, and thus the BL and enzyme may be entirely hybridised by complementary base pairing. In such cases, the enzyme will not catalytically modify the hybridised BL, as the BL will not comprise specific residue(s) (e.g. specific ribonucleotide(s)) that facilitate catalytic modification by the enzyme.

Compositions and kits of the present invention may comprise molecular complexes in which a linker joins one terminus of the blocker oligonucleotide to one terminus of the catalytic nucleic acid. For example, a 5' terminus of a DNAzyme or ribozyme may be linked to a 3' terminus of the BL, or a 3' terminus of a DNAzyme or ribozyme may be linked to a 5' terminus of the BL. Any suitable means may be used to link the BL to the DNAzyme or ribozyme (e.g. by use of a linking nucleic acid sequence or non-nucleic acid chemistry).

For example, the molecular complex may comprise a hairpin loop linking one terminus of the blocker oligonucleotide to one terminus of the DNAzyme or ribozyme. The hairpin loop may comprise a stem portion in which opposing nucleotides share base pair complementarity. Alternatively, the hairpin loop may comprise a stem portion in which one or more opposing nucleotides do not share base pair complementarity. The hairpin loop or a segment thereof (e.g. a strand of the stem portion or the loop portion) may comprise a binding site for a primer oligonucleotide.

Additionally or alternatively, the molecular complex may comprise at least one single-stranded overhang segment (e.g. a 3' overhang and/or a 5' overhang) extending from the complex. The single-stranded overhang segment(s) may be formed by an unhybridised segment of the BL or an unhybridised single-stranded segment of the DNAzyme or ribozyme. The single-stranded overhang segment(s) may comprise a binding site for another oligonucleotide, or a segment thereof (e.g. a primer, an NRF, an RL; or a segment of thereof).

In some embodiments, the compositions and kits may comprise all of the components necessary to activate a molecular switch as described herein, with the exception of a co-factor necessary for the catalytic function of an initiator catalytic nucleic acid enzyme and/or a catalytic nucleic acid enzyme of the switch (e.g. divalent metal ions such as, for example, $Ba^{2+}$, $Sr^{2+}$, $Mg^{2+}$, $Ca^{2+}$, $Ni^{2+}$, $Co^{2+}$, $Mn^{2+}$, $Zn^{2+}$, and/or $Pb^{2+}$, and/or monovalent cations). By way of non-limiting example only, the compositions and kits may comprise an initiator catalytic nucleic acid enzyme and a molecular switch comprising a first catalytic nucleic acid enzyme hybridised to a BL. In the presence of a specific co-factor the initiator catalytic nucleic acid enzyme may be capable of catalytically modifying the BL directly to cause dissociation of the BL and a first catalytic nucleic acid enzyme, thereby facilitating (directly or indirectly) the generation of a detectable signal. Alternatively, the initiator catalytic nucleic acid enzyme may, in the presence of a specific co-factor, be capable of catalytically modifying another component provided in the composition or kit. This catalytic modification may in turn provide a component (e.g. an RL, NRF, primer) capable of interacting with the molecular switch and (directly or indirectly) dissociate the enzyme and BL, thereby facilitating the generation of a detectable signal.

BL Molecules

Compositions and kits of the present invention may comprise blocker oligonucleotide (BL) molecules.

A BL is an oligonucleotide capable of hybridising to a second oligonucleotide by complementary base pairing, thereby preventing the second oligonucleotide from serving a function by either inhibiting its capacity to hybridise the second oligonucleotide from interacting with other molecules, and/or by inhibiting its capacity to form an active conformation. In this manner the presence of the BL prevents the second oligonucleotide from functioning as it would in the absence of the BL. The specific function of the second oligonucleotide which is inhibited in the presence of the BL may include the ability to catalytically modify a substrate; the ability to provide a component partzyme for an active MNAzyme; the ability to function as a "releaser oligonucleotide" capable of replacing one strand of a nucleic acid duplex; the ability to serve as a primer capable of polymerase mediated elongation; the ability to serve as a template for polymerase mediated synthesis of a complementary strand; and/or the ability to form a duplex capable of recognition and digestion by an endonuclease or endonuclease. The specific function of the second oligonucleotide which is inhibited in the presence of the BL may not include the ability to block binding of a ligand to an aptazyme. For example, a BL when hybridised to a second oligonucleotide may prevent the second oligonucleotide from hybridising with other oligonucleotide(s). A BL may be dissociated from a second oligonucleotide to which it is hybridised by the addition of another entity (e.g. a releaser oligonucleotide (RL)) having binding affinity with at least a segment of the BL that is complementary to the second oligonucleotide. The RL may in some cases facilitate strand displacement. In this case, the RL may have stronger, equal, or reduced binding affinity for the BL or a segment thereof, compared to the binding affinity of the second oligonucleotide for the same BL or segment thereof. Accordingly, the incorporation of BL into compositions and kits of the present invention facilitates the provision of molecular switches, wherein hybridisation of a BL may be used to functionally inactivate a given component, and removal of a BL may be used to functionally activate a given component.

The BL, or a segment of the BL, may share base pair complementarity with an entire target oligonucleotide or a segment of the oligonucleotide. The oligonucleotide which is complementary to the BL may be, for example, a primer, NRF, RL, oligonucleotide substrate, catalytic nucleic acid molecule or component thereof (e.g. a DNAzyme, a ribozyme or an MNAzyme, an apta-MNAzyme or an assembly facilitator). In some embodiments, the BL, or the segment of the BL, may not have base pair complementarity or be capable of hybridising with an aptzyme or an assembly facilitator.

The BL may be designed to be complementary to a second oligonucleotide along the full length of the BL. Alternatively, the BL may comprise one or more segments that do not hybridise with the second oligonucleotide by complementary base pairing.

The BL may be provided in the compositions and kits as a discrete oligonucleotide, in which case there is potential for it to hybridise with another oligonucleotide or a segment thereof. In such cases, the 3' end of one molecule may hybridise with the 5' end of the other and vice versa (see FIG. 1, panel i)). Alternatively, the same ends (i.e. 5' with 5' and 3' with 3' can hybridize to create a quasi-circular structure between the two components (see FIG. 1, panel ii)).

The BL may be provided as a component of another oligonucleotide, such as the oligonucleotide to which it is designed to hybridise including, for example, a primer, NRF, RL, oligonucleotide substrate, catalytic nucleic acid molecule or component thereof. In some embodiments, the BL may be joined to the other oligonucleotide by a linking nucleic acid or non-nucleic acid spacer sequence. For example, a 5' terminus of the BL may be linked to a 3' terminus of the other oligonucleotide, or a 3' terminus of the BL may be linked to a 5' terminus of the other oligonucleotide. Any suitable means may be used to link the BL to the other oligonucleotide (e.g. by use of a linking nucleic acid sequence or non-nucleic acid chemistry). The BL may be linked to the other oligonucleotide by a hairpin loop linking one terminus of the blocker oligonucleotide to one terminus of the other oligonucleotide. The hairpin loop may comprise a stem portion in which opposing nucleotides share base pair complementarity. The hairpin loop or a segment thereof (e.g. a strand of the stem portion or the loop portion) may comprise a binding site for a primer oligonucleotide.

The hybridisation between the BL and the primer, NRF, RL or catalytic nucleic acid molecule or component thereof can result in the reversible functional inactivation of the primer, NRF, RL or catalytic nucleic acid, thereby providing a molecular switch.

When a BL is provided in a complex hybridised to a second oligonucleotide, the complex may comprise at least one single-stranded overhang segment (e.g. a 3' overhang and/or a 5' overhang). The single-stranded overhang segment(s) may be formed by an unhybridised segment of the BL or an unhybridised single-stranded segment of the second oligonucleotide to which the BL is hybridised (e.g. a DNAzyme or ribozyme). The single-stranded overhang segment(s) may comprise a binding site for another oligonucleotide, or a segment of another oligonucleotide (e.g. a primer, and NRF or an RL).

The BL may comprise one substrate, or a plurality of substrates (e.g. one, two, three or more substrates), for catalytic nucleic acid enzymes (e.g. DNAzymes, ribozymes, and/or MNAzymes). In embodiments where a BL comprises multiple substrates, one or more of the substrate(s) may be substrate(s) for a first catalytic nucleic acid enzyme, and one or more of the substrate(s) may be substrate(s) for a second different catalytic nucleic acid enzyme having different substrate specificity to the first catalytic nucleic acid enzyme. Alternatively, the multiple substrates may each be recognised by catalytic nucleic acid enzymes having the same substrate specificity.

The BL may comprise one or more aptamer sequences. In the presence of a target analyte, the target analyte may bind to the aptamer, which may change conformation of the aptamer and may result in the separation of the catalytic nucleic acid, partzyme, RL, primer or NRF from the BL and the subsequent restoration of their catalytic, releasing, priming and nuclease initiation activities respectively.

RL Molecules

Compositions and kits of the present invention may comprise releaser oligonucleotide molecules (RL).

An RL is an oligonucleotide capable of hybridising with a first strand of a given nucleic acid duplex, thereby replacing the second strand of a given nucleic acid duplex and substantially or completely preventing reannealing of the second strand to the first strand. The RL may have stronger, equal, or in some cases reduced binding affinity for the first strand or segment thereof, compared to the binding affinity of the second oligonucleotide for the same first strand or segment thereof. Despite this binding affinity for the first strand, the RL may comprise one or more segments that do not hybridise with the first strand by complementary base pairing.

RL molecules may be wholly or partially complementary to a second molecule, including but not limited to a BL oligonucleotide.

RL may be provided in compositions and kits of the present invention as components capable of replacing (e.g. displacing) or removing BL previously hybridised to other oligonucleotides, thereby restoring the capacity of those other oligonucleotides to function. Accordingly, the RL may be provided as a discrete entity designed to sequester BL from complexes comprising hybridised BL, and thereby render molecular switches functionally active.

For example, when provided as a discrete entity the RL may be designed to bind to a 3' or 5' overhang segment formed by a BL duplexed with any of a catalytic nucleic acid or component thereof (e.g. DNAzyme, ribozyme, MNAzyme partzyme, assembly facilitator), an NRF, primer, oligonucleotide substrate, or second RL. In these embodiments the RL is designed to possess binding affinity with the BL in a region complementary to the oligonucleotide intended for release thus facilitating replacement of oligonucleotide(s) formerly hybridised to the BL (i.e. the RL hybridises to the BL instead of the oligonucleotide initially in the duplex). The binding affinity of the RL to the BL may be optimised and measured using standard techniques known to those of ordinary skill in the field. In some embodiments, the length of the RL may exceed the length of the oligonucleotide bound by the BL (e.g. by at least: 1, 2, 3, 4, 5, 6, 7, 8, 9 or 10 nucleotides).

Additionally or alternatively, the RL may be provided as a component of a molecular complex, and as such may be provided in a functionally inactive form (FIG. 4 panel i)). Without imposing any particular limitation, the RL may be an oligonucleotide that is linked to, or is a component of another oligonucleotide such as a BL, a catalytic nucleic acid enzyme or a component thereof (e.g. DNAzyme, ribozyme, partzyme, assembly facilitator). The RL may be joined to the other oligonucleotide by a linking nucleic acid or non-nucleic acid spacer sequence. For example, a 5' terminus of the RL may be linked to a 3' terminus of the other oligonucleotide, or a 3' terminus of the RL may be linked to a 5' terminus of the other oligonucleotide. Any suitable means may be used to link the RL to the other nucleotide (e.g. by use of a linking nucleic acid sequence or non-nucleic acid chemistry). The RL may be linked to the other oligonucleotide by a hairpin loop of nucleic acid sequence linking one terminus of the RL to one terminus of the other oligonucleotide. The hairpin loop may comprise a stem portion in which opposing nucleotides share base pair complementarity. Alternatively, the hairpin loop may comprise a stem portion in which one or more opposing nucleotides do not share base pair complementarity. The hairpin loop or a segment thereof (e.g. a strand of the stem portion or the loop portion) may comprise a binding site for a primer oligonucleotide.

NRF Molecules

Compositions and kits of the present invention may comprise nuclease recognition fragment (NRF) molecules.

NRF are oligonucleotides that can hybridise by complementary base pairing to a second oligonucleotide, and thereby create a recognition site for a nuclease enzyme. Creation of the recognition site initiates activity of the nuclease enzyme on a component of a duplex formed by hybridisation of the NRF and second oligonucleotide (e.g. digestion of the second oligonucleotide by an exonuclease, or the nicking of the second oligonucleotide by an endonuclease). The NRF may be complementary to the second oligonucleotide along its entire length. Alternatively, one or more segments of the NRF may be complementary to the second oligonucleotide, whilst one or more other segments may not be. NRF for inclusion in compositions and kits of the present invention may partially or wholly comprise a sequence of nucleotides identical to that of a target nucleic acid or complementary to that of a target nucleic acid.

NRF for inclusion in compositions and kits of the present invention may be designed to hybridise by, complementary base pairing to an overhang segment present in a duplex of two oligonucleotides (e.g. a duplex formed between a BL and another oligonucleotide). Hybridisation of the NRF to the overhang segment may provide or complete a sequence which is able to be recognized by a nuclease, thus facilitating nuclease digestion of at least one strand of the duplex so formed. Additionally, the NRF may be designed to include a segment (e.g. at least: 1, 2, 3, 4, 5, 6, 7, 8, 9 or 10 nucleotides long) that is not complementary to either oligonucleotide of the duplex. This may serve to provide an unhybridised single-stranded portion of the NRF when the remainder is hybridised to the overhang segment, thereby serving to render the NRF resistant to digestion by the nuclease. The hybridised and unhybridised segments of the NRF may be positioned at opposing termini of the NRF.

NRF in compositions and kits of the present invention may be provided as discrete components capable of hybridising to and activating molecular switches as described herein. For example, the NRF may be designed to hybridise to a 3' overhang segment formed by a BL in a molecular switch as described herein. A first 5' segment of the NRF may be designed to hybridise to the 3' overhang to the BL by complementary base pairing to thereby form a nuclease recognition template, whereas a second 3' segment of the NRF (e.g. at least: 1, 2, 3, 4, 5, 6, 7, 8, 9 or 10 nucleotides long) may be designed to share no sequence complementarity with the BL (or oligonucleotide to which the BL is hybridised in the switch).

Additionally or alternatively, the NRF may be provided as a component of a molecular complex and as such may be provided in a functionally inactive form. Without imposing any particular limitation, the NRF may be linked to, or be provided as a component of, another oligonucleotide such as a BL, an RL, a catalytic nucleic acid enzyme or a component thereof (e.g. DNAzyme, ribozyme, partzyme, assembly facilitator). For example, the NRF may be provided in a hairpinned structure hybridised to a BL. The NRF may comprise first and second segments hybridised by complementary base pairing to the BL, and an intermediate segment between the first and second segments that is not hybridised to the BL. The portion of the BL unhybridised to the NRF may comprise a substrate for a catalytic nucleic acid enzyme (e.g an initiator catalytic nucleic acid enzyme). The NRF may be joined to the other oligonucleotide by a linking nucleic acid or non-nucleic acid spacer sequence. For example, a 5' terminus of the NRF may be linked to a 3' terminus of the other oligonucleotide, or a 3' terminus of the NRF may be linked to a 5' terminus of the other oligonucleotide. Any suitable means may be used to link the NRF to the other nucleotide (e.g. by use of a linking nucleic acid sequence or non-nucleic acid chemistry). The NRF may be linked to the other oligonucleotide by a hairpin loop linking one terminus of the NRF to one terminus of the other oligonucleotide. The hairpin loop may comprise a stem portion in which opposing nucleotides share base pair complementarity. Alternatively, the hairpin loop may comprise a stem portion in which one or more opposing nucleotides do not share base pair complementarity. The hairpin loop or a segment thereof (e.g. a strand of the stem portion or the loop portion) may comprise a binding site for a primer oligonucleotide.

Primers

Compositions and kits of the present invention may comprise primer oligonucleotides.

Primers are short oligonucleotides (e.g. less than: 50, 40, 35, 30, 25, 20, 15, or 10 nucleotides in length) that can hybridise by complementary base pairing to a single-stranded segment of another nucleic acid, and thereby facilitate synthesis of a new strand of nucleic acid having base pair complementarity to the single-stranded segment by a polymerase enzyme. The single segment of another nucleic acid to which the primer hybridises may provide the template for the polymerase; also referred to herein as the polymerase template. The new strand of nucleic acid which is synthesised by the polymerase via extension of the primer comprises a sequence of nucleotides that is the complement to the template. The function of the template as such is to provide a sequence which is read by the polymerase thus directing insertion of complementary nucleotides in the correct sequence.

The primers included in compositions and kits of the present invention may be designed to hybridise to discrete oligonucleotides (e.g. single-stranded oligonucleotides, double-stranded oligonucleotides comprising an overhang segment or loop of non-complementary nucleotides). Non-limiting examples include RL, BL, NRF, substrate oligonucleotides, catalytic nucleic acids or components thereof (e.g. DNAzymes, ribozymes, MNAzymes, partzymes, assembly facilitators).

Additionally or alternatively, primers included in compositions and kits of the present invention may be designed to hybridise to oligonucleotides existing in a complex (e.g. a molecular switch). For example, the primers may be designed to hybridise with an overhang segment of double-stranded oligonucleotide in a complex, or, to a hairpin loop segment in the complex that comprises non-complementary nucleotides.

In some embodiments, the primer may be provided in a hairpinned structure hybridised to a BL. The BL may comprise first and second segments hybridised by complementary base pairing to the primer, and an intermediate segment between the first and second segments that is not hybridised to the primer. The portion of the BL unhybridised to the primer may comprise a substrate for a catalytic nucleic acid enzyme (e.g an initiator catalytic nucleic acid enzyme).

In other embodiments, the primer may be provided as a component of a substrate for a catalytic nucleic acid enzyme (e.g. DNAzyme, ribozyme, MNAzyme, aptazyme). The primer may exist within the substrate in a functionally inactive form (e.g by virtue of being sequestered in a molecular complex and/or by virtue of being a component of a longer substrate sequence). Cleavage of the substrate by the catalytic nucleic acid may lead to the release (i.e activation) of the primer. In some embodiments, cleavage of the substrate by the catalytic nucleic acid enzyme may alone be sufficient to release an activated primer. In other embodiments, modification of the primer after cleavage of the substrate may be necessary (e.g. modification of the primer at or in the proximity of its 3' end). By way of non-limiting example only, the primer may require modification to remove a 2'3' cyclic phosphate at its 3' end by an appropriate enzyme (e.g. T4 PNK).

The primers may be suitable for extension by polymerases or components thereof and/or comprise a complete or partial recognition site for a nuclease enzyme.

Primers included in compositions and kits of the present invention may be provided as discrete components. Additionally or alternatively, the primers may be provided as a component of a molecular complex and as such may be provided in a functionally inactive form. Without imposing any particular limitation, the primers may be linked to, or be provided as a component of, another oligonucleotide such as a BL, an RL, a catalytic nucleic acid enzyme or a component thereof (e.g. DNAzyme, ribozyme, partzyme, assembly facilitator), or a substrate of a catalytic nucleic acid enzyme (e.g. an MNAzyme substrate). The primers may be joined to the other oligonucleotide by a linking nucleic acid or non-nucleic acid spacer sequence. For example, a 5' terminus of the primer may be linked to a 3' terminus of the other oligonucleotide, or a 3' terminus of the primer may be linked to a 5' terminus of the other oligonucleotide. Any suitable means may be used to link the primer to the other nucleotide (e.g. by use of a linking nucleic acid sequence or non-nucleic acid chemistry). The primer may be linked to the other oligonucleotide by a hairpin loop linking one terminus of the primer to one terminus of the other oligonucleotide. The hairpin loop may comprise a stem portion in which opposing nucleotides share base pair complementarity.

Oligonucleotides

Oligonucleotides included in compositions and kits of the present invention, such as DNAzymes, ribozymes, aptazymes, MNAzymes, and their respective substrates, MNAzyme components (e.g. partzymes, assembly facilitators), primers, polymerase templates, NRFs, BL and RL molecules may contain one or more substitutions such as analogues (e.g. those listed in Table 1), derivatives, modified or altered bases, ribonucleotides, alterations of the sugar or phosphate backbone, various deletions, insertions, substitutions, duplications or other modifications, or any combination of these, well known to those skilled in the art. Such modifications, substitutions, deletions, insertions, etc may be made at any position provided the oligonucleotide retains its function. Substitutions and modifications to the oligonucleotides may be well tolerated and allow tailoring of the molecules to function under certain conditions or for improvement of the efficiency of reaction. For example, modification of a BL molecule by inclusion of one or more nucleotide analogues may facilitate the improved release of the DNAzyme or other catalytic nucleic acid molecule following the cleavage of the substrate region by a second DNAzyme or MNAzyme in the presence of its target.

The skilled addressee will appreciate that the DNAzymes, ribozymes, MNAzymes, and their respective substrates, MNAzyme components (e.g. partzymes, assembly facilitators), primers, substrates, polymerase templates, NRFs, BL or RL molecules may comprise either deoxyribonucleotides or ribonucleotides, or both. The oligonucleotides may comprise at least one deoxyribonucleotide, and may in some cases consist of deoxyribonucleotides and/or analogues thereof.

Restriction Enzymes

The compositions and kits may include one or more restriction enzymes. The restriction enzymes may be Type I, Type II, Type III or Type IV restriction enzymes. Restriction enzymes are generally classified into these types based on subunit composition, cleavage position, sequence specificity and cofactor requirements (see Table 2).

TABLE 2

Suitable Types of Restriction Enzymes

| Type | Attributes |
|---|---|
| Type I | Complex, multi-subunit enzymes<br>Cleave DNA at random at a position distant from their recognition sequence<br>e.g. Eco606ORF4215P (SEQ ID NO: 89 TGANNNNNNNNNTGCT) |
| Type II | Cleave DNA at defined positions near or within their recognition sequences to produce discrete restriction fragments e.g. HhaI, HindIII, Not I<br>Cleavage creates a 3'-hydroxyl and a 5'-phosphate<br>Only require magnesium for activity<br>Structure & Recognition sequences<br>Many are homodimers which recognize palindromic sequences<br>Some are heterodimers which recognize asymmetric DNA sequences (e.g., Bbv CI: CCTCAGC)<br>Some recognize continuous sequences (e.g., EcoRI: GAATTC)<br>Others recognize discontinuous sequences (e.g., Bgl I: SEQ ID NO: 90 GCCNNNNNGGC) where the half-sites are separated |
| Type IIS | Cleave at defined positions near their recognition sequences to produce discrete restriction fragments.<br>Recognize sequences that are continuous and asymmetric and cleave outside of their recognition sequence e.g. FokI and AlwI<br>Comprise two distinct domains for DNA binding and for DNA cleavage<br>Generally thought to bind as monomers but to cleave cooperatively through dimerization |
| Type IIG | Large combination restriction-and-modification enzymes, in which the two enzymatic activities reside in the same protein chain<br>Cleave outside of their recognition sequences<br>Some recognize continuous sequences (e.g., AcuI: CTGAAG) and cleave on only one side<br>Some recognize discontinuous sequences (e.g., BcgI: SEQ ID NO: 91 CGANNNNNNTGC) and cleave on both sides (thus releasing a small fragment containing the recognition sites)<br>When they bind their substrates, they switch into either restriction mode to cleave the DNA, or modification mode to methylate it |
| Type III | Large combination restriction-and-modification enzymes<br>Cleave outside of their recognition sequences and require two such sequences in opposite orientations within the same DNA molecule to accomplish cleavage outside of their recognition sequences |
| Type IV | Enzymes recognize modified, typically methylated DNA and are exemplified by the McrBC and Mrr systems of E. coli |

Non-limiting examples of restriction enzymes suitable for inclusion in compositions and kits of the invention are listed in Table 2. One skilled in the art will appreciate that a wide range of restriction enzymes will be compatible with reactions involving the synthesis of catalytic nucleic acids in concert with the activity of strand displacing polymerase enzymes, direct activation of catalytic nucleic acids once triggered by a NRF or the indirect activation of catalytic nucleic acids via recycling of RL molecules. For example, many restriction enzymes listed in the Restriction Enzyme Database, REBASE (http://rebase.neb.com/rebase/rebase.html) will be compatible with the development of such reactions. Table 3 below provides examples of restriction enzymes of the varied specificities and characteristics in the present invention.

TABLE 3

Examples of Restriction Enzymes (Groups are not mutually exclusive)

| Group | # in REBASE | Name | Recognition Sequence* (/ or ↓ indicate cleavage site(s)) |
|---|---|---|---|
| Type I | 240 | CfrAI, M.CfrAI, S.CfrAI | SEQ ID: 92<br>GCANNNNNNNGTGG |
| | | Eco37I, M.Eco37I, S.Eco37I, Eco377I, M.Eco377I, S.Eco377I | SEQ ID NO: 93<br>GGANNNNNNNATGC |

TABLE 3-continued

Examples of Restriction Enzymes (Groups are not mutually exclusive)

| Group | # in REBASE | Name | Recognition Sequence* (/ or ↓ indicate cleavage site(s)) |
|---|---|---|---|
| | | EcoprrI, M.EcoprrI, S.EcoprrI | SEQ ID NO: 94 CCANNNNNNNRTGC |
| | | KpnBI, M.KpnBI, S.KpnBI | SEQ ID NO: 95 CAAANNNNNNRTCA |
| | | StySBLI,, M.StySBLI, S.StySBL | SEQ ID NO: 96 CGANNNNNNTACC |
| | | StySQI, M.StySQI, S.StySQI | SEQ ID NO: 97 AACNNNNNNRTAYG |
| Type II | | AccIII | T↓CCGGA |
| | | BamHI | G↓GATCC |
| | | BglI | SEQ ID NO: 98 GCCNNNN↓NGGC |
| | | BglII | A↓GATCT |
| | | HpaII | C↓CGG |
| | | HaeIII | GG↓CC |
| | | MalI | G6mA↓TC |
| | | PstI | CTGCA↓G |
| | | Sau3AI | ↓GATC |
| | | Tsp509I | ↓AATT |
| Type IIS | 367 | AbeI | CCTCAGC (-5/-2) |
| | | AciI | CCGC (-3/-1) |
| | | Acc36I | ACCTGC (4/8) |
| | | Asp26HI | GAATGC (1/-1) |
| | | BauI | CACGAG (-5/-1) |
| | | BbsI | GAAGAC (2/6) |
| | | BbvCI | CCTCAGC (-5/-2) |
| | | Bpu10I | CCTNAGC (-5/-2) |
| | | BsmDI | SEQ ID NO: 99 ACNNNNNCTCC |
| | | BspACI | CCGC (-3/-1 |
| | | BtrI | CACGTC (-3/-3) |
| | | MnlI | CCTC (7/6) |
| | | TaqII | GACCGA (11/9) |
| Type IIG | 1445 | AcuI | CTGAAG (16/14) |
| | | BmuSORF1564P | SEQ ID NO: 100 GAGNNNNNGT |
| | | EliORF730P | CTGGAG |
| | | NhaXI | CAAGRAG |
| Nicking Enzymes | 333 | Nt.AlwI | GGATC (4/none) |
| | | Nb.BsmAI | GTCTC (none/5) |
| | | Nt.BbvCI | CCTCAGC (-5/none) |
| | | Nb.BbvCI | GC↓TGAGG |
| | | Nt.BhaIII | GAGTC (4/none) |
| | | NtBsmAI | GTCTC (1/none) |
| | | Nb.BsmI | G↓CATTC |
| | | Nt.CviPII | CCD (-3/none) |
| | | Nb.Mva1269I | GAATGC (none/-1) |
| | | Nb.BtsI | (1/none) CACTGC |
| | | Nb.BsrDI | (1/none) CATTGC |
| | | Nt.BstNBI | GAGTC (4/none) |
| | | Nt.BspQI | GCTCTTC (1/none) |
| Type IIB | 23 | AjuI | SEQ ID NO: 101 (7/12) GAANNNNNNNTTGG (11/6) |
| | | BsaXI | SEQ ID NO: 102 (9/12) ACNNNNNCTCC (10/7) |
| | | NmeDI | (12/7) RCCGGY (7/12) |
| | | TstI | SEQ ID NO: 103 (8/13) CACNNNNNNTCC (12/7) |
| Type III | 34 | BceSI | MMCGAAG (25/27) |
| | | EcoP15I | CAGCAG (25/27) |
| | | M.HpyAX | TCGA |
| Type IV | 10 | EcoKMcrA | Y5mCGR |
| | | EcoKMcrBC | — |

TABLE 3-continued

Examples of Restriction Enzymes (Groups are not mutually exclusive)

| Group | # in REBASE | Name | Recognition Sequence* (/ or↓ indicate cleavage site(s)) |
|---|---|---|---|
| Thermo-stable Enzymes (Optimal Temp) | Not listed as a separate group in REBASE | Acc III (65° C.) | TCCGGA |
| | | Bsc BI (55° C.) | GGNNCC |
| | | Bsi XI (65° C.) | ATCGAT |
| | | Bsl I (55° C.) | SEQ ID NO: 104 CCNNNNNNNGG |
| | | Bst BI (65° C.) | TTCGAA |
| | | Mwo I (60° C.) | SEQ ID NO: 105GCNNNNNNNGC |
| | | Taq I (65° C.) | TCGA |

*N = any nucleotide; R = A or G; M = A or C; Y = C or T; 5mC = 5 methylcytosine; 6mA = 6 methyladenosine One skilled in the art will appreciate that standard RE's can also be manipulated to function as nicking enzymes by protecting one strand of a DNA duplex via the incorporation of nucleotide analogs including but not limited to α-thio-deoxynucleotides (dNTPas).

In some embodiments, the nicking enzyme class of RE are provided in the compositions and kits. Restriction enzymes including nicking enzymes may be included together with strand displacing polymerase enzymes.

Enzymes with Exonuclease Activity

In addition to REs and catalytic nucleic acid enzymes, other protein enzymes with the ability to cleave nucleic acid sequences may be included in the compositions, and kits described herein. Some of these enzymes have exonuclease activity which results in removal of nucleotides from the termini of nucleic acids. Suitable and non-limiting examples of exonucleases include Nuclease BAL-31, Exonuclease I (E Coli), Exonuclease III (E. coli), T7 Exonuclease and Exonuclease T. Examples of endoncleases include T7 Endonuclease I and Mung Bean Nuclease. Properties of a subset of useful nucleases are listed in Table 4A.

Enzymes with Phosphatase Activity

The compositions and kits may include one or more enzymes comprising phosphatase activity. The enzymes comprising phosphatase activity may catalyse the removal of phosphate group(s) from nucleic acids. Non-limiting examples of enzymes displaying phosphatase activity on nucleic acids include T4 Polynucleotide Kinase (T4 PNK) and Calf Intestinal Alkaline Phosphatase (CIAP). The enzyme (e.g. T4 PNK) may catalyse the removal of phosphate group(s) from the 3' termini of polynucleotides.

TABLE 4A

Nuclease Properties

| Enzyme | Examples of potential activities which could be exploited in the current invention (ss—single stranded; ds—double stranded) |
|---|---|
| Nuclease BAL-31 | This exonuclease degrades both 3' and 5' termini of duplex DNA. It is also a highly specific single-stranded endonuclease which cleaves at nicks, gaps and single-stranded regions of duplex DNA and RNA |
| Exonuclease I (E Coli) | This 3' to 5' exonuclease removes nucleotides from ss DNA and thus will cleave ss overhang from ds DNA. |
| Mung Bean Nuclease | This endonuclease removes ss extensions (3' and 5') from the ends of ds DNA or ds RNA leaving blunt ends. |
| Exonuclease III (Exo III) (E. coli) | This exonuclease removes nucleotides from 3'-hydroxyl termini of duplex DNA with blunt or 3' recessed termini, and also at nicks in duplex DNA to produce ss gaps |
| T7 | This endonuclease cleaves non-perfectly matched DNA, |

TABLE 4A-continued

Nuclease Properties

| Enzyme | Examples of potential activities which could be exploited in the current invention (ss—single stranded; ds—double stranded) |
|---|---|
| Endonuclease I | cruciform DNA structures, Holliday structures or junctions, heteroduplex DNA and more slowly, nicked ds DNA. It has been used previously to detect or cleave heteroduplex and nicked DNA. |
| T7 Exonuclease | This exonuclease removes 5' nucleotides from duplex DNA in the 5' to 3' direction. It can initiate nucleotide removal from the 5' termini or at gaps and nicks of ds DNA. It has also been reported to degrade RNA and DNA from RNA/DNA hybrids in the 5' to 3' direction but is unable to degrade ds or ss RNA. |
| Exonuclease T | This exonuclease is a ss RNA or ss DNA specific nuclease that requires a free 3' terminus and removes nucleotides in the 3' to 5' direction. It can generate blunt ends from dsRNA or ds DNA molecules that have 3' extensions. |

Strand-Displacing Polymerase Enzymes

Compositions and kits of the present invention may comprise polymerases (e.g. polymerases with strand-displacing activity).

As known to those skilled in the field, strand displacement describes the ability of a polymerase to displace hybridised oligonucleotides (e.g. DNA) encountered during synthesis. These displaced downstream oligonucleotide strands are not degraded and remain intact. Non-limiting examples of suitable strand-displacing polymerases include the Klenow fragment of DNA polymerase I, Phi29 DNA polymerase, Bst DNA Polymerase large fragment, Pyrophage 3173, and Sequenase 2.0 polymerase or variants thereof.

Substrates

Compositions and kits of the present invention may comprise substrates capable of modification by enzymes (e.g. DNAzymes, ribozymes, aptazymes and/or MNAzymes or apta-MNAzymes).

The substrate may be any single- or double-stranded polymer of deoxyribonucleotide or ribonucleotide bases, or analogues, derivatives, variants, fragments or combinations thereof, including, but not limited to, DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof (including mixed polymers of deoxyribonucleotide and ribonucleotide bases), which is capable of being recognized, acted upon or modified by an enzyme including a catalytic nucleic acid enzyme.

The substrate may be modified by various enzymatic activities including but not limited to cleavage or ligation, wherein modification of the substrate by the enzyme may provide a detectable effect indicative of the catalytic activity of the enzyme.

Substrates for nucleic acid enzymes may also comprise non-nucleic acid constituents such as an amino acid, peptide or protein or any chemical constituent outlined in Table 6.1 of ("New strategies in Chemical synthesis and Catalysis", B. Pignataro in Wiley-VCH, 2012).

The substrate may be a reporter substrate comprising one or more features to facilitate the quantification and/or detection of a modified form of the substrate arising due to the catalytic activity of an enzyme. Reporter substrates can be free in solution or bound (or "tethered"), for example, to a surface, or to another molecule. A reporter substrate can be labelled by any of a large variety of means including, for example, fluorophores (with or without one or more additional components, such as quenchers), radioactive labels, biotin (e.g. biotinylation) or chemiluminescent labels. These various labels may provide a means of generating a detectable signal upon modification (e.g. cleavage) by a catalytic nucleic acid enzyme.

The substrate may be a universal substrate that is recognized by and acted on catalytically by a plurality of catalytic nucleic acid enzymes. The universal substrate may be tethered to a solid support. Substrates included in compositions and kits of the present invention may be provided as discrete components capable of recognition and modification by a catalytic nucleic acid. Other aspects of the present invention relate to substrates that can be recognized and cleaved by more than one catalytic nucleic acid. By way of example, a single nucleic acid substrate may be cleavable by both a DNAzyme and an MNAzyme provided the substrate binding arms of the DNAzyme, and the substrate binding arms of the partzyme components of the MNAzyme, are both complementary to the same said single nucleic acid substrate. In such cases the specific catalytic core sequence of the DNAzyme, and the catalytic core portions of the partzyme pair of the MNAzyme, may be compatible with cleavage at a "cleavage" site within the substrate.

Additionally or alternatively, the substrates may be provided as a component of a molecular complex and as such may be provided in a functionally inactive form. Without imposing any particular limitation, one or more substrates may be linked to, or be provided as a component of, another oligonucleotide such as a BL, an RL, an NRF, a catalytic nucleic acid enzyme or a component thereof (e.g. DNAzyme, ribozyme, partzyme, assembly facilitator). The substrates may be joined to the other oligonucleotide by a linking nucleic acid or non-nucleic acid spacer sequence. For example, a 5' terminus of the substrate may be linked to a 3' terminus of the other oligonucleotide, or a 3' terminus of the substrate may be linked to a 5' terminus of the other oligonucleotide. Any suitable means may be used to link the substrate to the other nucleotide (e.g. by use of a linking nucleic acid sequence or non-nucleic acid chemistry). The substrate may be linked to the other oligonucleotide by a hairpin loop linking one terminus of the substrate to one terminus of the other oligonucleotide. The hairpin loop may comprise a stem portion in which opposing nucleotides share base pair complementarity. Alternatively, the hairpin loop may comprise a stem portion in which one or more opposing nucleotides do not share base pair complementarity. The hairpin loop or a segment thereof (e.g. a strand of the stem portion or the loop portion) may comprise a binding site for a primer oligonucleotide.

Additionally or alternatively, the substrates may comprise one or more components that is/are capable of functioning as a primer. Generally, the primer may be in an inactive form when it exists as a component of the substrate (e.g by virtue of being sequestered in a molecular complex and/or by virtue of being a component of a longer substrate sequence). Cleavage of the substrate by a catalytic nucleic acid may lead to the release (i.e. activation) of the primer. In some embodiments, cleavage of the substrate by the catalytic nucleic acid enzyme may alone be sufficient to release an activated primer. In other embodiments, modification of the primer after cleavage of the substrate may be necessary (e.g. modification of the primer at or in the proximity of its 3' end). By way of non-limiting example only, the primer may require modification to remove a 2'3' cyclic phosphate at its 3' end by an appropriate enzyme (e.g. T4 PNK).

Methods for Detection, Quantification and Signal Amplification

The present invention provides various methods for the detection, identification, and/or quantification of at least one target.

Further, the present invention provides various cascades for the amplification of signals generated by these methods.

The methods utilise compositions of the present invention and components thereof. In particular, the methods make use of the molecular switches described herein to generate detection and signal amplification cascades.

Target Detection: BL with Internal Enzyme Substrates

According to the present invention, various methods for the detection of a target and amplifying signals generated from target detection utilise BL comprising catalytic nucleic acid enzyme substrates.

Accordingly, a BL used in the methods may contain a sequence which acts as one or more substrates for one or more catalytic nucleic acid molecules. This may exist as part of or in addition to a hairpin loop sequence linking the BL to another oligonucleotide (e.g. a primer, NRF, RL, polymerase template, or a catalytic nucleic acid). In such embodiments, cleavage of one or more substrate sequences may release the polymerase template, primer, NRF, RL or catalytic nucleic acid from the BL which may result in the re-instatement of functional capacity of the other oligonucleotide such as priming, nuclease initiation, releasing, synthesising from a template oligonucleotide or catalytic activity, respectively.

In certain embodiments more than one BL can be used to inactivate more than one catalytic nucleic acid molecule. In this instance, the substrate sequence of each can be identical and can be cleaved by a second catalytic nucleic acid molecule resulting in the re-instatement of all previously inactive catalytic nucleic acid molecules (FIG. 1, panel iii)). Alternatively, the substrate sequences may be different and cleaved by a second and third catalytic nucleic acid molecule.

In certain embodiments, one or more MNAzyme or aptazyme substrates may be incorporated within the BL molecules. This may facilitate the use of one or more MNAzymes and/or one or more aptazymes as an initiator enzyme to specifically detect a target molecule and modify a substrate of the BL upon doing so. In one embodiment, the BL contains the sequence for a substrate for an MNAzyme or aptazyme such that cleavage of this substrate by the MNAzyme or aptazyme may separate the BL from a second fully or partially complementary oligonucleotide. Cleavage of the substrate may result in cleavage of the BL into two or more shorter oligonucleotide fragments each of which has a lower melting temperature than the uncleaved BL. At the reaction temperature these short cleaved fragments no longer hybridize substantially to the second complementary oligonucleotide. The second complementary oligonucleotide may be, for example, another catalytic nucleic acid or partzyme component thereof, a primer, a polymerase template, NRF or a RL molecule, and release of these from the BL may thus restore the ability of these molecules to perform their respective functions, namely catalyse substrate modification, prime synthesis, provide a template for synthesis of a nucleic acid strand, or provide a sequence for initiation of nuclease activity or release oligonucleotides (e.g. by strand displacement). In some embodiments, the second complementary oligonucleotide is not an assembly facilitator for an MNAzyme.

Referring to FIG. 1, various detection strategies are exemplified in which an initiator catalytic enzyme (e.g. an MNAzyme) may be used to detect a target molecule and facilitate the generation of a detectable signal by catalytic modification of a substrate incorporated into a BL. The strategies depict various molecular complexes comprising DNAzymes hybridized to BL molecules. One skilled in the art will appreciate that one or more partzymes may also be hybridized to BL molecules in a similar manner. Strategy (i) involves the end-to-end hybridisation of the DNAzyme (Dz2) and BL molecule, whereby the 5' and 3' ends of each are paired, as would exist for a typical DNA duplex. Strategy (ii) involves the hybridisation of the same ends of each of the DNAzyme (Dz2) and BL, that is, the 5' ends of each molecule pair as do the 3' ends of each molecule. In order to maintain hybridisation with correct polarity however, each molecule must twist in the opposite direction and as a result, a 'quasi circle' or circle-like structure is then formed between Dz2 and the BL. Strategy (iii) demonstrates a feature unique to the quasi-circle design in that larger circles can be constructed with more than one DNAzyme present (e.g. DzA and DzB) where each can be released by the cleavage activity of a single MNAzyme (Mz1) of one or more BL (e.g. BLA and BLB).

In FIG. 1 panel i) a DNAzyme (Dz2; thick black line) is hybridized with a BL molecule (BL), drawn as two thin black lines linked by a substrate sequence (Substrate 1; thick black dashed line). The 3' end of the BL hybridizes with the 5' end of the Dz2 and vice versa. A second substrate (Substrate 2; thin black dashed line) may be labeled with a fluorophore (unfilled circle) and a quencher (filled circle) and is designed to be cleaved by Dz2. Initially Dz2 cannot cleave this substrate as it is hybridised to the BL. When an MNAzyme (Mz1; thick grey line) assembles in the presence of a target assembly facilitator (AF1; thick grey dashed line) this results in the cleavage of Substrate 1 and the subsequent release of Dz2 from the cleaved BL molecule. Dz2 is then able to bind and cleave Substrate 2 which can result in the separation of the fluorophore and quencher resulting in a detectable fluorescent signal.

FIG. 1 panel ii) demonstrates the quasi-circle strategy, whereby the 5' ends and 3' ends hybridize between the DNAzyme (Dz2; thick black line) and the BL molecule (BL), drawn as two thin black lines which are linked by a substrate sequence (Substrate 1a; thick black dashed line). When hybridized together these molecules then form a quasi-circle, which prevents Dz2 from binding and cleaving its substrate (Substrate 2; thin black dashed line). Substrate 2 may be labeled with a fluorophore (unfilled circle) and a quencher (filled circle). When an MNAzyme (Mz1; thick grey line) assembles in the presence of its target assembly facilitator (AF1; thick grey dashed line) this can result in the cleavage of Substrate 1a and the subsequent release of Dz2 from the cleaved BL, disrupting the quasi-circular structure. Dz2 is then able to bind and cleave Substrate 2 which may result in the separation of fluorophore and quencher and cause a detectable fluorescent signal.

FIG. 1 panel iii) demonstrates a quasi-circle containing two independent DNAzymes which are both temporarily inhibited by two BL molecules. The two DNAzymes, DzA (thick black line) and DzB (thick black dashed line) hybridize with each of the two BL molecules, BLA and BLB, both drawn as thin black lines that are linked with the Substrate 1 sequences (Substrate 1a and Substrate 1b), drawn as a thick black dashed line. Initially both DzA and DzB are unable to cleave their substrates, Substrate A and Substrate B respectively, both of which are drawn as thin black dashed lines. Substrate A and Substrate B may be labeled with different fluorophores (white unfilled circle for Substrate A and grey filled circle for Substrate B) and with quenchers drawn as black filled circles. In the presence of an MNAzyme (Mz1; thick grey lines) assembled in the presence of its target assembly facilitator (AF1; thick grey dashed line), where that Mz1 can cleave Substrate 1 present within the BLA and BLB molecules, cleavage of BLA and/or BLB can result in their separation from DzA and DzB respectively, thus disrupting the quasi-circular structure. As a result, both DzA and DzB may bind and cleave Substrate A and Substrate B respectively, causing the separation of the fluorophores and quenchers and producing a resultant detectable fluorescent signal. The fluorescent signal generated by cleavage of Substrate A and Substrate B could be the same or different.

The skilled person will recognize that another different catalytic nucleic acid enzyme (e.g. an aptazyme) may be used instead of the depicted MNAzyme in FIG. 1 (panels (i), (ii), and (iii)).

Figure 3:
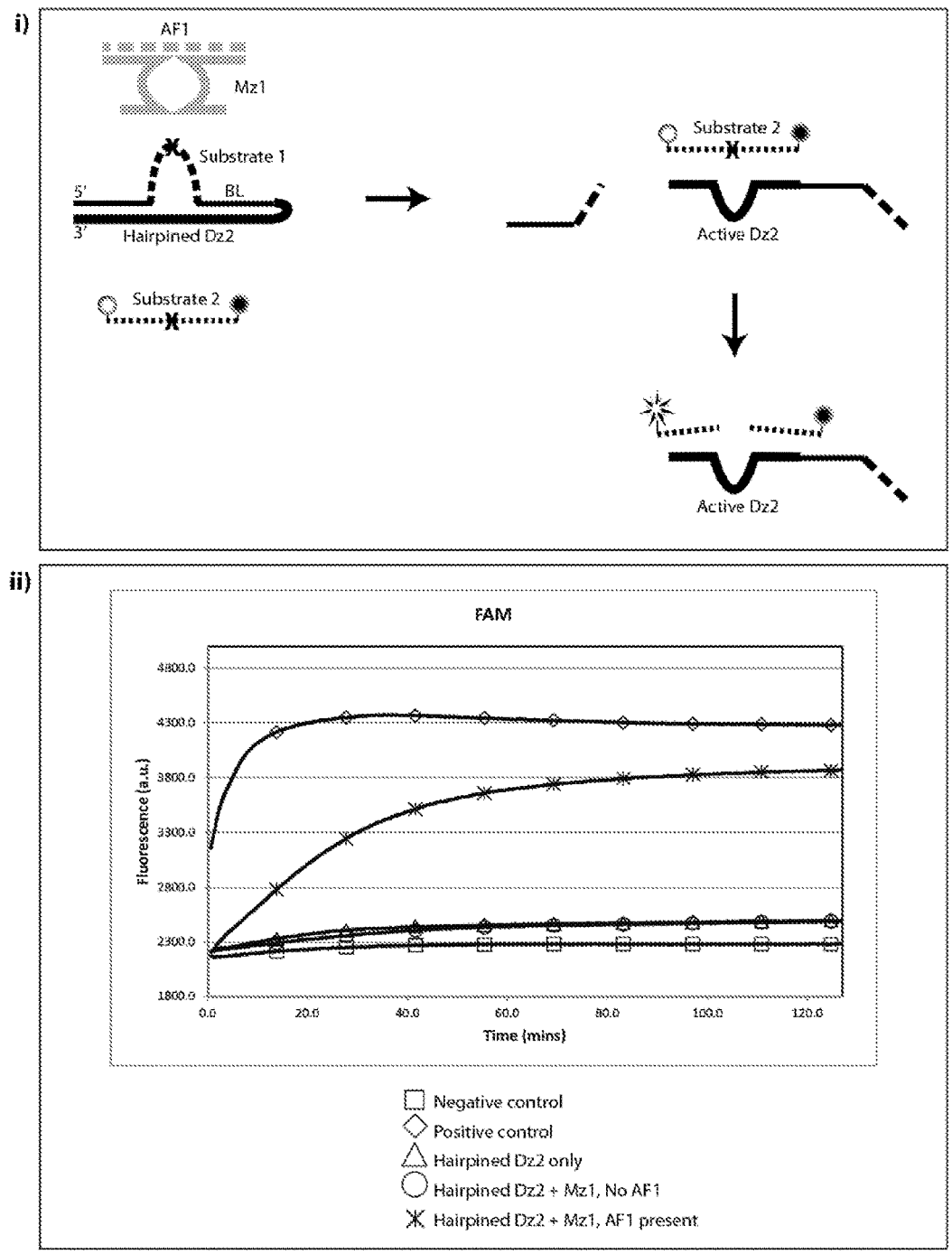
FIG. 3 panel i) depicts the use of the blocked DNAzyme strategy as outlined in FIG. 1 panel i) to demonstrate the ability of an MNAzyme (Mz1) to cleave the substrate (Substrate 1) present within the BL, thus activating/re-instating the catalytic activity of the DNAzyme (Dz2). Dz2 can then cleave Substrate 2 between a fluorophore and quencher and this cleavage can result in an increase in fluorescent signal. Panel ii) provides a timecourse graph depicting fluorescent signal achieved from the strategy depicted diagrammatically in panel i). Cascades involving the continual release and activation of DNAzyme molecules, which may be used for the amplification of signal are also illustrated. Two non-limiting examples of such strategies are illustrated (panels iii) and iv)). The first (panel iii) outlines an 'autocatalytic' cascade where the substrate sequence that exists within a BL molecule may be cleaved by an MNAzyme that is designed to cleave the same substrate as the DNAzyme which has been temporarily inactivated by the BL. The second (panel iv) outlines a 'cross-catalytic' cascade whereby two molecular switch complexes exist, each containing a DNAzyme that may potentially cleave the substrate sequence of the opposing molecular switch and vice versa. In both examples the molecular switches could exist in an inactive state due to inhibition by BL molecules (BLA and BLB) until cascade initiation occurs via cleavage of BLA by an active MNAzyme (Mz1) in the presence of a target molecule which could act as an assembly facilitator (AF1). In all of the illustrations of exemplary strategies in this figure the hybridization between DNAzymes and BLs exists as 5' and 3' end pairing between DNAzymes and BLs (as outlined in FIG. 1 panel i)), however in addition, one end of the duplex is linked by a non-complementary sequence forming a hairpined structure. The pairing may in fact exist without the linking hairpin loop or instead involve 5' and 5' end pairing between the DNAzyme and BL (including such pairings that consist of more than one DNAzyme and BL within the one structure), or a combination of hybridization methods, non-limiting examples of which appear in FIG. 1. In all of the illustrations of exemplary strategies in this figure, the initiating event is cleavage by Mz1, however, in all cases the initiating event can be facilitated by another different catalytic nucleic acid (e.g. a DNAzyme or aptazyme) capable of cleaving the same substrate (substrate 1). When an MNAzyme is used, the initiation can be made to be dependent on the presence of any specific target which can function as an assembly facilitator (AF) for any MNAzyme capable of cleaving substrate 1.
Figure 3:
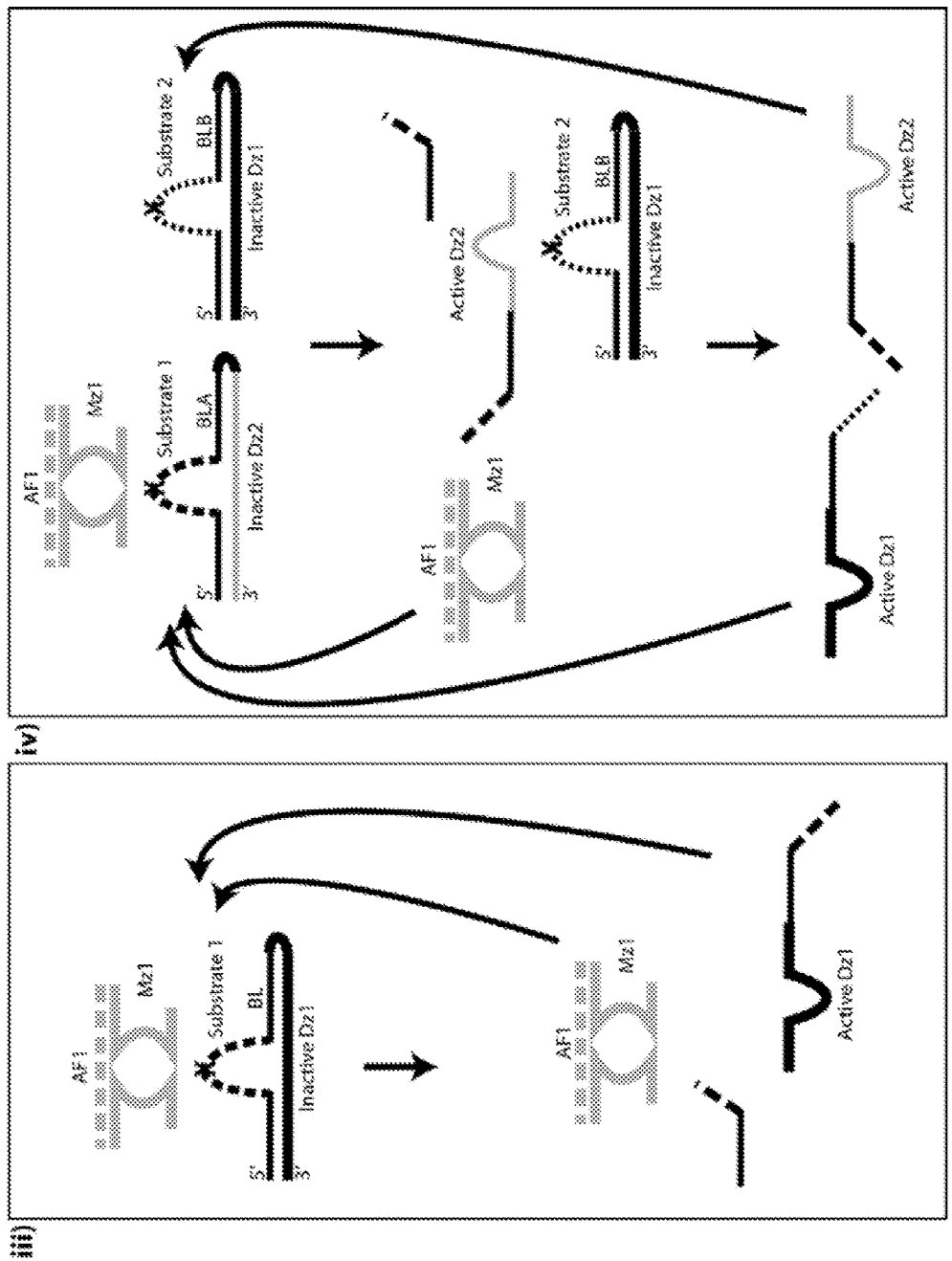

Referring now to FIG. 3 panel i), the exemplary blocked DNAzyme strategy as outlined in FIG. 1 panel i) is extended to include a hairpin loop sequence which links the Dz and the BL together as a single molecule. One skilled in the art will appreciate that a partzyme may also be hybridized to a BL in the same manner. The hairpined DNAzyme (Hairpined Dz2), comprises the DNAzyme portion shown as a thick black line, that is hybridised with a BL portion, drawn as two thin black lines linked by a substrate sequence (Substrate 1) which is drawn as a thick black dashed line. The DNAzyme sequence and BL sequence are linked together via a non-complementary loop sequence (also a thick black line) to form the hairpin structure, rendering the Dz2 inactive. A second substrate (Substrate 2), drawn as a thin black dashed line, may be labeled with a fluorophore (unfilled circle) and a quencher (filled black circle) and is designed to be cleaved by Dz2 once Dz2 is active. Initially Dz2 cannot cleave this substrate as it is hybridized to the BL. When an MNAzyme (Mz1; thick grey lines) assembles in the presence of its target assembly facilitator (AF1; thick grey dashed line) it can cleave Substrate 1 causing the subsequent release of the Dz2 from the hairpin molecule. The active Dz2 molecule may then bind and cleave Substrate 2 which can result in the separation of the fluorophore and quencher resulting in a detectable fluorescent signal. The skilled person will recognise that another different catalytic nucleic acid enzyme (e.g. an aptazyme) may be used instead of the depicted MNAzyme in FIG. 3 panel (i).

Figure 20:
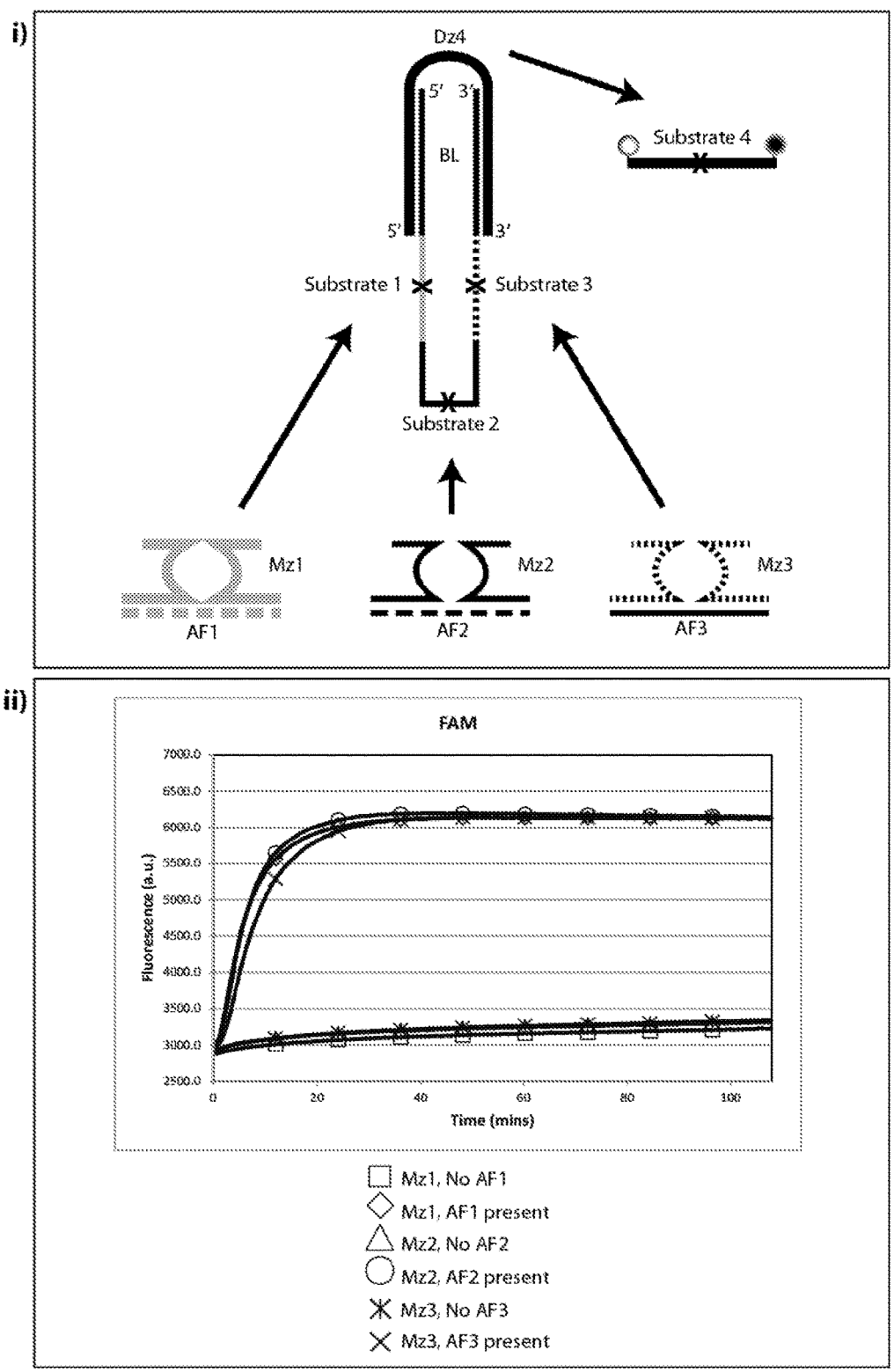
FIG. 20 exemplifies two strategies in which multiple initiator catalytic enzymes (e.g. MNAzymes Mz1, Mz2, Mz3)) may be used to each detect a target molecule and facilitate the generation of a detectable signal by catalytic modification of one of multiple substrates or substrate components incorporated into a BL of a quasi-circular DNAzyme (originally outlined in FIG. 1 panel ii)). The first strategy (panel i)) involves the inclusion of multiple independent, adjacent substrate sequences within the intermediate region of the BL, whereby each substrate sequence may be catalytically modified by an independent initiator catalytic enzyme (e.g. an MNAzyme). The second strategy (panel iii)) involves the inclusion of both independent substrate sequences and components thereof, whereby each substrate or substrate component may be catalytically modified by an independent initiator catalytic enzyme (e.g. an MNAzyme). Panels ii) and iv) demonstrate the fluorescent signal achieved from the strategies depicted in panels i) and iii) respectively.
Figure 20:
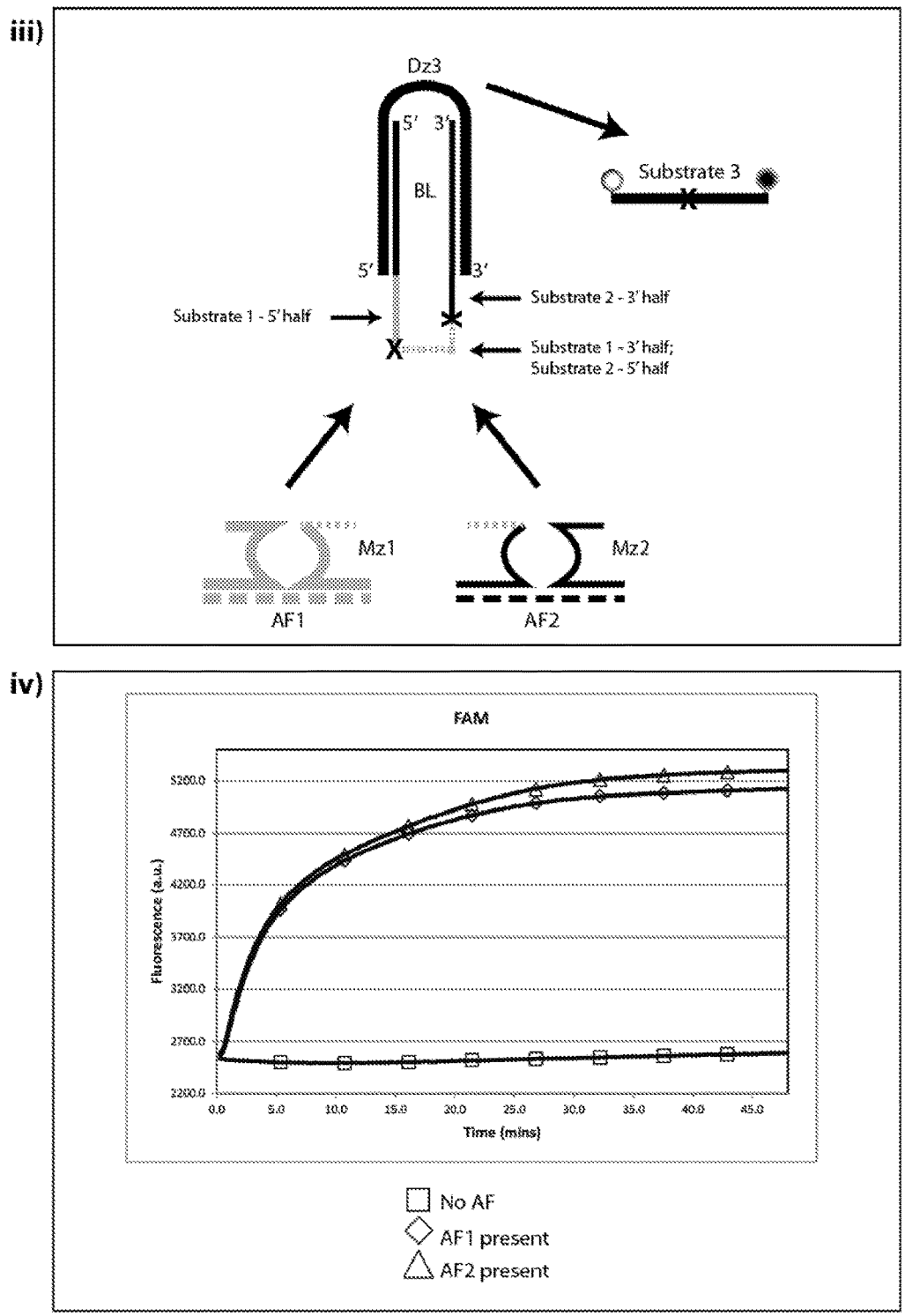

Referring now to FIG. 20, various detection strategies are exemplified in which multiple initiator catalytic enzymes (e.g. MNAzymes as illustrated, or alternatively aptazymes) may be used to each detect a single target molecule or multiple target molecules and facilitate the generation of a detectable signal by catalytic modification of one of multiple substrates incorporated into a BL. Panel (i) depicts a strategy that involves the inclusion of multiple independent, adjacent substrate sequences within the intermediate region of the BL, whereby each substrate sequence may be catalytically modified by an independent initiator catalytic enzyme (e.g. an MNAzyme or aptazyme). Panel (iii) depicts a strategy that involves the inclusion of independent substrate sequences or components thereof, whereby each substrate may be catalytically modified by an independent, initiator catalytic enzyme (e.g. an MNAzyme or aptazyme).

In FIG. 20 panel i) a quasi-circle containing three independent and adjacent substrate sequences is illustrated. Each of the 5' ends and 3' ends hybridize between the DNAzyme (Dz4; thick black line) and the BL molecule, drawn as two thin black lines which are linked by three substrate sequences; Substrate 1 (thin grey line), Substrate 2 (thin black line) and Substrate 3 (thin black dashed line). Both molecules then form a quasi-circle, preventing Dz4 from binding and cleaving its substrate (Substrate 4), drawn as a thick black line. Substrate 4 may be labelled with a fluorophore (unfilled circle) and a quencher (filled circle). Partzyme components for MNAzymes may be present, designed to cleave either Substrate 1 (Mz1, thick grey line), Substrate 2 (Mz2, thin black line), or Substrate 3 (Mz3, thin black dashed line). The MNAzymes assemble in the presence of their target assembly facilitators AF1 (thick grey dashed line), AF2 (thin black dashed line) and AF3 (thin black line) for Mz1, Mz2 and Mz3 respectively. This can result in the cleavage of Substrate 1 by Mz1, Substrate 2 by Mz2 and/or Substrate 3 by Mz3 causing the subsequent release of Dz4 from the cleaved BL, thus disrupting the quasi-circular structure. Dz4 is then able to bind and cleave Substrate 4 which may result in the separation of fluorophore and quencher and cause a detectable fluorescent signal.

In FIG. 20 panel iii) the DNAzyme (Dz3; thick black line) hybridises to a BL molecule, drawn as two thin black lines which are linked by the adjacent sequences of Substrates 1 and 2 which share common sequence, where Substrate 1 (Substrate 1; 5' half drawn as a thin grey line, 3' half drawn as a thin grey dashed line which also serves as the 5' half of Substrate 2) and the 3' half Substrate 2 (drawn as a thin black line). Ribonucleotide junctions (drawn as a thin black X) which serve as cleavage sites for catalytic initiator enzymes (eg the MNAzymes Mz1 and Mz2) within their substrates, Substrate 1 and Substrate 2 respectively, with the cleavage site for Substrate 1 located 5' of that for Substrate 2 within the BL. The BL is hybridizes to Dz3, forming a quasi-circle, thus preventing Dz3 cleaving its substrate (Substrate 3; thick black line). Substrate 3 may be labelled with a fluorophore (unfilled circle) and a quencher (filled circle). Partzyme components for MNAzymes may be present, designed to either bind and cleave the ribonucleotide junction between the Substrate 1 5' half and the shared common sequence (Substrate 1 3' half and the Substrate 2 5' half) (Mz1, drawn as thick grey line, except for the portion that binds to the shared common sequence which is drawn as a thin grey dashed line), or bind and cleave the ribonucleotide junction between the shared common sequence and the 3' half of Substrate 2 (Mz2, thin black line, except for the portion that binds to the shared common sequence which is drawn as a thin grey dashed line). Mz1 and Mz2 assemble in the presence of their target assembly facilitators AF1 (thick grey dashed line) and AF2 (thin black dashed line) respectively. Cleavage at either ribonucleotide junction can result in the release of Dz3 from the cleaved BL, disrupting the quasi-circular structure. Dz3 is then able to bind and cleave Substrate 3 which may result in the separation of fluorophore and quencher and cause a detectable fluorescent signal.

The skilled person will recognise that different catalytic nucleic acid enzyme/s (e.g. aptazyme/s) may be used instead of one or more of the depicted MNAzyme/s in FIG. 20 panel (i) or panel (iii).

Signal Detection and Amplification: BL with Internal Enzyme Substrates

In some embodiments, an autocatalytic cascade may be created whereby the substrate sequence that exists within a BL molecule may be cleaved by a catalytic nucleic acid that is designed to cleave the same substrate as the catalytic nucleic acid which has been temporarily inactivated by the BL. In other embodiments a cross-catalytic cascade may be created whereby two or more molecular switch complexes exist, each containing a catalytic nucleic acid molecule that can potentially cleave the substrate sequence of the opposing molecular switch and vice versa. In both embodiments the molecular switches may exist in an inactive state due to inhibition by BL molecules until cascade initiation by cleavage by an active catalytic nucleic acid. For example, the addition of an assembly facilitator (e.g. a target nucleic acid) may result in assembly of an active MNAzyme capable of cleaving one or more BL molecules to initiate a cascade reaction, wherein the BL contains a substrate sequence for the initiating MNAzyme. Alternatively, the presence of a ligand (e.g. a target ligand capable of binding to an aptamer portion of an aptazyme) could activate an aptazyme capable of cleaving one or more BL molecules to initiate a cascade reaction, wherein the BL could contain a substrate sequence for the initiating aptazyme. The initiating BL cleavage event may result in the continued activation of catalytic nucleic acid molecules and the subsequent amplification of signal. Alternatively, the presence of the ligand (e.g. target ligand capable of binding to an aptamer present within a BL) may bind to an aptamer and release the BL from the catalytic nucleic acid molecule. This separation may be used as an alternative method to initiate the cascade reaction whereby the liberated catalytic nucleic acid molecule may then cleave a second BL molecule hybridized to a second catalytic nucleic acid.

Referring now to FIG. 3 panels iii) and iv), the exemplary blocked DNAzyme strategy as outlined in FIG. 3 panel i) is used to create a cascade involving the continual release and activation of DNAzyme molecules, which may be used for the amplification of signal.

In FIG. 3 panel iii) an exemplary autocatalytic cascade strategy is illustrated where a first DNAzyme, shown as a thick black line is hybridized with a BL molecule (BL), drawn as two thin black lines linked by a substrate sequence (Substrate 1) which is drawn as a thick black dashed line. The Dz1 and BL are linked together via a non-complementary loop sequence (also a thick black line) to form a hairpin structure, rendering the Dz1 inactive (Inactive Dz1). Upon detection of a target molecule, an initiating MNAzyme (Mz1; thick grey lines) could form in the presence of its target assembly facilitator (AF1; thick grey dashed line), and cleave Substrate 1 causing the subsequent release of Dz1 from the hairpin molecule. The active Dz1 molecule may then bind and cleave Substrate 1 on additional Inactive Dz1/BL hairpined molecules, which could result in a cascade of BL cleavage and Dz1 activation events, which can be used for the amplification of signal. Alternatively, the presence of a ligand (e.g. a target ligand capable of binding to an aptamer portion of an aptazyme) could activate an aptazyme capable of cleaving one or more BL molecules to initiate a cascade reaction, wherein the BL could contain a substrate sequence cleavable by both the initiating aptazyme and active Dz1. Alternatively, the presence of the ligand (e.g. target ligand capable of binding to an aptamer present within a BL) may bind to an aptamer and release the BL from Dz1. This separation may be used as an alternative method to initiate the cascade reaction whereby the liberated Dz1 may then cleave Substrate 1 present within a BL of another complex.

In FIG. 3 panel iv) a cross-catalytic cascade strategy is illustrated where two DNAzymes, Inactive Dz1 and Inactive Dz2 (thick black and thin grey lines respectively), are both hybridized with a different BL molecule (BLB and BLA respectively), each drawn as two thin black lines and each linked by a different substrate sequence. Inactive Dz1 is linked with BLB and Substrate 2 (thin black dashed line) and Inactive Dz2 is linked with BLA and Substrate 1 (thick black dashed line). The two DNAzymes are linked to their respective BLs via a non-complementary loop sequence (also a thick black line) to form a hairpin structure, rendering the DNAzymes inactive. If an active MNAzyme (Mz1; thick grey lines) forms in the presence of its target assembly facilitator (AF1; thick grey dashed line) the MNAzyme may cleave Substrate 1, and cause the subsequent release of the Dz2 from the hairpin molecule. The now active Dz2 molecule may then bind and cleave Substrate 2, resulting in the release and activation of Dz1, which in turn could cleave Substrate 1 in BLA, thus triggering a cascade of BL cleavage and Dz1 and Dz2 activation events, which could be used for the amplification of signal. Alternatively, the presence of a ligand (e.g. a target ligand capable of binding to an aptamer portion of an aptazyme) could activate an aptazyme capable of cleaving BLA molecules to initiate a cascade reaction, wherein the BLA could contain a substrate 1 sequence cleavable by both the initiating aptazyme and the active Dz1. Alternatively, the presence of the ligand (e.g. target ligand capable of binding to an aptamer present within a BL) may bind to an aptamer and for example, release the BLA from Dz2. This separation may be used as an alternative method to initiate the cascade reaction whereby the liberated Dz2 may then cleave Substrate 2 present within BLB, thereby liberating Dz1.

Figure 16:
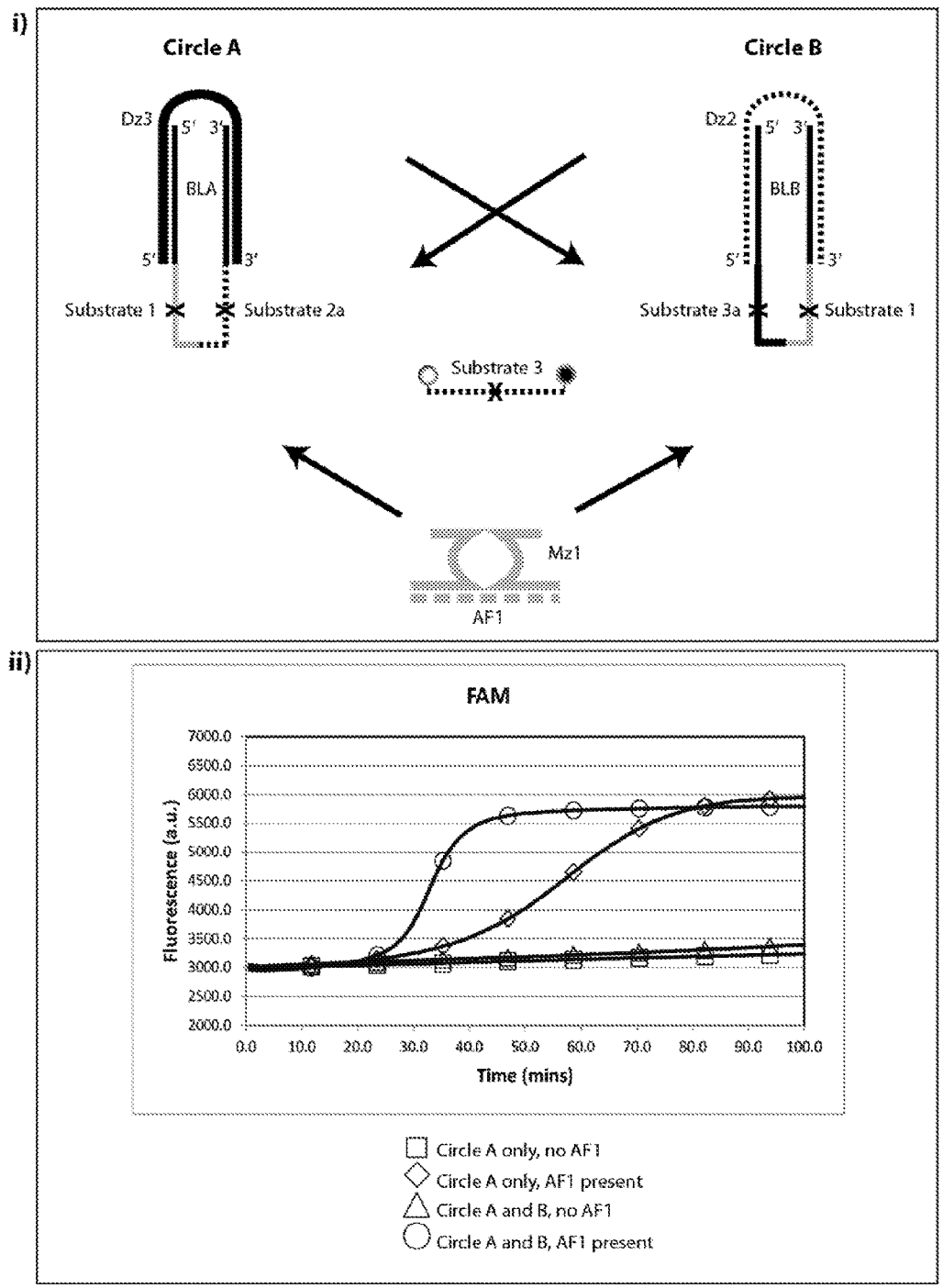
FIG. 16 Panel i) depicts a cross-catalytic cascade between two DNAzyme quasi circles, Circle A and Circle B. Circle A contains Dz3; a DNAzyme capable of cleaving Substrate 3a present within BLB of Circle B. Circle B contains Dz2; a DNAzyme capable of cleaving Substrate 2a present within BLA of Circle A. BLA and BLB also each contain Substrate 1 which can be cleaved by Mz1; an MNAzyme formed in the presence of a target assembly facilitator (AF1). Panel ii) provides a timecourse graph depicting fluorescent signal achieved from the cross-catalytic DNAzyme quasi-circle strategy outlined in panel i) comparing the fluorescent signal from the activation of Circle A only versus Circle A and B together, using a single concentration of MNAzyme assembly facilitator. Panel iii) provides a timecourse graph depicting fluorescent signal achieved from the cross-catalytic DNAzyme quasi-circle strategy outlined in panel i) with both Circle A and Circle B together and a titration of MNAzyme assembly facilitator concentration.
Figure 16:
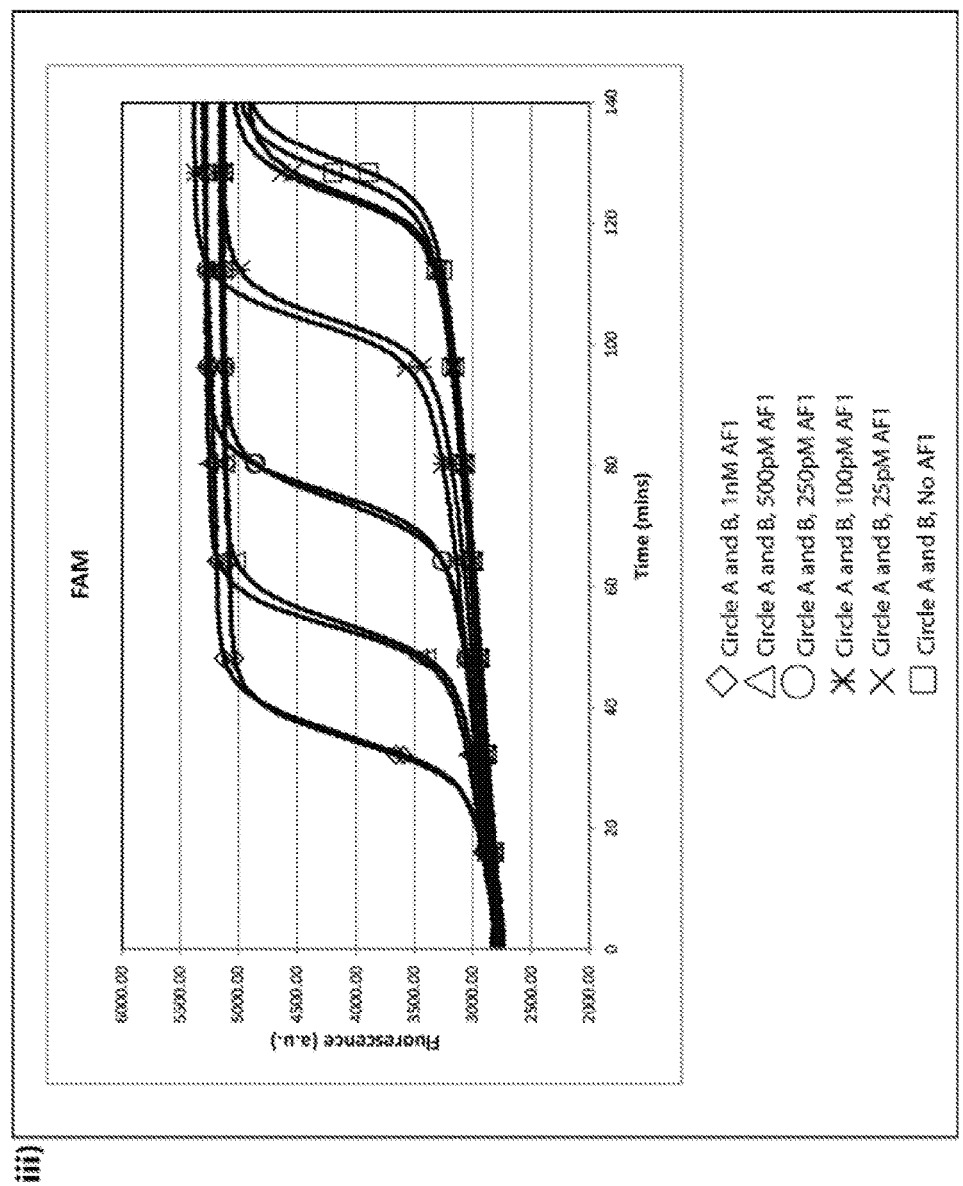

Referring now to FIG. 16, the exemplary DNAzyme quasi-circle strategy as outlined in FIG. 1 panel ii) is used to create a cascade involving the continual release and activation of DNAzyme molecules, which may be used for the amplification of signal. Two cross-catalytic circles are shown and the BLs for each circle contains two substrates. The first substrate can be cleaved by an MNAzyme in the presence of target assembly facilitator and the additional substrate can be cleaved by the DNAzyme of the opposing circle.

In FIG. 16 panel i) an exemplary cross-catalytic strategy between Circle A and Circle B is illustrated. The first substrate sequence (Substrate 1; thin grey line), which is present in both quasi circles A and B, is cleaved by an MNAzyme (Mz1; thick grey lines) only in the presence of a target assembly facilitator (AF1; thick dashed grey line). The two quasi circles each contain a second substrate sequence, Substrate 2 (Substrate 2a within Circle A; thin black dashed line) and Substrate 3 (Substrate 3a within Circle B; thick black line) which are capable of being cleaved by Dz2 from Circle B (thin black dashed line) and Dz3 from Circle A (thick black line) respectively. The two DNAzymes Dz3 and Dz2 are inactive when bound to BLA and BLB respectively. Cleavage of Substrate 1 on either circle A or B by Mz1 results in the release and subsequent re-activation of either Dz2 or Dz3 and triggers an exponential cascade of BL cleavage events between the two circles whereby Dz2 cleaves substrate 2 in Circle A and Dz3 cleaves substrate 3 in Circle B. Additional substrate sequences may also be included as reporter substrates, in this illustration, Substrate 3, which is labeled with a fluorophore (unfilled circle) and a quencher (filled circle). Alternatively, or additionally, a labeled Substrate 2 could be added. Cleavage of additional reporter substrate(s) results in the separation of fluorophore and quencher followed by a detectable fluorescent signal. Alternatively, the cross-catalytic cascade could be initiated by the presence of a ligand (e.g. a target ligand capable of binding to an aptamer portion of an aptazyme) which could activate an aptazyme capable of cleaving Substrate 1 within BLA and BLB to initiate a cascade reaction. Alternatively, the presence of the ligand (e.g. target ligand capable of binding to an aptamer present within a BL) may bind to an aptamer and for example, release the BLA from Dz3. This separation may be used as an alternative method to initiate the cascade reaction whereby the liberated Dz3 may then cleave Substrate 3 present within BLB, thereby liberating Dz2.

Figure 21:
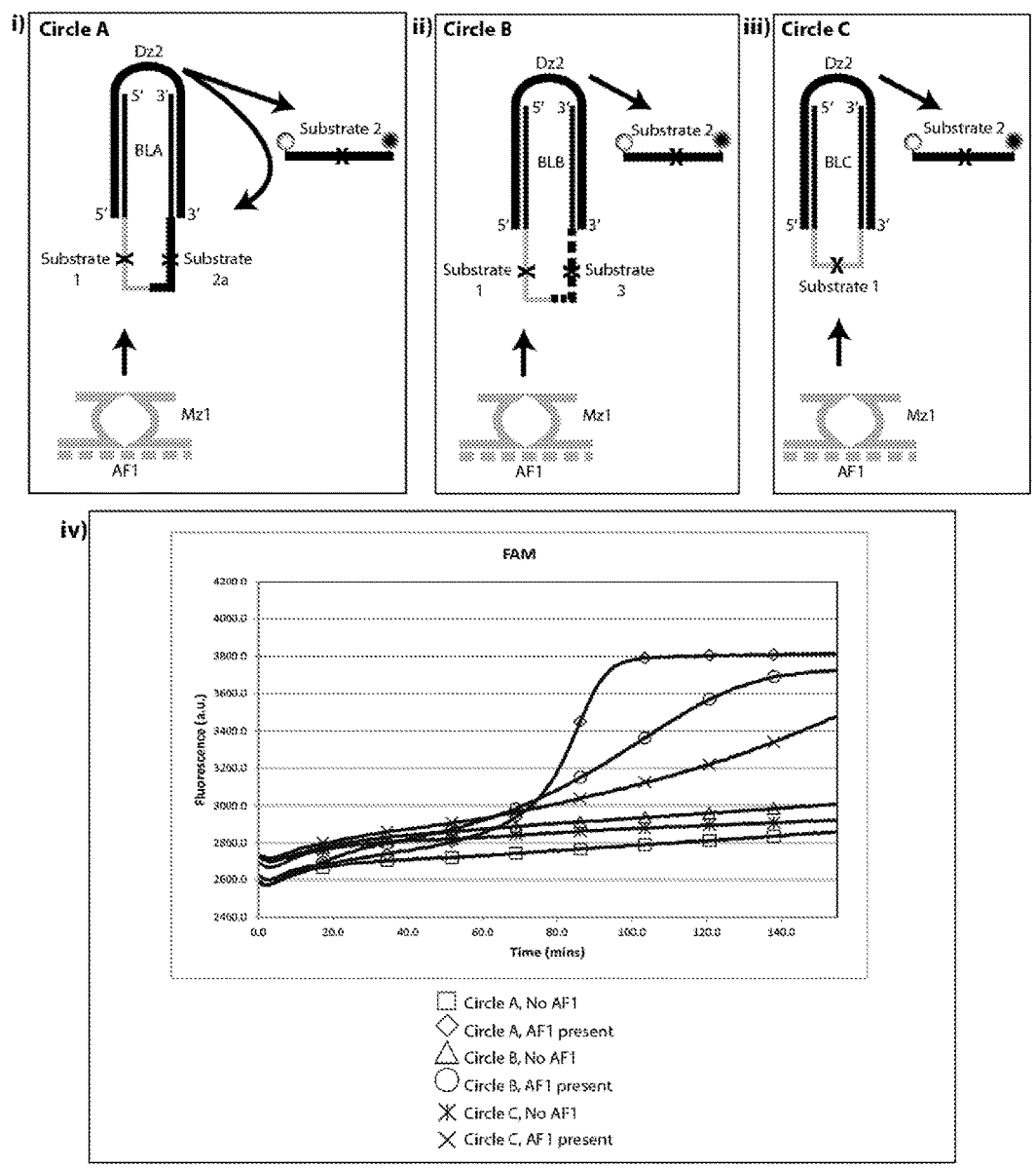
FIG. 21, panel i) demonstrates an auto-catalytic cascade reaction involving the quasi circle strategy originally outlined in FIG. 1 panel ii). The BLA of the quasi-circle comprises two adjacent substrate sequences; Substrate 1 and Substrate 2a. Substrate 1 may be cleaved by an MNAzyme (Mz1) in the presence of its target assembly facilitator (AF1), resulting in the release and activation of the DNAzyme (Dz2). Dz2 may then cleave Substrate 2. This may result in the release of additional Dz2 molecules if Substrate 2 is also present in the quasi-circle (Substrate 2a in panel i)) thus triggering an exponential cascade of BLA cleavage events. Dz2 may also cleave an independent fluorescently-labeled Substrate 2, leading to the generation and amplification of signal. In panels ii) and iii) quasi circles are depicted which do not have the potential to feedback in an auto-catalytic manner as the BLB and BLC molecules do not contain Substrate 2. Panel iv) demonstrates the fluorescent signal achieved from the strategies depicted in panels i)-iii).

Referring now to FIG. 21, the exemplary DNAzyme quasi-circle strategy as outlined in FIG. 1 panel ii) is used to create a cascade involving the continual release and activation of DNAzyme molecules, which may be used for the amplification of signal.

In FIG. 21 panel i) an auto-catalytic cascade is depicted whereby a quasi-circle (Circle A) consists of a DNAzyme (Dz2; thick black line) and a BL (BLA), drawn as two thin black lines which are linked by two substrate sequences; Substrate 1 (thin grey line) and Substrate 2 (Substrate 2a; thick black line). In addition, Substrate 2 can be provided as a separate independent molecule (also drawn as a thick black line) which can be labeled with a fluorophore (unfilled circle) and a quencher (filled circle). The quasi-circle formation that occurs due to the hybridization between Dz2 and BLA prevents Dz2 from binding and cleaving Substrate 2 present either within BLA or as a separate entity. When an MNAzyme, designed to cleave Substrate 1 (Mz1; thick grey line) assembles in the presence of its target assembly facilitator AF1 (thick grey dashed line) this can result in the cleavage of Substrate 1 by Mz1 and the subsequent release of Dz2 from the cleaved BLA, disrupting the quasi-circular structure. Dz2 is then able to bind and cleave the independent Substrate 2 molecule which may result in the separation of fluorophore and quencher and cause a detectable fluorescent signal. Dz2 may also bind and cleave Substrate 2 present within BLA, resulting in the release of additional Dz2 molecules and thus triggering an exponential cascade of BL cleavage events, leading to the amplification of signal. Alternatively, the presence of a ligand (e.g. a target ligand capable of binding to an aptamer portion of an aptazyme) could activate an aptazyme capable of cleaving substrate 1 within BLA to initiate a cascade reaction, wherein the BLA could contain a substrate sequence cleavable by both the initiating aptazyme and active Dz2. Alternatively, the presence of the ligand (e.g. target ligand capable of binding to an aptamer present within a BL) may bind, to an aptamer and for example, release the BLA from Dz2. This separation may be used as an alternative method to initiate the cascade reaction whereby the liberated Dz2 may then cleave Substrate 2 present within additional BLA molecules, thereby continually liberating Dz2.

In FIG. 21 panels ii) and iii) the quasi circles (Circle B and Circle C respectively) depicted do not have the potential to feedback in an auto-catalytic manner. For both quasi circles, Substrate 2 is no longer present within the BL. For Circle B, the BL (BLB) consists of Substrate 1 and Substrate 3 (thick black dashed line). For Circle C, the BL (BLC) consists only of Substrate 1.

The skilled person will recognise that the cascades described above utilise DNAzymes for the purpose of exemplification only, and that other catalytic nucleic acid enzymes (e.g. ribozymes), or catalytic nucleic acid enzyme components (eg partzymes), may be incorporated/substituted for the DNAzymes in the molecular switch structures where hybrisation of BL could inhibit catalytic activity.

Target Detection: Releaser Oligonucleotides

A BL oligonucleotide may exist as a separate molecule which may be hybridized to a complementary third oligonucleotide in a molecular switch complex or alternatively may exist as a BL portion of a molecular switch where the BL portion may be linked to the third complementary oligonucleotide via linker sequence to form a hairpin structure.

In this manner, a first RL oligonucleotide may hybridize with the BL oligonucleotide of a molecular switch and result in the displacement of a third complementary oligonucleotide. The third complementary oligonucleotide may be inactive when hybridized to the BL but once displaced from the BL, this third oligonucleotide may be able to function as a catalytic nucleic acid enzyme, a primer, a polymerase template, NRF or another RL. In embodiments where the third oligonucleotide comprises a catalytic nucleic acid, the BL is not designed to hybridize with the entire catalytic nucleic acid sequence in a molecular switch so that the RL will not contain the entire sequence required for catalytic activity and thus the RL molecules cannot function as nucleic acid enzymes themselves. In other embodiments, a single RL molecule can function to displace more than one catalytic nucleic acid from more than one BL, resulting in the simultaneous re-instatement of catalytic activity for multiple catalytic nucleic acid molecules which had previously been present in an inactive state.

Figure 4:
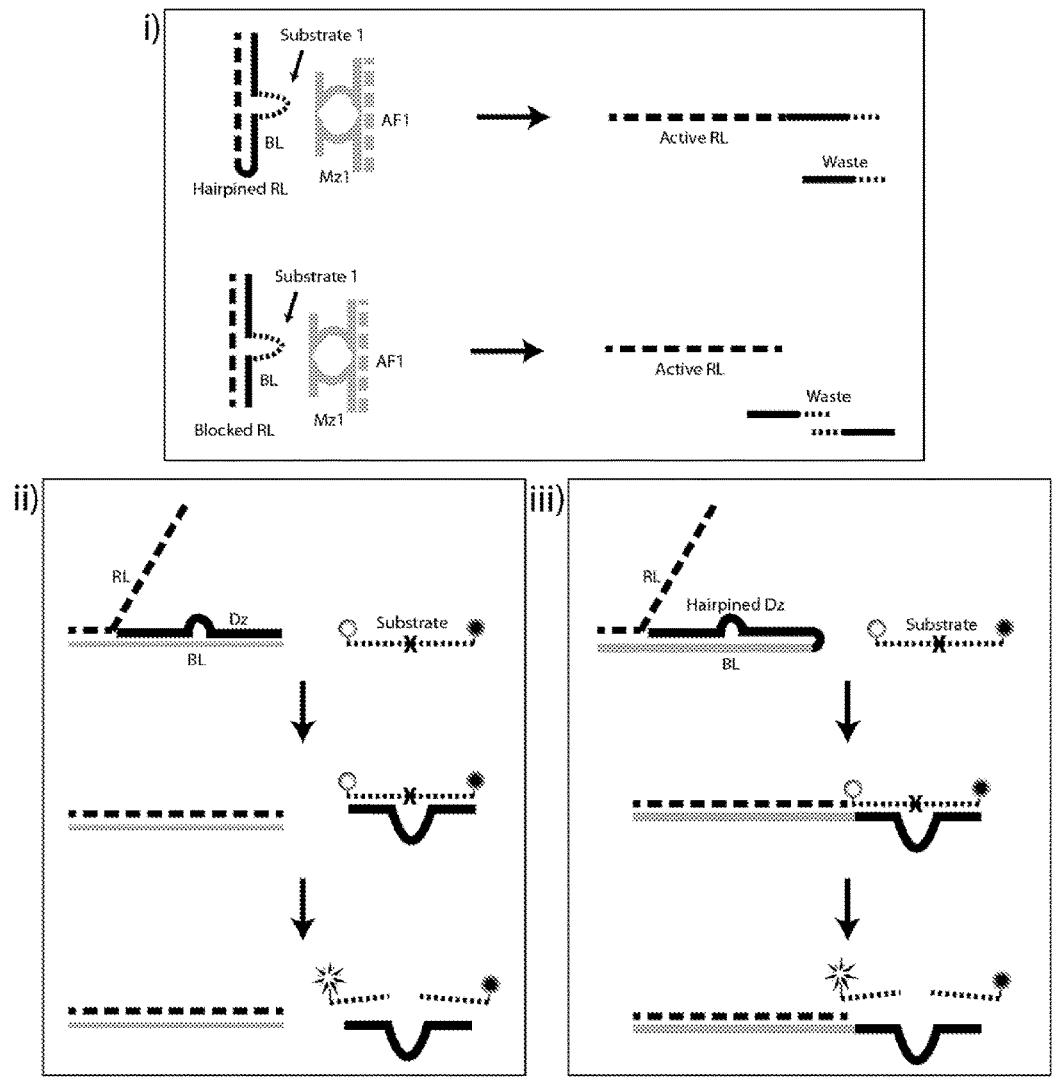
FIG. 4 illustrates methods of generating Releaser Oligonucleotide (RL) molecules (panel (i)) and the use of RL for activating DNAzyme molecules, which are initially inactive via hybridisation to a BL molecule (ii, iii and iv). In the non-limiting examples illustrated, the BL molecule does not contain a substrate sequence for cleavage by a separate DNAzyme or MNAzyme. Instead the DNAzyme is separated from the BL by the RL which binds to the BL at a single-stranded protrusion known as a 'toehold' and proceeds to hybridize with the remainder of the BL thus replacing the pre-bound DNAzyme. This results in a free DNAzyme which is now separated from the BL and which has re-instated catalytic activity. Methods of RL activation are depicted in panel i), which include the RL initially inactive in a hairpined complex or hybridised to a separate BL. Cleavage of the substrate present within the BL by an MNAzyme in the presence of its target results in the generation of an active RL molecule. The ability of an RL to activate DNAzymes is illustrated in three non-limiting examples (panels ii)-iv)). In a first strategy the DNAzyme and BL are two separate oligonucleotides and the action of the RL results in complete separation of the two oligonucleotides (panel ii)). In a second strategy the DNAzyme and BL molecules are linked such that they exist as a single oligonucleotide in a hairpined DNA structure and the action of the RL can result in the opening of the hairpin (panel iii)). In a third strategy, a complex linking two of the hairpined DNA structures together can be opened by the action of a single RL molecule (panel iv)).
Figure 4:
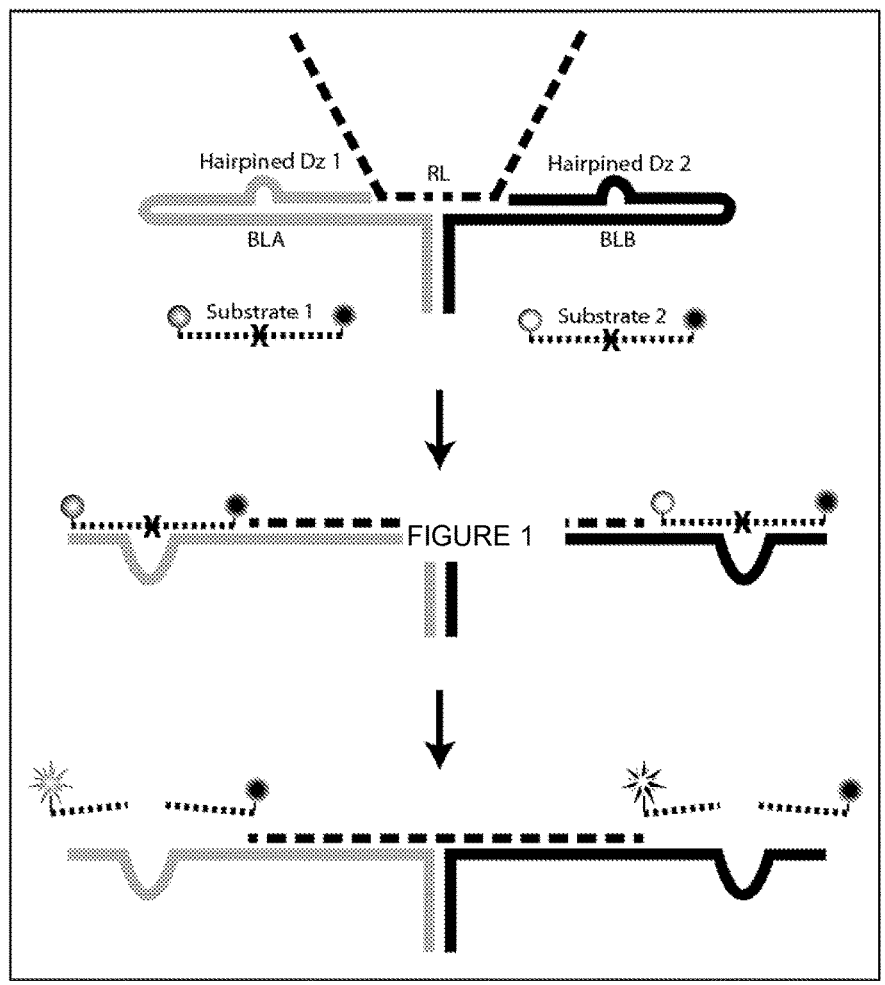

An RL may be provided by the catalytic activity of an initiator enzyme (e.g. an MNAzyme, DNAzyme, ribozyme or aptazyme) in a target-dependent manner, whereby a substrate for the initiator enzyme is modified to produce the RL only when a target molecule is present that induces catalytic activity of the initiator enzyme. By way of non-limiting example, generation of the RL in a target-dependent manner could be achieved as illustrated in FIG. 4 panel i). This mechanism could be used to initiate the downstream reactions illustrated in FIG. 4 panels ii), iii) and iv), in FIG. 6 panel i), FIG. 7 panel i), and FIG. 8 panel i).

Referring specifically to the embodiment described in FIG. 4 panel i), an RL (thick black dashed line) could be initially hybridised to a BL (solid black line) rendering the RL inactive. The RL may be linked to the BL via a non-complementary hairpin loop, drawn as a solid black line ('Hairpined RL') or remain as a separate entity ('Blocked RL'), which are shown at the top left and bottom left sections of the panel respectively. The BL portions may contain a substrate sequence, Substrate 1 (thin black dashed line) which may be cleaved by a catalytic nucleic acid enzyme, shown here as an MNAzyme (Mz1) which could assemble in the presence of a target assembly facilitator (AF1) drawn as solid grey and thick grey dashed lines respectively. Cleavage of the BL by the MNAzyme may result in the generation of an active RL (Active RL). Alternatively, the presence of a ligand (e.g. a target ligand capable of binding to an aptamer portion of an aptazyme) could activate an aptazyme capable of cleaving substrate 1 within the BL which could activate the RL. Active RL molecules which are no longer hybrided to BL due to cleavage of Substrate 1 by an MNAzyme or aptazyme could provide a mechanism to initiate the downstream reactions illustrated in FIG. 4 panels i), ii) and iii).

The embodiments described in FIG. 4 panels ii) to iv) depict DNAzymes hybridized to BL molecules, which are then separated from the BL molecules via the hybridization of an RL to the BL. One skilled in the art will appreciate that partzymes may also be hybridized to BL molecules and released in the same manner.

In the embodiment described in FIG. 4 panel ii), a DNAzyme (Dz; thick black line) is hybridised with a BL molecule (BL; thin grey line) to form a duplex. A small portion of the Dz sequence does not hybridise with the BL and is shown as a loop structure in the centre of the duplex. A substrate sequence (Substrate; thin black dashed line) is labelled with a fluorophore (unfilled circle) and a quencher (filled circle) and is designed to be cleaved by the Dz, however, due to the initial binding of the BL, the Dz cannot cleave its substrate. When an active RL (thick black dashed line) is present it can bind to the BL and displace the Dz from the BL molecule. The RL cannot function as a catalytic molecule as it lacks some essential sequence in the region where there is incomplete hybridization between the Dz and BL. The RL and BL can then form an inert duplex, whilst the Dz is then able to bind and cleave the substrate which results in the separation of the fluorophore and quencher and the generation of a detectable fluorescent signal.

In the embodiment shown in FIG. 4 panel iii), a hairpined DNAzyme (Hairpined Dz) exists which contains the DNAzyme portion (thick black line) and BL portion (thick grey line) in a single oligonucleotide which has been linked by a short non-complementary sequence acting as the hairpin loop (thick black line). In addition, a small portion of the Dz sequence does not hybridize to the remainder of the hairpin (BL sequence) and is shown as a loop structure in the center of the duplex. A substrate sequence (Substrate; thin black dashed line) is labelled with a fluorophore (unfilled circle) and a quencher (filled circle) and is designed to be cleaved by the Dz, however, as the Dz sequence is constrained within the hairpin structure, initially the Dz cannot cleave its substrate. When an active RL molecule (RL; thick black dashed line), is present, it can bind to the hairpin Dz toehold (strand containing the BL sequence) and can hybridize to the BL portion of the hairpin Dz molecule. The RL cannot function as a catalytic molecule as it lacks some sequence essential for catalytic activity (it lacks those bases which are present in the Dz but are looped out due to incomplete hybridization between the Dz and the BL region of the hairpin). The BL portion of the hairpin and the RL can then form an inert duplex, which frees the Dz portion. The Dz portion is then able to bind and cleave the substrate which results in the separation of the fluorophore and quencher and the generation of a detectable fluorescent signal.

FIG. 4 panel iv) outlines an exemplary strategy involving the linking of two hairpined DNAzymes (as described in FIG. 4 panel iii)) termed Hairpined Dz1, consisting of the DNAzyme portion and BLA portion (both drawn as a solid grey line) & Hairpined Dz2, consisting of the DNAzyme portion and BLB portion (both drawn as a solid black line) where both hairpin molecules are each extended to contain an additional stem sequences, which are complementary to the other, and thus link them together. Initially, Hairpined Dz1 and Hairpined Dz2 are unable to cleave their respective substrates, Substrate 1 and Substrate 2, both of which are drawn as thin black dashed lines. Both Substrate 1 and Substrate 2 are labelled with a different fluorophore (grey filled circle for Substrate 1 and white unfilled circle for Substrate 2) and both are also labelled with quenchers drawn as black filled circles. When a active RL is present, it can bind to the toehold sequences for each hairpined Dz (that have been brought close together due to the complementary stem region) and open both hairpined Dz's simultaneously. As a result, both Dz portions of the hairpined Dz molecules are able to bind and cleave their respective substrates, resulting in the separation of the fluorophore and quencher thus generating a detectable fluorescent signal for each of the two different fluorophores.

Signal Detection and Amplification: Releaser Oligonucleotides

RL generated by an initiator enzyme upon detection of a target may dissociate a BL from a hybridised catalytic nucleic acid enzyme (i.e. activate a molecular switch), thereby allowing the enzyme to catalytically modify a reporter substrate and generate a detectable signal. In doing so, the RL hybridises to the BL and is thereby rendered inactive.

Signal amplification cascades utilising RL are provided herein. In general, these cascades involve the use of components capable of dissociating BL from RL, thereby allowing the RL to dissociate more BL hybridised to catalytic nucleic acid enzymes. In this manner, a signal arising from a single target detection event may be amplified many times over by successive rounds of RL-mediated dissociation of BL/nucleic acid enzyme complexes.

In some embodiments, exonucleases, for example ExoIII can be used for signal amplification whereby a RL molecule is recycled by the activity of the ExoIII, leading to the continual release and subsequent activation of multiple catalytic nucleic acid molecules. In this instance, the RL-mediated activation of catalytic nucleic acid molecules is followed by the selective degradation of the BL in a molecular switch by ExoIII. The RL molecule therefore remains intact and is then able to hybridize with another BL. The activation cycle is then repeated, with a new catalytic nucleic acid molecule released each time during the process, leading to amplification of signal.

Figure 6:
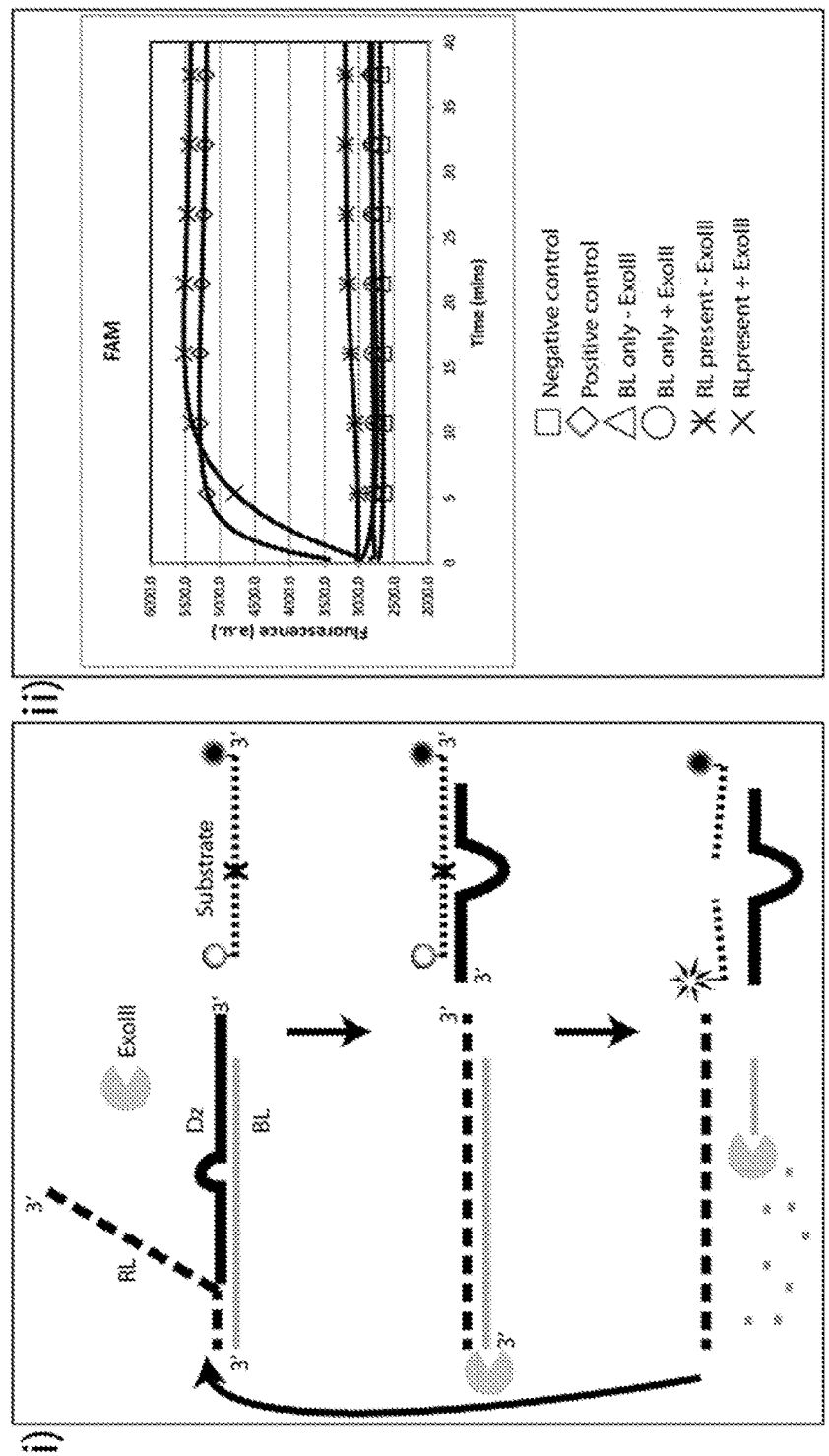
FIG. 6 panel i) demonstrates the RL-mediated displacement of a DNAzyme from a BL molecule (as described in FIG. 4) which further involves the use of a protein enzyme known as Exonuclease III (ExoIII). ExoIII catalyzes the step-wise removal of mononucleotides from the 3' end of blunt or recessed duplexed DNA and is used here to degrade the BL when it is hybridized to the RL. This promotes the 'recycling' of the RL molecule so that it can function to continually displace and activate several DNAzymes. Panel ii) demonstrates the fluorescent signal achieved from the ExoIII strategy depicted in panel i).

FIG. 6 provides one exemplary strategy of a signal detection and amplification cascade evoking the recycling of RL molecules. FIG. 6 panel i) depicts a strategy whereby the DNAzyme (Dz; thick black line) hybridizes to a BL molecule (BL; thin grey line). The 3' ends of each molecule are protruding from the duplex by at least 4 nucleotides so as to render the Dz/BL duplex resistant to ExoIII-mediated degradation. A substrate sequence (Substrate; a thin black dashed line) is labeled with a fluorophore (unfilled circle) and a quencher (filled circle) and is designed to be cleaved by the Dz, however while hybridized to the BL, the Dz is inactive and cannot cleave its substrate. An RL may be provided by the catalytic activity of an initiator enzyme (e.g. an MNAzyme, DNAzyme, ribozyme, or aptazyme) in a target-dependent manner, whereby a substrate for the initiator enzyme is modified to produce the RL only when a target molecule is present that induces catalytic activity of the initiator enzyme. By way of non-limiting example, generation of the RL in a target specific manner could be achieved as illustrated in FIG. 4 panel i).

When an active RL is present (RL; thick black dashed line) it can bind to the BL and displaces the Dz from the BL molecule (FIG. 6 panel i). The RL and BL can then form a duplex, whereby the 3' end of the RL is protruding from the duplex but the 3' end of the BL is now blunt as depicted (or alternatively recessed with respect to the 5' end of the RL). ExoIII (drawn as a grey segmented circle) is then able to digest the BL molecule from its 3' terminus whilst leaving the RL molecule intact. The RL is then recycled and able to repeat the process. Each Dz, once displaced, is then able to bind to its substrate (with the 3' ends of each protruding, rendering them resistant to ExoIII) and can cleave the substrate which results in the separation of the fluorophore and quencher and the generation of a detectable fluorescent signal. As this can occur multiple times, there is then an amplification of signal generated by a circular cascade reaction.

In other embodiments, a restriction enzyme (e.g. nicking enzyme) may be utilized for signal amplification whereby a RL molecule is recycled by the activity of the restriction enzyme, leading to the continual release and subsequent activation of DNAzymes. During the RL-mediated displacement of a catalytic nucleic acid molecule from a BL molecule, a new recognition site is then created within the duplex between the RL and BL molecules. A restriction enzyme is then able to recognize this site and selectively cleave the BL whilst the RL molecule remains intact. Cleavage of the RL may be avoided by generating a recognition site for (and using) a nicking restriction enzyme that will cleave only the BL strand of the recognition site and not the RL strand. Alternatively, a restriction enzyme capable of cleaving both strands may be used, in which case the RL strand of the recognition site may comprise a phosphorothioate linkage preventing cleavage of the RL strand by the restriction enzyme. Each shorter 'nicked' fragment of the BL now no longer has the same affinity to the RL as the intact BL did, and as a result will no longer form a stable duplex DNA structure with the RL. The RL is then able to bind to another BL and the cycle is repeated, with a catalytic nucleic acid activated each time during the process.

Figure 7:
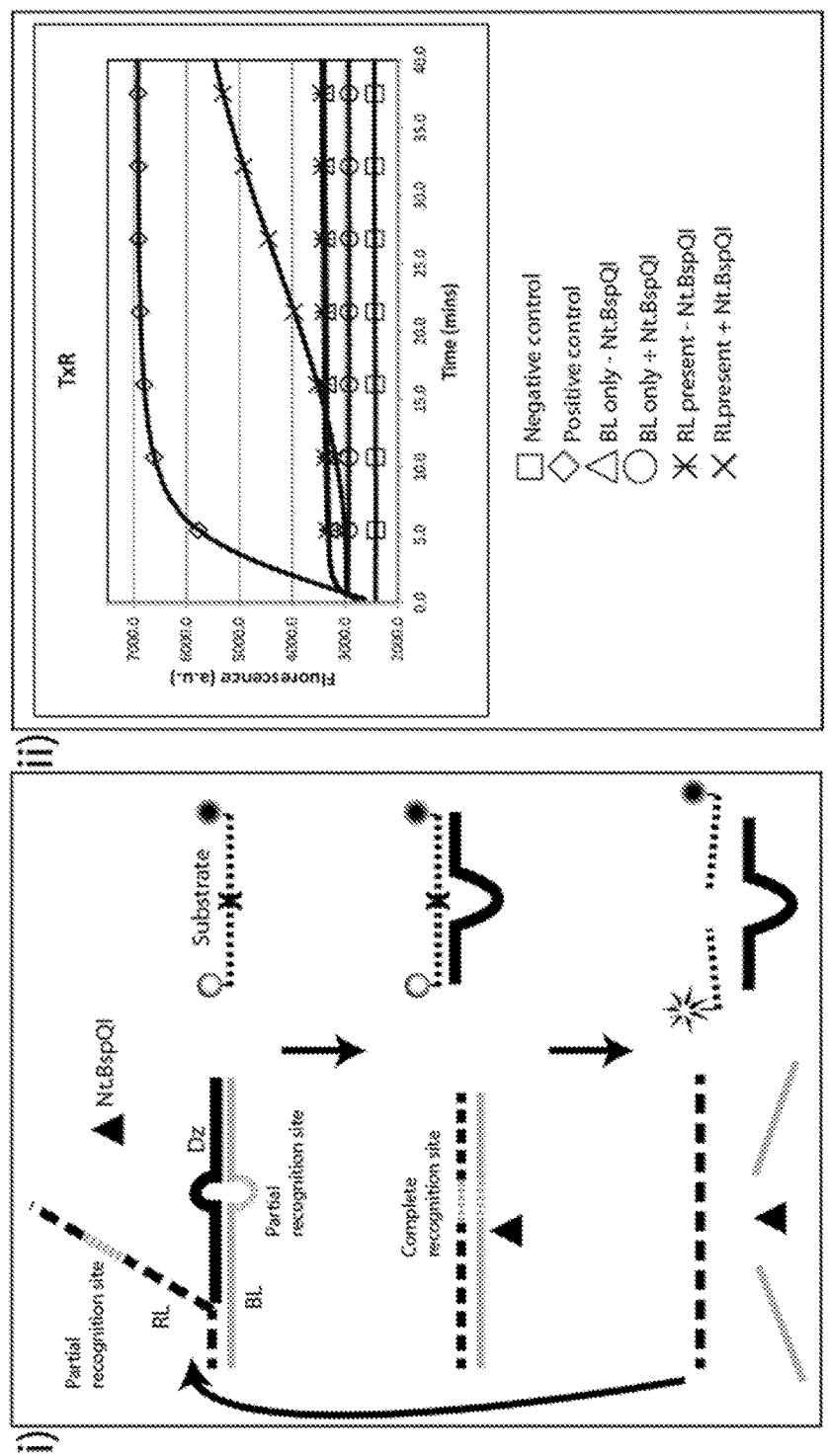
FIG. 7 panel i) demonstrates the RL-mediated displacement of a DNAzyme away from a BL molecule (as described in FIG. 4) but involves the use of a restriction enzyme that selectively cleaves only one strand of a DNA duplex, known as a 'Nicking enzyme'. Nicking enzymes are used here to selectively cleave the BL strand when it is duplexed with the region of RL containing one strand of the double stranded recognition sequence. This promotes the 'recycling' of the RL molecule as it is no longer thermodynamically favorable for it to re-hybridize with the BL. The RL can then function to continually displace and activate additional DNAzymes. Panel ii) demonstrates the fluorescent signal achieved from the Nicking enzyme strategy depicted in panel i).

Turning to FIG. 7, panel i), an exemplary strategy is depicted whereby the DNAzyme (Dz; thick black line) hybridizes to a BL (BL; thin grey line). The BL contains some additional sequence that is non-complementary to the DNAzyme and that forms one strand of a double stranded recognition sequence for a Nicking enzyme (drawn as a thin grey dashed line) which loops out from the Dz/BL duplex. The Nicking enzyme, e.g. Nt.BspQI (drawn as a black filled triangle) is also present, but cannot cleave the BL as its complete double-stranded recognition sequence does not exist within the Dz and BL duplex. A substrate sequence (Substrate; thin black dashed line) is labeled with a fluorophore (unfilled circle) and a quencher (filled circle) and is designed to be cleaved by the Dz, however due to the hybridization with the BL, the Dz cannot cleave its substrate. An RL may be provided by the catalytic activity of an initiator enzyme (e.g. an MNAzyme, DNAzyme, ribozyme, or aptazyme) in a target-dependent manner, whereby a substrate for the initiator enzyme is modified to produce the RL only when a target molecule is present that induces catalytic activity of the initiator enzyme. By way of non-limiting example, generation of the RL in a target specific manner could be achieved as illustrated in FIG. 4 panel i). When an active RL molecule (RL; thick black dashed line) containing the other strand of the double stranded Nicking enzyme recognition sequence (itself drawn as a grey dashed line in the middle of the RL molecule) is present, it binds to the BL and displaces the Dz from the BL molecule as depicted in FIG. 7 panel i). The RL and BL then form a duplex which now contains the complete Nicking enzyme recognition sequence. Consequently, the Nicking enzyme can now cleave the BL whilst leaving the RL molecule intact. The RL is then recycled and able to repeat the process. Each Dz, once displaced, is then able to bind and cleave the substrate which results in the separation of the fluorophore and quencher and generation of a detectable fluorescent signal. As this can occur multiple times, there is thus an amplification of signal. The skilled person will recognise that although the exemplary strategies above use a nicking enzyme, the processes could be modified to accommodate the use of a restriction enzyme capable of cleaving both strands of the recognition site formed by hybridisation of the RL and BL. In such cases, cleavage of the RL may be avoided by modifying the RL strand of the recognition site to incorporate a phosphorothioate linkage, thus preventing cleavage of the RL strand by the restriction enzyme.

In other embodiments, a strand-displacing polymerase may be used for signal amplification. When provided in combination with a suitable primer oligonucleotide, strand displacing polymerases which have the ability to synthesize new strands of nucleic acids by extension of primer sequences can be used for the purpose of displacing downstream strands of nucleic acid thus rendering the displaced strand single stranded. This can be used as a mechanism for activation of the function of molecules which are non-functional when double stranded but which regain functionality when single stranded. The process of primer/polymerase mediated strand displacement can be used to promote the activation of catalytic nucleic acid molecules that have been previously rendered inactive when bound to BL molecules. In one embodiment, the primer can hybridize with the BL molecule following the displacement of the catalytic nucleic acid by the RL molecule and can be extended at its 3' end by a strand displacing polymerase enzyme. This results in the displacement of the RL from the BL and a waste complex is then formed between the BL and the extended primer. The RL is then recycled and can function to displace additional catalytic nucleic acids from BL molecules, resulting in the amplification of signal.

Figure 8:
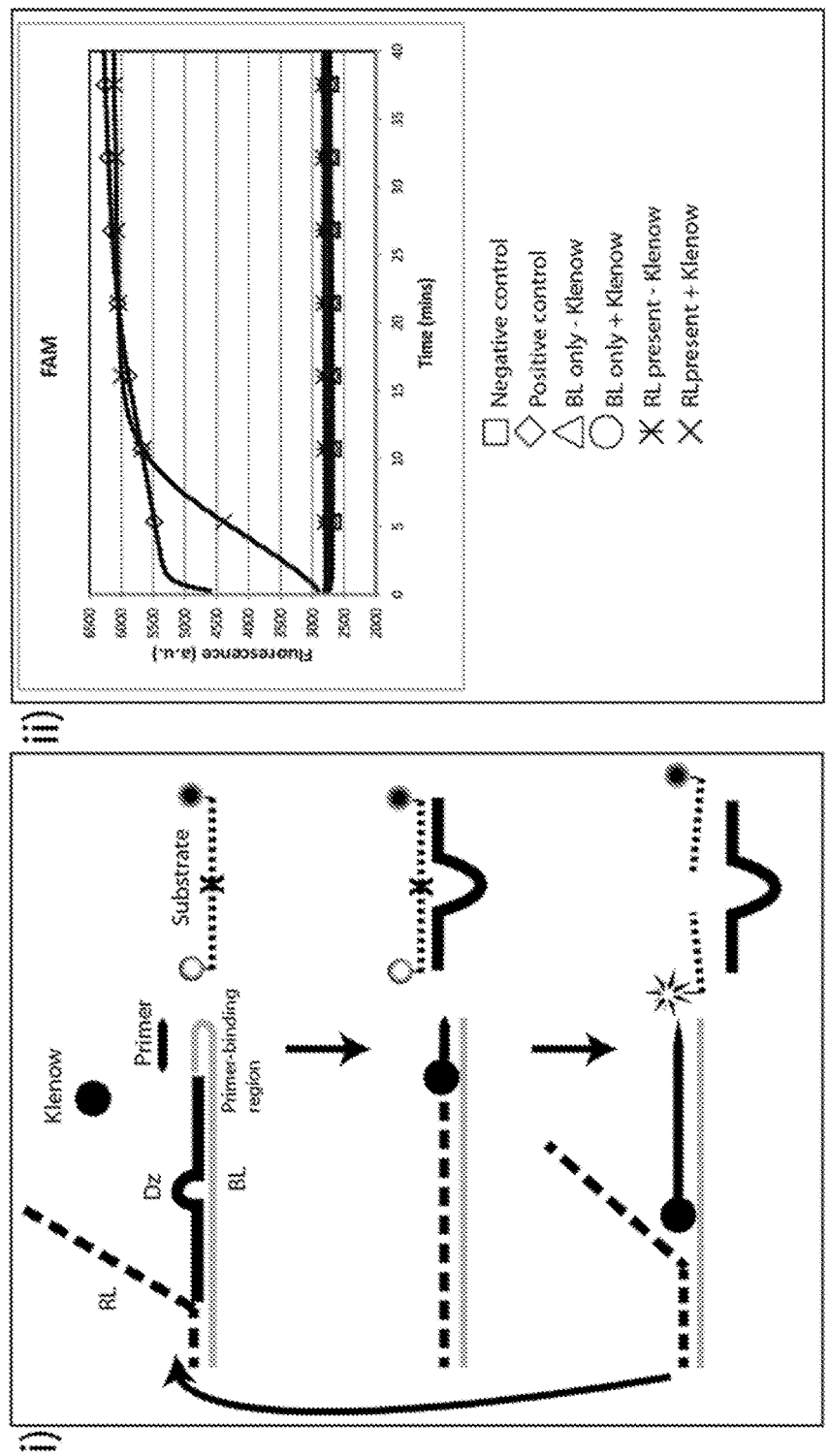
FIG. 8 panel i) demonstrates the RL-mediated displacement of a DNAzyme away from a BL molecule (as described in FIG. 4) but further involves the use of a DNA polymerase enzyme that has the ability to displace DNA strands that are pre-bound to the template strand during polymer synthesis. A strand-displacing polymerase is therefore used to displace the RL from an RL/BL duplex and synthesize a strand complementary to the BL which prevents the re-hybridization of the DNAzyme or the RL to the BL. This promotes the 'recycling' of the RL molecules so that they can function to continually displace and activate additional DNAzymes. Panel ii) demonstrates the fluorescent signal achieved from the strand-displacing polymerase strategy depicted in panel i).

Referring to FIG. 8, panel i) an exemplary strategy is depicted whereby the DNAzyme (Dz; thick black line) hybridizes to a BL molecule (BL; thin grey line). The BL contains some additional sequence at one of its ends that forms a small hairpin, but the DNAzyme and the BL are separate oligonucleotides. The stem of this small hairpin contains a primer-binding region, however the primer (drawn as a short black line with pointed ends) cannot bind to this region as the region is blocked within the hairpin stem. When a strand-displacing polymerase such as Klenow fragment (3'-5' exo') is used (drawn as a filled black circle) it also cannot extend the primer initially as the primer cannot bind to its binding site. Of all the oligonucleotides in the region mix, only the primer has the potential to be extended by the polymerase as the remaining oligonucleotides have been 3' phosphorylated to block their extension by polymerase. A substrate sequence (Substrate; thin black dashed line) is labeled with a fluorophore (unfilled circle) and a quencher (filled circle) and is designed to be cleaved by the Dz, however due to hybridization to the BL, the Dz cannot cleave its substrate. An RL may be provided by the catalytic activity of an initiator enzyme (e.g. an MNAzyme, DNAzyme, ribozyme, or aptazyme) in a target-dependent manner, whereby a substrate for the initiator enzyme is modified to produce the RL only when a target molecule is present that induces catalytic activity of the initiator enzyme. By way of non-limiting example, generation of the RL in a target specific manner could be achieved as illustrated in FIG. 4 panel i). Referring to FIG. 8 panel i), when the active, single stranded RL molecule (RL; thick black dashed line) is present, it binds to the BL and displaces the Dz from the BL molecule and also facilitates the opening of the hairpin at the end of the BL, thus exposing the primer-binding site. Consequently, the primer binds at the end of the BL and is extended by the strand displacing polymerase, displacing the RL in the process. The extended primer and BL then form an inert duplex whilst the RL is then recycled and able to repeat the process. Each Dz, once displaced, is then able to bind and cleave the substrate which results in the separation of the fluorophore and quencher and a detectable fluorescent signal will follow. As this can occur multiple times, there is then an amplification of signal.

Signal Detection and Amplification: Blocked RL

Figure 9:
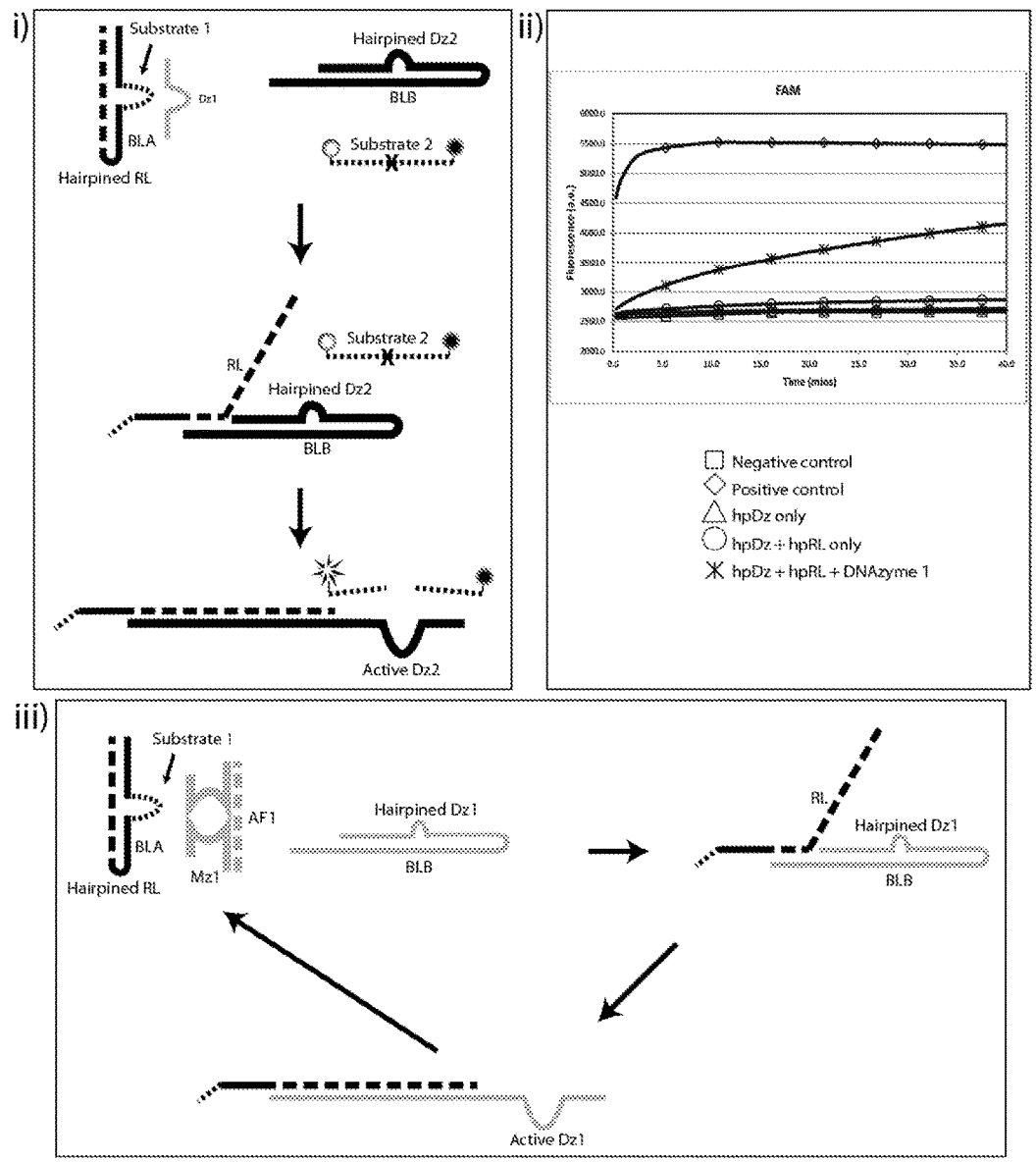
FIG. 9 panel i) demonstrates the pre-hybridization of an RL to a BL molecule (BLA) in order to initially inactivate the RL. This BL may contain a substrate for a catalytic nucleic acid (e.g. a DNAzyme (Dz1) as illustrated or, an MNAzyme, so that the reaction is target dependent), such that cleavage of this substrate results in the activation of the RL molecule so that it can then function to activate another functional molecule, such as a second DNAzyme (Dz2) by separating the second DNAzyme it from its own BL (BLB) (as initially described in FIG. 4). Panel ii) demonstrates a fluorescent signal achieved from the strategy outlined in panel i). This strategy may also be used to create a circular cascade (panel iii)) whereby the catalytic nucleic acid that is activated by the RL could then function to cleave the substrate present within the BLA molecule from the RL/BL molecular switch, which may result in the continuous activation of both RL molecules and catalytic nucleic acids and thus be used for the amplification of signal.

In some embodiments, RL molecules may themselves be initially inactivated by hybridization to another BL molecule. The BL may exist as a separate oligonucleotide or may exist within the same oligonucleotide as the RL, where they may be joined by a linking nucleic acid or non-nucleic acid spacer sequence which may form the loop of a hairpin structure. The hybridisation between the BL and the RL may result in the reversible inactivation of the RL and in this state is referred to here as a "molecular switch". The BL molecule may contain a substrate sequence for a catalytic nucleic acid. This may exist as part of or in addition to the hairpin loop sequence when both the RL and BL are linked together. In such embodiments, cleavage of the substrate sequence may release the RL from the BL which may result in the re-instatement of the RL's ability to "release" other oligonucleotides (e.g. by strand displacement activity). In such embodiments, a feedback cascade may be created whereby one or more inactive RL molecules co-exist with one or more inactive catalytic nucleic acid molecules, where both the RL and the catalytic nucleic acid have been inactivated via hybridization to their respective BL molecules (FIG. 9, panel iii). The addition of an active catalytic nucleic acid molecule, or the final component to complete an active catalytic nucleic acid molecule such as an assembly facilitator for an MNAzyme, may result in cleavage of one or more BL molecules that results in the activation of either RL functionality and/or catalytic nucleic acid catalysis. This may initiate a cascade of BL cleavage and RL-mediated displacement events between the two different molecular switches resulting in the continued activation of RL and catalytic nucleic acid molecules and the subsequent amplification of signal.

For example, FIG. 9 panel i) depicts a strategy whereby the Releaser (RL; dashed thick black line) is pre-hybridized to a BL molecule (BLA, drawn as a thick black line), and the two are linked together by a non-complementary sequence forming the loop of a hairpined structure (the whole complex is termed a Hairpined RL). BLA contains a substrate sequence, Substrate 1, drawn as a thin black dashed line, that can be cleaved by an initiator catalytic nucleic acid enzyme in a target-dependent manner. In addition, a hairpined DNAzyme (Hairpined Dz2, thick solid black line) is present and contains both the DNAzyme, and a corresponding BL sequence (BLB) in a single oligonucleotide which has been linked by a short non-complementary sequence acting as the hairpin loop. As initially described in FIG. 4 panel iii), a small portion of the Dz sequence does not hybridize to the remainder of the hairpin (BLB sequence) and is shown as a loop structure in the centre of the duplex. Referring to FIG. 9 panel i) a substrate sequence (Substrate 2; thin black dashed line) is labeled with a fluorophore (unfilled circle) and a quencher (filled circle) and is designed to be cleaved by Dz2, however, while the Dz2 sequence is constrained within the hairpin structure, it initially cannot cleave its substrate. When the BLA-portion of the Hairpined RL complex is cleaved by a catalytic nucleic acid (illustrated as Dz1 (thick solid grey line), but a different catalytic nucleic acid enzyme such as an MNAzyme or an aptazyme could also be used), the BLA dissociates from the RL. The RL is then active and free to hybridize to the BLB portion of the hairpined Dz2 where it functions to open the hairpin Dz2 molecule. The RL cannot function as a catalytic molecule itself as it lacks some essential sequence for catalytic activity (it lacks those bases which are present in the Dz2 but are looped out due to incomplete hybridization between the Dz2 and the BLB region of the hairpin). The BLB portion of the Hairpined Dz2 complex and the RL then form an inert duplex, which frees the Dz2 portion. The Dz2 portion is then able to bind and cleave Substrate 2 which results in the separation of the fluorophore and quencher and the generation of a detectable fluorescent signal.

FIG. 9 panel iii) outlines an exemplary circular cascade reaction which may occur when the substrate sequence present within the BLA region of the Hairpined RL, is designed to be cleaved by the catalytic nucleic acid which is subsequently activated by the RL. The Hairpined RL, includes the RL portion (thick dashed black line) and BL portion (BLA, thick black line) and these can be linked together by a non-complementary sequence forming the loop of the hairpined structure (thick black line). The BLA portion contains a substrate sequence (Substrate 1; thin black dashed line) that could be cleaved by an MNAzyme (illustrated as Mz1 (thick solid grey line), but a different catalytic nucleic acid enzyme such as an aptazyme or DNAzyme could also be used) assembled in the presence of a target assembly facilitator (AF1 thick grey dashed line). In addition, DNAzyme 1 (Dz1) may also exist in an inactive state due to hybridisation to a BL sequence (BLB) within a hairpin structure (the whole complex is termed Hairpined Dz1, drawn as a thin grey line). In the absence of any active Mz1, the two hairpined molecules exist together in an inactive state and do not interact with one another. When active Mz1 is present however, this may result in the cleavage of the BLA portion of the Hairpined RL and the subsequent activation of the RL portion of the molecule. The RL may then function to hybridize with the BLB portion of the Hairpined Dz1 and open the hairpin structure to activate the Dz1 portion of the molecule. The active Dz1 may then function to cleave the substrate 1 within another Hairpined RL molecule, thus resulting in the activation of additional RL molecules. A circular cascade may then be created whereby RL molecules continuously activate DNAzymes and vice versa and this cascade may be used for the amplification of signal.

Target Detection and Signal Amplification: NRF

As noted above, NRF are oligonucleotides that can provide a sequence for recognition by a nuclease, thus allowing initiation of the activity of a nuclease enzyme. In some embodiments, the NRF may wholly or partly hybridize with the BL thus generating a substrate for a nuclease, for example an exonuclease such as ExoIII, leading to selective cleavage or degradation of the BL. When a BL is hybridized to a third functional molecule such as a catalytic nucleic acid, the nuclease cleavage or digestion of the BL may then result in the activation of the catalytic nucleic acid and restoration of its function. The NRF may then be recycled to hybridize with another BL molecule and the process is repeated. In further preferred embodiments, the NRF may be hybridized to another BL molecule, resulting in its temporary inactivation i.e loss of ability to function to provide the sequence template necessary to initiate nuclease activity. The BL may exist as a separate oligonucleotide or may exist within the same oligonucleotide as the NRF where they may be joined by a linking nucleic acid or non-nucleic acid spacer sequence which forms the loop of a hairpin structure. In one embodiment, the BL may also contain a sequence which acts as a substrate for a catalytic nucleic acid molecule. This may exist as part of, or in addition to, the hairpin loop sequence when both the NRF and BL are linked together. In such embodiments, cleavage of the substrate sequence may release the NRF from the BL which may result in the re-instatement of its ability to function as a NRF.

In other embodiments, a cascade may be created whereby both a NRF and a catalytic nucleic acid are both present in an inactive state due to hybridization with their respective BL molecules. The NRF has the potential to hybridize with the opposing BL of the BL/catalytic nucleic acid molecular switch and initiate its digestion by an exonuclease. The catalytic nucleic acid also has the potential to cleave the substrate present within the opposing BL of the BL/NRF molecular switch and result in activation of the NRF. The addition of an active catalytic nucleic acid molecule, or the final component to complete an active catalytic nucleic acid molecule such as an assembly facilitator for an MNAzyme, may result in cleavage of one or more BL molecules that results in the activation of either NRF functionality or catalytic nucleic acid catalysis. This may initiate a cascade of BL cleavage and NRF-mediated BL nuclease digestion events between the two different molecular switches resulting in the continued activation of NRF and catalytic nucleic acid molecules.

Figure 10:
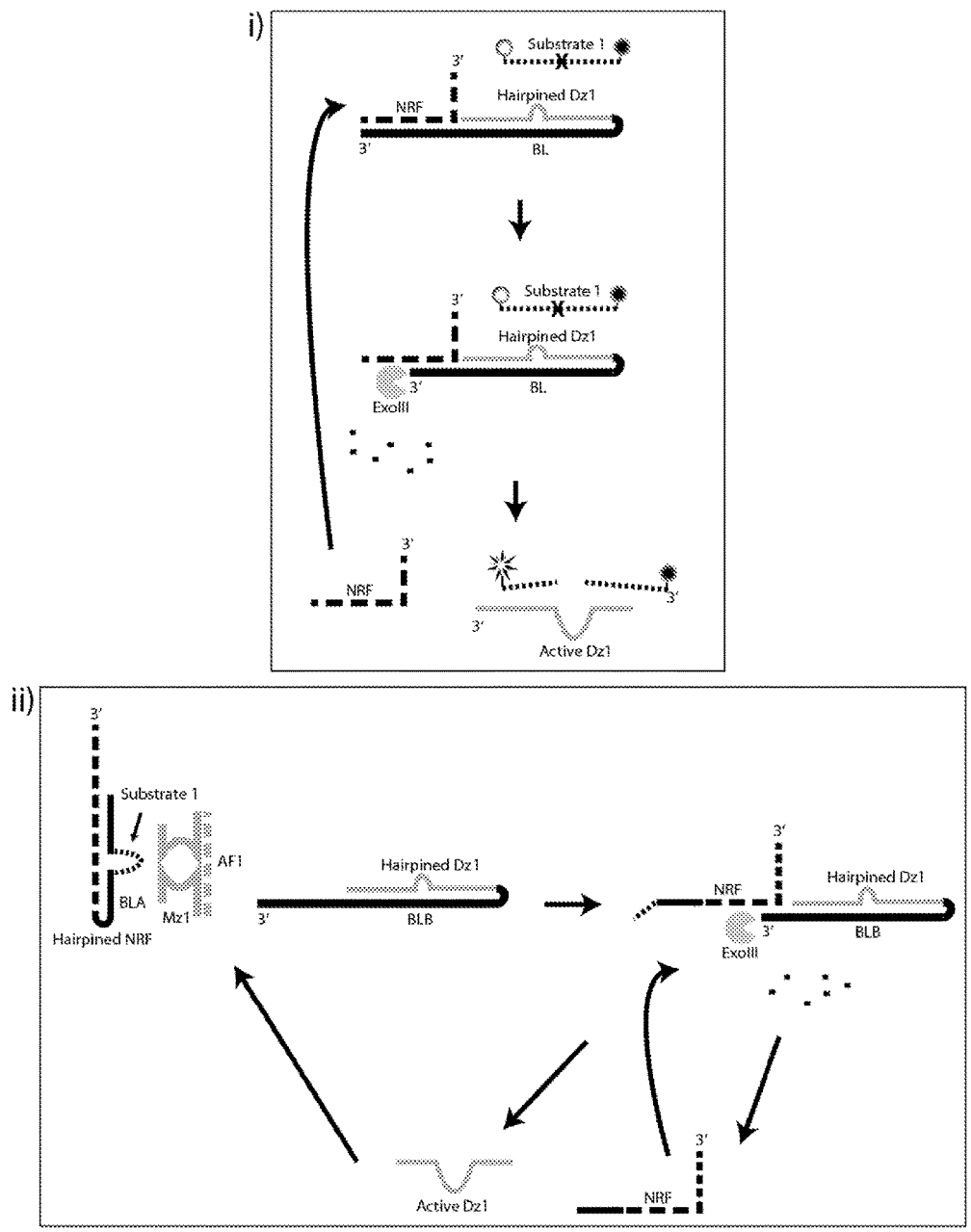
FIG. 10 demonstrates the direct activation of a catalytic nucleic acid, such as a DNAzyme, by the use of a nuclease enzyme such as Exonuclease III (ExoIII). ExoIII catalyzes the step-wise removal of mononucleotides from the 3' end of blunt or recessed duplexed DNA and is used here to degrade the BL portion of a BL/DNAzyme molecular switch. ExoIII activity is triggered by the presence of an active Nuclease Recognition Fragment (NRF) which may partially hybridize to a portion of the BL and promote its degradation by ExoIII. This may result in the activation of the DNAzyme and the recycling of the NRF so that it can function to continuously activate additional DNAzymes via the same method (panel i)). This strategy may also be used to create a circular cascade whereby the DNAzyme that is activated by the NRF-promoted ExoIII degradation event can then function to cleave the substrate present within the BLA molecule from the NRF/BL molecular switch. This may result in the continuous activation of both NRF molecules (which are also recycled) and activation of DNAzymes and may be used for the amplification of signal (panel ii)).

Turning to FIG. 10, panel i) depicts the strategy diagrammatically, whereby a hairpined DNAzyme molecule (Hairpined Dz1) exists and is drawn as a thin grey line indicating the DNAzyme portion and thick black line indicating the remaining BL, toehold and hairpin loop portions). A substrate sequence (Substrate 1), drawn as a thin black dashed line, is labeled with a fluorophore (unfilled circle) and a quencher (filled circle) and is designed to be cleaved by the Dz1 portion of the Hairpined Dz1 molecule, however while hybridized to the BL portion, the Dz1 would be inactive and cannot cleave its substrate. An NRF may be provided by the catalytic activity of an initiator enzyme (e.g. an MNAzyme, DNAzyme, ribozyme, or aptazyme) in a target-dependent manner, whereby a substrate for the initiator enzyme could be modified to produce the NRF only when a target molecule is present that induces catalytic activity of the initiator enzyme. By way of non-limiting example, generation of the NRF in a target specific manner could be achieved as illustrated in FIG. 10 panel ii). Referring to FIG. 10 panel i), an active NRF is drawn as a thick dashed black line, hybridized to the 3' end of the BL portion of the Hairpined Dz1, which initially has its 3' end protruding from the duplex by at least 4 nucleotides so as to render it resistant to ExoIII degradation. However, hybridisation of the NRF to the BL would provide a double-stranded substrate with a suitable blunt or 3' recessed termini for ExoIII (grey segmented circle). ExoIII could selectively digest the BL molecule from its 3' terminus whilst leaving the NRF molecule intact rendering the Hairpined Dz molecule single stranded, thus degrading the BL portion but leaving behind the Dz1 portion, which would now be active. The NRF could then be recycled and able to repeat the process. Once active, each Dz1 could bind to its substrate (with the 3' ends of each protruding, rendering them resistant to ExoIII) and cleave the substrate resulting in the separation of the fluorophore and quencher and the generation of a detectable fluorescent signal.

The embodiment shown in FIG. 10 panel ii) depicts a circular cascade reaction which may occur when a substrate sequence, present within the BL region of a Hairpined NRF, is designed to be cleaved by the catalytic nucleic acid which is subsequently activated by the NRF-initiated nuclease activity. The Hairpined NRF consists of the NRF portion, drawn as a thick dashed black line, and BL portion, BLA drawn as a thick black line, and may be linked together by a non-complementary sequence forming the loop of the hairpined structure (also a thick black line). The BLA portion may contain a substrate sequence (Substrate 1; thin black dashed line) that may be cleaved by an active MNAzyme (Mz1; thick grey line) assembled in the presence of its target assembly facilitator (AF1; thick grey dashed line). In addition, the DNAzyme may exist in an inactive state within a hairpin structure (Hairpined Dz1; thin grey line indicating the DNAzyme portion and thick black line indicating the hairpin loop and BLB portions). In the absence of any active MNAzyme, the two hairpined molecules may exist together in an inactive state and do not interact with one another. However, when an active MNAzyme is present, this could result in the cleavage of the Substrate 1 within the BLA portion of the Hairpined NRF and the subsequent activation of the NRF portion of the molecule. This step provides a non-limiting example of a method for providing an NRF by the catalytic activity of an initiator enzyme (e.g. an MNAzyme or apatazyme) in a target-dependent manner as discussed in FIG. 10 panel i). Referring to FIG. 10 panel ii) the NRF may then function to hybridize with the BLB portion of the Hairpined Dz1 and open the hairpin structure to activate the Dz1 portion of the molecule (as outlined in panel i)). In addition to the recycling of the NRF, the active Dz1 may then also function to cleave the substrate of another hairpined NRF molecule, thus resulting in the activation of additional NRF molecules. A circular cascade may then be created whereby NRF molecules (which are recycled) continuously activate DNAzymes and vice versa and may be used for the amplification of signal.

Figure 27:
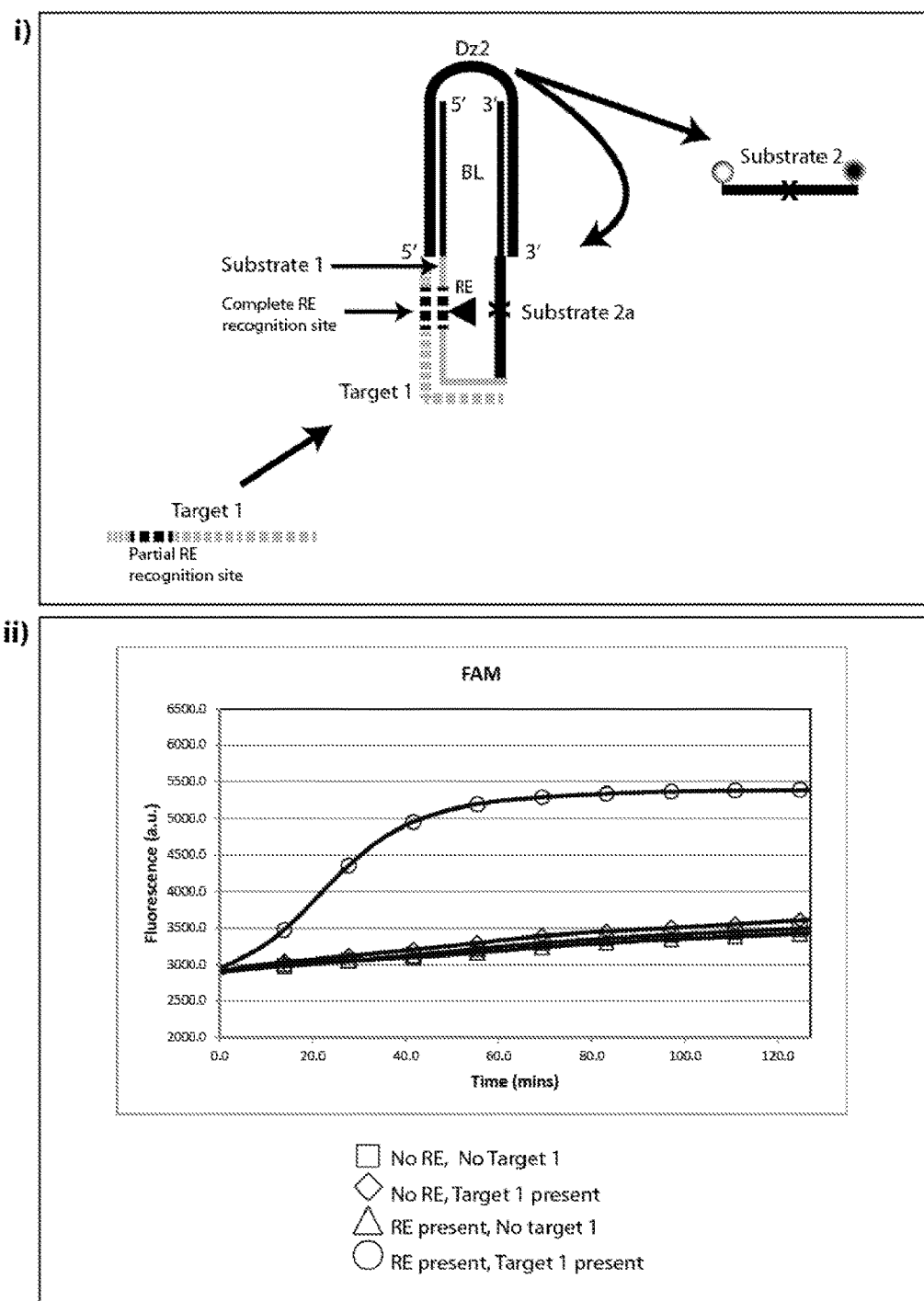
FIG. 27 panel i) depicts an auto-catalytic, quasi-circular structure (FIG. 21 panel i)) whereby the cascade is initiated via the hybridization of a target sequence (Target 1) to a RE substrate (Substrate 1) within the BL, recruiting the activity of an RE to selectively nick the BL. Substrate 1 and Target 1 each comprise one strand of a RE recognition sequence, such that the binding of the two together results in the formation of the complete recognition site and triggers the nicking of the BL by the RE. Substrate 2 within the BL (Substrate 2a), and free Substrate 2 (labelled with a fluorophore/quencher dye pair), can both be cleaved by Dz2 following its RE-mediated release from the circle. Panel ii) provides a timecourse graph demonstrating the fluorescent signal achieved from the strategy depicted in panel i).

In other embodiments, the NRF can wholly or partially comprise the target. Referring specifically to FIG. 27 panel i), an auto-catalytic, quasi-circle cascade (such as that in FIG. 21 panel i)) is initiated via the hybridization of a target sequence (Target 1; thick grey dashed line) to a substrate (Substrate 1; thin grey line) within the BL of the quasi circle. Substrate 1 and Target 1 each comprise one strand of a RE recognition sequence (thick black dashed line), such that the binding of the two together results in the formation of the complete recognition site. Target 1 therefore functions as an NRF as it recruits the activity of an RE (filled black triangle) to selectively nick the BL. The BL molecule consists sequence at its 5' and 3' ends (thin black lines), which hybridize to a DNAzyme (Dz2; thick black line), resulting in the temporary inactivation of Dz2. The BL also contains a second substrate sequence Substrate 2 (Substrate 2a, thick black line), adjacent to Substrate 1, which is capable of being cleaved by Dz2, once Dz2 has been released from the BL via nicking of Substrate 1. In addition, Substrate 2 is also provided as an independent entity which has been modified with a fluorophore (unfilled circle) and quencher (filled black circle) to monitor the DNAzyme cleavage reaction. Only when Target 1 and the RE are both present will Substrate 1 be nicked, resulting in the initiation of the auto-catalytic cascade and generation of fluorescent signal.

Target Detection and Signal Amplification: Hairpined DNAzymes

In another strategy, restriction enzymes (e.g. nicking enzymes) can be included together and used in concert with strand displacing polymerase enzymes to continually synthesize and displace catalytic nucleic acid molecules from a complementary BL template. In such embodiments, the extension of a primer by a strand displacing polymerase results in the formation of an upstream recognition site for a RE. The endonuclease activity of a RE can result in the production of a nick upstream of the catalytic nucleic acid molecule (e.g. by using a nicking enzyme or incorporating a phosphorothioate linkage in one strand of the recognition site) thus forming a new primer which can extend by a strand displacing polymerase enzyme to synthesize a new copy of the catalytic nucleic acid molecule and simultaneously displace the existing catalytic nucleic acid molecule. The two protein enzymes can then continue to work in concert to continually synthesize and displace new catalytic nucleic acid molecules, which can be used for the amplification of signal.

Figure 11:
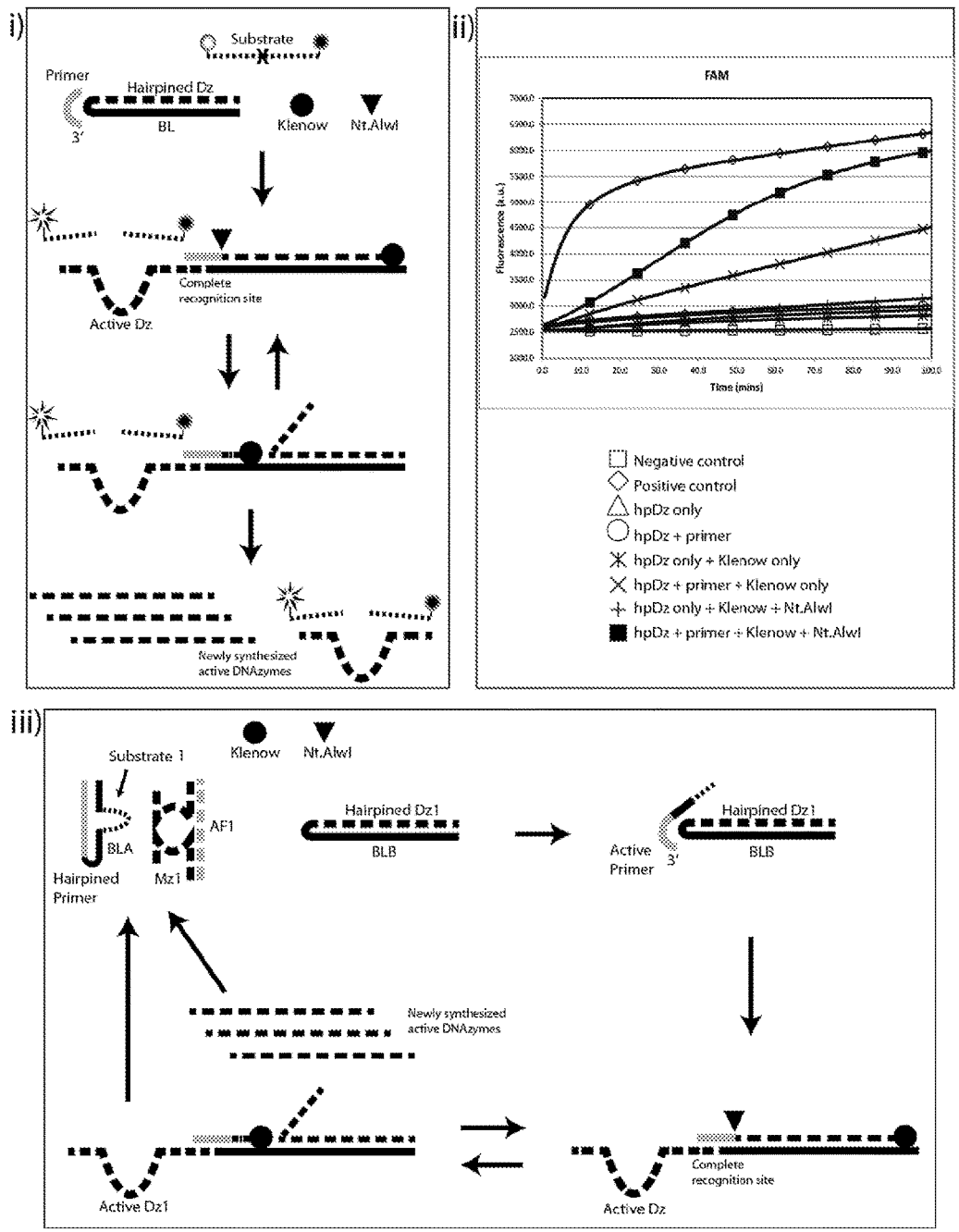
FIG. 11 demonstrates the direct activation of a catalytic nucleic acid, such as a DNAzyme, by the use of a strand displacing polymerase enzyme such as Klenow fragment (3'-5' exo-). As shown in panel i) the enzyme is used here to displace the DNAzyme portion from a Dz/BL molecular switch via the extension of a primer which can hybridize to either a portion of the BL, or, to the loop sequence in embodiments where the Dz/BL are linked together in a hairpined structure. Strand displacing primer extension uses the BL portion as a template and results in, an inactive duplex between the extended primer and the BL, whilst the Dz is now single stranded and active. In addition, the use of a Restriction Enzyme (RE) is also depicted, with its activity resulting in the production of new primers which can be extended by polymerase to synthesize and displace additional copies of active DNAzymes. Panel ii) demonstrates the fluorescent signal achieved from the strategy depicted in panel i). This strategy may also be used to create a circular cascade whereby the DNAzymes that are activated and synthesized (from the activity of polymerase alone or polymerase in combination with an RE) and can then function to cleave the substrate present within a BL molecule from a primer/BL molecular switch (panel iii)). This may result in the continuous activation of both primers and DNAzymes (in addition to the synthesis of new active DNAzymes if the RE is also used) and may be used for the amplification of signal.

For example, FIG. 11, panel i) depicts a strategy of this nature whereby a hairpined DNAzyme molecule (Hairpined Dz) is present, with the Dz portion drawn as a thick black dashed line and the BL portion and hairpin loop drawn as a thick black line. The hairpin loop contains some, but not all, of the bases required for one strand of a RE recognition site for a RE e.g. the nicking enzyme Nt.AlwI (solid back triangle) and therefore the RE recognition site in the Hairpined Dz is incomplete. A substrate sequence (Substrate; thin black dashed line) is labeled with a fluorophore (unfilled circle) and a quencher (filled circle) and is designed to be cleaved by the Dz portion of the Hairpined Dz molecule, however due to the hybridization of the Dz to the BL portion, the Dz is inactive and cannot cleave its substrate. A primer may be provided by the catalytic activity of an initiator enzyme (e.g. an MNAzyme, DNAzyme, ribozyme, or aptazyme) in a target-dependent manner, whereby a substrate for the initiator enzyme is modified to produce the primer only when a target molecule is present that induces catalytic activity of the initiator enzyme. By way of non-limiting example, provision of the primer may be achieved using the strategy illustrated in FIG. 12 i) and ii). Referring to FIG. 11 panel i), when a primer is present, drawn as a thick grey line, it can hybridise to the single stranded loop of the hairpined Dz and can be extended by a strand displacing polymerase, such as Klenow fragment (3'-5' exo−) drawn as a filled black circle. The polymerase can use the BL portion of the Hairpined Dz as a template and synthesize a new copy of the Dz, thus opening the hairpin and allowing the existing Dz to be single-stranded and active. In addition, primer extension completes the Nt.AlwI recognition site, promoting Nt.AlwI to selectively nick the newly synthesized strand in between the upstream primer and downstream Dz sequence. The nick therefore creates a new primer which can be extended by Klenow to synthesize a new Dz copy and displace the existing Dz. Both enzymes can then function together to continuously synthesize and displace Dz molecules. Each Dz, once displaced and active, is then able to bind to the Substrate and can cleave the Substrate which results in the separation of the fluorophore and quencher and the generation of a detectable fluorescent signal. The skilled person will recognise that although the exemplary strategies above use a nicking enzyme, the processes can be modified to accommodate the use of a restriction enzyme capable of cleaving both strands of the recognition site formed by hybridisation and/or extension of the primer, and the hairpin loop segment linking the enzyme to the BL. In such cases, cleavage of the hairpin loop strand of the recognition site may be avoided by modifying the hairpin loop strand to incorporate a phosphorothioate linkage, thus preventing cleavage of the hairpin loop strand by the restriction enzyme.

In other embodiments, a cascade may be created whereby both a primer and a catalytic nucleic acid are initially both present in an inactive state due to hybridization with their respective BL molecules. For example, the primer may be initially hybridized to a BL molecule, resulting in its temporary inactivation. The BL may exist as a separate oligonucleotide to the primer, or may exist within the same oligonucleotide as the primer where they are joined by a linking nucleic acid or non-nucleic acid spacer sequence which forms the loop of a hairpin structure. The BL bound to the primer may also contain a sequence which acts as a substrate for a catalytic nucleic acid molecule. This may exist as part of, or in addition to, the hairpin loop sequence when both the primer and BL are linked together. Cleavage of the substrate sequence may release the primer from the BL which may result in the re-instatement of its priming activity. The primer may have the potential to hybridize with a portion of the opposing BL of the BL/catalytic nucleic acid molecular switch, such as the hairpin loop sequence and initiate the extension of the primer by a polymerase enzyme, which may result in the separation of the catalytic nucleic acid from the BL and re-instate its catalytic activity. The catalytic nucleic acid may also have the potential to cleave the substrate present within the opposing BL of the BL/primer molecular switch and result in activation of the primer. Both molecular switches however, are inactive until the addition of an active catalytic nucleic acid molecule, or the final component to complete an active catalytic nucleic acid molecule such as an assembly facilitator for an MNAzyme, which may result in cleavage of one or more BL molecules that results in the activation of either primer functionality or catalytic nucleic acid catalysis. This may initiate a cascade of BL cleavage and primer extension events between the two different molecular switches resulting in the continued activation of primers and catalytic nucleic acid molecules and the subsequent amplification of signal.

By way of non-limiting example, FIG. 11 panel iii) outlines a circular cascade reaction which may occur when the substrate sequence (Substrate 1) present within the BL region of a Hairpined Primer, is designed to be cleaved by the DNAzyme which is subsequently activated by the primer-polymerase activity. The Hairpined Primer includes the primer portion (thick grey line) and BL portion (BLA, thick black line) linked together by a non-complementary sequence forming the loop of the hairpin structure (also a thick black line). The BLA portion contains the Substrate 1 sequence (thin black dashed line) that may be cleaved by an active MNAzyme (Mz1; thick black dashed lines) assembled in the presence of its target assembly facilitator (AF1 thick dashed grey line). In addition, Dz1 may exist in an inactive state within a hairpin structure (Hairpined Dz1), the Dz1 portion of which is drawn as a thick black dashed line and the BL portion (BLB) and hairpin loop is drawn as a thick black line. The Klenow polymerase (Klenow; filled black circle) and a RE, for example, Nt.AlwI nicking enzyme (filled black triangle) may also present in the reaction. In the absence of any active Mz1, the two hairpin molecules may exist together in an inactive state and not interact with one another. When an active Mz1 is present however, this may result in the cleavage of Substrate 1 of the BLA portion of the Hairpined Primer and the subsequent activation of the primer portion of the molecule. The Active Primer may then function to hybridize with the loop of the Hairpined Dz1 and open the hairpin structure to activate the Dz1 portion of the molecule. In addition, primer binding and/or extension may complete the RE (e.g. Nt.AlwI) recognition site, promoting the RE to selectively nick the newly synthesised strand in between the upstream primer and downstream Dz sequence. The nick would therefore create a new primer which may be extended by Klenow to synthesize a new Dz copy and displace the existing Dz. Both enzymes can then function together to synthesize and displace Dz1 molecules (as outlined in panel i)), each of which can function to cleave Substrate 1 present in the BLA portion of the Hairpined Primer, thus creating new Active Primers. A circular cascade may then be created whereby Active Primer molecules are responsible for the continuous activation and synthesis of Active Dz1 molecules and vice versa and may be used for the amplification of signal. The skilled person will recognise that although the exemplary strategy above uses a nicking enzyme, the process can be modified to accommodate the use of a restriction enzyme capable of cleaving both strands of the recognition site formed by hybridisation and/or extension of the primer and the loop of the hairpined Dz1. In such cases, cleavage of the loop strand of the recognition site may be avoided by modifying the loop strand to incorporate a phosphorothioate linkage, thus preventing cleavage of the loop strand by the restriction enzyme.

In other embodiments, the hairpined structure which forms the template for continual synthesis of catalytic nucleic acid molecules (for example, DNAzymes), may instead comprise of a Dz region consisting of only partial catalytic nucleic acid sequence. When this occurs, the activity of both the polymerase and the RE are essential for there to be any active catalytic nucleic acid present in the reaction. The use of such templates may be useful for eliminating background 'primer-independent' signal, thus resulting in greater specificity.

Figure 19:
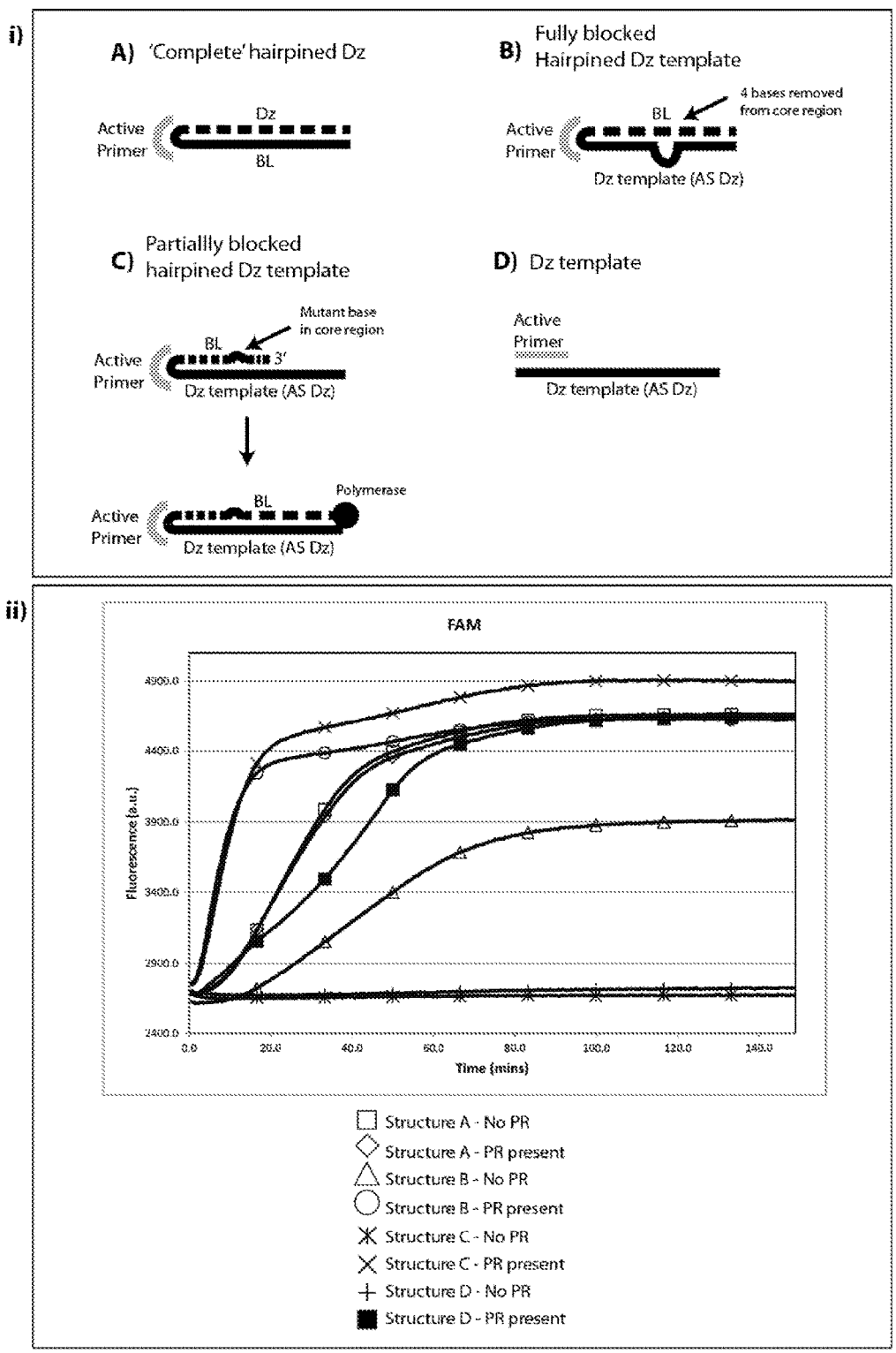
FIG. 19 panel i) depicts four different structures that can be used to synthesize catalytic nucleic acid sequences (e.g. DNAzymes) in a continuous manner as outlined in FIG. 11. Structure A consists of a 'Complete' hairpined DNAzyme/BL whereby the Dz region of the hairpin comprises the complete sequence required for catalytic activity and may become active once the hairpin has been opened via the displacement action of a primer and strand-displacing polymerase. Structure B consists of a BL containing an inactive oligonucleotide comprising an inactive partial DNAzyme sequence (with essential bases absent from the catalytic core) which blocks an antisense DNAzyme (ASDz) sequence capable of functioning as a template for DNAzyme synthesis. Structure C consists of a BL containing, an inactive oligonucleotide comprising an inactive, partial DNAzyme sequence (with an essential base mutated within the catalytic core) which blocks an ASDz sequence capable of functioning as a template for DNAzyme synthesis. In the presence of the polymerase, the BL strand may be extended, but the mutated base pair within the Dz core region will still render this oligonucleotide inactive. As such, both structures B and C will not expose functional DNAzymes when they are opened by the primer. Structure D comprises an unblocked Dz template (ASDz) and an adjacent primer-binding site. Each of the Structures B, C and D are capable of providing a template for DNAzyme synthesis but considerable variation in signal is achieved from the active DNAzymes produced. Panel ii) demonstrates the fluorescent signal achieved from the active DNAzymes produced from each of the structures A-D depicted in panel i).

For example, FIG. 19 panel i) depicts four unique structures (structures A, B, C and D) which can form the template for continual synthesis of a DNAzyme. The template portion for Dz synthesis is also the BL for Structure A (depicted a thick black line) and this hybrided to a DNAzyme (Dz; thick dashed line) which is initially inactive due to hybridization of the BL. The template for syntheses of new DNAzymes in Structures B-D (Dz template (ASDz; anti-sense DNAzyme sequence; thick black line) comprises the antisense of a functional DNAzyme. The BL portions for Structures B and C are drawn as a thick black dashed line. An Active Primer (short thick grey line) is shown binding to the primer-binding region (the hairpin loop portions) of Structures A-C and to the primer-binding region of Structure D. Structure A is termed a 'Complete' hairpined Dz whereby the Dz portion of the molecule comprises the complete catalytic Dz sequence (originally depicted in FIG. 11 panel i)). Referring to FIG. 19 panel i) Structure B is referred to as a 'Fully Blocked' hairpined Dz template and comprises a BL containing a Dz Portion consisting of all except for 4 nucleotides of the complete Dz sequence, with the bases removed from the catalytic core region. The Dz template (ASDz) of Structure B, contains the complete complement (antisense) of a DNAzyme including those nucleotides removed from the Dz Portion of the BL. This therefore results in the formation of a bulge within the Dz template where there are 4 unpaired nucleotides. Structure C is referred to as a 'Partially' blocked hairpined Dz template' and may contain a mutated mis-matched base pairing with the Dz core portion of the BL, shown as a small bulge within the BL. In the presence of the polymerase (filled black circle), the 3' end of the Partially blocked hairpined Dz template may be extended using the ASDz template as a template for copying, but due to the mutated base pair within the core region of BL, does not expose a functional Dz when it is opened by the later extension of the primer. Structure D is referred to as an 'Dz-template' (ASDz) and comprises solely of sequence complementary to a Dz, with an adjacent primer-binding site. The Dz-template molecule is not bound to a BL.

In further embodiments, both the hairpined primer (outlined in FIG. 12 panel i)) and hairpined DNAzyme molecule (outlined in FIG. 11 panel iii)) may instead be partial hairpined primer and partial hairpined DNAzyme molecules respectively. The partial hairpined primer may initially comprise only a portion of the primer region and therefore may have a reduced complementarity with the partially hairpined Dz template (originally described in FIG. 19 panel i)) minimizing any unwanted binding between the two molecules before the reaction can be initiated in a target-dependent manner. In the presence of the polymerase, the partial primer region is extended using the BL region as a template thus completing the sequence of the hairpined primer. The use of two partial molecules (a partial hairpined primer and a partially blocked hairpin Dz template), as illustrated in FIG. 23, may be useful for eliminating background 'target-independent' signal, thus resulting in greater specificity.

Figure 23:
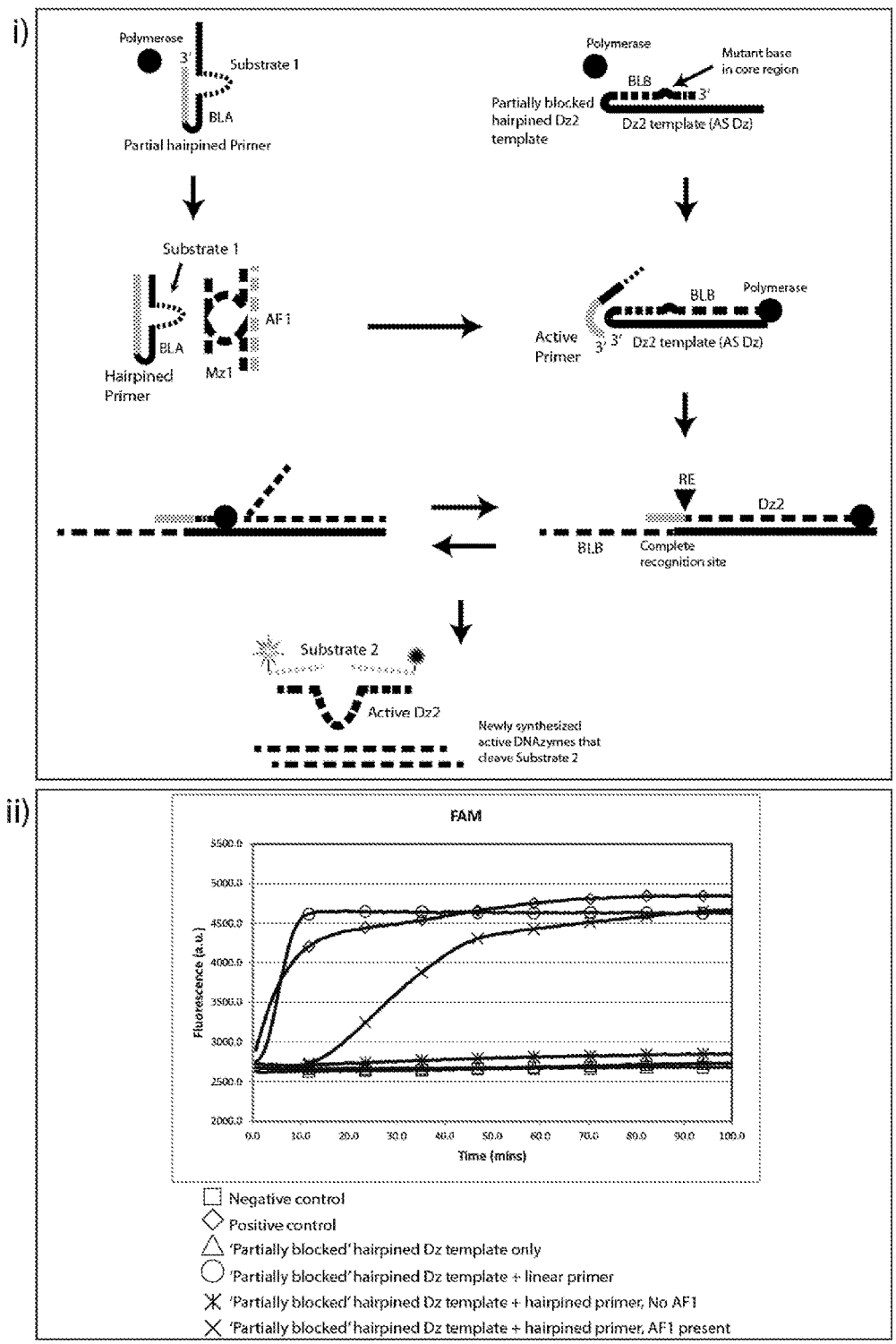
FIG. 23 panel i) depicts the use of both a partial hairpined primer and partially blocked hairpined Dz-template (antisense DNAzyme; ASDz) molecule to initiate the synthesis of new DNAzyme molecules in a target-dependent manner. The BLB is an incomplete Dz sequence with at least one inactivating mutation within the core region, such that its extension by polymerase can not produce active DNAzymes. Initially, both partial hairpined molecules may be extended by polymerase from the 3' ends to produce fully hairpined structures. An MNAzyme (Mz1) can form in the presence of its target assembly facilitator (AF1) to cleave Substrate 1 present within the BLA of the hairpined primer. This cleavage can result in the release of a functional primer, which in turn binds to the hairpined Dz-template where it can extend and synthesise active DNAzyme molecules that can cleave fluorescently-labeled substrates, generating a detectable fluorescent signal. Panel ii) demonstrates the fluorescent signal achieved from the strategy depicted in panel i).

In FIG. 23 panel i) a Partial hairpined Primer is present, with the partial primer region shown as a thin grey line, the BL region (BLA) as two thin black lines linked by Substrate 1 which is drawn as a thin black dashed line. In the presence of a polymerase enzyme (filled large black circle), the 3' end of the partial hairpined primer may be extended using the BLA region as a template, thus completing the primer region and resulting in the formation of a complete Hairpined Primer. In addition, Partially blocked hairpined Dz2 template is also present, with the BL region (BLB) drawn as a thick dashed black line and Dz2 template (ASDz) region as a thick black dashed line. The BLB comprises a partial sequence of a DNAzyme which contains mutated base(s) within Dz core of the BLB which constitutes a catalycally inactivating mutation with respect to a complete DNAzyme. The mutant core bases in the BLB, are shown as a small bulge. In the presence of the polymerase, the 3' end of the Partially hairpined Dz template strand may be extended using the Dz2 template portion as a template for copying, but due to the mis-mutated bases within the BLB, a functional Dz is not exposed when Partially hairpined Dz template structure is opened by the extension by the primer. An MNAzyme can be present, designed to cleave Substrate 1 (Mz1; thick black dashed line) which assembles in the presence of its target assembly facilitator (AF1; thick grey dashed line). This can result in the cleavage of Substrate 1 by Mz1 and the subsequent release of the primer region from the Partially hairpined Primer, resulting in the restoration of its priming ability. The Active Primer may then hybridise to the loop of the Partially blocked hairpined Dz2 template structure and prime the synthesis of Active Dz2 molecules (thick black dashed lines) via the polymerase extension and RE nicking activities (RE drawn as a filled black triangle) outlined in FIG. 11. Referring to FIG. 23 panel i), the Active Dz2 molecules may then cleave Substrate 2 (thin grey dashed line) which may be labeled with a fluorophore (grey star) and quencher (filled small black circle), resulting in a detectable fluorescence signal.

Figure 12:
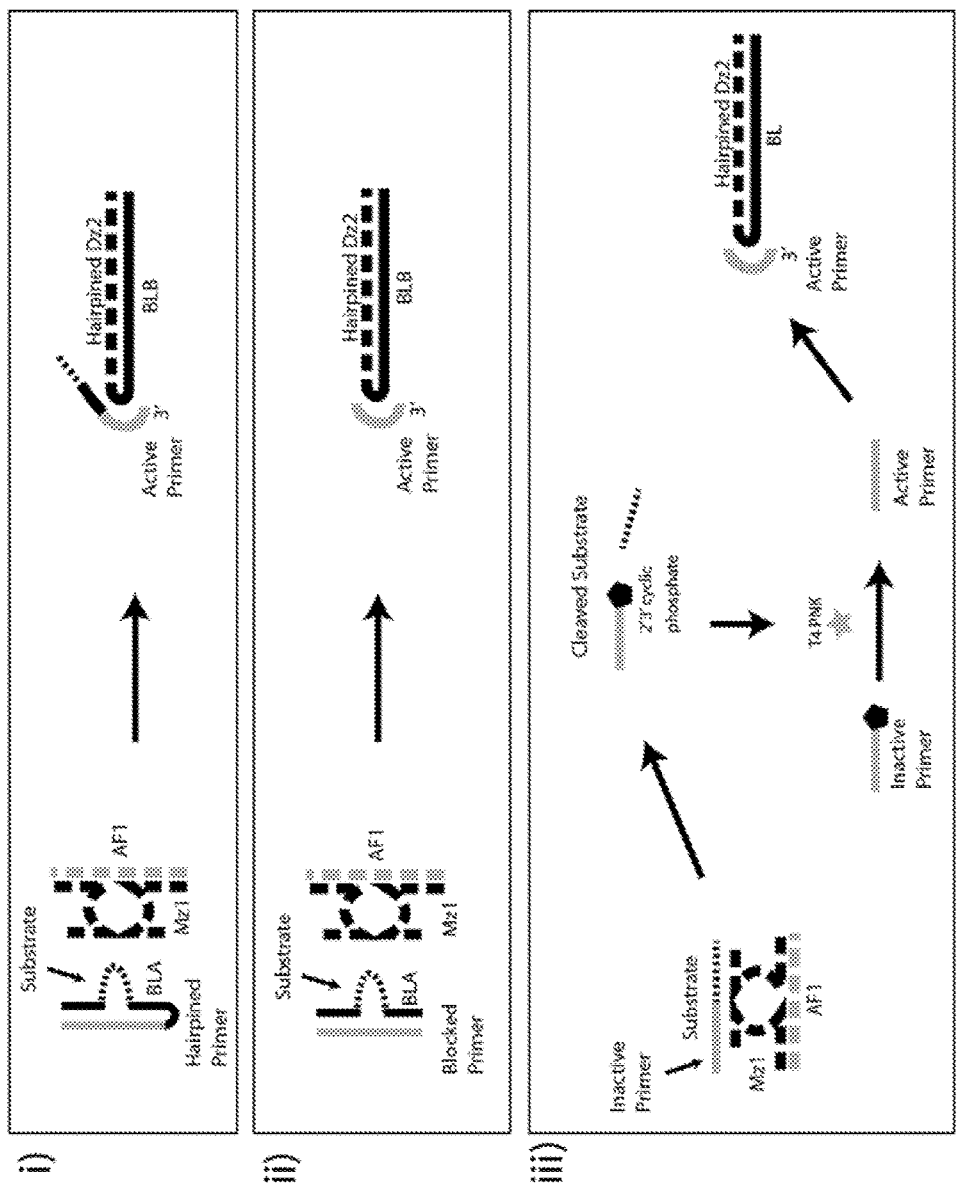
FIG. 12 outlines exemplary methods for the generation of active primer molecules. In each case (panel i), panel ii) and panel iii)), an active primer may be produced by cleavage of a substrate by a catalytic nucleic acid (e.g. an active DNAzyme, an active aptazyme or by an active MNAzyme assembled in the presence of its target (as illustrated)).

FIG. 12 provides exemplary strategies for the generation of primer oligonucleotides relying on the target-dependent activity of catalytic nucleic acid enzymes. In panel i) the primer (thick grey line) may be initially hybridized to a BL molecule (BLA, thick black line) and both may be linked by a non-complementary sequence which forms the loop of a hairpined molecule (also a thick black line). The BLA may contain a substrate sequence (thin dashed black line) which may be cleaved by an MNAzyme (Mz1) (thick dashed black line) in the presence of its target (AF1: thick grey dashed line). Cleavage of the Substrate may release the primer from the BLA and render the primer active. The Active Primer may then hybridize with the loop of the complete hairpined DNAzyme structure (Hairpined Dz2; Dz2 drawn as a thick dashed black line, BLB drawn as a thick solid black line) and proceed to activate and/or synthesize new DNAzymes (e.g. as outlined in FIG. 11). In panel ii) the primer (thick grey line) may be initially hybridized to a separate BL molecule (BLA, thick black line), however both may not be linked together as in panel i), but exist as two separate oligonucleotides. The primer may then be activated in the same manner as that outlined in panel i). In panel iii) the primer may be present as a component of a substrate for an MNAzyme (the primer is depicted as a thick grey line on the left portion of the Substrate molecule, with the remainder of the substrate shown as a thin blacked dashed line on the right). The MNAzyme, (Mz1; thick dashed black line) in the presence of its target (AF1; thick grey dashed line) can cleave the Substrate resulting in the separation of the primer from the other cleaved fragment. The primer remains inactive following cleavage due to the presence of a 2'3' cyclic phosphate at the 3' terminus (solid black pentagon shape) which is a product of the MNAzyme cleavage reaction. T4 Polynucleotide kinase (T4 PNK, shown as a solid grey star shape) or another appropriate enzyme may be used to catalyse the removal of the 2'3' cyclic phosphate resulting in the activation of the primer. The Active Primer may then hybridize with the loop of the complete hairpined DNAzyme (Hairpined Dz2; Dz2 drawn as a thick dashed black line, BL drawn as a thick solid black line) and proceed to activate and/or synthesize new DNAzymes as outlined, for example, in FIG. 11.

Figure 17:
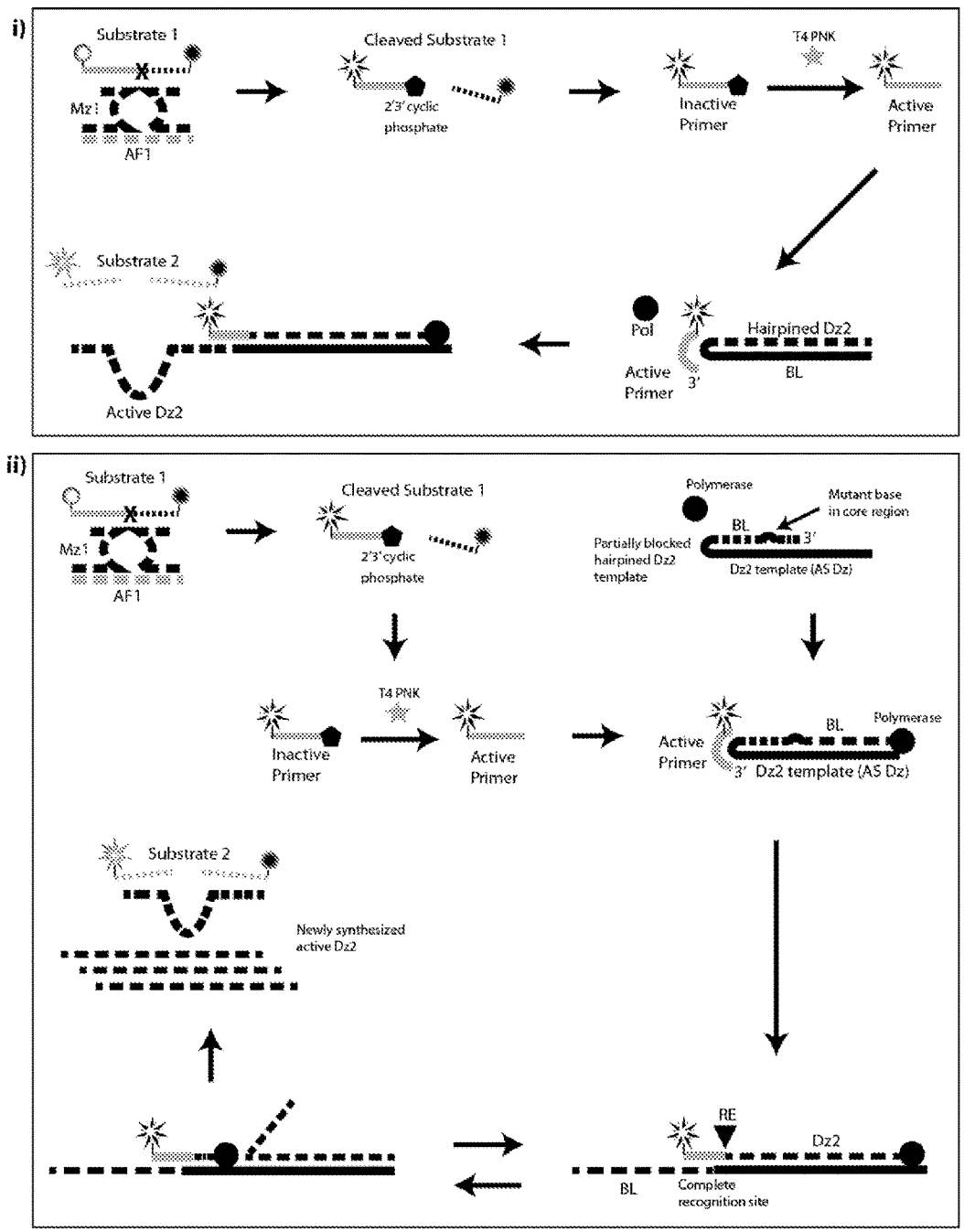
FIG. 17 demonstrates the activation (panel i)) of, or the synthesis of (panel ii), a catalytic nucleic acid, such as a DNAzyme, by the use of a strand displacing polymerase enzyme together with an enzyme with phosphatase activity (e.g. T4 PNK) and optionally an RE (as shown in Panel ii)). When an MNAzyme cleaves a substrate, a latent primer is released that is inactivate due to the presence of a 2'3' cylic phosphate group at its 3' end. T4 PNK can then be used to remove the 2'3' cylic phosphate group thereby rendering the primer active. The active primer can then hybridize to either a portion of the BL, or, to the loop sequence in embodiments where the BL is duplexed within a hairpined structure (panels i) and ii)). In panel i), primer extension via a strand displacing polymerase uses the BL portion as a template and results in an inactive duplex between the extended primer and the BL, whilst the Dz is now single stranded and active and hence capable of cleaving a substrate to provide a signal. Panel ii) shows an exemplary embodiment in which extension of the activated primer by a strand displacing polymerase creates a nicking endonuclease recognition site. The BL is duplexed with an oligonucleotide which contains the inactive antisense of a DNAzyme (ASDz) as well as one strand of the duplex recognition site of a nicking RE. The BL contains an inactive partial and/or mutated DNAzyme but does not contain the complementary sequence that would be required to form the second strand of the duplex recognition site of the nicking RE. An appropriate RE may be used to nick one strand at a complete recognition site of a new duplex formed by extension of the primer, thus generating a new primer from which the strand displacing polymerase can synthesise a new Dz molecule using the ASDz as a template. The system provides for the continual synthesis of new Dz molecules, and Panel ii) shows an exemplary linear cascade whereby the synthesized DNAzymes can cleave a different substrate to that cleaved by the MNAzyme. Panel iii) shows the fluorescent signal achieved from the linear cascade strategy outlined in panel ii).
Figure 17:
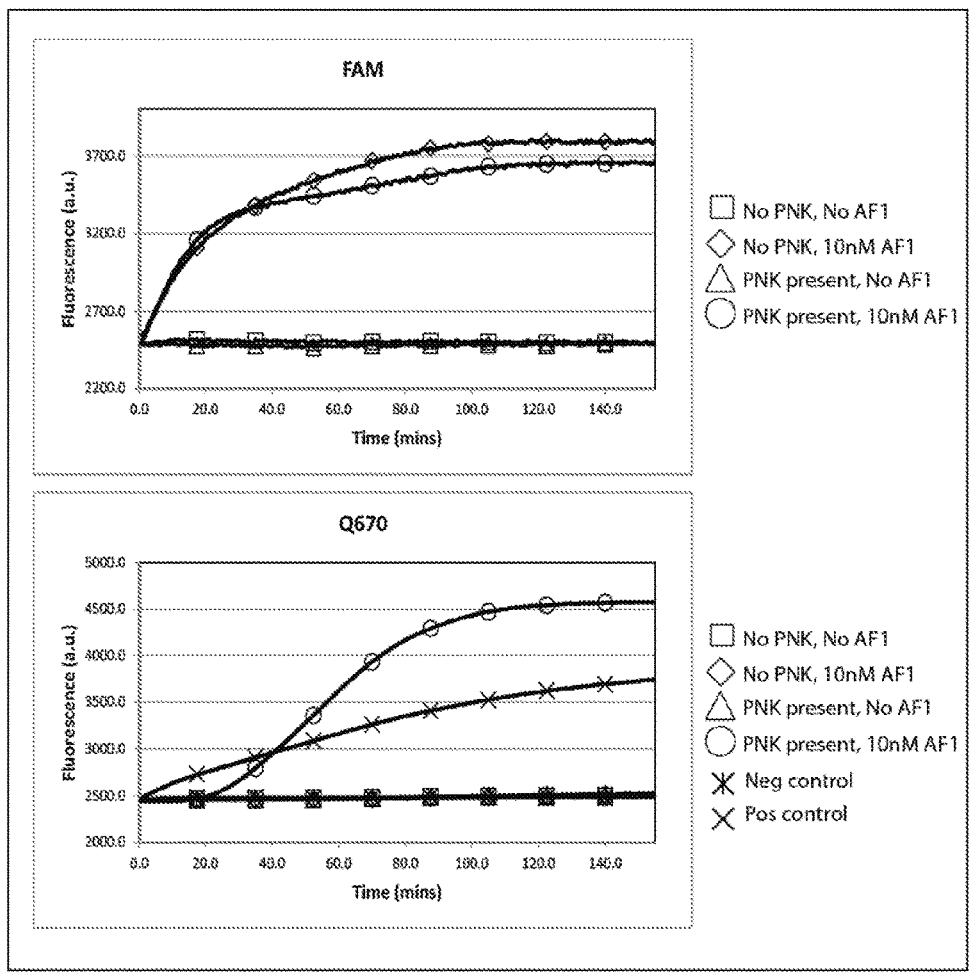

In further embodiments, a linear cascade can be triggered by the activation of, a primer via MNAzyme cleavage of a substrate and the subsequent de-phosphorylation of the cleaved substrate fragment (e.g. as outlined in FIG. 12, panel iii), and FIG. 17, panel i) and ii)). In these linear cascades, the substrate comprising the primer cleaved by the initial MNAzyme differs from the substrate eventually cleaved by the Dz released from the hairpin Dz/BL complex or synthesised by copying the Dz template in the partially hairpinned Dz template/BL complex.

FIG. 17 depicts two exemplary linear cascades utilising a strategy for primer activation for initiation. The cascades are based upon the use of an active primer to hybridize with the loop of the complete hairpined (panel i)) or a partially hairpined Dz template structure in order to activate and/or synthesize new DNAzymes as outlined in FIG. 11. In FIG. 17 panel i) an MNAzyme (Mz1; thick dashed black line) could assemble in the presence of its target (AF1; thick grey dashed line) and could cleave its substrate (Substrate 1, drawn as a line containing left and right portion; the left contains a thick grey line, representing the inactive primer and the right is shown as a thin black dashed line). Substrate 1 can be labeled with a fluorophore (unfilled circle) and a quencher (filled small black circle). Cleavage of Substrate 1 by the MNAzyme may result in separation of the primer from the other cleaved fragment, and in doing so may create a detectable signal. The primer may remain inactive following cleavage due to the presence of a 2'3' cyclic phosphate at the 3' terminus (solid black pentagon shape), which may be a product of the MNAzyme cleavage reaction. T4 Polynucleotide kinase (T4 PNK; solid grey star shape) or a similarly appropriate enzyme may be used to catalyse the removal of the 2'3' cyclic phosphate resulting in activation of the primer (i.e. in the sense that it may be capable of hybridizing to a complementary nucleic acid and being utilized to initiate synthesis of a new strand of nucleic acid by a suitable polymerase enzyme). The Active Primer may thus hybridize with the loop of the complete hairpined DNAzyme (Hairpined Dz2; Dz2 portion drawn as a thick black dashed line, BL portion and hairpin loop drawn as a thick black line) and could be extended by a strand displacing polymerase (Pol; large filled black circle). The polymerase can use the BL portion as a template and synthesize a new copy of the Dz2, thus opening the hairpin and allowing the existing Dz2 to become single-stranded and active. Each Dz2, once displaced and active can then bind and cleave its substrate (Substrate 2; thin grey dashed line). Substrate 2 may be labeled with the same, or a different, fluorophore to Substrate 1 (shown as a filled grey star shape) and a quencher (filled black circle). Cleavage of Substrate 1 by Mz1 and Substrate 2 by the Active Dz2 may result in the separation of the fluorophore and quencher and the generation of one or two detectable fluorescent signals depending on whether one of two fluorophores are used to label Substrates 1 and 2.

Another linear cascade can be expanded upon to incorporate a RE, resulting in the continual synthesis of new DNAzyme molecules (as is outlined in FIG. 11). In FIG. 17 panel ii), the 'Partially blocked' hairpined Dz template (originally outlined in FIG. 19 panel i) C) may be used (Partially blocked hairpined Dz2 template (ASDz); thick black line). A partial Dz portion drawn as a thick black dashed line is present in the BL portion and the hairpin loop is drawn as a thick black line). The Dz2 template (ASDz) portion is the antisense of a functional DNAzyme, Dz2. The BLB comprises a partial sequence of a DNAzyme which contains mutated bases (shown as a small bulge) within Dz core of the BL which constitute catalycally inactivating mutations with respect to a complete DNAzyme. In the presence of the polymerase, the BL strand of may be extended, but due to the mutation, may not synthesise a functional Dz when it is opened by the primer. In the embodiment shown in panel ii), the Dz template strand also contains one strand of a recognition site for an RE, such that extension of the primer along the loop and Dz template portion may result in the formation of the complete RE recognition site. Consequently, an RE (shown as a solid black triangle shape) can selectively nick the newly synthesised strand in between the upstream primer and downstream Dz2 sequence. The nick may create a new primer which can be extended by the strand displacing polymerase to synthesize a new Dz2 copy and displace the existing Dz2. Both enzymes can then function together to synthesize and displace Dz2 molecules, each of which can function to cleave the Substrate 2, separating the fluorophore and quencher, providing a detectable fluorescent signal.

Figure 18:
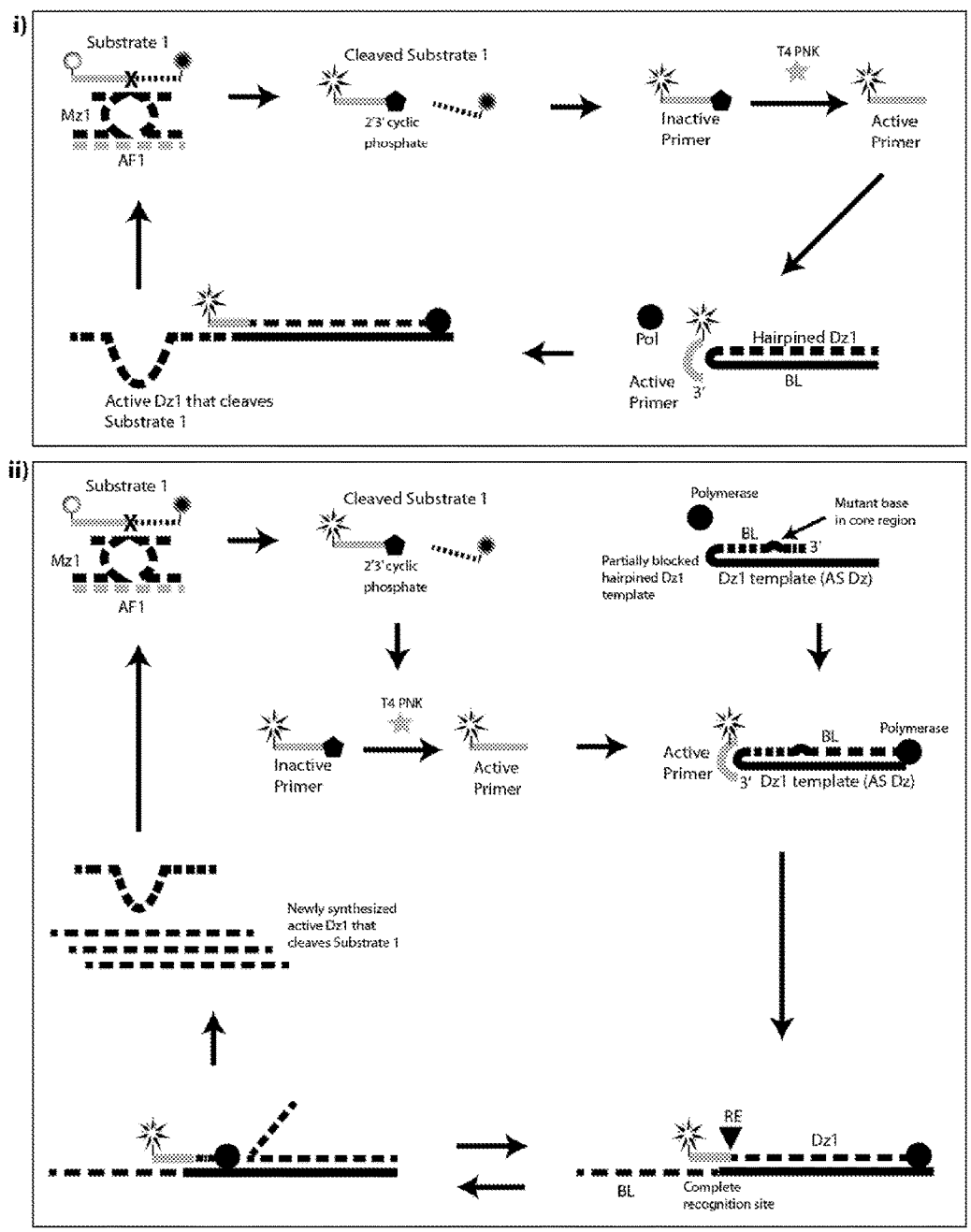
FIG. 18 Panels i) and ii) demonstrate circular feedback cascades from the strategies outlined in FIG. 17 panels i) and ii) respectively, whereby the newly activated or synthesised catalytic nucleic enzymes (depicted in this case as DNAzymes) are designed to cleave the same substrate as the MNAzyme which initiates the cascade reaction.

In still further embodiments, the linear cascades outlined in FIG. 17 panels i) and ii) may be modified to generate circular feedback cascades, and thereby result in the amplification of signal following the MNAzyme target recognition event. FIG. 18 panels i) and ii) depict a closed feedback loop the linear cascades outlined in FIG. 17 panels i) and iii) respectively. In each instance, the active Dz that is generated may be designed to recognise and cleave the same substrate as the MNAzyme (Substrate 1), thus leading to the generation of new Active Primer molecules.

Figure 13:
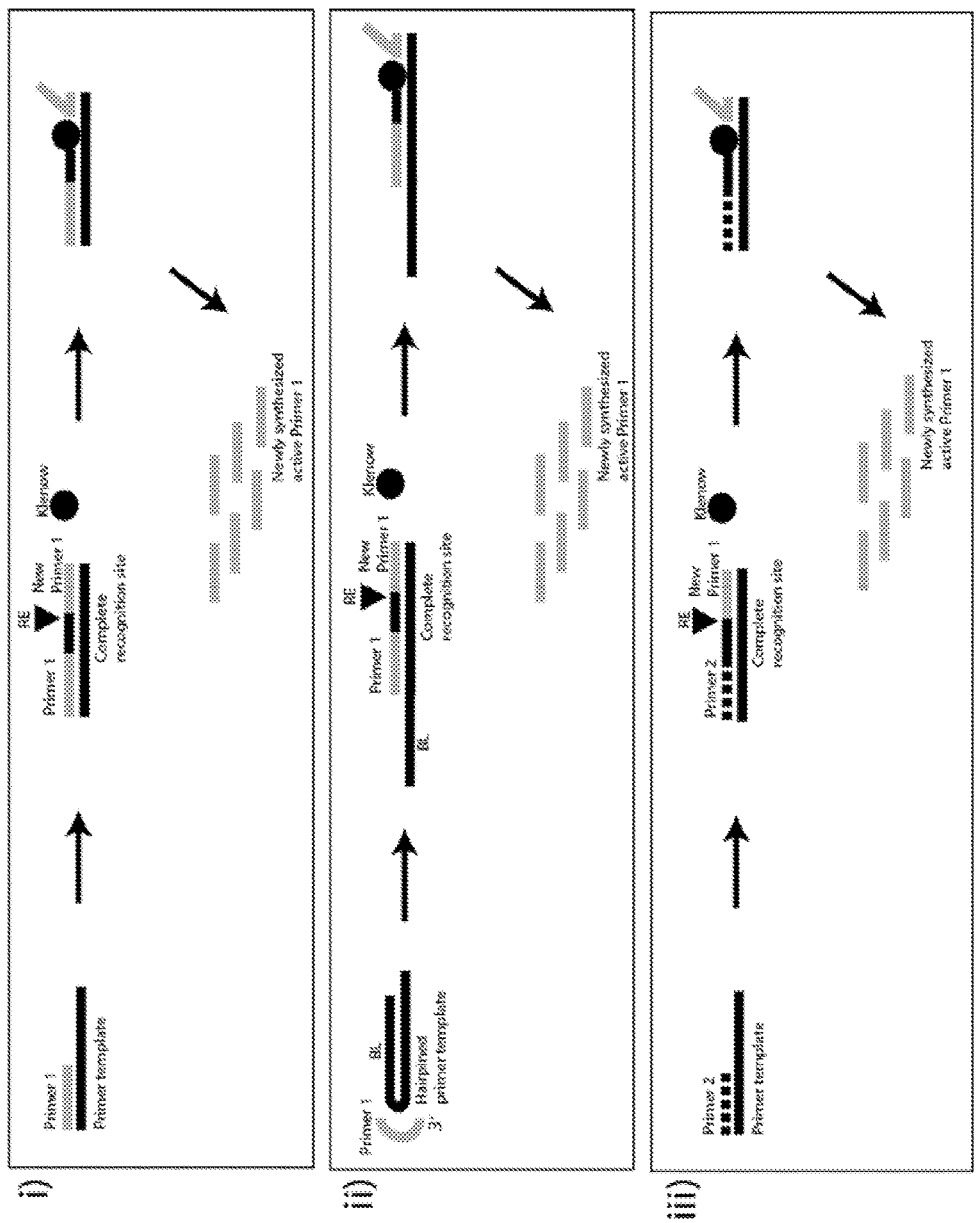
FIG. 13 outlines exemplary methods for the amplification of primers which may then, be used to activate and/or synthesize new DNAzymes as outlined in FIG. 11. The exemplary methods shown in panels i)-iii) involve the hybridization of an initial primer (Active Primer) to a template, which is extended by a strand displacing polymerase to create a new copy of the primer (New Primer) preceded by a RE recognition site. A continual cycle of RE nicking and polymerization may then occur to continuously synthesize new primers.

In further exemplary embodiments, additional molecule(s) may be present within the reaction which may act as a template for the synthesis and amplification of the primer. Referring to the exemplary strategies shown in FIG. 13, the template contains two regions which are complementary to primers and which are separated by one strand of a the recognition site of a RE. Referring to FIG. 13 panel i) hybridisation of the primer, referred to as 'Primer 1 to the first complementary region of the Primer template is initially favored as it is designed such that there is a greater number of nucleotides which can be hybridized. The primer may then be extended by a polymerase and this may result in the synthesis of the complete double stranded RE recognition site followed by an additional Primer 1 sequence. RE activity may then allow for the continual synthesis of Primer 1 via a cycle of RE cleavage, and then extension by the strand displacing polymerase. The additional primer-producing template molecule may exist as a linear single-stranded template as depicted in FIG. 13 panel i) or as a hairpined DNA molecule as depicted in FIG. 13 panel ii), whereby one strand contains the template for primer synthesis and the other is partially complementary to the primer template and helps to prevent the initial primer from hybridising to the second complementary region, since this event will not result in additional primer 1 synthesis. The additional primer-producing template molecule may also be initiated by the extension of a different primer, for example where primer 2 produces primer 1, as depicted in FIG. 13 panel iii).

Referring to the exemplary embodiments shown in FIG. 13 in more detail, panel i) shows how an initial primer (Primer 1; solid grey line) may hybridise to the primer template (Primer template; solid black line) where the Primer 1 may then be extended by the strand displacing polymerase (e.g. Klenow; filled black circle) to synthesize both a complete RE recognition site (solid black lines) followed by a new Primer 1 (solid grey line). The RE (filled black triangle) may then cleave the newly synthesized strand between the RE site and the New Primer 1 to create a nick which may then be extended by the polymerase to synthesize another New Primer 1, whilst displacing the previously bound Primer 1. This may result in a continual cycle of RE cleavage and polymerization and strand displacement to continuously synthesize new primers.

In panel ii) of FIG. 13 the initial Primer 1 may be used to initiate the continual synthesis of more New Primer 1, similar to the scheme outlined in panel i) however panel ii) illustrates a strategy that may use a Hairpined primer template (solid black line). The bottom strand of the hairpin molecule may contain the primer template and the top strand may contain a sequence partially complementary to the Primer template, with both linked by a non-complementary sequence forming the loop of the hairpin. The initial Primer 1 may hybridise to the loop and then may be extended by polymerase using the Primer template (the bottom strand of the hairpin) as template to copy.

In FIG. 13 panel iii), a different primer (Primer 2; dashed black line) may be used to initiate the continual synthesis of New Primer 1 via the same, process as outlined in panel i).

Figure 25:
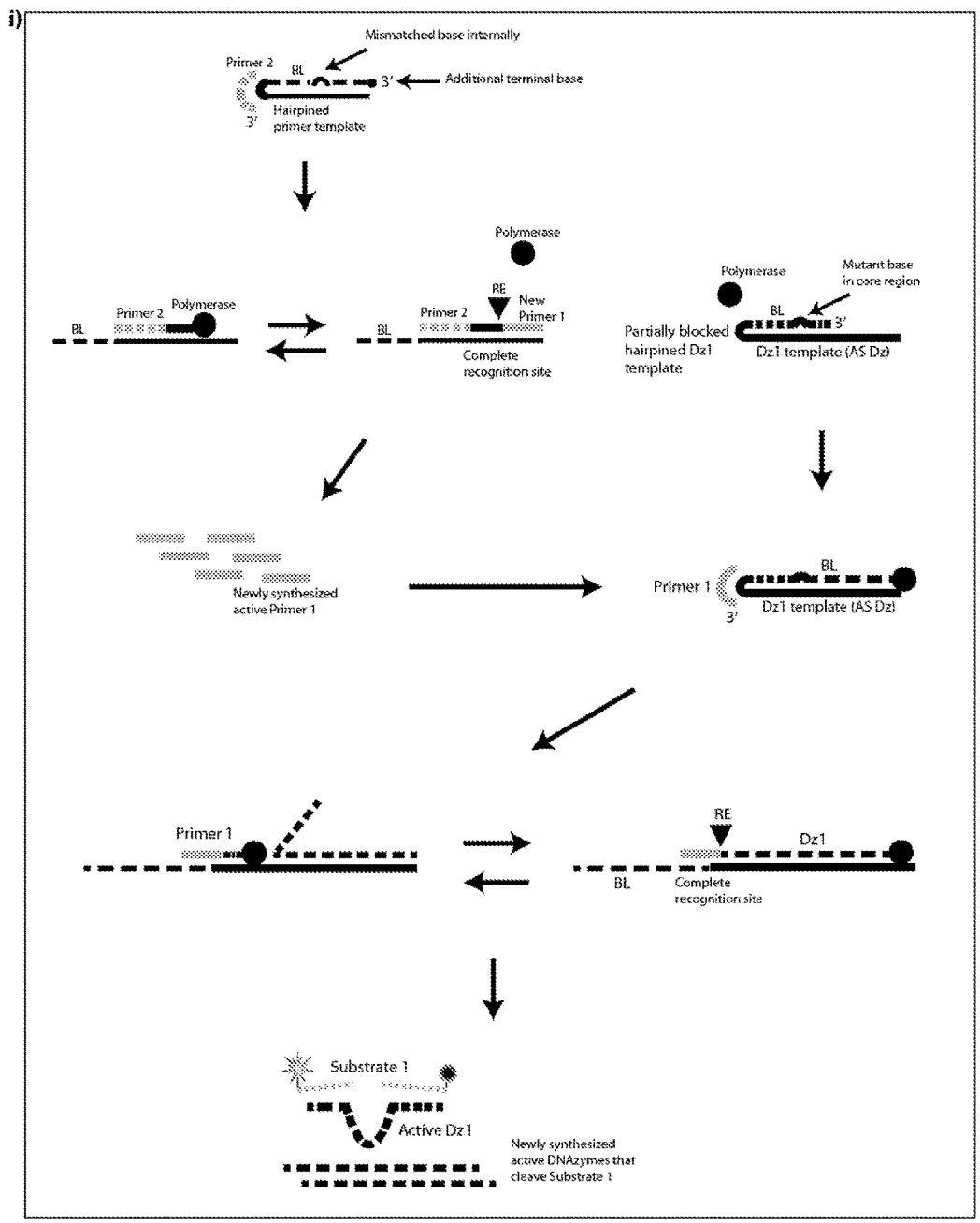
FIG. 25 panel i) broadens the strategy depicted in FIG. 13 panel iii) whereby a primer (Primer 2) can hybridize with a hairpined primer template molecule to initiate the synthesis of a different primer (Primer 1). Each Primer 1 can then initiate the synthesis of active DNAzyme (Dz1) molecules by hybridizing with a partially blocked hairpined Dz-template (previously outlined in FIG. 17 panel ii) and FIG. 23 panel i). Each Dz1 can then cleave Substrate 1, which may be labeled with a fluorophore and quencher dye pair, such that cleavage results in a detectable increase in fluorescent signal. Panel ii) provides a timecourse graph demonstrating the fluorescent signal achieved from the strategy depicted in panel i).
Figure 25:
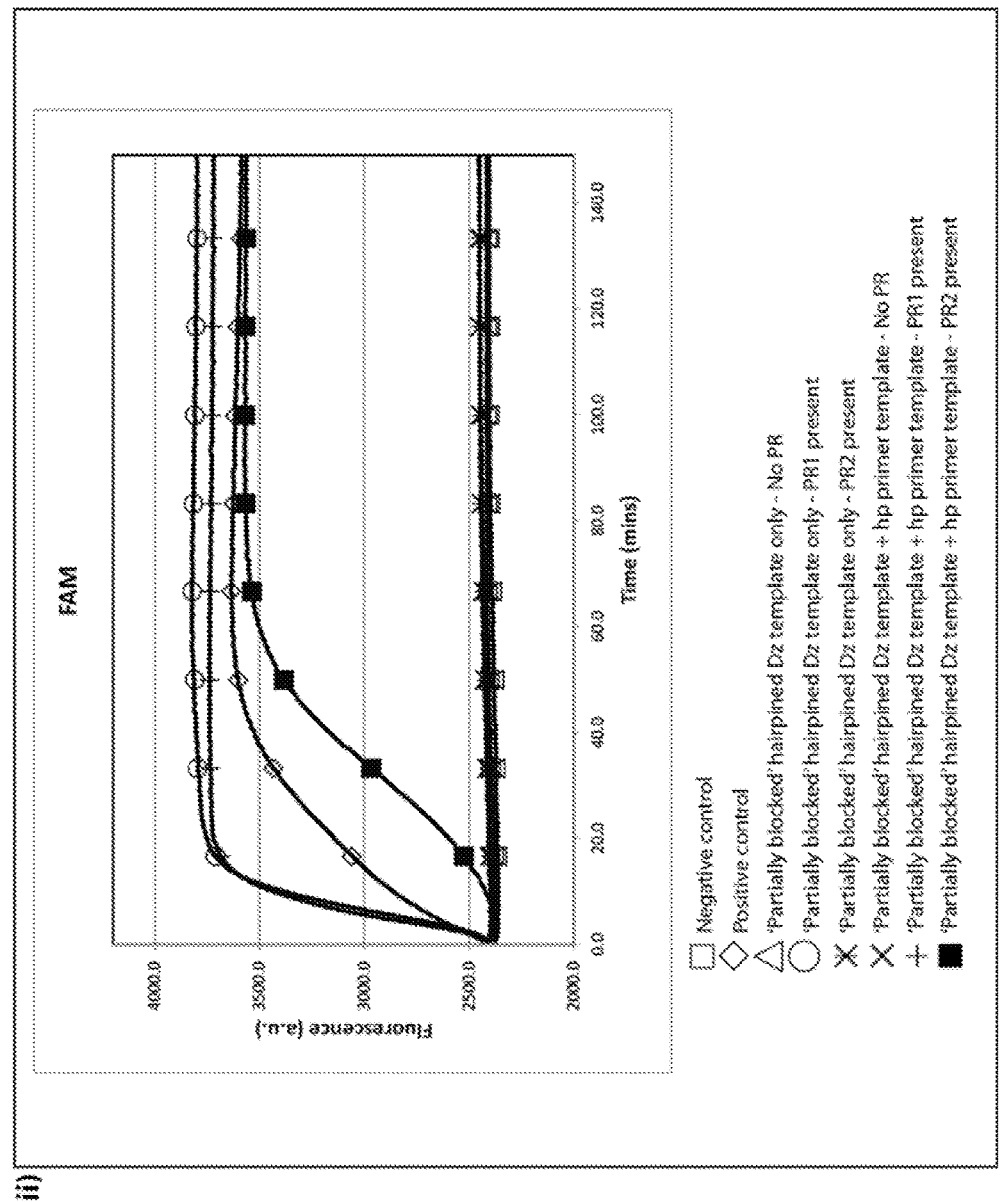

In FIG. 25 panel i) the strategy depicted in FIG. 13 panel iii) is broadened to demonstrate the use of a primer template molecule to facilitate the initiation of DNAzyme synthesis, using the method originally outlined in FIG. 11 panel i). Here the primer template (Hairpined primer template) is composed of a hairpined structure whereby one strand contains the template for synthesis of Primer 1 adjacent to one strand of a RE recognition site (all denoted by a thin black line), whilst the other strand of the primer hairpin (thin dashed black line) is partially complementary to the template. The partially complementary strand contains a mismatched base pairing between it and the template strand (drawn as a small bulge) as well as an additional base at the 3' terminus (small black circle) where the latter is not a part of the primer sequence. The internal mis-matched base pair reduces the affinity between the partially complementary strand of the hairpined primer template with the Primer 1 binding site of the Partially hairpined Dz1 template molecule. The additional base at the 3' terminus prevents the partially complementary strand from acting as a primer as this base does not share complementarity with the Primer 1 binding site. The purpose of the partially complementary strand is therefore to keep the primer template strand in a double-stranded formation, in the absence of extension of Primer 2, so as to prevent it from sequestration of newly-synthesized Primer 1 molecules.

Figure 14:
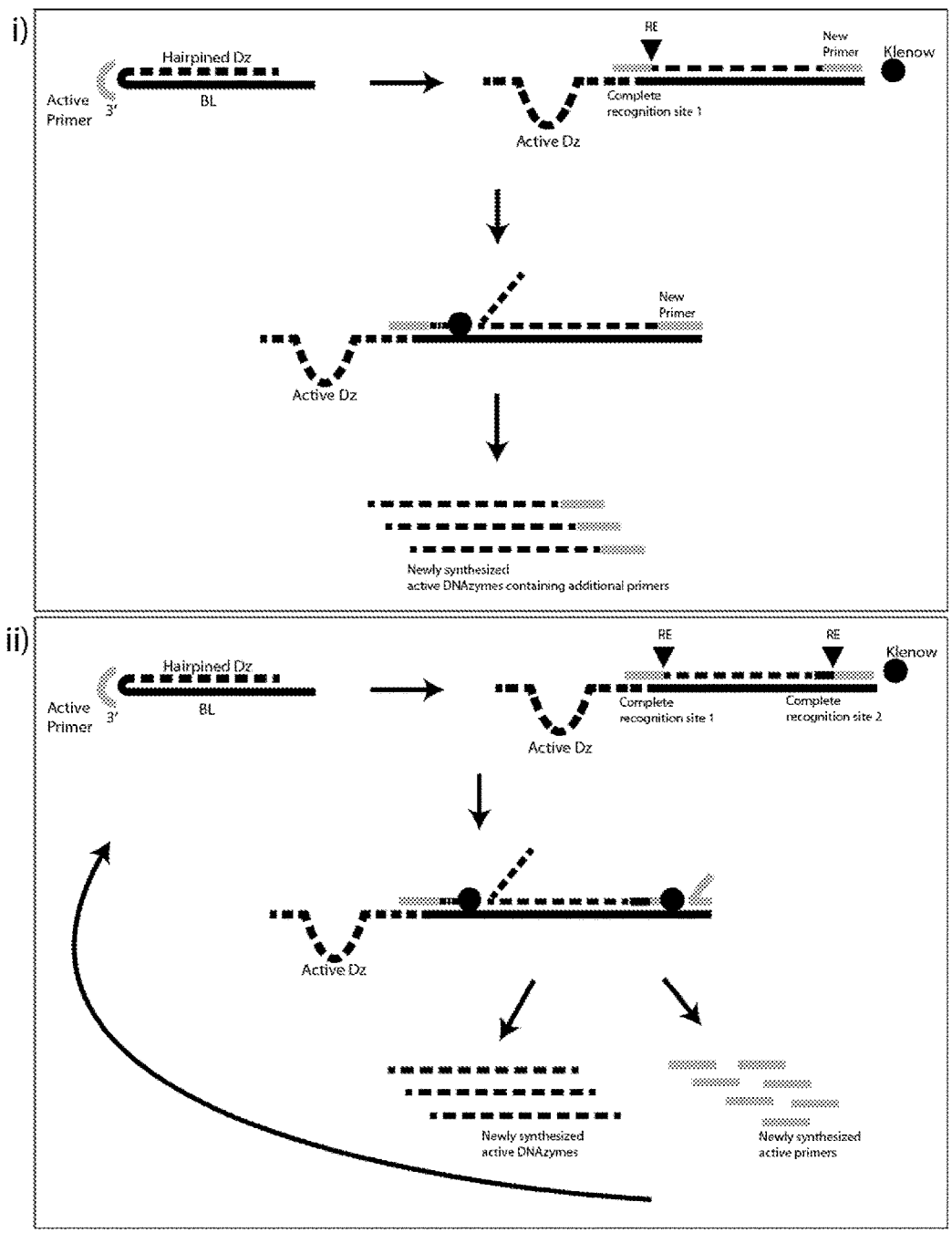
FIG. 14 outlines exemplary methods for the amplification of both DNAzymes and primers, both of which may then be used to activate and/or synthesize new DNAzymes as initially outlined in FIG. 11. The exemplary methods shown in panels i) and ii) involve the hybridization of an initial primer (Active Primer) to the hairpined DNAzyme/BL, which may be extended by a strand displacing polymerase to activate the DNAzyme that had been previously inactive due to the BL, and to create a newly synthesised copy of the DNAzyme, which could further be followed by a new copy of the primer (New Primer). The new primer may also be preceded by a nicking RE recognition site, such that the continual cycle of nicking and polymerization could be used to not only continuously synthesize new DNAzymes but also new primers.

The loop strand (thick black line) of the Hairpined primer template structure is complementary to Primer 2 (thick grey dashed line), such that when Primer 2 binds to this loop, Primer 2 can be extended by a strand-displacing polymerase, resulting in the simultaneous opening of the Hairpined primer template and synthesis of both a complete RE recognition site and adjacent Primer 1 (thick grey line). When a nicking restriction enzyme is present (filled black triangle), it can recognise the completed RE recognition site and selectively nick the newly synthesized strand at a region between the upstream Primer 2 and downstream Primer 1 sequence. Nicking therefore generates a new primer, which is extended by a strand displacing polymerase (filled black circle) to both synthesize another Primer 1 copy and displace the pre-existing copy from the template strand. This cycle of nicking, polymerization and displacement can then occur autonomously to generate multiple active Primer 1 molecules. Each Primer 1 can then initiate the synthesis of active DNAzyme molecules using the partially blocked hairpined Dz template method, which has been previously outlined in FIG. 17 panel ii) and FIG. 23 panel i). In other exemplary embodiments, the BL molecule may also contain the complementary sequence of an additional primer, such that extension of the original primer on the BL template may synthesize both a new copy of a complete DNAzyme linked to an additional primer (FIG. 14 panel i)). As illustrated in FIG. 14 panel i) the initial Active Primer (thick grey line) hybridizes to the loop of a Hairpined DNAzyme (Hairpined Dz)/BL complex. The top strand of the Hairpined Dz/BL complex is a DNAzyme (thick dashed black line) and is shown hybridized to the bottom strand containing the BL (thick black line), where both are linked together via a non-complementary loop (also a thick black line). Extension of the Active Primer by a strand displacing polymerase (Klenow; filled black circle) opens the Hairpined DNAzyme/BL complex and synthesizes a new strand using the BL as a template. The newly synthesised strand contains an additional copy of the DNAzyme and a New Primer. The new DNAzyme copy is preceded by a complete recognition site for a restriction enzyme, such that cleavage by an RE (filled black triangle) creates a nicked oligonucleotide which can be extended by Klenow to create a new copy of the DNAzyme and New Primer, whilst displacing the existing copy. The nick may be generated by creating a recognition site for (and using) a nicking enzyme that is only capable of cleaving the strand in the recognition site formed by primer hybridisation and/or extension. Alternatively, the nick may be generated by creating a recognition site for a restriction enzyme capable of cleaving both strands, and modifying the loop strand to incorporate a phosphorothioate linkage, thus preventing cleavage of the loop strand by the restriction enzyme. This cycle of nicking and extension acts to continuously synthesize new DNAzymes containing primers at one end. The New Primer portion of each DNAzyme/primer strand can then hybridize to a new hairpined DNAzyme loop to re-initiate the cycle.

The newly synthesised primer may also be preceded by an additional RE recognition site, such that RE activity allows for the continual synthesis of the additional primers (FIG. 14 ii)). As illustrated in FIG. 14 panel ii) the same process of additional DNAzyme and primer synthesis from panel i) is outlined, however the additional primer itself is preceded by a complete recognition sequence for an RE. As a result, in addition to the cycle of nicking and extension to create new DNAzyme copies, this can also occur to create new primers which are separated oligonucleotides from the new DNAzyme, with the two cycles occurring simultaneously. The nicking may be facilitated by using a nicking enzyme or incorporating a phosphorothioate linkage to prevent cleavage of the loop strand by a non-nicking restriction enzyme.

Detection of Ionic Compounds

In another strategy, methods are provided for determining the absence of ionic compounds, detecting the presence of ionic compounds, and/or quantifying ionic compounds, in a sample (e.g. an environmental sample or a biological sample). The ionic compounds may be monovalent or divalent ions. The ionic compounds may be metal ion cofactors required for the activity of a catalytic nucleic acid enzyme.

The methods comprise providing a molecular complex as described herein (a molecular switch) and at least one additional component capable of activating the switch to thereby provide a detectable signal. The functional activity of the additional component may be reliant on the presence of the ionic compound in a sample to be tested. For example, the methods may comprise contacting a sample suspected of containing ionic compounds with a molecular switch comprising a first catalytic nucleic acid enzyme hybridised to and functionally inactivated by a blocker oligonucleotide, and an initiator catalytic nucleic acid enzyme (e.g. a DNAzyme, ribozyme, assembled MNAzyme, or components capable of assembly into an MNAzyme).

In the presence of the ionic compound, the initiator catalytic nucleic acid enzyme may be capable of directly dissociating the BL and first catalytic nucleic acid enzyme of the complex, thereby rendering the first catalytic nucleic acid enzyme functionally active and capable of (directly or indirectly) providing a detectable signal (e.g. as illustrated in any one of FIG. 1, 3, 4, 6, 7, 8, 9, 10, 11, 13, 14, 16, 17 or 18).

Alternatively, in the presence of the ionic compound the initiator catalytic nucleic acid enzyme may be capable of catalytically modifying another additional component that is contacted with the sample to thereby provide a component (e.g. an RL, NRF, primer, polymerase template) capable of interacting with the molecular complex and (directly or indirectly) dissociating the first catalytic nucleic acid enzyme and BL. The dissociation may render the first catalytic nucleic acid enzyme functionally active and capable of (directly or indirectly) providing a detectable signal. (e.g. as illustrated in any one of FIG. 1, 3, 4, 6, 7, 8, 9, 10, 11, 13, 14, 16, 17 or 18).

In either case, the catalytic function of the initiator catalytic nucleic acid is dependent on the presence of the ionic compound, which is required as a co-factor for catalytic function of the initiator enzyme. In the absence of the ionic compound, the initiator catalytic nucleic acid enzyme cannot function and therefore cannot affect dissociation of the first catalytic nucleic acid enzyme, or the RL or the NRF from the BL.

The ionic compound may additionally be a co-factor required for catalytic activity of the first catalytic nucleic acid enzyme of the complex.

Consequently the methods may utilise catalytic nucleic acids (e.g. DNAzymes, ribozymes, aptazymes and/or MNAzymes) which require a specific metal ion cofactor for catalytic activity, to detect the presence or determine the absence of the metal ion in a sample (e.g. environmental or biological samples). For example, the methods may facilitate DNAzyme-mediated detection of $Pb^{2+}$ in an environmental sample such as water.

Methods Using Multiple Enzymes to Analyze Multiple Targets

The skilled person will recognize that the methods provided herein may be used to detect a single target per reaction, or to detect multiple targets in a single reaction. When detecting multiple targets, one or more MNAzymes may be used depending on the assay and what is to be detected. For example, a single MNAzyme may suffice when detecting multiple related structures such as, for example, a group of sequences sharing a critical sequence (recognized by the MNAzyme) and varying only, for example, in length, or in sequence outside of the critical sequence. Any sequence with the critical sequence could be detected. Multiple MNAzymes are contemplated to be useful when detecting related sequences differing by as little as a single nucleotide or even where vastly different targets are to be detected, and it is desirable to know the presence or absence of each. Similarly, in some embodiments a single MNAzyme substrate will suffice, while in others a unique MNAzyme substrate is required for a unique BL to allow detection of each of several targets. In some embodiments, the methods may allow detection of a variety of different types of target in one reaction (e.g. a nucleic acid target and a protein).

Figure 26:
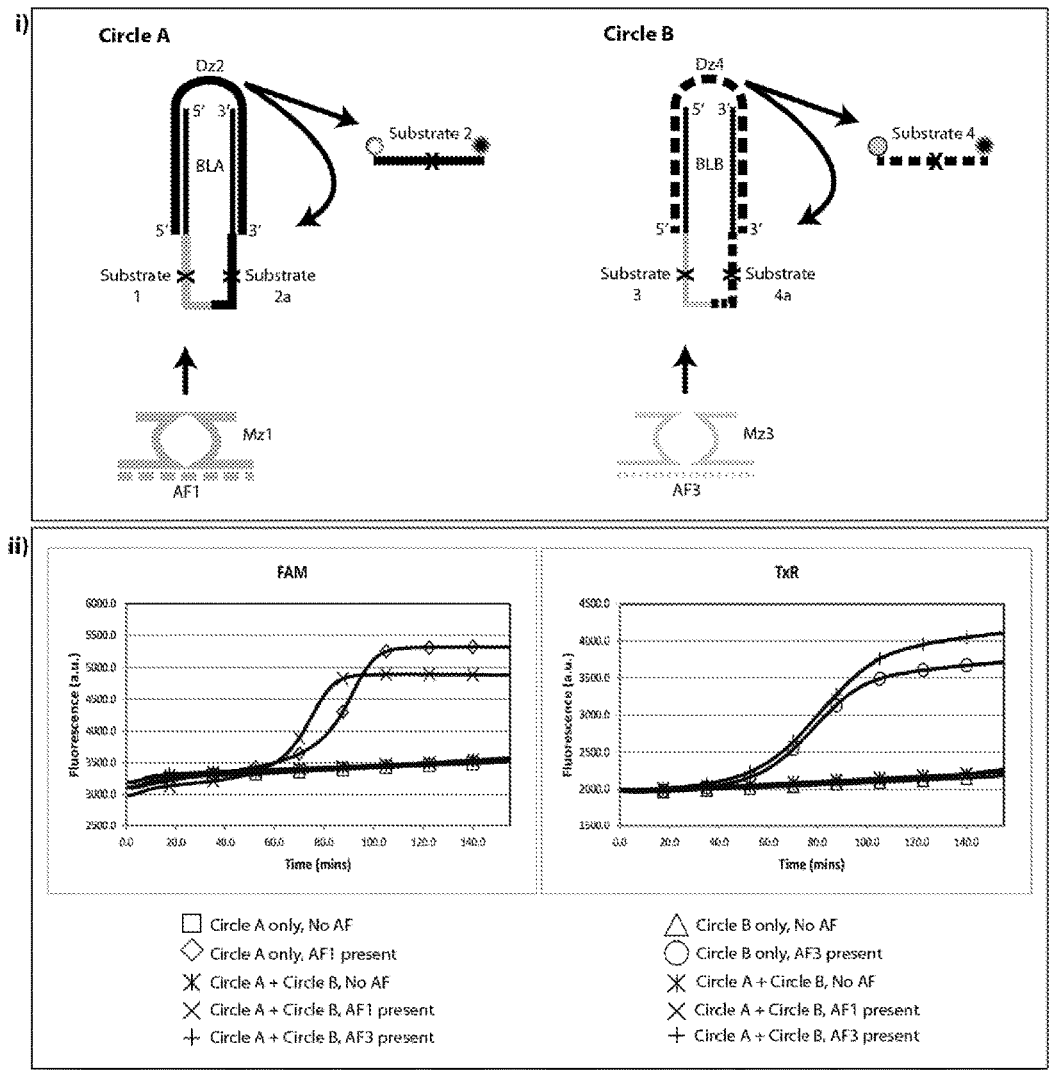
FIG. 26 panel i) exemplifies a multiplex detection reaction involving two independent, auto-catalytic quasi circles (Circle A and Circle B). Each cascade reaction is shown to function independently despite all components being together in the same reaction chamber. The cascades are initiated by the cleavage of a different substrate present within each BL that are cleaved by different MNAzymes, each of which can function following assembly with their unique target sequences. Each cascade results in the modification of a different fluorescent reporter substrate, with different fluorescent dyes also used for each probe to distinguish between the two reactions and to indicate the presence of each target. Panel ii) provides two timecourse graphs demonstrating the fluorescent signal from both fluorescent reporter probes in the multiplex reaction strategy depicted in panel i).

Referring specifically to FIG. 26, a multiple target detection schema is demonstrated whereby two independent, auto-catalytic quasi circles (FIG. 21 panel i)) are placed together in the same reaction chamber. The two quasi circles (Circle A and Circle B) can function independently and are utilised to amplify the signal following the detection of two independent target sequences. Circle A is comprised of a DNAzyme (Dz2, thick black line) and BLA, consisting of sequence at its 5' and 3' ends (thin black line), which hybridizes to Dz2 resulting in the temporary inactivation of Dz2. BLA also contains an intermediate region consisting of the adjacent sequences of Substrate 1 (thick grey line) and Substrate 2 (Substrate 2a; thick black line). Substrate 1 can be cleaved by Mz1 (thick grey line), in the presence of its target assembly facilitator (AF1, thick grey dashed line). Substrate 2 is capable of being cleaved by Dz2, once it has been released from BLA via Mz1 cleavage of Substrate 1.

Circle B is comprised of a DNAzyme (Dz4, thick black dashed line) and BLB, which consists of sequence at its 5' and 3' ends (thin black line), which hybridizes to Dz4, resulting in the temporary inactivation of Dz4. BLB also contains an intermediate region consisting of the adjacent sequences of Substrate 3 (thin grey line) and Substrate 4 (Substrate 4a; thick black dashed line). Substrate 3 can be cleaved by Mz3 (thin grey line), in the presence of its target assembly facilitator (AF3, thin grey dashed line). Substrate 4 is capable of being cleaved by Dz4, once it has been released from BLB via Mz3 cleavage of Substrate 3. To monitor each cascade reaction independently, Substrate 2 and Substrate 4 are also provided as linear sequences which have been modified with different fluorophores (unfilled circle for Substrate 2 and filled grey circle for Substrate 4) and a quencher (filled black circle) to individually monitor cleavage by Dz2 and Dz4 respectively.

Methods Using Insoluble and Solid Supports

It is also to be understood that generally the methods, whether multiplexed or not, are applicable in solution, or when combined with an insoluble support or solid support on which one or more of the group including BL molecule, RL molecule, primer, NRF, DNAzyme, MNAzyme component (substrate, partzyme or assembly facilitator/target), RE, polymerase template, exonuclease and/or strand displacing polymerase may be bound, attached or tethered. The features of such systems will be generally understood by the skilled person in the knowledge of the methods and variations discussed herein. Thus, the invention is not to be considered limited to the literal teachings herein, but is capable of being modified and varied consistent with the principles and scope of the teachings provided herein and the knowledge in the art.

For example, methods for detecting targets using an MNAzyme, whereby either a BL containing an MNAzyme substrate, a DNAzyme or any other catalytic nucleic acid to which the BL is designed to be hybridized may be anchored to a support, are contemplated herein. In some embodiments, the BL is attached to a support. The support may be an insoluble material, or a matrix which retains the substrate and excludes it from freely moving in the bulk of the reaction mixture. Such supports are known in the art for immobilizing or localizing substrates, including nucleic acid targets. The skilled person will appreciate that the support can be selected from a wide variety of matrices, polymers, and the like, in a variety of forms including beads convenient for use in microarrays, as well as other materials compatible with the reaction conditions. In certain embodiments, the support may be a plastic material, such as plastic beads or wafers, or that of the well or tube in which a particular assay is conducted. In certain embodiments the support may be microcarriers or nanocarriers. In certain embodiments the support may be encoded.

The attachment of the BL to a support may be designed such that upon hybridization of the BL with the DNAzyme or other catalytic nucleic acid to form the molecular switch complex, excess DNAzyme or other catalytic nucleic acid can be washed away from the solid support leaving, for example, a 1:1 ratio between the two molecules that make up the molecular switch. Cleavage of a BL labelled with a fluorophore (F) and quencher (Q) by a second DNAzyme or MNAzyme may result in fluorophore being released into the bulk of the reaction mixture, leaving the quencher attached to the support. Thus, the detectable signal may vastly increase as the quencher portion and the detectable portion are separated upon cleavage. In an alternate embodiment the fluorophore-containing detectable portion may remain attached after cleavage. This may allow localization of the signal on the support. In certain instances it is contemplated that the fluorophore may be free in solution. In addition, the DNAzyme or other catalytic nucleic acid may also be released into solution away from the BL which remains attached to the solid support, preventing any unwanted re-hybridization following BL cleavage.

Figure 24:
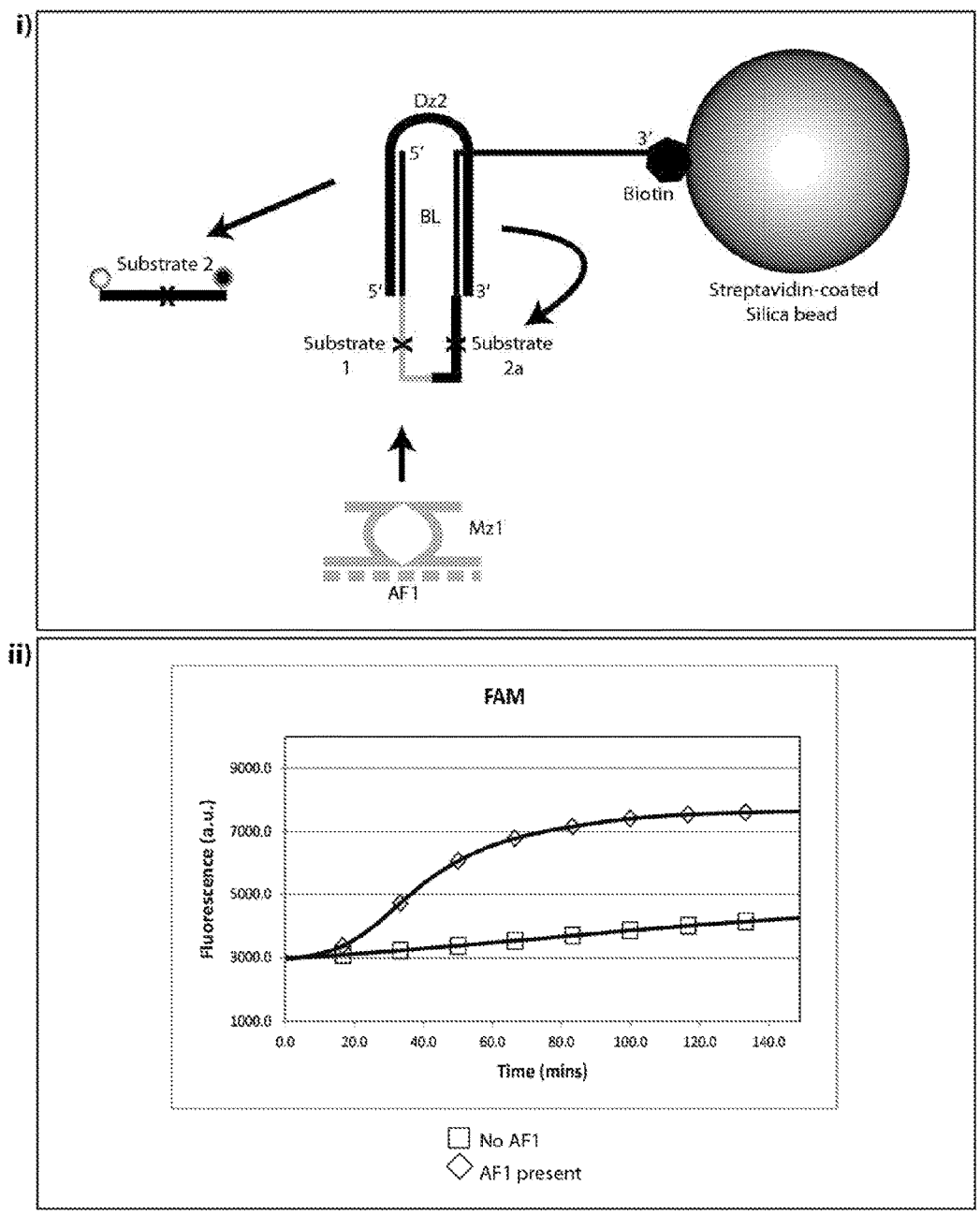
FIG. 24 panel i) depicts the attachment of an auto-catalytic DNAzyme quasi-circle (FIG. 21 panel i)) to a solid support. An exemplary strategy is outlined whereby the BL of the quasi-circle is tethered to a solid support by an attachment strategy, for example, via use of biotin to attach the BL to a streptavidin-coated silica microsphere. The BL of the circle comprises an additional spacer region with the 3' terminus modified with a biotin moiety, such that the BL can attach to the microsphere via a biotin-streptavidin bond. The DNAzyme then hybridizes with the BL via Watson-Crick base pairing. An MNAzyme (Mz1) that assembles in the presence of its target assembly facilitator (AF1), can be utilised to initiate the auto-catalytic cascade reaction that may occur whilst the quasi-circles remain attached to the solid surface. Panel ii) provides a timecourse graph demonstrating the fluorescent signal achieved from the strategy depicted in panel i).

FIG. 24 panel i), outlines an example of a solid support strategy whereby the BL of an auto-catalytic, DNAzyme quasi-circle (outlined in FIG. 21) is tethered to a silica microsphere. Here, the BL of the quasi circle is comprised of two DNAzyme binding regions (thin black lines), linked by the adjacent sequences of Substrate 1 (thin grey line) and Substrate 2 (Substrate 2a; thick black line). An additional spacer region exists 3' of the DNAzyme-binding region and is modified at its very 3' terminus with a biotin moiety (filled black hexagon). The BL can hybridise with a DNAzyme (Dz2; thick black line) and both are incubated with the silica microspheres (beads) that have been streptavidin-coated (drawn as a large grey circle). The BL and the microsphere therefore attach to one another via a biotin-streptavidin bond and the Dz2 hybridizes with the BL via Watson-Crick base pairing. When microspheres containing tethered quasi circles are placed in contact with an MNAzyme (Mz1; thick solid grey lines) that assembles in the presence of its target assembly facilitator (AF1; thick dashed grey line), the Mz1 can cleave Substrate 1 in the BL, which initiates an auto-catalytic cascade whereby Dz2 is released from the BL and can cleave Substrate 2 within other attached BL molecules. Dz2 may also cleave a separate, independent Substrate 2 (thick black line), which in this example is not attached to a microsphere, but may be labeled with a fluorophore (unfilled circle) and quencher (filled black circle), such that cleavage results of Substrate 2 in a detectable fluorescent signal.

Alternatively, the BL which is attached to the bead could be directly labeled such that cleavage of either Substrate 1 by the MNAzyme and/or Substrate 2 by Dz2 could result in signal which is free in solution (if the quencher is closer than the fluorophore to the attachment site); or it could result in signal which is associated with the bead (if the fluorophore is closer than the quencher to the attachment site).

Optimisation of Methods

The skilled person will readily understand that the methods described herein may be optimized using a variety of experimental parameters in order to enhance the detection, identification and/or quantification of a target. The particular experimental parameters that are optimized, and the level of such optimization, will depend upon the particular method being employed and the particular target being sought to be detected, identified and/or quantified. Such parameters include, but are not limited to time, temperature, pH, concentration and identity of salts and buffers, concentrations of oligonucleotides, concentration of protein enzymes (RE, exonuclease, strand displacing polymerase), co-factors, detergents, cations and other reagents including, but not limited to, dimethylsulfoxide (DMSO), EDTA, ATP, glycerol, length of complementarity, GC content and melting point (Tm) of nucleic acids components of MNAzymes, molecular switch complexes, BL/RL complexes, BL/NRF complexes, Dz template/BL complexes and BL/primer complexes.

In some embodiments, for example, those methods involving detection of specific nucleic acid sequences, experimental parameters including the temperature at which the method is performed, may be optimized so as to discriminate between binding of an MNAzyme component to a target nucleic acid that does or does not comprise a sequence variation. The temperature at which such methods may be performed may be in the range of about 20° C. to about 96° C., about 20° C. to about 75° C., 20° C. to about 60° C. or about 20 to about 55° C.

In certain embodiments, optimized reactions for practicing the methods described herein are provided. In such optimized reactions, the signal detected is increased by up to 10%, 20%, or 30% above un-optimized reactions. More preferred reaction conditions may improve signal detected by at least 35%, or 40%, and preferably up to 50% or more. In other embodiments, optimized reactions may provide an increase of catalytic activity of more than 50%, and up to 66%, 75% or even 100%. In still other embodiments, a fully optimized reaction method may offer 100%, 200% or even 300% or more increase in signal detection. Other preferred reaction conditions can improve the catalytic activity by up to 1000% or more over methods practiced with unoptimized reaction conditions. A highly preferred reaction condition for optimizing the methods provided herein is the inclusion of certain divalent cations. The catalytic activity of most nucleic acid enzymes and protein nucleic acid-modifying enzymes may be influenced in a concentration-dependent fashion by the concentration of divalent cations. Preferred optimized reactions are optimized for one or more of $Ba^{2+}$, $Sr^{2+}$, $Mg^{2+}$, $Ca^{2+}$, $Ni^{2+}$, $Co^{2+}$, $Mn^{2+}$, $Zn^{2+}$, and $Pb^{2+}$.

Aptamers

Persons skilled in the art will readily appreciate that the methods described herein may be performed with aptamers, wherein said aptamers may facilitate the detection, identification and/or quantification of targets including targets other than nucleic acids.

Methods of using MNAzymes to detect targets, including non-nucleic acid entities are contemplated. Such methods may use aptamers which may comprise a nucleic acid or protein, polypeptide, or peptide or combination thereof that has the ability to recognize one or more ligands. Aptamers may bind target ligands, for example, proteins, polypeptides, peptides or nucleic acids, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivatives, portions or combinations thereof, or any other entity.

Preferred aptamers herein may comprise short single-stranded DNA or RNA oligomers or peptides that can be isolated from complex libraries of synthetic nucleic acids or peptides by an iterative process of adsorption, recovery, and reamplification. Aptamers may therefore be generated against almost any target/ligand, ranging from small molecules such as amino acids or antibiotics, to protein and nucleic acid structures. In some embodiments, aptamers include, for example, nucleic acid binding molecules which are preferably generated by evolution and selection techniques. Aptamers may comprise DNA or RNA molecules, or a combination of both, including but not limited to the nucleotide analogues as per, for example, Table 1 above.

Figure 28:
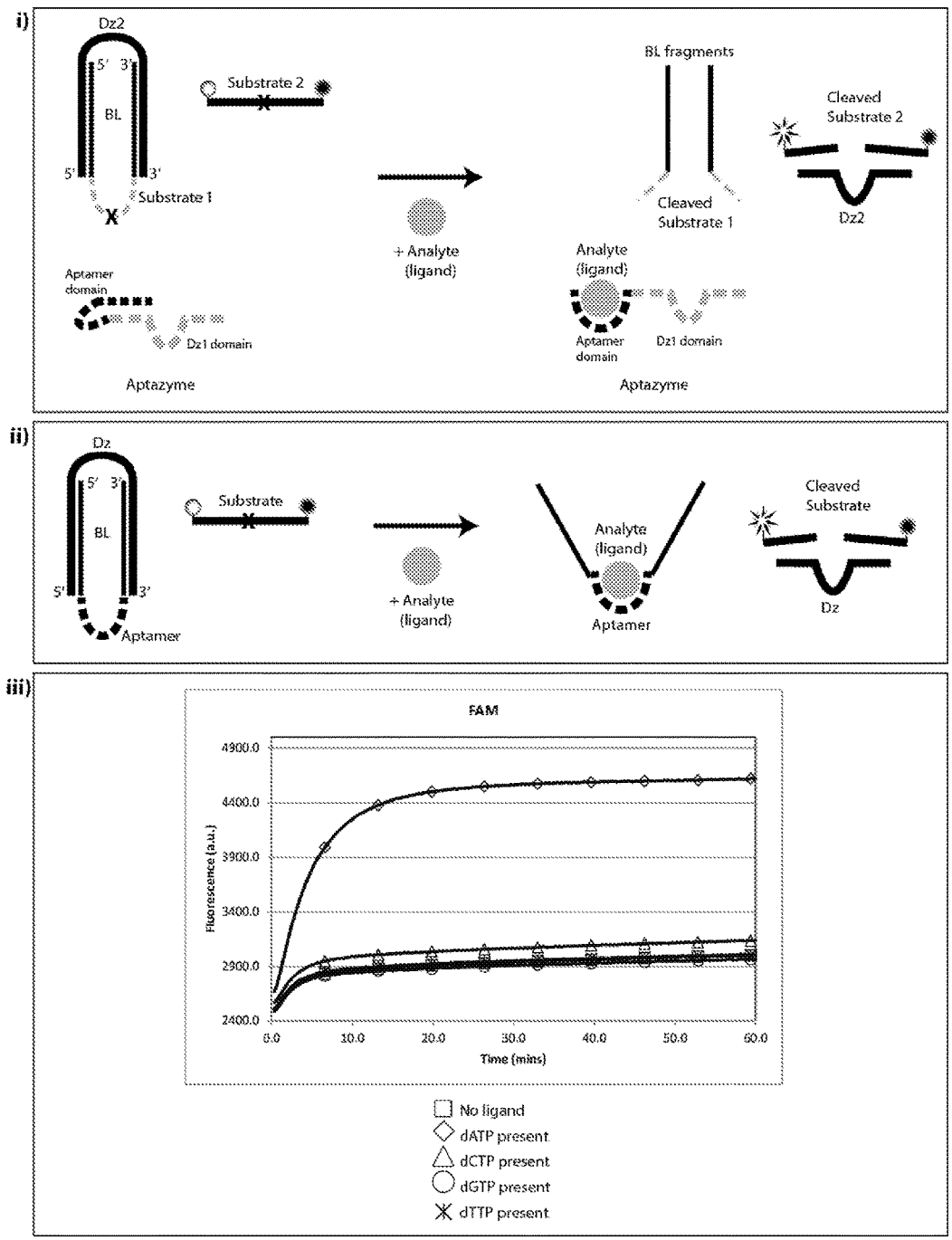
FIG. 28 depicts strategies for the use of an aptamer to recognise a target analyte/ligand and promote the dissociation of a BL from another functional molecule, in this case a DNAzyme, which may result in the restoration of the DNAzymes catalytic activity. Two non-limiting examples of this strategy are depicted in panels i-ii). Panel i) outlines the use of an Aptazyme to cleave a substrate (Substrate 1) present within a BL of a molecular switch complex, which functions only in the presence of its target analyte/ligand. The Aptazyme is comprised of a DNAzyme domain (Dz1 domain) and an Aptamer domain. The presence of the Aptamer domain results in the temporary inactivation of the DNAzyme domain of the Aptazyme. In the presence of the target analyte/ligand, the Aptamer region binds to the analyte, resulting in a conformational change of the Aptazyme structure which in turn allows the DNAzyme domain to adopt an active conformation thus restoring its catalytic activity. Cleavage of Substrate 1 (Substrate 1) by the active Aptazyme results in the release of a second DNAzyme (Dz2), which was initially hybridized to the BL. The active Dz2 can then cleave its substrate (Substrate 2) which, if labeled with a fluorophore and quencher moiety, results in an increase in fluorescent signal.

Persons skilled in the art will appreciate that the aptamer may be incorporated into a DNAzyme, ribozyme or any of the MNAzyme components. DNAzymes and ribozymes which are coupled to aptamers are known in the art as aptazymes. Such aptazymes may have their catalytic activity switched on or off by the presence of ligands with affinity to their aptamer components. Further it will be appreciated that multiple aptamers can be incorporated into one or more of the partzyme oligonucleotide components. Referring specifically to FIG. 28 Panel i) an Aptazyme is depicted, which is comprised of a DNAzyme domain (Dz1 domain, thick grey dashed line) and an Aptamer domain (thick black dashed line). In this example, the presence of the Aptamer domain results in the temporary inactivation of the DNAzyme domain of the Aptazyme. In the presence of the analyte (ligand, large grey circle), the Aptamer domain binds to the ligand, resulting in a conformational change of the Aptazyme structure which in turn allows the DNAzyme domain to adopt an active conformation thus activating the catalytic activity of the DNAzyme domain. The active Aptazyme can then function to cleave a substrate (Substrate 1, thin grey dashed line) present within the BL (thin black lines) of a second molecular switch, consisting, for example, of a quasi-circular structure whereby the BL is hybridized to a second DNAzyme (Dz2, thick black line). Cleavage of Substrate 1 by the Aptazyme results in the separation of Dz2 from the BL, restoring the catalytic activity of Dz2. The active Dz2 can then cleave its substrate (Substrate 2, also a thick black line) which, if labeled with a fluorophore (small unfilled circle) and quencher (small filled black circle), results in an increase in fluorescent signal, depicted as the fluorophore now drawn as a star shape.

In further exemplary embodiments an aptamer sequence may be incorporated at the end of a partzyme (apta-partzyme) in a configuration whereby an active MNAzyme is only formed in the presence of the target analyte. In this case the partzymes for the MNAzyme detection strategy include; a standard partzyme; an apta-partzyme which is a partzyme with an aptamer incorporated into one of its ends; an assembly facilitator which binds to both the apta-partzyme and the partzyme enabling assembly of an active MNAzyme (in the presence of target); a substrate; and an assembly inhibitor which hybridises to the apta-partzyme in a region which spans at least part of the aptamer sequence and part of the partzyme sequence. In the absence of a target the assembly inhibitor binds to the apta-partzyme thus blocking binding (and cleavage) of the reporter probe substrate. In the presence of a target, the target binds to the aptamer sequence of the apta-partzyme, preventing the binding of the assembly inhibitor and allowing the binding and cleavage of the MNAzyme substrate. As such, an active MNAzyme can only form and modify an MNAzyme substrate in the presence of target.

In other exemplary embodiments where the target is not required for the assembly of an MNAzyme an aptamer may be incorporated into an assembly facilitator. A related strategy is also envisaged where an aptamer sequence is incorporated at the end of a partzyme (apta-partzyme) in a configuration whereby an active MNAzyme is only formed in the presence of the target. The oligonucleotide components for such a detection strategy include; a standard partzyme; an apta-partzyme which is a partzyme with an aptamer incorporated into one of its ends; an assembly facilitator which binds to both the apta-partzyme and the partzyme enabling assembly of an active MNAzyme (in the presence of target); an MNAzyme substrate; and an assembly inhibitor, which hybridises to the apta-partzyme in a region which spans at least part of the aptamer sequence and part of the partzyme sequence. In the absence of a target ligand, the assembly inhibitor binds to the apta-partzyme thus blocking binding (and cleavage) of the MNAzyme substrate. In the presence of a ligand, the ligand binds to the aptamer sequence of the apta-partzyme, preventing the binding of the assembly inhibitor and allowing the binding and cleavage of the MNAzyme substrate. As such, an active MNAzyme can only form and cause fluorescent signal generation in the presence of target ligand.

Further, it will be appreciated by one skilled in the art that the assembly inhibitor may be a separate molecule or may be incorporated into one of the components that participate in the MNAzyme complex.

It will be also appreciated by one skilled in the art that in the above strategy an inhibitor sequence may be a separate molecule or may be incorporated into one of the components that participate in the MNAzyme complex. Further, one or more aptamers may be incorporated into any of the oligonucleotide components, including the partzymes, the assembly facilitator or the substrate. Further the aptamer may be incorporated into either end of any one of these oligonucleotides.

Persons skilled in the art will appreciate that the aptamer may share base pair complementarity to a DNAzyme, ribozyme or any of the MNAzyme components, which may result in temporary inactivation of their catalytic activity. When the target analyte is present, it may bind to the aptamer, separating it from the DNAzyme, ribozyme or MNAzyme component, which may result in the restoration of catalytic activity of the DNAzyme, ribozyme or MNAzyme component, which may then be used to initiate the cascade reactions described herein by acting as the catalytic nucleic acid which may modify substrates present within BL molecules.

In further exemplary embodiments, one or more aptamer sequences or portions thereof may be present within a BL molecule. In the presence of a target ligand, the target ligand may bind to the aptamer, which may change conformation of the aptamer and may result in the separation of the catalytic nucleic acid, RL, primer, polymerase template or NRF from the BL and the subsequent restoration of their catalytic, releasing, priming, template and nuclease initiation activities respectively. Referring specifically to FIG. 28, panel ii) depicts the inclusion of an Aptamer within a BL of a molecular switch. In panel ii) a DNAzyme (Dz, thick black line) is hybridized with a BL, resulting in its temporary inactivation. The BL consists of 5' and 3' ends which hybridize to the Dz (thin black lines), connected by a central portion which is not complementary to the Dz, but is comprised of an Aptamer sequence (thick black dashed line). In the presence of the target analyte (or ligand, large filled grey circle), the Aptamer may bind to the ligand which may result in a conformational change of the BL resulting in the separation of the BL from the Dz, restoring the catalytic activity of the Dz. The active Dz may then function to cleave its substrate (Substrate, thick black line) which may be labeled with a fluorophore (small unfilled circle) and quencher (small filled black circle) and may result in an increase in fluorescent signal, depicted as the fluorophore now drawn as a star shape.

Kits

The present invention also provides kits for practising the methods disclosed herein. Typically, kits for carrying out the methods of the present invention contain all the necessary reagents to carry out the method.

The kits may comprise any composition according to the present invention or component(s) thereof. By way of non-limiting example only, the kits may comprise catalytic nucleic acid enzymes (e.g. MNAzymes and/or partzyme components thereof, DNAzymes, aptazymes and/or ribozymes), exonucleases, endonucleases, RL, BL, NRF, primers, polymerase templates and substrates (e.g. substrates for catalytic nucleic acid enzymes, exonucleases, endonucleases). The substrates may comprise one or more primers.

The kits may be fragmented kits or combined kits as defined herein. Fragmented kits comprise reagents housed in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion. Such kits may also include a container which will accept the test sample, a container which contains the reagents used in the assay, containers which contain wash reagents, and containers which contain a detection reagent. Typically, a kit of the present invention will also include instructions for using the kit components to conduct the appropriate methods. Kits and methods of the invention may be used in conjunction with automated analysis equipment and systems, for example, including but not limited to, real time PCR machines.

For example, the kit may comprise a first container and second container. The first container may comprise a molecular switch comprising a catalytic nucleic acid (e.g. a DNAzyme) existing in a functionally inactivated form due to hybridisation with a BL. The second container may comprise one or more oligonucleotide or protein components capable of dissociating the BL from the enzyme in a target dependent or a target-independent manner. The kits may be fragmented kits or combined kits as defined herein.

The kits may also comprise one or more other containers, containing for example, wash reagents, and/or other reagents as required in the performance of the methods of the invention.

For application of detection, identification or quantitation of different targets, a single kit of the invention may be applicable, or alternatively different kits, for example containing reagents specific for each target, may be required. Methods and kits of the present invention find application in any circumstance in which it is desirable to detect, identify or quantitate any entity.

The present invention will now be further described in greater detail by reference to the following specific examples, which should not be construed as in any way limiting the scope of the invention.

EXAMPLES

Example 1

The following example demonstrates the inactivation of a DNAzyme by hybridization to a complementary blocking oligonucleotide (BL). The BL contains two regions of sequence complementarity to the DNAzyme, which are connected by a non-complementary region that acts as a substrate for a second, independent catalytic nucleic acid (in this case, another DNAzyme). The 5' and 3' ends of the BL were designed to either (i) hybridize with the 3' and 5' ends, respectively, of the DNAzyme (Dz2) to form a linear duplex structure with a looped out cleavable substrate sequence (depicted schematically in FIG. 1 panel i)) or, (ii) they were designed to hybridize with the 5' and 3' ends respectively, forming a quasi-circular structure (depicted schematically in FIG. 1 panels ii) and iii)). In this example, the quasi-circular structure is demonstrated and cleavage of the substrate region (Substrate 1a) is performed by a DNAzyme (Dz1), rather than the MNAzyme depicted in FIG. 1 panel ii). Cleavage of the substrate region should result in the release and subsequent re-activation of the previously inactive DNAzyme (Dz2).

Oligonucleotides

In the current example, the BL (SEQ ID NO: 1; C(4)Sub45(24:24)(2)-FB) is composed of (i) 5' and 3' ends that are complementary to a portion of Dz2 (SEQ ID NO: 2; DzK(10:9)) and (ii) a central portion, connecting the 5' and 3' ends, that consists of Substrate 1a, which is equivalent to the sequence of Substrate 1 (SEQ ID NO: 3; Sub45) but lacks the 5' terminal 'A' nucleotide and the 3' terminal 'GAA' nucleotides. The BL was internally labeled with a 6-fluorescein ("6-FAM") moiety at the 15$^{th}$ nucleotide (a. 'T') from the 5' end and a Black Hole Quencher 1 ("BHQ1") moiety at the 34$^{th}$ nucleotide (a 'T') from the 5' end. Thus the fluorophore and quencher moieties were located at the junction of the Substrate 1a region and DNAzyme-complementary regions. The BL is utilized to block the activity of Dz2 by pre-hybridizing the BL with Dz2.

A DNAzyme (Dz1—SEQ ID NO: 4; Dz45(9:10)), is utilized to cleave the Substrate 1a portion of the BL. This cleavage event facilitates the release of Dz2, allowing it to act upon Substrate 2 (SEQ ID NO: 5; Sub2). In this example, Substrate 2 was end-labeled with a Texas Red moiety on the 5' end and a Black Hole Quencher 2 ("BHQ2") moiety on the 3' end.

To measure the effectiveness of the cleavage of the BL by Dz1, the signal from the cleavage of the BL was compared to a Positive Control 1 signal of the cleavage of the independent substrate Substrate 1 by Dz1. Substrate 1 does not contain any additional 5' and 3' sequence complementary to Dz1 and was end-labeled with a 6-FAM moiety on the 5' end and an Iowa Black (IB) quencher moiety on the 3' end.

The sequences of these oligonucleotides are listed from 5' to 3' below. Bases in uppercase are deoxyribonucleotides and bases in lowercase are ribonucleotides. Underlined bases represent regions in the BL that are complementary to a portion of Dz2. Bases in italics refer to regions corresponding to a substrate sequence within the BL molecule. Boxed bases represent the catalytic core of the DNAzymes. Nucleotides highlighted in grey represent the bases in Dz2 that are complementary to and blocked by, the underlined bases in the BL molecule.

```
Blocker oligonucleotide (BL):
C(4)Sub45(24:24)(2)-FB
                                          SEQ ID NO: 1
AGCCTCCCTGGGCAT CGGGTCCCguCTCCTTTGTAAGGTTTCCTCTCG, Dz2: DzK(10:9)
                                          SEQ ID NO: 2
GCCCAGGGA GGCTAGCTACAACGA GAGGAAACCT Substrate 1: Sub45-FIB
                                          SEQ ID NO: 3
ACGGGTCCCguCTCCTTTGGAA Dz1: Dz45(9:10)
                                          SEQ ID NO: 4
CCAAAGGAGA GGCTAGCTACAACGA GGGACCCGT Substrate 2: Sub2-TRB2
                                          SEQ ID NO: 5
AAGGTTTCCTCguCCCTGGGCA
```

Reaction Components

Reactions A, B, C, D, E and F were set up to contain the following oligonucleotides as listed in Table 4B, with reference to oligonucleotides listed in the previous section and structures illustrated in FIG. 1 panel ii). For reactions E and F, the BL and Dz2 were initially pre-hybridized together for 30 minutes at room temperature before the addition of any further oligonucleotide components.

TABLE 4B

| Reaction A (Negative control 1) | Reaction B (Positive control 1) | Reaction C (Negative control 2) | Reaction D (Positive control 2) | Reaction E (BL only) | Reaction F (Trigger present) |
|---|---|---|---|---|---|
| Sub45-FIB 200 nM | Sub45-FIB 200 nM | Sub2-TRB2 200 nM | Sub2-TRB2 200 nM | Sub2-TRB2 200 nM | Sub2-TRB2 200 nM |
| | Dz45(9:10) 100 nM | | | | Dz45(9:10) 20 nM |
| | | | DzK(10:9) 100 nM | DzK(10:9) 100 nM | DzK(10:9) 100 nM |
| | | | | C(4)Sub45(24:24)(2)-FB 200 nM | C(4)Sub45(24:24)(2)-FB 200 nM |

Oligos were purchased from Integrated DNA Technologies (IDT) or Biosearch technologies. All reactions contained 1×PCR buffer II (Applied Biosystems), nuclease free water (Ambion) and 25 mM of $MgCl_2$ (Ambion). The total volume of all reactions was 25 μL. All reactions were performed in duplicate at 45° C. in a Bio-Rad® CFX96 thermocycler and fluorescence signal was measured simultaneously in both Channel 1 (FAM) and Channel 3 (TxR) to monitor FAM and Texas Red, respectively and was programmed to be read every 5 seconds (scan mode: all channels) for a total of 40 minutes.

Results

Figure 2:
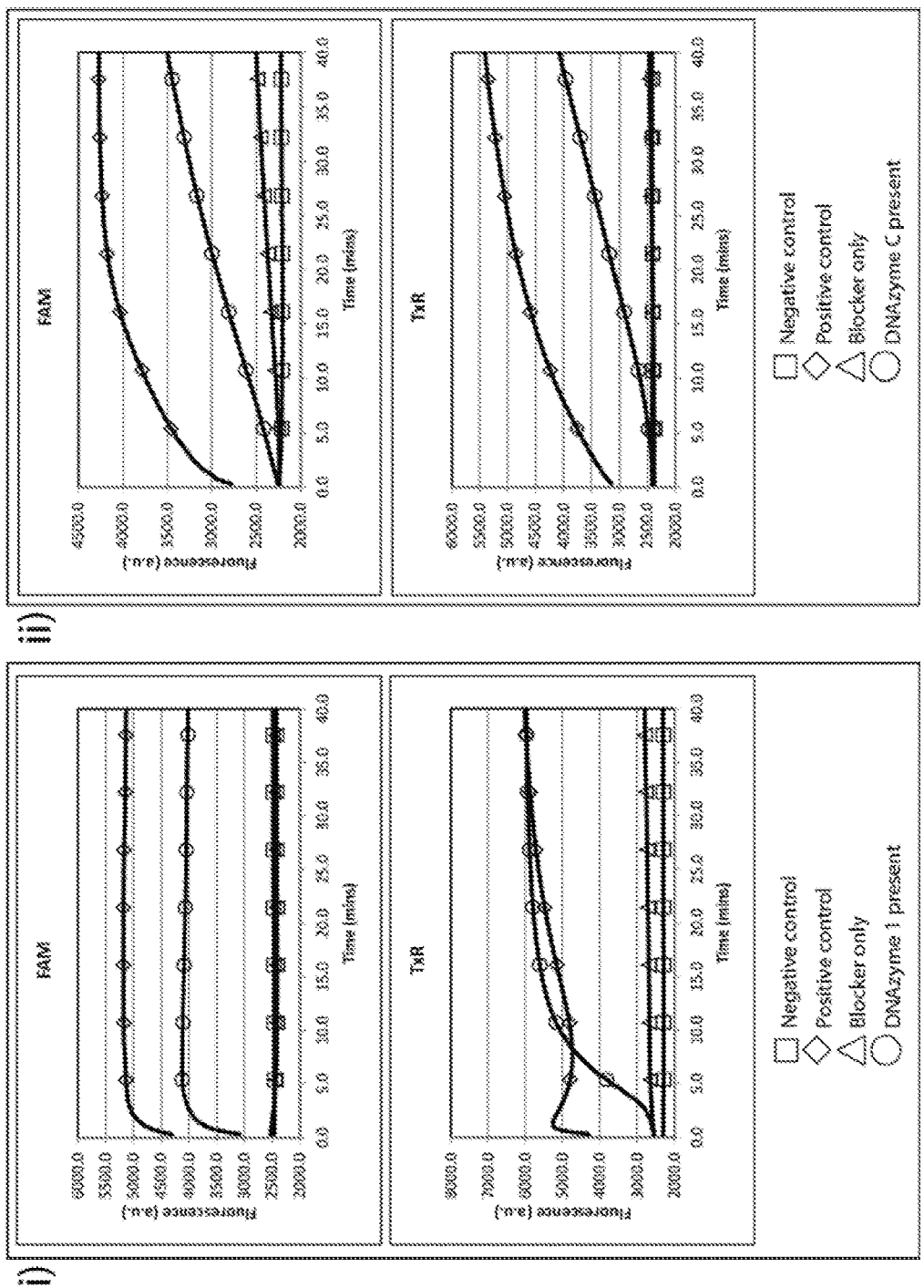
FIG. 2 provides timecourse graphs depicting fluorescent signal achieved from the DNAzyme quasi-circle strategy from circles with either 1 and 2 inactivated DNAzymes (depicted diagrammatically in FIG. 1 panels ii) and iii) respectively). In these cases, reactions were initiated by DNAzymes.

FIG. 2 panel i) shows results from the quasi-circle containing one DNAzyme molecule. Here, Substrate 1a that exists as part of the BL molecule is itself labelled with a FAM fluorophore and quencher. Substrate 2 which can be cleaved by Dz2 is labelled with a TxR fluorophore and quencher and hence the release and activation of Dz2 can be monitored by changes in fluorescence for TxR. As a result, both cleavage events can be monitored separately by measuring the fluorescent signal from both fluorophore emission wavelengths. The top graph in panel i) outlines the fluorescent signal from the FAM fluorophore and the bottom graph from the TxR fluorophore. For reaction E, where the quasi-circle exists on its own ('Blocker only' shown as a line with triangle symbols), there is no cleavage of Substrate 1a and as a result, no increase in FAM signal, in addition there is no significant increase in TxR signal during the reaction indicating that Dz2 is inactive when complexed with the BL. This is shown in comparison to the negative controls for FAM and TxR corresponding to reactions A & C respectively ('Negative control', line containing square symbols) which contains Substrate 1 and Substrate 2 only. For reaction F, where Dz1 is present and can cleave Substrate 1a however ('DNAzyme 1 present'; line containing circle symbols), there is an immediate increase in FAM signal, indicating Substrate 1a has been cleaved. This also results in a gradual increase in TxR signal indicating that Dz2 has now been released from the BL and is cleaving Substrate 2. This is shown in comparison to the positive controls for FAM and TxR, corresponding to reactions B & D respectively ('Positive control', line containing diamond symbols) which each contain the same concentration of Substrate 1 and Dz1 for FAM and Substrate 2 and Dz2 for TxR respectively as present in Reaction F.

Example 2

The following example demonstrates:
(i) the inactivation of two independent DNAzymes, Dz(A) and Dz(B), by hybridization to two complementary blocking oligonucleotides (BL), BL(A) and BL(B).
(ii) the subsequent activation of Dz(A) and Dz(B), in the presence of a third DNAzyme, Dz(C), capable of cleaving the substrate portion of BL(A) and BL(B), resulting in the release of Dz(A) and Dz(B). The example demonstrates a system as illustrated in FIG. 1 panel iii) where Dz(C) of this example is equivalent to the first catalytic nucleic acid (Mz1 as per the Figure).

Oligonucleotides

BL(A) (SEQ ID NO: 6; C4Sub45(22:23)) is composed of (i) a 5' end complementary to the 5' end of Dz(A) (SEQ ID NO: 7; DzK(8:7)), (ii) a central portion that consists of Substrate 1a, which is equivalent to the sequence of Substrate 1 (SEQ ID NO: 3, Sub45) but lacks the 5' terminal 'A' nucleotide and the 3' terminal 'GAA' nucleotides and (iii) a 3' end complementary to the 3' end of Dz(B) (SEQ ID NO: 8; Dz6(8:7)).

BL(B) (SEQ ID NO: 9; C4Sub45T(21:24)) is composed of (i) a 5' end complementary to the 5' end of Dz(B), (ii) a central portion that consists of Substrate 1b which is equivalent to the sequence of Substrate 1 but lacks the 5' terminal 'AC' nucleotides and the 3' terminal 'GAA' nucleotides and (iii) a 3' end complementary to the 3' end of Dz(A).

In this example, the 5' and 3' ends of BL(A) and BL(B) are designed to hybridize with the 5' and 3' ends of the Dz(A) and Dz(B), such that a quasi-circular structure containing two inactive DNAzymes held together by two BL molecules forms (as outlined in FIG. 1 panel iii)).

A third DNAzyme, Dz(C) (SEQ ID NO: 10; Dz45(8:9)), is capable of cleaving the Substrate 1a portion of BL(A) and Substrate 1 b portion of BL(B), resulting in the release of Dz(A) and Dz(B) from the quasi-circular structure.

Dz (A) cleaves Substrate A (SEQ ID NO: 5, Sub 2), which in this example is labeled with a 6-fluorescein ("6-FAM") moiety at the 5' end and a Black Hole Quencher 1 ("BHQ1") at the 3' end.

Dz (B) cleaves Substrate B (SEQ ID NO: 11, Sub 6) which in this example is labeled with a TxR moiety at its 5' end and a Black Hole Quencher 2 ("BHQ2") moiety at its 3' end.

The sequences of the above oligonucleotides are listed from 5' to 3' below.

Bases in uppercase are deoxyribonucleotides and base in lowercase are ribonucleotides. Underlined bases represent regions in the BL that are complementary to a portion of DNAzyme. Bases in italics refer to regions corresponding to a substrate sequence within the BL molecule. Boxed bases represent the catalytic core of the DNAzyme. Nucleotides highlighted in grey represent the bases in the DNAzyme that are complementary to and blocked by, the underlined bases in the BL molecule.

```
Substrate A: Sub2-FB
                                           SEQ ID NO: 5
AAGGTTTCCTCguCCCTGGGCA BL(A): C4Sub45(22:23)
                                           SEQ ID NO: 6
TAGCCTCCCTGGGCGGGTCCCguCTCCTTTGTCACGCCTCTCGTT Dz(A): DzK(8:7)
                                           SEQ ID NO: 7
CCAGGGAGGCTAGCTACAACGAGAGGAAAC Dz(B): Dz6(8:7)
                                           SEQ ID NO: 8
GGAGGAAGGCTAGCTACAACGAGAGGCGTG BL(B): C4Sub45T(21:24)
                                           SEQ ID NO: 9
TAGCCTTCCTCCCGGGTCCCguCTCCTTTGGGTTTCCTCTCGTTG Dz(C): Dz45(8:9)
                                           SEQ ID NO: 10
CAAAGGAGAGGCTAGCTACAACGAGGGACCC Substrate B: Sub6-TRB2
                                           SEQ ID NO: 11
ATCACGCCTCguTCCTCCCAG
```

Reaction Components

Reactions A, B, C, D, E and F were set up to contain the following oligonucleotides as listed in Table 5, with reference to oligonucleotides listed in the previous section and structures illustrated in FIG. 1 panel iii). For reactions E and F, the BL molecules; BL(A), BL(B) and the DNAzymes Dz(A) and Dz(B) were initially pre-hybridized together for 30 minutes at room temperature before the addition of any further oligonucleotide components.

TABLE 5

| Reaction A (Negative control 1) | Reaction B (Positive control 1) | Reaction C (Negative control 2) | Reaction D (Positive control 2) | Reaction E (BL only) | Reaction F (Trigger present) |
|---|---|---|---|---|---|
| Sub2-FB 200 nM | Sub2-FB 200 nM | | | Sub2-FB 200 nM | Sub2-FB 200 nM |
| | | Sub6-TRB2 200 nM | Sub6-TRB2 200 nM | Sub6-TRB2 200 nM | Sub6-TRB2 200 nM |
| | DzK(8:7) 10 nM | | | DzK(8:7) 10 nM | DzK(8:7) 10 nM |
| | | | Dz6(8:7) 10 nM | Dz6(8:7) 10 nM | Dz6(8:7) 10 nM |
| | | | | C4Sub45(22:23) 20 nM | C4Sub45(22:23) 20 nM |
| | | | | C4Sub45T(21:24) 20 nM | C4Sub45T(21:24) 20 nM |
| | | | | | Dz45(8:9) 10 nM |

Oligos were purchased from IDT or Biosearch Technologies. All reactions contained 1×PCR buffer II (Applied Biosystems), nuclease free water (Ambion) and 25 mM of $MgCl_2$ (Ambion). The total volume of all reactions was 25 µL. All reactions were performed in duplicate at 45° C. in a Bio-Rad® CFX96 thermocycler. Fluorescence signal was measured simultaneously in both Channel 1 (FAM) and Channel 3 (TxR) to monitor FAM and Texas Red, respectively and was programmed to be read every 5 seconds (scan mode: all channels) for a total of 40 minutes.

Results

FIG. 2 panel ii) shows the results from the quasi-circle containing two DNAzymes present. In this case, the substrate sequences (Substrate 1a for BLA and Substrate 1b for BLB) that exists as part of both BL molecules was unlabelled. The substrate sequence (Substrate A) that can be cleaved by Dz(A), following its release and activation, is labelled with a FAM fluorophore and quencher dye and the substrate (Substrate B) that can be cleaved by Dz(B), following its release and activation, is labelled with a TxR fluorophore and quencher. As a result, both cleavage events can be monitored separately by visualizing the fluorescent signal from both fluorophore emission wavelengths. The top graph outlines the fluorescent signal from the FAM fluorophore and the bottom graph from the TxR fluorophore. For Reaction E, when the quasi-circle exists on its own ('Blocker only' shown as a line with triangle symbols), there is no cleavage of Substrate 1a or Substrate 1b and as a result, little to no increase in FAM or TxR signal, indicating that both Dz(A) and Dz(B) are inactive when complexed with the intact BL molecules. This is shown in comparison to the negative controls for both FAM and TxR, corresponding to reactions A & C respectively ('Negative control', line containing square symbols) which contain the same fluorescently-labelled Substrate A and Substrate B sequences only. For Reaction F, where DNAzyme C is present; (line containing circle symbols) there is a gradual increase in signal from both the FAM and TxR fluorophores indicating that both Dz(A) and Dz(B) are released from the quasi-circle and are now cleaving their respective substrates. This is shown in comparison to the positive controls for FAM and TxR corresponding to Reactions B and D respectively ('Positive control', line containing diamond symbols) which each contain the same concentrations of Substrate A and Dz(A) for FAM and Substrate B and Dz(B) for TxR respectively as in Reaction F.

Example 3

The following example demonstrates the inactivation of a DNAzyme by incorporation of the DNAzyme into a hairpin structure (Hairpined Dz) as outlined in (FIG. 4 panel iii). The DNAzyme can be rendered active in the presence of a Releaser oligonucleotide (RL) that is fully complementary to the BL portion of the hairpin (where the BL is only partially complementary to the full DNAzyme sequence). The RL lacks the complete DNAzyme sequence and therefore does not function as a catalytic DNAzyme itself.

Oligonucleotides

In the present example hairpined DNAzyme (SEQ ID NO: 12; hp(R6)Dz45BUB0(4)) capable of cleaving the Substrate (SEQ ID NO: 3; Sub45) was utilized. In this example Sub45 was labeled with a 6-fluorescein ("6-FAM") moiety at the 5' end and an Iowa Black quencher moiety ("IB") at the 3' end. A RL (SEQ ID NO: 13; RL-Dz45BUB0(4)) was employed to activate the hairpined DNAzyme. The catalytic activity of the hairpined DNAzyme was compared to that of a corresponding non-hairpined DNAzyme, (SEQ ID NO: 4; Dz45(9:10)).

The sequences of these oligonucleotides are listed from 5' to 3' below. Bases in uppercase are deoxyribonucleotides and bases in lowercase are ribonucleotides. Underlined bases represent the BL region in the hairpin that is complementary to the RL. Bases in italics refer to DNAzyme sequence within the hairpin structure. Boxed bases represent part of the catalytic core of the DNAzyme which is non-complementary to the BL portion of the hairpin and is thus looped out of the stem of the hairpin.

```
Substrate: Sub45-FIB
                                      SEQ ID NO: 3
ACGGGTCCCguCTCCTTTGGAA Non-hairpined control DNAzyme: Dz45(9:10)
                                      SEQ ID NO: 4
CCAAAGGAGAGGCTAGCTACAACGAGGGACCCGT hairpined DNAzyme: hp(R6)Dz45BUB0(4)
                                      SEQ ID NO: 12
CAAAGGAGAGGCTA GCTA CAACGAGGGACCCGTTTTTTACGGGTCCCTCG
TTGTAGCCTCTCCTTTGGTGATGACCTG Releaser (RL): RL-Dz45BUB0(4)
                                      SEQ ID NO: 13
CAGGTCATCACCAAAGGAGAGGCTACAACGAGGGACCCGT
```

Reaction Components

Reactions A, B, C and D were set up to contain the following oligonucleotides as listed in Table 6, with reference to oligonucleotides listed in the previous section and structures illustrated in FIG. 4 panel iii).

TABLE 6

| Reaction A (Negative control) | Reaction B (Positive control) | Reaction C (Hairpin only) | Reaction D (RL present) |
|---|---|---|---|
| Sub45-FIB 200 nM | Sub45-FIB 200 nM | Sub45-FIB 200 nM | Sub45-FIB 200 nM |
|  | Dz45(9:10) 10 nM |  |  |
|  |  | hp(R6)Dz45BUB0(4) 100 nM | hp(R6)Dz45BUB0(4) 100 nM |
|  |  |  | RL-Dz45BUB0(4) 100 nM |

Oligos were purchased from IDT or Biosearch technologies. All reactions contained 1×PCR buffer II (Applied Biosystems), nuclease free water (Ambion) and 25 mM of $MgCl_2$ (Ambion). The total volume of all reactions was 25 All reactions were performed in duplicate at 45° C. in a Bio-Rad® CFX96 thermocycler. Fluorescence signal was measured on Channel 1 (FAM) and was programmed to be read every 10 seconds (scan mode: FAM only) for a total of 40 minutes.

Results

Figure 5:
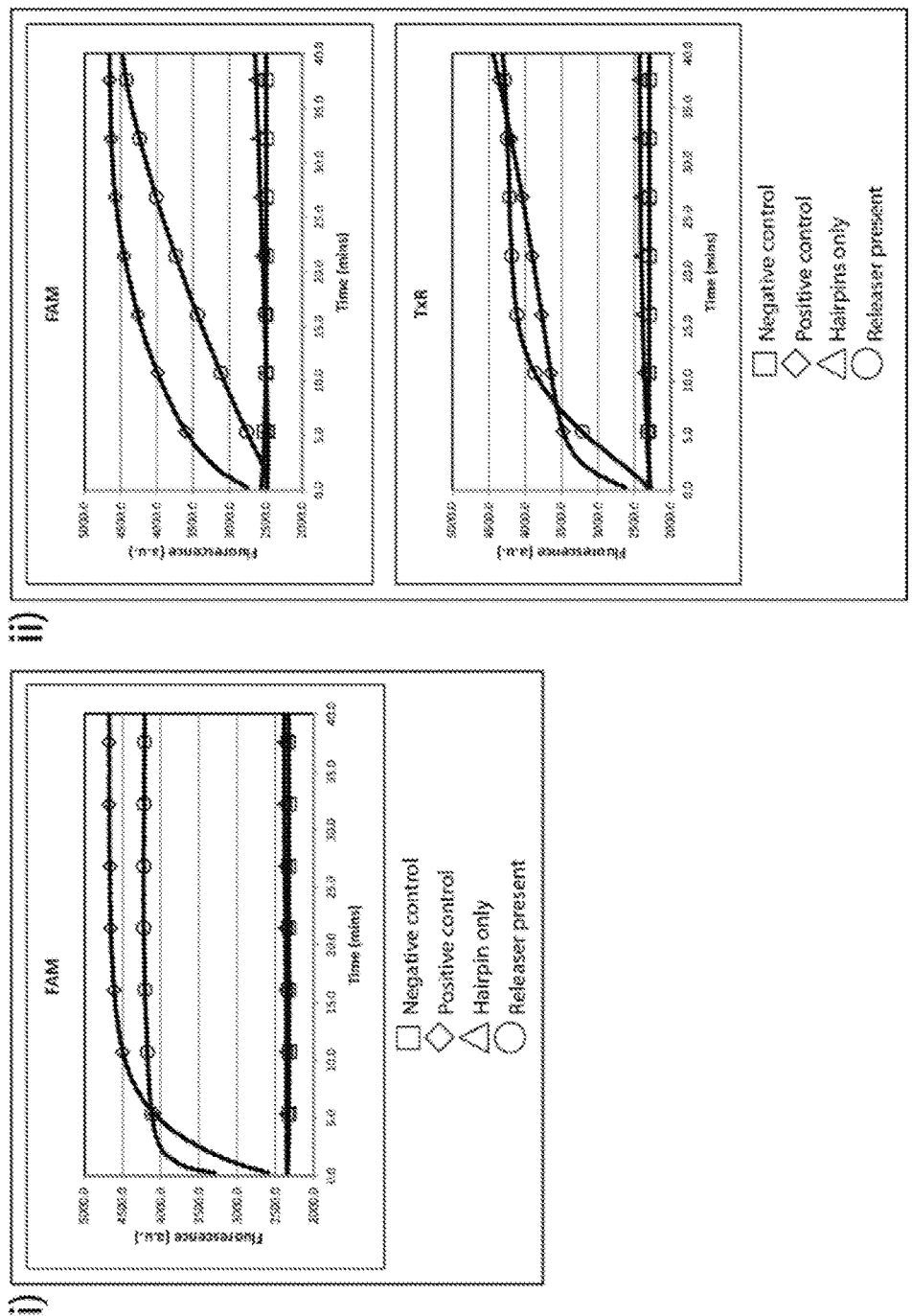
FIG. 5 provides timecourse graphs depicting the fluorescent signal achieved from the RL-mediated DNAzyme activation strategy from both a single hairpined DNAzyme and two linked hairpined DNAzymes (depicted diagrammatically in FIG. 4 panels iii) and iv) respectively).

FIG. 5, panel i) shows the results from a hairpined DNAzyme containing a single DNAzyme molecule. The substrate sequence that can be cleaved by the DNAzyme, following its activation by the RL, is labelled with a FAM fluorophore and quencher. The graph (FAM) outlines the fluorescent signal from this FAM fluorophore. For Reaction C when the hairpined Dz exists on its own ('Hairpin only' shown as a line with triangle symbols), there is no cleavage of the Substrate and as a result, no increase in FAM signal, indicating that the DNAzyme portion is kept inactive within the hairpined structure. This is shown in comparison to the negative control corresponding to Reaction A ('Negative control', line containing square symbols) which contains the same fluorescently-labelled substrate sequence only. For Reaction D, when a RL is present to open the hairpin ('Releaser present; line containing circle symbols), there is an immediate increase in FAM signal, indicating the DNAzyme portion is free and the Substrate has been cleaved. This is shown in comparison to the positive control corresponding to reaction B ('Positive control', line containing diamond symbols) which contains the same concentration of Substrate and non-hairpined control DNAzyme as present in Reaction D.

Example 4

The following example demonstrates the inactivation of two independent DNAzymes, by placing them within two hairpin DNA structures: Hairpined Dz1 and Hairpined Dz2 (as outlined in FIG. 4 panel iv). Each hairpin contains additional sequence, for Hairpined Dz1 the additional sequence is at the 5' end of its BLA stem and for Hairpined Dz2 the additional sequence is at the 3' end of its BLB stem. These additional sequences are complementary to each other, such that the two hairpin DNAzymes are linked together. This brings the DNAzymes into close proximity such that a single RL molecule can bind to its complementary sequence that exists on both the BLA and BLB and simultaneously open both of the hairpins, releasing each DNAzyme, so they are then able to cleave their substrates. The RL cannot act as DNAzyme itself as it is does not contain sufficient DNAzyme sequence to be catalytically active.

Oligonucleotides

In the present example, hairpined Dz1 (SEQ ID NO: 14; dhp6Dz2(5)M4) contains DNAzyme sequence capable of cleaving Substrate 1 (Sub2, SEQ ID NO: 5) and hairpined Dz2 (SEQ ID NO: 15; dhp5Dz6(3)) contains DNAzyme sequence capable of cleaving Substrate 2 (Sub6, SEQ ID NO: 11). Substrate 1 was labeled with a 6-fluorescein ("6-FAM") moiety at the 5' end and a Black Hole Quencher 1 ("BHQ1") at the 3' end (Sub2-FB) and Substrate 2 was labeled with a Texas Red moiety at its 5' end and a Black Hole Quencher 2 ("BHQ2") moiety at its 3' end (Sub6-TRB2). An RL (SEQ ID NO:16; RL-dhp6) was used to release the DNAzymes from the hairpin structure. The activity of each hairpined DNAzyme was compared to the corresponding non-hairpined control DNAzymes, Control DNAzyme 1 (Dz2, SEQ ID NO: 17) and Control DNAzyme 2 (Dz6, SEQ ID NO: 18).

The sequences of these oligonucleotides are listed from 5' to 3' below. Bases in uppercase are deoxyribonucleotides and bases in lowercase are ribonucleotides. Underlined bases represent the region in the hairpin that is complementary to the RL. Bases in italics refer to full DNAzyme sequence within the hairpin structure, whereas boxed bases represent part of the DNAzyme which is locked into the hairpin stem (complementary to BL portion). Grey highlighted sequences in Hairpined Dz1 and Hairpined Dz2 are complementary.

```
Substrate 1: Sub2-FB
                                        SEQ ID NO: 5
AAGGTTTCCTCguCCCTGGGCA Substrate 2: Sub6-TRB2
                                        SEQ ID NO: 11
ATCACGCCTCguTCCTCCCAG Hairpined Dz1: dhp6Dz2(5)M4
                                        SEQ ID NO: 14
GCCTCGACTGCACGGGTCGAGCTCACGAGGTTTCCTCTCGTTGTAGCTGCC
CAGGGAGGCTAGCTACAACGAGAGGAAACCTCGTG Hairpined Dz2: dhp5Dz6(3)
                                        SEQ ID NO: 15
TGGGAGGAAGGCTAGCTACAACGAGAGGCGTGAGTTGTAGCTAGCCTT
CCTCCCACTCAGCGTCCGTGCAGTCGAGGC RL-dhp6
                                        SEQ ID NO: 16
ACGCTGAGTGGGAGGAAGGCTAGCTACAACAGCTACAACGAGAGGAAACCT
CGTGAGCTCGAC Control DNAzyme 1: Dz2
                                        SEQ ID NO: 17
TGCCCAGGGAGGCTAGCTACAACGAGAGGAAACCTT Control DNAzyme 2: Dz6
                                        SEQ ID NO: 18
CTGGGAGGAAGGCTAGCTACAACGAGAGGCGTGAT
```

Reaction Components

Reactions A, B, C, D, E and F were set up to contain the following oligonucleotide fragments as listed in Table 7, with reference to oligonucleotides listed in the previous section and structures illustrated in FIG. 4 panel iv).

was programmed to be read every 5 seconds (scan mode: all channels) for a total of 40 minutes.

Results

In FIG. 5 panel ii) the results of the dual hairpined DNAzyme molecules are shown. The substrate sequence (Substrate 1) that can be cleaved by the hairpined Dz1 following its opening and activation is labelled with a FAM fluorophore and quencher and the substrate (Substrate 2) that can be cleaved by the hairpined Dz2 following its opening and activation is labelled with a TxR fluorophore and quencher. As a result, both cleavage events can be monitored separately by visualising the fluorescent signal from both fluorophore emission wavelengths. The top graph outlines the fluorescent signal from the FAM fluorophore and the bottom graph from the TxR fluorophore. For Reaction E, when both hairpined Dz structures exist on their own ('Hairpins only' shown as a line with triangle symbols), there is little or no cleavage of each substrate and as a result, little or no increase in FAM and TxR signal, indicating that both DNAzyme portions are kept inactive within their respective hairpined structures. This is shown in comparison to the negative controls for FAM and TxR, corresponding to Reactions A and C respectively ('Negative control', line containing square symbols) which contains the same fluorescently-labelled substrate sequences only. However, for Reaction F when a single RL is present it simultaneously opens both hairpins ('Releaser present; line containing circle symbols), and thus there is an increase in both FAM and TxR signal, indicating that both DNAzyme portions are now free to cleave their respective substrates. This is shown in comparison to the positive control for FAM and TxR, corresponding to Reactions B and D respectively ('Positive control', line containing diamond symbols) which each contain the same concentration of each substrate and non-hairpined control DNAzyme as present in Reaction F.

Example 5

The current example demonstrates a method of signal amplification whereby a RL is recycled by the activity of

TABLE 7

| Reaction A (Negative control 1) | Reaction B (Positive control 1) | Reaction C (Negative control 2) | Reaction D (Positive control 2) | Reaction E (Hairpins only) | Reaction F (RL present) |
|---|---|---|---|---|---|
| Sub2-FB 200 nM | Sub2-FB 200 nM | | | Sub2-FB 200 nM | Sub2-FB 200 nM |
| | | Sub6-TRB2 200 nM | Sub6-TRB2 200 nM | Sub6-TRB2 200 nM | Sub6-TRB2 200 nM |
| | Dz2 10 nM | | | | |
| | | | Dz6 10 nM | | |
| | | | | dhp6Dz2(5)M4 10 nM | dhp6Dz2(5)M4 10 nM |
| | | | | dhp5Dz6(3) 10 nM | dhp5Dz6(3) 10 nM |
| | | | | | RL-dhp6 10 nM |

Oligos were purchased from IDT or Biosearch technologies. All reactions contained 1×PCR buffer II (Applied Biosystems), nuclease free water (Ambion) and 25 mM of MgCl$_2$ (Ambion). The total volume of all reactions was 25 µL. All reactions were performed in duplicate at 40° C. in a Bio-Rad® CFX96 thermocycler. Fluorescence signal was measured on Channel 1 (FAM) and Channel 3 (TxR) and ExoIII, leading to the continual release and subsequent activation of a DNAzyme (outlined in FIG. 6 panel i)). Similar to Example 3, the DNAzyme is inactivated by a being hybridized to a BL, however in the current Example 5; a single mis-match exists between the DNAzyme and BL sequence in contrast to Example 3 where more than one nucleotide of the DNAzyme has no compliment in the BL and is thus looped out when the DNAzyme sequence binds the BL. The single mis-match between the DNAzyme and the BL in the current Example 5 means that the RL does not contain the entire sequence required for catalytic activity of a DNAzyme. In Example 5, the DNAzyme can be activated by a RL, andonce the BL is bound to the RL, the BL may listed in Table 8, with reference to oligonucleotides listed in the previous section and structures illustrated in FIG. 6 panel i). For reactions C-F, the DNAzyme and BL were pre-hybridized together for 30 minutes at room temperature prior to the addition of further oligonucleotide components.

TABLE 8

| Reaction A (Negative control) | Reaction B (Positive control) | Reaction C (BL only, −ExoIII) | Reaction D (BL only, +ExoIII) | Reaction E (RL present, −ExoIII) | Reaction F (RL present, +ExoIII) |
|---|---|---|---|---|---|
| Sub2h-FB 200 nM | Sub2h-FB 200 nM Dz2(21:10) 100 nM | Sub2h-FB 200 nM Dz2(21:10) 100 nM BL(MM1)-Dz2 200 nM | Sub2h-FB 200 nM Dz2(21:10) 100 nM BL(MM1)-Dz2 200 nM ExoIII (0.1 U) | Sub2h-FB 200 nM Dz2(21:10) 100 nM BL(MM1)-Dz2 200 nM RL(MM1)(+5)-Dz2 50 nM | Sub2h-FB 200 nM Dz2(21:10) 100 nM BL(MM1)-Dz2 200 nM RL(MM1)(+5)-Dz2 50 nM ExoIII (0.1 U) | bedegraded by ExoIII whilst the RL molecule remains intact. The RL is then able to bind to another BL and the cycle is repeated, with a DNAzyme released each time during the process.

Oligonucleotides

In the present example, a hybridizing BL (SEQ ID NO: 19; BL(MM1)-Dz2) is used to block the catalytic activity of a Dz (SEQ ID NO: 20; Dz2(21:10) on its substrate (SEQ ID NO: 22; Sub2h-FB). Sub2h-FB was labelled with a 6-FAM moiety at its 5' end and a Black Hole Quencher 1 ("BHQ1") moiety internally on an A base at position 6 from its 3' end. Following hybridisation of the Dz and BL, the 3' ends of both the DNAzyme and the BL overhang by at least five nucleotides, allowing each to be resistant to ExoIII activity. A RL (SEQ ID NO: 22; RL(MM1)(+5)-Dz2) is used to release the DNAzyme from the BL. When hybridised to the BL, the 5' end of the RL is designed to hybridize with the 3' end of the BL to form a blunt end, thus making the BL susceptible to ExoIII degradation.

The sequences of these oligonucleotides are listed from 5' to 3' below. Bases in uppercase are deoxyribonucleotides and bases in lowercase are ribonucleotides. Underlined bases represent regions of complementarity between the DNAzyme and BL. Boxed bases represent the region in the RL complimentary to the BL.

```
BL: BL(MM1)-Dz2
                                         SEQ ID NO: 19
AAGGTTTCCTCTCGTTGTAGCTGGCCTCCCTGGGCAGTGCATACTCTA

Dz: Dz2(21:10)
                                         SEQ ID NO: 20
TGCCCAGGGAGGCTAGCTACAACGAGAGGAAACCTTCACCTGACTG

Substrate: Sub2h-FB
                                         SEQ ID NO: 21
AAGGTTTCCTCguCCCTGGGCACGAGG FL: RL(MM1)(+)5-Dz2
                                         SEQ ID NO: 22
TAGAGTATGCACTGCCCAGGGAGGCCAGCTACAACGAGAGGAAACCTTCAC
CT
```

Reaction Components

Reactions A, B, C, D, E and F were set up to contain the following oligonucleotides and ExoIII enzyme as Oligos were purchased from IDT or Biosearch technologies. Exonuclease III (ExoIII) was purchased from New England Biolabs. All reactions contained 1×NEB buffer 2 (New England Biolabs) and nuclease free water (Ambion). The total volume of all reactions was 25 μL. All reactions were performed in duplicate at 45° C. in a Bio-Rad® CFX96 thermocycler. Fluorescence signal was measured on Channel 1 (FAM) and was programmed to be read every 10 seconds (scan mode: FAM only) for a total of 40 minutes.

Results

FIG. 6 panel ii) demonstrates the fluorescent signal achieved from the ExoIII strategy depicted in FIG. 6 panel i). The substrate sequence that can be cleaved by the DNAzyme following its activation is labelled with a FAM fluorophore and quencher dye. The graph (FAM) outlines the fluorescent signal from this FAM fluorophore. For Reactions C and D when the Dz and BL duplex exist on their own ('BL only−ExoIII' shown as a line with triangle symbols and 'BL only+ExoIII' shown as a line with circle symbols), there is no displacement of the Dz and therefore no cleavage of the substrate and no corresponding increase in FAM signal. This is shown in comparison to the negative control, Reaction A ('Negative control', line containing square symbols) which contains the same fluorescently-labelled substrate sequence only. For Reactions E and F where a low concentration of RL (50 nM) is present respective to the concentration of BL (200 nM) and Dz (100 nM) ('RL present−ExoIII', line containing a symbol that consists of two diagonal and one vertical intersecting lines and 'RL present+ExoIII', line containing a symbol that consists of two diagonal intersecting lines), there is a small increase in signal for Reaction E containing RL without ExoIII, but a much larger and immediate increase in signal for Reaction F containing both RL and ExoIII. In both instances, the RL is functioning to displace the DNAzyme, however when ExoIII is absent, there is very little displacement occurring as each of the few RL molecules will only have a very low rate of dissociation from the and will therefore create largely inert duplexes with the BL. When ExoIII is, present, it functions to degrade the BL from a BL/RL duplex and as a result, each RL is recycled and can continuously displace more Dz molecules. This is shown in comparison to Reaction B containing the positive control ('Positive control', line containing diamond symbols) which contains only the substrate and free control DNAzyme in the same concentrations as in Reaction F.

Example 6

The following example demonstrates a method of signal amplification whereby a RL is recycled by the activity of a Nicking enzyme, leading to the continual release and subsequent activation of a DNAzyme (as outlined in FIG. 7 panel i)). Similar to Example 3, the DNAzyme is inactivated by a BL and can be re-activated by a RL, however in the current Example 5, once the BL is bound to the RL, a complete double-stranded recognition site for a Nicking enzyme is created within the RL/BL duplex. The Nicking enzyme recognizes this site and selectively nicks the BL whilst the RL molecule remains intact. Each 'nicked' fragment of the BL now no longer has the same affinity to the RL as the intact BL and as a result the complex dissociates. This allows the RL to bind to another BL and the cycle is repeated, with a DNAzyme released each time during the process.

```
Substrate: Sub2-TRB2
                                        SEQ ID NO: 5
AAGGTTTCCTCguCCCTGGGCA Dz: Dz2
                                        SEQ ID NO: 17
TGCCCAGGGAGGCTAGCTACAACGAGAGGAAACCTT BL: BL-Dz2Nic7-FB
                                        SEQ ID NO: 23
AAGGTTTCCTCTCGCTCTTCTAGCCTCCCTGGGCA RL: RL-Dz2Nic7a
                                        SEQ ID NO: 24
TGCCCAGGGAGGCTAGAAGAGCGAGAG
```

Reaction Components

Reactions A, B, C, D, E and F were set up to contain the following oligonucleotides and Nicking enzyme (Nt.BspQI) as listed in Table 9, with reference to oligonucleotides in the previous section and structures illustrated in FIG. 7 panel i). For reactions C-F, the DNAzyme and BL were pre-hybridized together for 30 minutes at room temperature prior to the addition of further oligonucleotide components.

TABLE 9

| Reaction A (Negative control) | Reaction B (Positive control) | Reaction C (BL only, −Nic) | Reaction D (BL only, +Nic) | Reaction E (RL present, −Nic) | Reaction F (RL present, +Nic) |
|---|---|---|---|---|---|
| Sub2-TRB2 200 nM | Sub2-TRB2 200 nM | Sub2-TRB2 200 nM | Sub2-TRB2 200 nM | Sub2-TRB2 200 nM | Sub2-TRB2 200 nM |
|  | Dz2 10 nM | Dz2 100 nM | Dz2 100 nM | Dz2 100 nM | Dz2 100 nM |
|  |  | BL-Dz2Nic7-FB 200 nM | BL-Dz2Nic7-FB 200 nM | BL-Dz2Nic7-FB 200 nM | BL-Dz2Nic7-FB 200 nM |
|  |  |  |  | RL-Dz2Nic7a 10 nM | RL-Dz2Nic7a 10 nM |
|  |  |  | Nt.BspQI 10 U |  | Nt.BspQI 10 U |

Oligonucleotides

In the present example, a hybridizing BL (SEQ ID NO: 23; BL-Dz2Nic7-FB) is used to block the catalytic activity of a Dz (SEQ ID NO: 17; Dz2) on its Substrate (SEQ ID NO: 5; Sub2-TRB2). Sub2-TRB2 was end-labeled with a Texas Red moiety at its 5' end and a Black Hole Quencher 2 ("BHQ2") moiety at its 3' end. The BL contains sequence that is not complementary to the DNAzyme and which forms one strand of the double stranded Nicking enzyme recognition sequence. When the BL is hybridized to the DNAzyme, this additional BL sequence exists as a single-stranded loop protruding from the duplex. Furthermore, the BL was internally labeled with a 6-fluorescein ("6-FAM") moiety at the 7th nucleotide (a 'T' nucleotide) from the 5' end and a Black Hole Quencher 1 ("BHQ1") moiety at the 30th nucleotide (a 'T' nucleotide) from the 5' end. A RL (SEQ ID NO: 24; RL-Dz2Nic7a) is used to release the DNAzyme from the BL and at the same time generate a complete double stranded recognition site for the restriction enzyme Nt.BspQI from the RL/BL complex.

The sequences of these oligonucleotides are listed from 5' to 3' below. Bases in uppercase are deoxyribonucleotides and base in lowercase are ribonucleotides. Underlined bases represent regions of complementarity between the DNAzyme and BL. Boxed bases represent the region in the BL complementary to the RL.

Oligos were purchased from IDT or Biosearch technologies. The nicking enzyme, Nt.BspQI was purchased from New England Biolabs. All reactions contained 1×NEB buffer 3 (New England Biolabs) and nuclease free water (Ambion). The total volume of all reactions was 25 μL. All reactions were performed in duplicate at 52° C. in a Bio-Rad® CFX96 thermocycler. Fluorescence signal was measured on Channel 3 (TxR) and was programmed to be read every 10 seconds (scan mode: all channels) for a total of 40 minutes.

Results

FIG. 7 panel ii) demonstrates the fluorescent signal achieved from the Nicking enzyme strategy depicted in FIG. 7 panel i) and as described above. The substrate sequence that can be cleaved by the DNAzyme once it has been released from the BL and thus activated, is labelled with a TxR fluorophore and quencher. The graph (TxR) outlines the fluorescent signal from this TxR fluorophore. For Reactions C and D, where the Dz and BL duplex exists on its own ('BL only−Nt.BspQI' shown as a line with triangle symbols and 'BL only+BspQI' shown as a line with circle symbols), there is no displacement of the Dz and therefore no cleavage of the substrate and no corresponding increase in TxR signal. This is shown in comparison to Reaction A containing the negative control ('Negative control', line containing square symbols) which contains the same fluorescently-labelled substrate sequence only. For Reactions E and F where a low concentration of RL (10 nM) is present respective to the concentration of BL (200 nM) and Dz (100 nM) ('RL present−Nt.BspQI', line containing a symbol that consists of two diagonal and one vertical intersecting lines and 'RL present+Nt.BspQI', line containing a symbol that consists of two diagonal intersecting lines), there is little to no increase in signal for Reaction E containing RL without Nicking enzyme, but a gradual increase in signal over time for Reaction F containing both RL and Nt.BspQI. In both instances, the RL is functioning to displace the DNAzyme, however when Nicking enzyme is absent, there is very little displacement occurring as each of the few RL molecules will only have a very low rate of dissociation from the BL and will therefore create largely inert duplexes with the BL. When the Nicking enzyme is present, it functions to selectively cleave the BL from a BL/RL duplex and as a result, each RL is recycled and can continuously displace Dz molecules. This is shown in comparison to the positive control ('Positive control', line containing diamond symbols) which contains the same concentration of substrate and free control DNAzyme as present in Reaction F.

Example 7

The following example demonstrates a method of signal amplification whereby a RL is recycled by the activity of a strand-displacing polymerase enzyme, leading to the continual release and subsequent activation of a DNAzyme (as outlined in FIG. 8 panel i)). As in Example 3, the DNAzyme is initially inactivated by hybridisation to a BL and can be re-activated by a RL. In this current Example 7 the BL contains sequence that forms a hairpin at the end of the BL which can be opened by the RL. The hairpin stem contains a primer-binding site which is only exposed in the presence of the RL. Once the primer can bind to this site, it is then extended by a polymerase enzyme which is capable of displacing any upstream pre-hybridized strands from the BL template. Consequently, primer extension by a strand-displacing polymerase enzyme will result in the displacement of the RL from the BL and a waste duplex will be created between the BL template and the newly synthesized strand. The RL is then able to bind to another BL and the cycle is repeated, with a DNAzyme released each time during the process.

Oligonucleotides

The BL (SEQ ID NO: 25; hpBLr-Dz2BUB0(4)-P) was designed to block the activity of the Dz (SEQ ID NO: 26; Dz2(9:8)) capable of cleaving its Substrate (Sub2, SEQ ID NO: 5). In this example Sub2-FB was internally labeled with a 6-FAM moiety on a T nucleotide in position 6 and a Black Hole Quencher 1 ("BHQ1") moiety at the 3' end. A RL (SEQ ID NO: 27; RLr-Dz2BUB0(4)(-2)-P) was employed to release the DNAzyme and expose the binding site for the primer (SEQ ID NO: 28; PR(3)-BLDz2(10))

The sequences of these oligonucleotides are listed from 5' to 3' below. Bases in uppercase are deoxyribonucleotides and base in lowercase are ribonucleotides. Underlined bases represent regions of complementarity between the DNAzyme and BL. Boxed bases represent the region in the BL complementary to the RL. Regions highlighted in grey represent the sequence in the BL that acts as the primer binding site. /3Phos/ indicates 3' end phosphorylation, a modification that prevents extension of the oligonucleotide by a polymerase enzyme.

```
Substrate: Sub2i-FB
                                              SEQ ID NO: 5
AAGGTTTCCTCguCCCTGGGCA BL: hpBLr-Dz2BUB-(4)-P
                                              SEQ ID NO: 25
GTGCATACTCTAGGTTTCCTCTCGTTGTAGCCTCCCTGGGATCGACCAGGT
TTTTTACGTGGTCGAT/3Phos/

Positive Control DNAzyme: Dz2(9:8)
                                              SEQ ID NO: 26
CCCAGGGAGGCTAGCTACAACGAGAGGAAACC/3Phos/

RL: RLr-Dz2BUB0(R)(-2)-P
                                              SEQ ID NO: 27
GTGGTCGATCCCAGGGAGGCTACAACGAGAGGAAACCTAGAGTATGCAC
/3Phos/

Primer: PR(3)-BLDz2(10)
                                              SEQ ID NO: 28
GCATATCGACCACG
```

Reaction Components

Reactions A, B, C, D, E and F were set up to contain the following oligonucleotide and Polymerase enzyme as listed in Table 10, with reference to oligonucleotides in the previous section and structures illustrated in FIG. 8 panel i). For reactions C-F, the DNAzyme, BL and primer were pre-incubated for 30 minutes at room temperature before the addition of the polymerase to reactions D and F and the addition of the RL to reactions E and F.

TABLE 10

| Reaction A (Negative control) | Reaction B (Positive control) | Reaction C (BL only, −Pol) | Reaction D (BL only, +Pol) | Reaction E (RL present, −Pol) | Reaction F (RL present, +Pol) |
|---|---|---|---|---|---|
| Sub2i-FB 200 nM | Sub2i-FB 200 nM | Sub2i-FB 200 nM | Sub2i-FB 200 nM | Sub2i-FB 200 nM | Sub2i-FB 200 nM |
| | | PR(3)-BLDz2(10) 200 nM | PR(3)-BLDz2(10) 200 nM | PR(3)-BLDz2(10) 200 nM | PR(3)-BLDz2(10) 200 nM |
| | Dz2(9:8)-P 150 nM | Dz2(9:8)-P 150 nM | Dz2(9:8)-P 150 nM | Dz2(9:8)-P 150 nM | Dz2(9:8)-P 150 nM |
| | | hpBLr-Dz2BUB0(4)-P 200 nM | hpBLr-Dz2BUB0(4)-P 200 nM | hpBLr-Dz2BUB0(4)-P 200 nM | hpBLr-Dz2BUB0(4)-P 200 nM |
| | | | | RLr-Dz2BUB0(4)(−2)-P 10 nM | RLr-Dz2BUB0(4)(−2)-P 10 nM |
| | | | Klenow Fragment (4 U) | | Klenow Fragment (4 U) |

Oligos were purchased from IDT or Biosearch technologies. The strand-displacing polymerase enzyme, Klenow Fragment (3'→5' exo⁻) was purchased from New England Biolabs. All reactions contained 1×NEB buffer 2 (New England Biolabs), 200 µM dNTPs (Bioline) and nuclease free water (Ambion). The total volume of all reactions was 25 µL. All reactions were performed in duplicate at 40° C. in a Bio-Rad® CFX96 thermocycler. Fluorescence signal was measured on Channel 1 (FAM) and was programmed to be read every 10 seconds (scan mode: FAM only) for a total of 40 minutes.

Results

FIG. 8 panel ii) demonstrates the fluorescent signal achieved from the strand-displacing polymerase strategy depicted in FIG. 8 panel i). The substrate sequence, which can be cleaved by the DNAzyme following its activation, is labelled with a FAM fluorophore and quencher. The graph (FAM) outlines the fluorescent signal from this FAM fluorophore. For Reactions C and D where the Dz and BL duplex exist on their own ('BL only-Klenow' shown as a line with triangle symbols and 'BL only+Klenow' shown as a line with circle symbols), there is no displacement of the Dz and therefore no cleavage of the substrate and no corresponding increase in FAM signal. This is shown in comparison to Reaction A containing the negative control ('Negative control', line containing square symbols) which contains the same fluorescently-labelled substrate sequence only. For Reactions E and F where a low concentration of RL (10 nM) is present respective to the concentration of BL (200 nM) and Dz (150 nM) ('RL present-Klenow', line containing a symbol that consists of two diagonal and one vertical intersecting lines and 'RL present+Klenow', line containing a symbol that consists of two diagonal intersecting lines), there is no increase in signal for Reaction E containing RL without Klenow, but an immediate increase in signal for Reaction F containing both RL and Klenow. When the polymerase is absent (Reaction E), there is very little displacement occurring as each of the few RL molecules will only have a very low rate of dissociation from the BL and will therefore create largely inert duplexes with the BL. The primer will be able to bind to its binding site, but will not be able to be extended. When the polymerase is present however, (Reaction F) it can extend the primer and displace the RL. Consequently, each RL is recycled and can continuously displace Dz molecules. The extension of the primer also creates a waste hairpin duplex between the BL template and the newly synthesized strand. This is shown in comparison to Reaction B containing the positive control ('Positive control', line containing diamond symbols) which consists of the same concentration of substrate and free control DNAzyme as present in Reaction F.

Example 8

The following example demonstrates the initial inactivation of a RL by its incorporation into a hairpin RL/BL structure as depicted in FIG. 9, panel i). The BL portion of the Hairpined RL (BLA) contains a substrate sequence (Substrate 1) which can be cleaved by a DNAzyme 1 (Dz1) and results in the activation of the RL. The active RL can then function to open another hairpin containing DNAzyme 2 (Hairpined Dz2) by hybridizing to the BL portion (BLB). The Dz2 portion of the hairpined Dz2/BLB structure is then active and can then function to cleave fluorescently labeled Substrate 2, resulting in the generation of fluorescent signal.

Oligonucleotides

In the present example, Hairpined Dz2 (SEQ ID NO: 29; hp(R3a)Dz45BUB0(4)) capable of cleaving Substrate 2 (SEQ ID NO: 3; Sub45) was utilized. In this example Substrate 2 (Sub45-FIB) was labeled with a 6-fluorescein ("6-FAM") moiety at the 5' end and an Iowa Black quencher moiety ("IB") at the 3' end. A Hairpined RL (SEQ ID NO: 30; hpRLb(R4)-Sub2) was employed to activate the Hairpined Dz2, once Substrate 1 within the BLA component of the Hairpined RL is cleaved by Dz1, (DzK(8:7) SEQ ID NO: 7). The catalytic activity of the hairpined DNAzyme was compared to that of a corresponding non-hairpined Dz2, (Positive control Dz2: SEQ ID NO: 4; Dz45(9:10)).

The sequences of these oligonucleotides are listed from 5' to 3' below. Bases in uppercase are deoxyribonucleotides and bases in lowercase are ribonucleotides. Underlined bases represent the regions that are complementary between the Hairpined RL and Hairpined Dz2. Bases in italics refer to DNAzyme sequence within the hairpined DNAzyme. Boxed bases represent part of the catalytic core of the DNAzyme which is non-complementary to the BL portion of the Hairpined Dz2 and is thus looped out of the stem of the hairpin.

---

Substrate 2: Sub45-FIB
                                  SEQ ID NO: 3
ACGGGTCCCguCTCCTTTGGAA Positive control Dz2: Dz45(9:10)
                                  SEQ ID NO: 4
CCAAAGGAGAGGCTAGCTACAACGAGGGACCCGT Dz1: DzK(8:7)
                                  SEQ ID NO: 7
CCAGGGAGGCTAGCTACAACGAGAGGAAAC hairpined Dz 2: hp(R3a)Dz45BUB0(4)
                                 SEQ ID NO: 29
*CAAAGGAGAGGCTAGCTACAA*CGAGGGACCCGTTAGGGACGGGTCCTTGTAGCTAGCCTCTCCT hairpined RL (containing Substrate 1):
hpRLb(R4)-Sub2
                                 SEQ ID NO: 30
GGTCCTTGTAGCGTTTCCTCguCCCTGGGAGCCTCTCTTTTTGAGAGGCTAGCTACAAGGACC

---

Reaction Components

Reactions A, B, C, D and E were set up to contain the following oligonucleotide fragments as listed in Table 11, with reference to oligonucleotides listed in the previous section and structures illustrated in FIG. 9 panel i).

TABLE 11

| Reaction A (Negative control) | Reaction B (Positive control) | Reaction C (Hairpin Dz only) | Reaction D (Hairpined Dz and Hairpined RL only) | Reaction E (DNAzyme 1) present) |
|---|---|---|---|---|
| Sub45-FIB 200 nM | Sub45-FIB 200 nM Dz45(9:10) 10 nM | Sub45-FIB 200 nM | Sub45-FIB 200 nM | Sub45-FIB 200 nM |

TABLE 11-continued

| Reaction A (Negative control) | Reaction B (Positive control) | Reaction C (Hairpin Dz only) | Reaction D (Hairpined Dz and Hairpined RL only) | Reaction E (DNAzyme 1) present) |
|---|---|---|---|---|
| | | hp(R3a)Dz45BUB0(4) 100 nM | hp(R3a)Dz45BUB0(4) 100 nM hpRLb(R4)-Sub2 100 nM | hp(R3a)Dz45BUB0(4) 100 nM hpRLb(R4)-Sub2 100 nM DzK(8:7) 20 nM |

Oligos were purchased from IDT or Biosearch technologies. All reactions contained 1×PCR buffer II (Applied Biosystems), nuclease free water (Ambion) and 25 mM of MgCl$_2$ (Ambion). The total volume of all reactions was 25 µL. All reactions were performed in duplicate at 45° C. in a Bio-Rad® CFX96 thermocycler. Fluorescence signal was measured on Channel 1 (FAM) and was programmed to be read every 10 seconds (scan mode: FAM only) for a total of 40 minutes.

Results

FIG. 9 panel ii) demonstrates a fluorescent signal achieved from the strategy outlined in FIG. 9 panel i). Substrate 2, which can be cleaved by the hairpined Dz2 following its activation upon release from its hairpin structure, is labelled with a FAM fluorophore and quencher. The graph (FAM) outlines the fluorescent signal from this FAM fluorophore. For Reaction C, where the Hairpined Dz2 exists on its own ('hpDz only' shown as a line with triangle symbols), there is no cleavage of the Substrate 2 and as a result, no increase in FAM signal, indicating that the DNAzyme portion is kept inactive within the hairpined structure. Similarly, for Reaction D where the Hairpined RL and Hairpined Dz are both present ('hpDz+hpRL only' shown as a line containing circle symbols), there is very little Increase in FAM signal, indicating that both the RL and Dz2 portions of the respective hairpins are kept inactive within their hairpined structures. This is shown in comparison to Reaction A containing the negative control ('Negative control', line containing square symbols) which contains Substrate 2 only. For Reaction E where Dz1 is present to cleave Substrate 1 ('hpDz+hpRL+DNAzyme 1'; line containing a symbol that consists of two diagonal and one vertical intersecting lines), there is a gradual increase in FAM signal, indicating that cleavage of Substrate 1 activates the RL portion of the hairpined RL and the RL can then function to activate hairpined Dz2, which can then cleave Substrate 2. This is shown in comparison to Reaction B containing the positive control ('Positive control', line containing diamond symbols) which consists of the same concentration of Substrate 2 and non-hairpined positive control DNAzyme 2 as present in Reaction E.

Example 9

Example 9 demonstrates the use of a primer to directly activate DNAzyme molecules as depicted in FIG. 11, panel i) without the use of a RL molecule. A hairpined molecule containing an inactive DNAzyme exists, as outlined in Example 3. In this current Example 9 however, the BL portion of the Hairpined Dz/BL complex is completely hybridized to the entire DNAzyme sequence, with the two linked by a non-complementary loop. The hairpin loop in this structure consists of nucleotides which form a partial recognition sequence for a nicking enzyme. When a primer is present, it hybridizes to the loop sequence and is extended at its 3' end by a strand displacing polymerase. Primer extension results in the simultaneous displacement of the DNAzyme from the hairpin structure and the synthesis of a new copy of the DNAzyme, via the use of the BL sequence as a template. The displaced DNAzyme is now active and can cleave its substrate. The extension of the primer also results in the completion of a double-stranded nicking enzyme recognition site. The nicking enzyme can recognize this site and selectively nick the newly synthesized strand at a region between the upstream primer and downstream newly synthesized DNAzyme sequence. Nicking therefore generates a new primer, which is extended by polymerase to both synthesize another DNAzyme copy and displace the pre-existing copy from the BL template. This cycle of nicking, polymerization and displacement can then occur autonomously to generate several multiple DNAzyme molecules.

Oligonucleotides

The Hairpined Dz/BL complex (SEQ ID NO: 31; hp(R6b)Dz45) contains a Dz, when released from the BL and thus active, capable of cleaving the Substrate (Sub45, SEQ ID NO: 3). In this example Sub45 was labeled with a 6-fluorescein ("6-FAM") moiety at the 5' end and an Iowa Black quencher moiety ("IB") at the 3' end. A primer (SEQ ID NO: 32; PR(R6)Dz45(10)) was employed to activate and synthesize additional copies of the DNAzyme. The catalytic activity of the hairpined DNAzyme was compared to that of a corresponding non-hairpined positive control DNAzyme, (SEQ ID NO: 4; Dz45(9:10)).

The sequences of these oligonucleotides are listed from 5' to 3' below. Bases in uppercase are deoxyribonucleotides and base in lowercase are ribonucleotides. Bases in italics refer to DNAzyme sequence within the Hairpined Dz/BL structure. Underlined bases represent regions of complementarity between the primer and the hairpined DNAzyme. Boxed bases represent the partial nicking enzyme recognition site present within the Hairpined Dz/BL and the primer.

```
Substrate: Sub45-FIB
                                          SEQ ID NO: 3
ACGGGTCCCguCTCCTTTGGAA Positive Control Dz: Dz45(9:10)
                                          SEQ ID NO: 4
CCAAAGGAGAGGCTAGCTACAACGAGGGACCCGT Hairpined Dz: hp(R6b)-Dz45
                                          SEQ ID NO: 31
ACGGGTCCCTCGTTGTAGCTAGCCTCTCCTTTGGTCGTCGATCCTGAGACC
AAAGGAGAGGCTAGCTACAACGAGGGACCCGT Primer: PR(R6)Dz45(10)
                                          SEQ ID NO: 32
TCAGGATCGA
```

Reaction Components

Reactions A, B, C, D, E, F, G and H were set up to contain the following oligonucleotides, Polymerase and nicking enzyme as listed in Table 12, with reference to oligonucleotides in the previous section and structures illustrated in FIG. 11 panel i).

primer (Reaction H–'hpDz+primer+Klenow+Nt.AlwI', line containing a symbol that consists of a filled black square), there is an increase in signal for Reaction H containing primer, which is proceeding more rapidly than Reaction F with only the Klenow, indicating that the presence of the Nt.AlwI enzyme is promoting the synthesis of additional Dz

TABLE 12

| Reaction A (Negative control) | Reaction B (Positive control) | Reaction C (hpDz only) | Reaction D (hpDz + primer only) | Reaction E (hpDz only + Pol) | Reaction F (hpDz + primer + Pol) | Reaction G (hpDz only + Pol + Nicker) | Reaction H (hpDz + primer + Pol + Nicker) |
|---|---|---|---|---|---|---|---|
| Sub45-FIB 200 nM | Sub45-FIB 200 nM | Sub45-FIB 200 nM hp(R6b)Dz45 100 nM | Sub45-FIB 200 nM hp(R6b)Dz45 100 nM | Sub45-FIB 200 nM hp(R6b)Dz45 100 nM | Sub45-FIB 200 nM hp(R6b)Dz45 100 nM | Sub45-FIB 200 nM hp(R6b)Dz45 100 nM | Sub45-FIB 200 nM hp(R6b)Dz45 100 nM |
|  | Dz45 100 nM |  |  |  |  |  |  |
|  |  |  | PR(R6)Dz45(10) 20 nM |  | PR(R6)Dz45(10) 20 nM |  | PR(R6)Dz45(10) 20 nM |
|  |  |  |  | Klenow Fragment (0.5 U) | Klenow Fragment (0.5 U) | Klenow Fragment (0.5 U) | Klenow Fragment (0.5 U) |
|  |  |  |  |  |  | Nt.AlwI (2 U) | Nt.AlwI (2 U) |

Oligos were purchased from IDT or Biosearch technologies. The strand-displacing polymerase enzyme, Klenow Fragment (3'→5' exo⁻) and the nicking enzyme, Nt.AlwI were purchased from New England Biolabs. All reactions contained 1×NEB buffer 2 (New England Biolabs), 100 μM dNTPs (Bioline) and nuclease free water (Ambion). The total volume of all reactions was 50 μL. All reactions were performed in duplicate at 37° C. in a Bio-Rad® CFX96 thermocycler. Fluorescence signal was measured on Channel 1 (FAM) was programmed to be read every 10 seconds (scan mode: FAM only) for a total of 100 minutes.

Results

FIG. 11 Panel ii) demonstrates the fluorescent signal achieved from the strategy depicted in FIG. 11 panel i). The substrate sequence, which can be cleaved by the DNAzyme following its activation, is labelled with a FAM fluorophore and quencher. The graph (FAM) outlines the fluorescent signal from this FAM fluorophore. For Reactions C and D where no protein enzymes are present but the Hairpined Dz exists on its own ('hpDz only' shown as a line with triangle symbols) and the Hairpined Dz with primer ('hpDz+primer' shown as a line with circle symbols), there is little increase in signal indicating no extension of the primer, no subsequent activation of the Dz and therefore no cleavage of the substrate and corresponding increase in FAM signal. This is shown in comparison to Reaction A containing the negative control ('Negative control', line containing square symbols) which contains the same fluorescently-labelled substrate sequence only. For Reactions E and F where Klenow is present and the Hairpined Dz exists without primer ('hpDz only+Klenow only', line containing a symbol that consists of two diagonal and one vertical intersecting lines) and with primer ('hpDz+primer+Klenow only', line containing a symbol that consists of two diagonal intersecting lines), there is a gradual increase in signal for Reaction F containing the primer indicating the primer is extended by Klenow and results in the activation of the Dz portion of the Hairpined Dz. When however, both Klenow and Nt.AlwI are present and the Hairpined Dz is in solution without primer (Reaction G–'hpDz only+Klenow+Nt.AlwI', line containing a symbol with one vertical intersecting line) and with copies in addition to activating the existing copy within the hairpin. This is shown in comparison to Reaction B containing the positive control ('Positive control', line containing diamond symbols) which consists of the same concentration of substrate and free positive control DNAzyme as present in Reaction H. Each of the reactions containing the Hairpined Dz in the presence or absence of primer but containing only the Nt.AlwI were also performed to confirm that this enzyme alone was not responsible for the additional signal generation. These reactions did not result in an increase in FAM fluorescence (data not shown).

Example 10

The following example demonstrates the inactivation of a DNAzyme by hybridization to a complementary blocking oligonucleotide (BL). The BL contains two regions of sequence complementary to the DNAzyme, which are connected by a non-complementary region that acts as a substrate for a second, independent catalytic nucleic acid (in this case, an MNAzyme). The 5' and 3' ends of the BL can be designed to either (i) hybridize with the 3' and 5' ends, respectively, of the DNAzyme to form a linear duplex structure with a looped out cleavable substrate sequence or, (ii) they can be designed to hybridize with the 5' and 3' ends respectively, forming a quasi-circular structure (as in this example and outlined diagrammatically in FIG. 1 panels ii) and iii) respectively). Cleavage of the substrate (Substrate 1a) region by an MNAzyme (Mz1) in the presence of its target (AF1) results in the release and subsequent re-activation of the previously inactive DNAzyme.

Oligonucleotides

In the current example, the BL (SEQ ID NO: 1; C(4) Sub45(24:24)(2)-FB) is composed of (i) 5' and 3' ends that are complementary to a portion of Dz2 (SEQ ID NO: 2; DzK(10:9)) and (ii) a central portion connecting the 5' and 3' ends that consists of Substrate 1a, which is equivalent to the sequence of Substrate 1 (SEQ ID NO: 3; Sub45) but lacks the 5' terminal 'A' nucleotide and the 3' terminal 'GAA' nucleotides. The BL was internally labeled with a 6-fluorescein ("6-FAM") moiety at the 15$^{th}$ nucleotide from the 5' end (a 'T' nucleotide) and a Black Hole Quencher 1 ("BHQ1") moiety at the 34$^{th}$ nucleotide from the 5' end (a 'T' nucleotide). Thus the fluorophore and quencher were located at the junction of the substrate region and DNAzyme-complementary regions. The BL is utilized to block the activity of Dz2, by pre-hybridizing the BL with Dz2.

An MNAzyme (Mz1) consisting of partzymes (Partzyme A, SEQ ID NO: 33; TFRCA4/45-P and Partzyme B, SEQ ID NO: 34 TFRCB5/45-P), and an assembly facilitator target (AF1, SEQ ID NO: 35 AF-TFRC) is utilized to cleave the Substrate 1a portion of the BL. This target dependent cleavage event facilitates the release of Dz2, allowing it to act upon Substrate 2 (SEQ ID NO: 5; Sub2). In this example, Sub2 was end-labeled with a Texas Red moiety on the 5' end and a Black Hole Quencher 2 ("BHQ2") moiety on the 3' end.

```
Partzyme B: TFRCB5/45-P
                                               SEQ ID NO: 34
TTCCAAAGGAGAGGCTAGCTCCTCTGACTGGAAAACAGACT/3Phos/

Assembly facilitator (AF1): AF-TFRC
                                               SEQ ID NO: 35
AGTCTGTTTTCCAGTCAGAGGGACAGTCTCCTTCCATATTCC
```

Reaction Components

Reactions A, B, C, D, E, F and G were set up to contain the following oligonucleotides as listed in Table 13, with reference to oligonucleotides listed in the previous section and structures illustrated in FIG. 1 panel ii). For reactions E, F and G, the BL and DNAzyme were initially pre-hybridized together for 30 minutes at room temperature before the addition of any further oligonucleotide components.

TABLE 13

| Reaction A (Negative control 1) | Reaction B (Positive control 1) | Reaction C (Negative control 2) | Reaction D (Positive control 2) | Reaction E (Blocker only) | Reaction F (Partzymes present (No AF1)) | Reaction G (Partzymes + AF1 present) |
| --- | --- | --- | --- | --- | --- | --- |
|  |  | Sub2-TRB2 200 nM | Sub2-TRB2 200 nM | Sub2-TRB2 200 nM | Sub2-TRB2 200 nM | Sub2-TRB2 200 nM |
| TFRCA4/45-P 100 nM | TFRCA4/45-P 100 nM |  |  |  | TFRCA4/45-P 100 nM | TFRCA4/45-P 100 nM |
| TFRCB5/45-P 100 nM | TFRCB5/45-P 100 nM |  |  |  | TFRCB5/45-P 100 nM | TFRCB5/45-P 100 nM |
|  | AF-TFRC 20 nM |  |  |  |  | AF-TFRC 20 nM |
|  |  |  | DzK(10:9) 100 nM | DzK(10:9) 100 nM | DzK(10:9) 100 nM | DzK(10:9) 100 nM |
| C(4)Sub45(24:24X2)-FB 200 nM | C(4)Sub45(24:24X2)-FB 200 nM |  |  | C(4)Sub45(24:24)(2)-FB 200 nM | C(4)Sub45(24:24)(2)-FB 200 nM | C(4)Sub45(24:24)(2)-FB 200 nM |

The sequences of these oligonucleotides are listed from 5' to 3' below. Bases in uppercase are deoxyribonucleotides and base in lowercase are ribonucleotides. Underlined bases represent regions in the BL that are complementary to a portion of the DNAzyme. Bases in italics refer to regions corresponding to a substrate sequence within the BL molecule. Boxed bases represent the catalytic core or partial catalytic cores of the DNAzyme or partzymes respectively. Nucleotides highlighted in grey represent the bases in the DNAzyme that are complementary to and blocked by the underlined bases in the BL molecule. /3Phos/ indicates 3' end phosphorylation.

```
Blocker oligonucleotide (BL):
C(4)Sub45(24:24)(2)-FB
                                               SEQ ID NO: 1
AGCCTCCCTGGGCATCGGGTCCCguCTCCTTTGTAAGGTTTCCTCTCG Dz2: DzK(10:9)
                                               SEQ ID NO: 2
GCCCAGGGAGGCTAGCTACAACGAGAGGAAACCT Substrate 2: Sub2-TRB2
                                               SEQ ID NO: 5
AAGGTTTCCTCguCCCTGGGCA Partzyme A: TFRCA4/45-P
                                               SEQ ID NO: 33
GGAATATGGAAGGAGACTGTCACAACGAGGGACCCGT/3Phos/
```

Oligos were purchased from IDT or Biosearch technologies. All reactions contained 1×PCR buffer II (Applied Biosystems), nuclease free water (Ambion) and 25 mM of $MgCl_2$ (Ambion). The total volume of all reactions was 25 µL. All reactions were performed in duplicate at 45° C. in a Bio-Rad® CFX96 thermocycler and fluorescence signal was measured simultaneously in both Channel 1 (FAM) and Channel 3 (TR) to monitor FAM and Texas Red, respectively and was programmed to be read every 5 seconds (scan mode: all channels) for a total of 40 minutes.

Results

Figure 15:
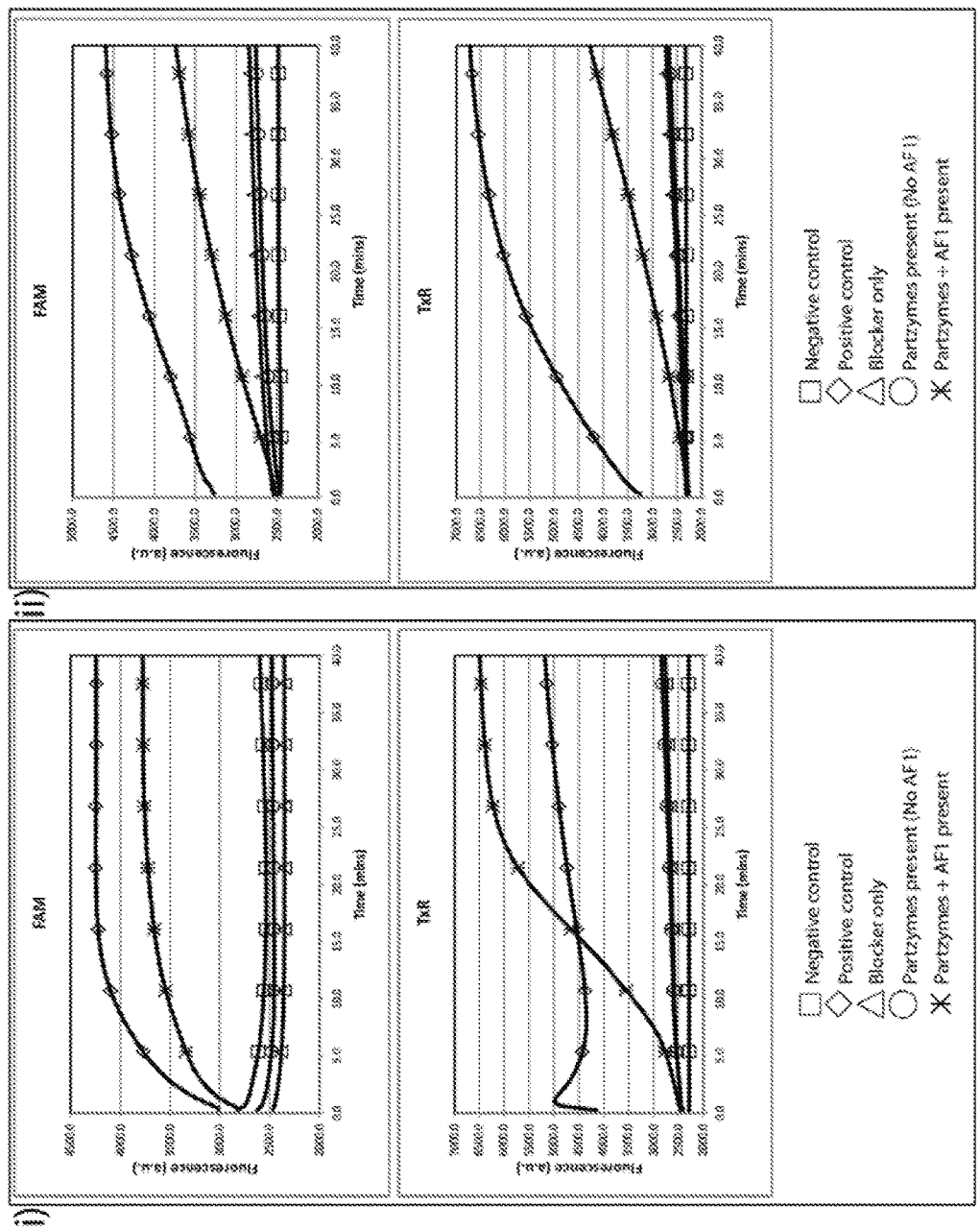
FIG. 15 shows the fluorescent signal achieved from the DNAzyme quasi-circle strategy from circles with both 1 and 2 inactivated DNAzymes, that have been activated by the cleavage of the BL portions of the circles by an MNAzyme in the presence of its target assembly facilitator (depicted diagrammatically in FIG. 1 panels ii) and iii) respectively).

FIG. 15 panel i) shows the fluorescent signal achieved from the DNAzyme quasi-circle strategy from a circle containing a single inactivated DNAzyme, that has been activated by the cleavage of the BL portion of the circle by an MNAzyme in the presence of its target assembly facilitator.

Here, the substrate sequence (Substrate 1a) that exists as part of the BL molecule is itself labelled with a FAM fluorophore and quencher. The substrate sequence, which can be cleaved by Dz2 following its release and activation (Substrate 2), is labelled with a TxR fluorophore and quencher. As a result, both cleavage events can be monitored separately by visualizing the fluorescent signal from both fluorophore emission wavelengths. The top graph outlines the fluorescent signal from the FAM fluorophore and the bottom graph from the TxR fluorophore. For Reaction E where the quasi-circle exists on its own ('Blocker only' shown as a line with triangle symbols) and Reaction F, in the presence of partzymes lacking an assembly facilitator (Partzymes present (no AF1)' shown as a line with circle symbols) there is no cleavage of Substrate 1a and as a result, no increase in FAM signal. Further there is no significant increase in TxR signal during these reactions indicating that Dz2 is inactive when complexed with the BL. This is shown in comparison to the negative controls for FAM and TxR corresponding to Reactions A and C respectively ('Negative control', line containing square symbols) which contain only the two fluorescently-labelled substrate sequences. However, for Reaction G where the assembly facilitator for the MNAzyme is present, ('Partzymes+AF1 present'; line containing a symbol that consists of two diagonal and one vertical intersecting lines) there is an immediate increase in FAM signal, indicating Substrate 1a in the BL has been cleaved. This also results in a gradual increase in TxR signal indicating that Dz2 has now been released from the BL and is cleaving Substrate 2. This is shown in comparison to the positive controls for FAM and TxR, corresponding to Reactions B and D respectively ('Positive control', line containing diamond symbols) which contain the same concentrations of Substrate 1a and MNAzyme cleaving Substrate 1a for FAM and Substrate 2 and MNAzyme cleaving Substrate 2 for TxR respectively as present in Reaction G.

Example 11

The following example demonstrates:
(i) the inactivation of two independent DNAzymes, Dz(A) and Dz(B), by hybridization to two complementary blocking oligonucleotides (BL), BL(A) and BL(B)
(ii) the subsequent activation of two independent DNAzymes, Dz(A) and Dz (B), in the presence of an active MNAzyme capable of cleaving the substrate portion of BL(A) and BL(B), resulting in the release of Dz(A) and Dz (B).

Oligonucleotides

BL(A) (SEQ ID NO: 6; C4Sub45(22:23)) is composed of (i) a 5' end complementary to the 5' region of Dz(A) (SEQ ID NO: 7; DzK(8:7)), (ii) a central portion that consists of Substrate 1a, which is equivalent to the sequence of Substrate 1 (SEQ ID NO: 3; Sub45) but lacks the 5' terminal 'A' nucleotide and the 3' terminal 'GAA' nucleotides and (iii) a 3' end complementary to the 3' region of Dz(B) (SEQ ID NO: 8; Dz6(8:7)). BL(B) (SEQ ID NO: 9; C4Sub45T(21: 24)) is composed of (i) a 5' end complementary to the 5' region of Dz(B) (ii) a central portion that consists of Substrate 1b, which is equivalent to the sequence of Substrate 1 but lacks the 5' terminal 'AC' nucleotides and 3' terminal 'GAA' nucleotides and (iii) a 3' end complementary to the 3' region of Dz(A).

In this example, the 5' and 3' ends of BL(A) and BL(B) are designed to hybridize with the 5' and 3' ends of the Dz(A) and Dz(B), such that a quasi-circular structure containing two inactive DNAzymes held together by two BL molecules forms (as outlined in FIG. 1 panel iii)). An MNAzyme (Mz1) consisting of the partzymes (Partzyme A, SEQ ID NO: 33; TFRCA4/45-P and Partzyme B, SEQ ID NO: 34 TFRCB5/ 45-P), and the assembly facilitator (AF1, SEQ ID NO: 35 AF-TFRC) is capable of cleaving the Substrate 1a portion of BL(A) and the Substrate 1b portion of BL(B), resulting in the release of Dz(A) and Dz(B) from the quasi-circular structure. Dz(A) cleaves Substrate A (SEQ ID NO: 5, Sub 2), which in this example is labeled with a 6-fluorescein ("6-FAM") moiety at the 5' end and a Black Hole Quencher 1 ("BHQ1") at the 3' end. Dz(B) cleaves Substrate B (SEQ ID NO: 11, Sub 6) which in this example is labeled with a Texas Red moiety at its 5' end and a Black Hole Quencher 2 ("BHQ2") moiety at its 3' end.

The sequences of the above oligonucleotides are listed from 5' to 3' below. Bases in uppercase are deoxyribonucleotides and base in lowercase are ribonucleotides. Underlined bases represent regions in the BL that are complementary to a portion of DNAzyme. Bases in italics refer to regions corresponding to a substrate sequence within the BL molecule. Boxed bases represent the catalytic core of the DNAzyme or partzyme. Nucleotides highlighted in grey represent the bases in the DNAzyme that are complementary to and blocked by, the underlined bases in the BL molecule. /3Phos/ indicates 3' end phosphorylation.

```
Substrate A: Sub2-FB
                                           SEQ ID NO: 5
AAGGTTTCCTCguCCCTGGGCA BL(A): C4Sub45(22:23)
                                           SEQ ID NO: 6
TAGCCTCCCTGGGCGGGTCCCguCTCCTTTGTCACGCCTCTCGTT Dz(A): DzK(8:7)
                                           SEQ ID NO: 7
CCAGGGAGGCTAGCTACAACGAGAGGAAAC Dz(B): Dz6(8:7)
                                           SEQ ID NO: 8
GGAGGAAGGCTAGCTACAACGAGAGGCGTG BL(B): C4Sub45T(21:24)
                                           SEQ ID NO: 9
TAGCCTTCCTCCCGGGTCCCguCTCCTTTGGGTTTCCTCTCGTTG Substrate B: Sub6-TRB2
                                           SEQ ID NO: 11
ATCACGCCTCguTCCTCCCAG Partzyme A: TFRCA4/45-P
                                           SEQ ID NO: 33
GGAATATGGAAGGAGACTGTCACAACGAGGGACCCGT/3Phos/

Partzyme B: TFRCB5/45-P
                                           SEQ ID NO: 34
TTCCAAAGGAGAGGCTAGCTCCTCTGACTGGAAAACAGACT/3Phos/

Assembly facilitator (AF1): AF-TFRC
                                           SEQ ID NO: 35
AGTCTGTTTTCCAGTCAGAGGGACAGTCTCCTTCCATATTCC
```

Reaction Components

Reactions A, B, C, D, E, F and G were set up to contain the following oligonucleotides as listed in Table 14, with reference to oligonucleotides listed in the previous section and structures illustrated in FIG. 1 panel iii). For reactions E, F and G, the BL molecules; BL(A), BL(B) and the DNAzymes Dz(A) and Dz(B) were initially pre-hybridized together for 30 minutes at room temperature before the addition of any further oligonucleotide components.

TABLE 14

| Reaction A (Negative control 1) | Reaction B (Positive control 1) | Reaction C (Negative control 2) | Reaction D (Positive control 2) | Reaction E (B locker only) | Reaction F (Partzymes present (No AF1)) | Reaction G (Partzymes + AF1 present) |
|---|---|---|---|---|---|---|
| Sub2-FB 200 nM | Sub2-FB 200 nM | Sub6-TRB2 200 nM | Sub6-TRB2 200 nM | Sub2-FB 200 nM Sub6-TRB2 200 nM DzK(8:7) 10 nM Dz6(8:7) 10 nM C4Sub45(22:23) 20 nM C4Sub45T(21:24) 20 nM | Sub2-FB 200 nM Sub6-TRB2 200 nM DzK(8:7) 10 nM Dz6(8:7) 10 nM C4Sub45(22:23) 20 nM C4Sub45T(21:24) 20 nM TFRCA4/45-P 100 nM TFRCB5/45-P 100 nM | Sub2-FB 200 nM Sub6-TRB2 200 nM DzK(8:7) 10 nM Dz6(8:7) 10 nM C4Sub45(22:23) 20 nM C4Sub45T(21:24) 20 nM TFRCA4/45-P 100 nM TFRCB5/45-P 100 nM AF-TFRC 20 nM |
|  | DzK(8:7) 20 nM |  | Dz6(8:7) 20 nM |  |  |  |

Oligos were purchased from IDT or Biosearch technologies. All reactions contained 1×PCR buffer II (Applied Biosystems), nuclease free water (Ambion) and 25 mM of MgCl$_2$ (Ambion). The total volume of all reactions was 25 µL. All reactions were performed in duplicate at 48° C. in a Bio-Rad® CFX96 thermocycler. Fluorescence signal was measured simultaneously in both Channel 1 (FAM) and Channel 3 (TxR) to monitor FAM and Texas Red, respectively and was programmed to be read every 5 seconds (scan mode: all channels) for a total of 40 minutes.

Results

FIG. 15 panel ii) shows the results from the quasi-circle with two DNAzymes present. In this case, the substrate sequences (Substrate 1a for BLA and Substrate 1b for BLB) remains unlabelled. The substrate sequence (Substrate A) that can be cleaved by Dz(A), following its release and activation, is labelled with a FAM fluorophore and quencher dye and the substrate (Substrate B) that can be cleaved by Dz(B), following its release and activation, is labelled with a TxR fluorophore and quencher. As a result, both cleavage events can be monitored separately by visualizing the fluorescent signal from both fluorophore emission wavelengths. The top graph outlines the fluorescent signal from the FAM fluorophore and the bottom graph from the TxR fluorophore. For Reaction E, when the quasi-circle exists on its own ('Blocker only' shown as a line with triangle symbols), and Reaction F where the quasi-circle and partzymes are present but no AF1 ('Partzymes present (No AF1)' shown as a line with circle symbols) there is no cleavage of Substrate 1a or Substrate 1 b and as a result, little to no increase in FAM or TxR signal, indicating that both Dz(A) and Dz(B) are inactive when complexed with the intact BL molecules. This is shown in comparison to the negative controls for both FAM and TxR, corresponding to reactions A & C respectively ('Negative control', line containing square symbols) which contain the same fluorescently-labelled Substrate A and Substrate B sequences only. For Reaction G, which contains the quasi-circle, partzymes and AF1; ('Partzymes+ AF1 present', line containing a symbol that consists of two diagonal and one vertical intersecting lines) there is a gradual increase in signal from both the FAM and TxR fluorophores indicating that both Dz(A) and Dz(B) are released from the quasi-circle and are now cleaving their respective substrates. This is shown in comparison to the positive controls for FAM and TxR corresponding to Reactions B and D respectively ('Positive control', line containing diamond symbols) which contain the same concentrations of Substrate A and Dz(A) for FAM and Substrate B and Dz(B) for TxR respectively as present in Reaction G.

Example 12

The following example demonstrates the inactivation of DNAzymes by hybridization to complementary BL molecules within quasi-circular structures, as previously demonstrated in Example 1. In this example however, two circles are present, each containing i) a DNAzyme capable of cleaving the substrate present within the BL of the opposing circle and ii) a BL containing two adjacent, independent substrates. The first substrate sequence (Substrate 1) sequence, which is present in both quasi circles, is cleaved by an MNAzyme (Mz1) in the presence of a target assembly facilitator (AF1). The two quasi circles each contain a second substrate sequence (either Substrate 2a or Substrate 3a) which is capable of being cleaved by the DNAzyme incorporated into the opposing circle (Dz2 or Dz3 respectively). The two DNAzymes are kept inactive by the presence of both BL molecules. Cleavage of Substrate 1 on either circle by the active Mz1 results in the release and subsequent re-activation of the previously inactive DNAzymes. Since each DNAzyme is capable of cleaving the opposing circles BL, this initial activation also triggers an exponential cascade of BL cleavage events between the two circles (depicted schematically in FIG. 16 panel i)) and increases the speed of DNAzyme activation compared to cleavage of a single quasi-circle. This will lead to signal amplification.

Oligonucleotides

In the current example, Circle A consists of BLA (SEQ ID NO: 36; C(R15a)Sub45_2) which is composed of (i) 5' and 3' ends that are complementary to a portion of Dz3 (SEQ ID NO: 37; Dz6(9:9)) and (ii) a central portion connecting the 5' and 3' ends that consists of the adjacent sequences of both Substrate 1 and Substrate 2a, BLA is utilized to block the activity of Dz3 by pre-hybridizing the BLA with Dz3. Circle B consists of BLB (SEQ ID NO: 38; C(R16d)Sub45_6) which is composed of (i) 5' and 3' ends that are complementary to a portion of Dz2 (SEQ ID NO: 26; Dz2(9:8)) and (ii) a central portion connecting the 5' and 3' ends that consists of the adjacent sequences of both Substrate 1 and Substrate 3a, which is equivalent to the sequence of Substrate 3 (SEQ ID No: 11; Sub6) but lacks the 5' terminal 'A' nucleotide and the 3' terminal 'G' nucleotide. BLB is utilized to block the activity of Dz2 by pre-hybridizing the BLB with Dz2.

An MNAzyme (Mz1), consisting of partzymes (Partzyme A, SEQ ID NO: 33; TFRCA4/45-P and Partzyme B, SEQ ID NO: 34 TFRCB5/45-P), and an assembly facilitator target (AF1, SEQ ID NO: 35 AF-TFRC), is utilized to cleave the Substrate 1 portion of either BLA or BLB. This target dependent cleavage event facilitates the release of either or both Dz3 or Dz2, allowing them to act upon BLB or BLA respectively. Dz3 can also act upon a Substrate 3, which is not a component of a quasi-circle. In this example, this independent Substrate 3 was end-labeled with a FAM moiety on the 5' end and a Black Hole Quencher 1 ("BHQ1") moiety on the 3' end.

The sequences of these oligonucleotides are listed from 5' to 3' below. Bases in uppercase are deoxyribonucleotides and bases in lowercase are ribonucleotides. Underlined bases represent regions in the BLA that are complementary to a portion of Dz3 and regions in the BLB that are complementary to a portion of Dz2. Bases in italics refer to regions corresponding to a substrate sequence within the BL molecule. Boxed bases represent the catalytic core of the DNAzymes and Partzymes. Nucleotides highlighted in grey represent the bases in Dz3 and Dz2 that are complementary to and blocked by, the underlined bases in the BLA and BLB molecules respectively. /3Phos/ indicates 3' end phosphorylation.

```
Substrate 3: Sub6-FB
                                           SEQ ID NO: 11
ATCACGCCTCguTCCTCCCAG Partzyme A: TFRCA4/45-P
                                           SEQ ID NO: 33
GGAATATGGAAGGAGACTGTCACAACGAGGGACCCGT/3Phos/

Partzyme B: TFRCB5/45-P
                                           SEQ ID NO: 34
TTCCAAAGGAGAGGCTAGCTCCTCTGACTGGAAAACAGACT/3Phos/

Assembly facilitator (AF1): AF-TFRC
                                           SEQ ID NO: 35
AGTCTGTTTTCCAGTCAGAGGGACAGTCTCCTTCCATATTCC BLA: C(R15a)Sub45_2
                                           SEQ ID NO: 36
TAGCCTTCCTCCCGGGTCCCguCTCCTTTGGTTTCCTCguCCCTGGGCAC
GCCTCTCGT Dz3: Dz6(9:9)
                                           SEQ ID NO: 37
TGGGAGGAAGGCTAGCTACAACGAGAGGCGTGA BLB: C(R16d)Sub45_6
                                           SEQ ID NO: 38
CTAGCCTCCCTGGTCGGGTCCCguCTCCTTTGTCACGCCTCguTCCTCCC
AGTTTCCTCTCGTT Dz2: Dz2(9:8)
                                           SEQ ID NO: 26
CCCAGGGAGGCTAGCTACAACGAGAGGAAACC
```

Reaction Components

Reactions A, B, C, and D were set up to contain the following oligonucleotides as listed in Table 15, with reference to oligonucleotides listed in the previous section and structures illustrated in FIG. 16 panel i). For all reactions, the BL and DNAzyme were initially pre-hybridized together for 30 minutes at room temperature before the addition of any further oligonucleotide components.

TABLE 15

| Reaction A (Circle A only, No AF1) | Reaction B (Circle A only, AF1 present) | Reaction C (Circle A and B, no AF1) | Reaction D (Circle A and B, AF1 present) |
| --- | --- | --- | --- |
| Sub6-FB 200 nM | Sub6-FB 200 nM | Sub6-FB 200 nM | Sub6-FB 200 nM |
| C(R15a)Sub45_2 200 nM | C(R15a)Sub45_2 200 nM | C(R15a)Sub45_2 200 nM | C(R15a)Sub45_2 200 nM |
| Dz6 (9:9) 100 nM | Dz6 (9:9) 100 nM | Dz6 (9:9) 100 nM | Dz6 (9:9) 100 nM |
|  |  | C(R16d)Sub45_6 150 nM | C(R16d)Sub45_6 150 nM |
|  |  | Dz2 (9:8) 100 nM | Dz2 (9:8) 100 nM |
| TFRCA4/45-P 100 nM | TFRCA4/45-P 100 nM | TFRCA4/45-P 100 nM | TFRCA4/45-P 100 nM |
| TFRCB5/45-P 100 nM | TFRCB5/45-P 100 nM | TFRCB5/45-P 100 nM | TFRCB5/45-P 100 nM |
|  | AF-TFRC 1 nM |  | AF-TFRC 1 nM |

Oligos were purchased from Integrated DNA Technologies (IDT) or Biosearch technologies. All reactions contained 1×PCR buffer II (Applied Biosystems), nuclease free water (Ambion) and 25 mM of MgCl$_2$ (Ambion). The total volume of all reactions was 25 μL. All reactions were performed in duplicate at 50° C. in a Bio-Rad® CFX96 thermocycler and fluorescence signal was measured in Channel 1 (FAM) and was programmed to be read every 30 seconds (scan mode: FAM only) for a total of 100 minutes.

Results

FIG. 16 panel ii) shows results comparing the fluorescent signal when one versus two DNAzyme quasi-circles was present. In these reactions, Substrate 3 which is labelled with a FAM fluorophore and quencher can be cleaved by Dz3 and hence the release and activation of Dz3 can be monitored by changes in fluorescence for FAM. For reactions A and C, where Substrate 3 and partzymes are present and either only quasi-circle A for Reaction A, ('Circle A only, no AF1' shown as a line with square symbols) or both quasi circles A and B for Reaction C ('Circle A and B, no AF1' shown as a line containing triangle symbols) there is very little cleavage of Substrate 3 and as a result, minimal increase in FAM signal over time. This indicates that the DNAzymes are inactive when complexed with the BLs where there is no MNAzyme assembly facilitator (AF1) present to trigger cleavage of Substrate 1 by the MNAzyme. Reaction B contains the same components as Reaction A, but with the addition of MNAzyme assembly facilitator ('Circle A only, AF1 present', line with diamond symbols) and results in an initial lag phase followed by a gradual increase in FAM signal over time, which eventually reaches a plateau at approximately 90 minutes towards the end of the reaction time. Reaction D contains the same components as Reaction C, but with the addition of MNAzyme assembly facilitator ('Circle A and B, AF1 present', line containing circle symbols) and results in an initial lag phase followed by a rapid increase in FAM signal reaching a plateau at approximately 40 minutes, indicating that a cross-catalytic feedback cascade is occurring when both circles are present, which increases the speed of Dz3 activation and thus cleavage of Substrate 3.

Example 13

The following example demonstrates a cross-catalytic DNAzyme quasi-circle cascade as originally outlined in Example 12. In this example however, the concentration of MNAzyme assembly facilitator was titrated down to determine the cascade's limit of detection above background and to demonstrate exponential amplification of signal at all assembly facilitator concentrations. Circle A and Circle B are both present (depicted schematically in FIG. 16 panel i)) however, the fluorescently labeled Substrate 3 is instead replaced by a fluorescently labeled Substrate 2, which is cleaved by Dz2, following its release and activation from Circle B.

Oligonucleotides

In the current example, Circle A consists of the BLA (SEQ ID NO: 36; C(R15a)Sub45_2) which is composed of (i) 5' and 3' ends that are complementary to a portion of Dz3 (SEQ ID NO: 40; Dz6(9:8)) and (ii) a central portion connecting the 5' and 3' ends that consists of the adjacent sequences of both Substrate 1 (SEQ ID NO: 3; Sub45) and Substrate 2a, which is equivalent to Substrate 2 (SEQ ID No: 5; Sub2) but lacks the 5' terminal 'AGG' nucleotides. BLA is utilized to block the activity of Dz3 by pre-hybridizing the BLA with Dz3. Circle B consists of the BLB (SEQ ID NO: 38; C(R16d)Sub45_6) which is composed of (i) 5' and 3' ends that are complementary to a portion of Dz2 (SEQ ID NO: 26; Dz2(9:8)) and (ii) a central portion connecting the 5' and 3' ends that consists of the adjacent sequences of both Substrate 1 and Substrate 3a. BLB is utilized to block the activity of Dz2 by pre-hybridizing the BLB with Dz2.

An MNAzyme (Mz1) consisting of partzymes (Partzyme A, SEQ ID NO: 33; TFRCA4/45-P and Partzyme B, SEQ ID NO: 34 TFRCB5/45-P), and an assembly facilitator target (AF1, SEQ ID NO: 35 AF-TFRC) is utilized to cleave the Substrate 1 portion of either BLA or BLB. This target dependent cleavage event facilitates the release of either or both Dz3 or Dz2, allowing them to act upon BLB or BLA respectively or for Dz2 to act upon a separate Substrate 2, which in this example, was end-labeled with a FAM moiety on the 5' end and a Black Hole Quencher 1 ("BHQ1") moiety on the 3' end.

The sequences of these oligonucleotides are listed from 5' to 3' below. Bases in uppercase are deoxyribonucleotides and bases in lowercase are ribonucleotides. Underlined bases represent regions in the BLA that are complementary to a portion of Dz3 and regions in the BLB that are complementary to a portion of Dz2. Bases in italics refer to regions corresponding to a substrate sequence within the BL molecule. Boxed bases represent the catalytic core of the DNAzymes and Partzymes. Nucleotides highlighted in grey represent the bases in Dz3 and Dz2 that are complementary to and blocked by, the underlined bases in the BLA and BLB molecules respectively. /3Phos/ indicates 3' end phosphorylation.

```
Substrate 2: Sub2-FB
                                               SEQ ID NO: 5
AAGGTTTCCTGguCCCTGGGCA Partzyme A: TFRCA4/45-P
                                               SEQ ID NO: 33
GGAATATGGAAGGAGACTGTCACAACGAGGGACCCGT/3Phos/

Partzyme B: TFRCB5/45-P
                                               SEQ ID NO: 34
TTCCAAAGGAGAGGCTAGCTCCTCTGACTGGAAAACAGACT/3Phos/

Assembly facilitator (AF1): AF-TFRC
                                               SEQ ID NO: 35
AGTCTGTTTTCCAGTCAGAGGGACAGTCTCCTTCCATATTCC BLA: C(R15a)Sub45_2
                                               SEQ ID NO: 36
TAGCCTTCCTCCCGGGTCCCguCTCCTTTGGTTTCCTCguCCCTGGGCAC
GCCTCTCGT BLB: C(R16d)Sub45_6
                                               SEQ ID NO: 38
CTAGCCTCCCTGGTCGGGTCCCguCTCCTTTGTCACGCCTCguTCCTCCC
AGTTTCCTCTCGTT Dz2: Dz2(9:8)
                                               SEQ ID NO: 26
CCCAGGGAGGCTAGCTACAACGAGAGGAAACC Dz3: Dz6(9:8)
                                               SEQ ID NO: 40
GGGAGGAAGGCTAGCTACAACGAGAGGCGTGA
```

Reaction Components

Reactions A, B, C, D, E and F were set up to contain the following oligonucleotide fragments as listed in Table 16, with reference to oligonucleotides listed in the previous section and structures illustrated in FIG. 16 panel i). For all reactions, the BL and DNAzyme were initially pre-hybridized together for 30 minutes at room temperature before the addition of any further oligonucleotide components.

TABLE 16

| Reaction A (Circle A and B, 1 nM AF1) | Reaction B (Circle A and B, 500 pM AF1) | Reaction C (Circle A and B, 250 pM AF1) | Reaction D (Circle A and B, 100 pM AF1) | Reaction E (Circle A and B, 25 pM AF1) | Reaction F (Circle A and B, No AF1) |
|---|---|---|---|---|---|
| Sub2-FB 200 nM C(R15a)Sub45_2 200 nM Dz6 (9:8) 100 nM C(R16d)Sub45_6 150 nM Dz2 (9:8) 100 nM TFRCA4/45-P 40 nM TFRCB5/45-P 40 nM ||||||
| AF-TFRC 1 nM | AF-TFRC 500 pM | AF-TFRC 250 pM | AF-TFRC 100 pM | AF-TFRC 25 pM | |

Oligos were purchased from Integrated DNA Technologies (IDT) or Biosearch technologies. All reactions contained 1×PCR buffer II (Applied Biosystems), nuclease free water (Ambion) and 45 mM of $MgCl_2$ (Ambion). The total volume of all reactions was 25 All reactions were performed in duplicate at 48.5° C. in a Bio-Rad® CFX96 thermocycler and fluorescence signal was measured in Channel 1 (FAM) and was programmed to be read every 30 seconds (scan mode: FAM only) for a total of 140 minutes.

Results

FIG. 16 panel iii) shows the fluorescent signal from the two DNAzyme quasi-circles with MNAzyme assembly facilitator titration. Here, Substrate 2 which can be cleaved by Dz2 is labelled with a FAM fluorophore and quencher, and hence the release and activation of Dz2 can be monitored by changes in fluorescence for FAM. For each of the reactions: Reaction A ('Circle A and B, 1 nM AF1' shown as a line with diamond symbols), Reaction B ('Circle A and B, 500 pM AF1' shown as a line containing triangle symbols), Reaction C ('Circle A and B, 250 pM AF1', line containing circle symbols), Reaction D ('Circle A and B, 100 pM AF1' line containing a symbol that consists of two diagonal and one vertical intersecting lines), Reaction E ('Circle A and B, 25 pM AF1' line containing a symbol that consists of two diagonal intersecting lines) and Reaction F ('Circle A and B, No AF1' line containing square symbols) there is an initial lag phase consisting of a small linear increase in fluorescence, followed by a steep increase in FAM signal (indicating an exponential phase of signal amplification) after which it reaches a plateau. The time at which each reaction undergoes exponential phase is correlated to the concentration of MNAzyme assembly facilitator, with Reaction A undergoing exponential phase the earliest, followed in order by Reactions B, C, D, and E. The control Reaction F, which lacks the target assembly facilitator, does not produce a signal until after all the reactions containing assembly facilitator have produced signal, thereby allowing discrimination between reaction with the lowest concentrations of target AF1 from those lacking target AF1.

Example 14

Example 14 demonstrates the use of a primer to synthesize DNAzyme molecules as earlier outlined in Example 9. In this example however, the primer is initially present in an inactive form as a component of an MNAzyme substrate (as depicted in FIG. 12 panel iii). When a target assembly facilitator (AF1) is present, the MNAzyme (Mz1) is active and can cleave its Substrate, resulting in two cleaved fragments (Cleaved Substrate) corresponding to the 5' and 3' ends of the substrate. The 5' end now contains a new 3' terminus, which remains blocked from extension by polymerases due to a 2'3' cyclic phosphate group. T4 Polynucleotide kinase (T4 PNK) is an enzyme that can catalyse the removal of phosphate groups from the 3' termini of nucleic acids. In the presence of T4 PNK, the 2'3' cyclic phosphate is removed from the cleaved MNAzyme substrate and consequently, the primer is now an Active Primer. In this reaction outlined in FIG. 17 panel ii), a hairpined molecule exists consisting of a BL portion comprising a partial DNAzyme containing one substrate-binding arm and approximately half of the catalytic core sequence. This partial catalytic core also contains an inactivating mutated base. In the presence of a polymerase enzyme, it is able to extend this sequence using the Dz template as a template for copying, thus completing the sequence of the inactive DNAzyme at the 3' end of the hairpin molecule. Due to the mutation in the core region however, the DNAzyme remains inactive even when the hairpin is open. The hairpin loop in this example consists of nucleotides which form a partial recognition sequence for a nicking enzyme When a primer is activated by both MNAzyme substrate cleavage and T4 PNK activity, it hybridizes to the loop sequence of the hairpin and is extended at its 3' end by a strand displacing polymerase using the Dz template strand as template to copy. Primer extension results in the synthesis of a new and complete copy of the DNAzyme. The extension of the primer also results in the completion of a double-stranded nicking enzyme recognition site. The nicking enzyme can recognize this site and selectively nick the newly synthesized strand at a region between the upstream primer and downstream DNAzyme sequence. Nicking therefore generates a new primer, which is extended by polymerase to both synthesize another DNAzyme copy and displace the pre-existing copy from the Dz template. This cycle of nicking, polymerization and displacement can then occur autonomously to generate several active DNAzyme molecules capable of cleaving their own substrates.

Oligonucleotides

An MNAzyme (Mz1), consisting of the partzymes (Partzyme A, SEQ ID NO: 41; TFRCA4/2-P and Partzyme B, SEQ ID NO: 42 TFRCB5/2-P), and an assembly facilitator (AF1) target (SEQ ID NO: 35 AF-TFRC) is utilized to cleave Substrate 1 (SubK1(14:12), SEQ ID NO: 43). In this example SubK1(14:12) was labeled with a 6-fluorescein ("6-FAM") moiety at the 5' end and a Black Hole Quencher 1 ("BHQ1") at the 3' end. The 'Partially blocked' hairpined Dz template (SEQ ID NO: 44; hp(R22a)ADz45) providing a template for DNAzymes to be synthesized that are capable of cleaving Substrate 2 (Sub45, SEQ ID NO: 3) was utilized. In this example Sub45 was labeled with a Quasar 670 ("Q670") moiety at the 5' end and a Black Hole Quencher 2 ("BHQ2") at the 3' end. The catalytic activity of the DNAzymes synthesized from the 'Partially blocked' hairpined Dz template was compared to that of a corresponding positive control Dz, (SEQ ID NO: 45; Dz45(9:9)).

The sequences of these oligonucleotides are listed from 5' to 3' below. Bases in uppercase are deoxyribonucleotides and bases in lowercase are ribonucleotides. Bases in italics refer to DNAzyme sequence within the hairpined DNAzyme structure. Underlined bases represent regions of complementarity between the primer and the hairpined DNAzyme. Highlighted bases represent the partial nicking enzyme recognition site. Boxed bases represent the catalytic core of DNAzymes and partzymes. /3Phos/ indicates 3' end phosphorylation.

```
Substrate 1: SubK1(14:12)-FB
                                        SEQ ID NO: 43
CGAAGGTTTCCTCguCCCTGGGCACG Partzyme A: TFRCA4/2-P
                                        SEQ ID NO: 41
GGAATATGGAAGGAGACTGTCACAACGAGAGGAAACCTT/3Phos/

Partzyme B: TFRCB5/2-P
                                        SEQ ID NO: 42
TGCCCAGGGAGGCTAGCTCCTCTGACTGGAAAACAGACT/3Phos/

Assembly Facilitator (AF1): AF-TFRC
                                        SEQ ID NO: 35
AGTCTGTTTTCCAGTCAGAGGGACAGTCTCCTTCCATATTCC 'Partially blocked' hairpined Dz template:
hp(R22a)ADz45
                                        SEQ ID NO: 44
GATCCGACTAGGACGGGTCCTCGTTGTAGCTAGCCTCTCCTTTGGGCTGA
TCCGAGGAAACCTTCCAAAGGAGAAGCTA Positive Control Dz: Dz45(9:9)
                                        SEQ ID NO: 45
CAAAGGAGAGGCTAGCTACAACGAGGGACCCGT Substrate 2: Sub45-Q670B2
                                        SEQ ID NO: 3
ACGGGTCCCguCTCCTTTGGAA
```

Reaction Components

Reactions A, B, C, D, E and F, were set up to contain the following oligonucleotides, Polymerase, T4 PNK and nicking enzymes as listed in Table 17, with reference to oligonucleotides in the previous section and structures illustrated in FIG. 17 panel ii).

TABLE 17

| Reaction A (No PNK, No AP1) | Reaction B (No PNK, 10 nM AF1) | Reaction C (PNK present, No AF1) | Reaction D (PNK present, 10 nM AF1) | Reaction E (Negative control) | Reaction F (Positive control) |
|---|---|---|---|---|---|
| Sub45-Q670B2 200 nM | Sub45-Q670B2 200 nM | Sub45-Q670B2 200 nM | Sub45-Q670B2 200 nM | Sub45-Q670B2 200 nM | Sub45-Q670B2 200 nM |
| SubK1(14:12)-FB 100 nM | SubK1(14:12)-FB 100 nM | SubK1(14:12)-FB 100 nM | SubK1(14:12)-FB 100 nM | | |
| TFRCA4/2-P 50 nM | TFRCA4/2-P 50 nM | TFRCA4/2-P 50 nM | TFRCA4/2-P 50 nM | | |
| TFRCB5/2-P 50 nM | TFRCB5/2-P 50 nM | TFRCB5/2-P 50 nM | TFRCB5/2-P 50 nM | | |
| | AF-TFRC 10 nM | | AF-TFRC 10 nM | | |
| | | | | | Dz45(9:9) 10 nM |
| Bst 2.0 warm start (0.6 U) | Bst 2.0 warm start (0.6 U) | Bst 2.0 warm start (0.6 U) | Bst 2.0 warm start (0.6 U) | | |
| Nt.AlwI (2.2 U) | Nt.AlwI (2.2 U) | Nt.AlwI (2.2 U) | Nt.AlwI (2.2 U) | | |
| | | T4 PNK (4 U) | T4 PNK (4 U) | | |

Oligos were purchased from IDT or Biosearch Technologies. The polymerase enzyme, Bst 2.0 warm start, the nicking enzyme, Nt.AlwI and T4 PNK were all purchased from New England Biolabs. All reactions contained 1×NEB buffer 2 (New England Biolabs), 200 μM dNTPs (Bioline) and nuclease free water (Ambion). The total volume of all reactions was 25 μL. All reactions were performed in duplicate at 51° C. in a Bio-Rad® CFX96 thermocycler. Fluorescence signal was measured on Channel 1 (FAM) and Channel 4 (Q670) and was programmed to be read every 30 seconds (scan mode: all channels) for a total of 154 minutes.

Results

FIG. 17 panel iii) demonstrates the fluorescent signal achieved from the strategy depicted in FIG. 17 panel ii). Substrate 1, which can be cleaved by the active MNAzyme is labelled with a FAM fluorophore and quencher moiety. The graph (FAM) outlines the fluorescent signal from this FAM fluorophore. Substrate 2, which can be cleaved by the synthesized DNAzymes is labelled with a Q670 fluorophore and quencher moiety. The graph (Q670) outlines the fluorescent signal from this Q670 fluorophore. For Reactions A ('No PNK, no AF1' shown as a line with square symbols) and C ('PNK present, No AF1', shown as a line with triangle symbols) no AF1 is present to assemble an active MNAzyme. Consequently, there is no increase in FAM signal indicating no cleavage of Substrate 1 as well as no increase in Q670 signal, indicating that there are no active DNAzymes synthesized to cleave Substrate 2. This Q670 signal is shown in comparison to Reaction E containing the negative control ('Negative control', line containing a symbol that consists of two diagonal and one vertical intersecting lines) which contains Substrate 2 only.

For Reactions B ('No PNK, 10 nM AF1', shown as a line with diamond symbols) and D ('PNK present, 10 nM AF1', shown as a line with circle symbols) the AF1 is present, resulting in the formation of an active MNAzyme. As a result, there is a gradual increase in FAM signal, indicating that Substrate 1 is being cleaved by the MNAzyme. After a short delay, there is then a gradual increase in Q670 signal for Reaction D, indicating that the T4 PNK is removing the phosphate group from the cleaved Substrate 1, allowing it to act as a primer and result in the synthesis of DNAzymes that subsequently cleave Substrate 2. This Q670 signal is shown in comparison to Reaction F containing the positive control ('Positive control', line containing a symbol that consists of two diagonal intersecting lines) which consists of Substrate 2 and the same concentration of a free positive control DNAzyme as that of the MNAzyme AF1. The signal from Reaction D plateaus faster than that of the positive control indicating more DNAzymes are being synthesized during the reaction time than that which are provided in the positive control. There is no increase in Q670 signal for Reaction B because it does not contain the T4 PNK enzyme indicating that the cleaved Substrate 1 cannot then act as a primer unless its 3' terminus is modified.

Example 15

Example 15 demonstrates the use of a primer to directly activate DNAzyme molecules as originally described in Example 9. However, this example specifically demonstrates the improved specificity that occurs with hairpined molecules which instead contain incomplete and inactive DNAzyme sequences. It also demonstrates the improved speed that occurs using a hairpined molecule compared to using an antisense Dz template. Four different molecular complexes depicted in FIG. 19 panel i) are compared. The first (part A) is a 'Complete' hairpined Dz, as originally described in Example 9. The second (part B) is referred to as a 'Fully Blocked' hairpined Dz template as the BL portion contains a DNAzyme sequence lacking four nucleotides of catalytic core sequence and this BL blocks an anti-sense DNAzyme template which can be copied by polymerase to produce an active DNAzyme. In the third, 'Partially Blocked' hairpined Dz template (part C), the BL portion contains a partial DNAzyme containing one substrate-binding arm and approximately half of the catalytic core sequence. The catalytic core also contains an inactivating mutated base in a region that renders the DNAzyme formed by extension of the BL to be catalytically inactive. The BL of part C blocks an anti-sense DNAzyme template which can be copied by polymerase to produce an active DNAzyme. In the presence of a polymerase enzyme, the BL is able to extend this sequence using the Dz template as the template for copying, however due to the mutation in the core region no active DNAzyme is exposed when the hairpin is open.

For both the 'Fully blocked' and 'Partially Blocked' hairpined Dz template molecules, the Dz template (ASDz) sequence contains the complete complement of an active DNAzyme sequence including the complement of the nucleotides in the core region which were lacking or mutated in the BL in the 'Fully' and 'Partially' blocked hairpin Dz templates respectively. For all three hairpined molecules, the hairpin loop linking the BL and the DNAzyme sequences, or complement thereof, consists of nucleotides which form a partial recognition sequence for a nicking enzyme. The final complex (part D) is an unblocked antisense DNAzyme sequence adjacent to a primer-binding site and partial recognition sequence for a nicking enzyme. In this complex there is no BL sequence present initially and no hairpin formation.

When a primer is present, it hybridizes to the primer-binding region (which is the loop sequence for the three hairpined structures), and is extended at its 3' end by a strand displacing polymerase. Primer extension results in the synthesis of a new DNAzyme containing the complete sequence required for catalytic activity, via the use of the BL (part A) or antisense Dz template sequence as a template (parts B, C and D). The extension of the primer also results in the completion of a double-stranded nicking enzyme recognition site. The nicking enzyme can recognize this site and selectively nick the newly synthesized strand at a region between the upstream primer and downstream DNAzyme sequence. Nicking therefore generates a new primer, which is extended by polymerase to both synthesize another complete DNAzyme sequence and displace the pre-existing DNAzyme from the BL (part A) or antisense Dz template (parts B, C and D). This cycle of nicking, polymerization and displacement can then occur autonomously to generate several active DNAzyme molecules. The improvement in specificity for the 'Fully blocked hairpined Dz' and 'Partially blocked hairpined Dz" molecules and for the 'Unblocked Dz template' primarily comes from the absolute requirement of both primer extension and nicking enzyme activity before an active DNAzyme is present in the reaction. The improvement in speed from the 'Fully blocked hairpined Dz' and 'Partially blocked hairpined Dz' over that of the 'Unblocked Dz template' is postulated to primarily occur because the Fully and Partially blocked Dz templates are hybridized to an opposing BL strand when the hairpins are in their initial closed conformation, and to an opposing newly synthesised Dz strand (an extension of the primer) when the hairpins are in an open conformation. This minimises the ability of the Dz template strand to sequester newly synthesized single-stranded Dz molecules as the Dz template is always in a double stranded formation.

Oligonucleotides

The 'Complete' hairpined Dz (SEQ ID NO: 31; hp(R6b) Dz45), the 'Fully Blocked' hairpined Dz template (SEQ ID NO: 46; hp(R8b)ADz45), the 'Partially Blocked' hairpined Dz template (SEQ ID NO: 47; hp(R11b)ADz45) and the Unblocked Dz-template (SEQ ID NO: 48; (R15a)-Dz45), either capable of directly cleaving, or synthesizing DNAzymes which cleave the Substrate (Sub45, SEQ ID NO: 3), was utilized. In this example Sub45 was labeled with a 6-fluorescein ("6-FAM") moiety at the 5' end and an Iowa Black quencher moiety ("BHQ1") at the 3' end. Primer 1 (SEQ ID NO: 32; PR(R6)Dz45(10)) was employed to activate the 'Complete' hairpined Dz and synthesize additional copies of the DNAzyme. Primer 2 (SEQ ID NO: 49; PR(R8b)Dz45(14)) was employed to synthesize copies of the DNAzyme from the 'Fully blocked hairpined Dz template' and 'Partially blocked hairpined Dz template' and from the 'Unblocked Dz-template'.

The sequences of these oligonucleotides are listed from 5' to 3' below. Bases in uppercase are deoxyribonucleotides and base in lowercase are ribonucleotides. Bases in italics refer to DNAzyme sequence within the hairpined DNAzyme structures. Underlined bases represent regions of complementarity between the primer and the hairpined DNAzyme or antisense DNAzyme template. Shaded bases represent the partial nicking enzyme recognition site. Boxed bases represent bases corresponding to the catalytic core of a DNAzyme.

```
Substrate: Sub45-FIB
                                                SEQ ID NO: 3
ACGGGTCCCguCTCCTTTGGAA 'Complete' hairpined Dz: hp(R6b)-Dz45
                                                SEQ ID NO: 31
ACGGGTCCCTCGTTGTAGCTAGCCTCTCCTTTGGTCGTCGATCCTGAGAC
CAAAGGAGAGGCTAGCTACAACGAGGGACCCGT Primer 1: PR(R6)Dz45(10)
                                                SEQ ID NO: 32
TCAGGATCGA 'Fully Blocked' hairpined Dz template:
hp(R8b)-ADz45
                                                SEQ ID NO: 46
ACGGGTCCCTCGTTGTAGCTAGCCTCTCCTTTGGTCGCTGATCCTGTACT
TGACCAAAGGAGAGGCTACAACGAGGGACCCGT 'Partially Blocked' hairpined Dz template:
hp(R11b)-ADz45
                                                SEQ ID NO: 47
ACGGGTCCCTCGTTGTAGCTAGCCTCTCCTTTGGTCGCTGATCCTGTACT
TGACCAAAGGAGATGCTAGC 'Unblocked' Dz-template: (R15a)-Dz45
                                                SEQ ID NO: 48
ACGGGTCCCTCGTTGTAGCTAGCCTCTCCTTTGGAATCGCTGATCCTGTA
CTT Primer 2: hp(R11b)-ADz45
                                                SEQ ID NO: 49
AAGTACAGGATCAG
```

Reaction Components

Reactions A, B, C, D, E, F, G and H were set up to contain the following oligonucleotide fragments, Polymerase and nicking enzymes as listed in Table 18, with reference to oligonucleotides in the previous section and structures illustrated in FIG. 19 panel i).

TABLE 18

| Reaction A (Structure A, No PR) | Reaction B (Structure A, PR present) | Reaction C (Structure B, No PR) | Reaction D (Structure B, PR present) | Reaction E (Structure C, No PR) | Reaction F (Structure C, PR present) | Reaction G (Structure D, No PR) | Reaction H (Structure D, PR present) |
|---|---|---|---|---|---|---|---|
| Sub45-FIB 200 nM | Sub45-FIB 200 nM | Sub45-FIB 200 nM | Sub45-FIB 200 nM | Sub45-FIB 200 nM | Sub45-FIB 200 nM | Sub45-FIB 200 nM | Sub45-FIB 200 nM |
| hp(R6b)Dz45 100 nM | hp(R6b)Dz45 100 nM | | | | | | |
| | | hp(R68b)ADz45 100 nM | hp(R68b)ADz45 100 nM | | | | |
| | | | | hp(R611b)ADz45 100 nM | hp(R611b)ADz45 100 nM | | |
| | | | | | | (R15a)-Dz45 100 nM | (R15a)-Dz45 100 nM |
| | PR(R6)Dz45(10) 20 nM | | PR(R8b)Dz45(14) 20 nM | | PR(R8b)Dz45(14) 20 nM | | PR(R8b)Dz45(14) 20 nM |
| Bst 2.0 warm start (0.8 U) | Bst 2.0 warm start (0.8 U) | Bst 2.0 warm start (0.8 U) | Bst 2.0 warm start (0.8 U) | Bst 2.0 warm start (0.8 U) | Bst 2.0 warm start (0.8 U) | Bst 2.0 warm start (0.8 U) | Bst 2.0 warm start (0.8 U) |
| Nt.AlwI (2.5 U) | Nt.AlwI (2.5 U) | Nt.AlwI (2.5 U) | Nt.AlwI (2.5 U) | Nt.AlwI (2.5 U) | Nt.AlwI (2.5 U) | Nt.AlwI (2.5 U) | Nt.AlwI (2.5 U) |

Oligos were purchased from IDT or Biosearch technologies. The polymerase enzyme, Bst 2.0 warm start and the nicking enzyme, Nt.AlwI were purchased from New England Biolabs. All reactions contained 1×NEB buffer 2 (New England Biolabs), 200 µM dNTPs (Bioline) and nuclease free water (Ambion). The total volume of all reactions was 25 µL. All reactions were performed in duplicate at 54° C. in a Bio-Rad® CFX96 thermocycler. Fluorescence signal was measured on Channel 1 (FAM) was programmed to be read every 30 seconds (scan mode: FAM only) for a total of 148 minutes.

Results

FIG. 19 panel ii) demonstrates the fluorescent signal achieved from the strategies depicted in FIG. 19 panel i). The substrate sequence, which can be cleaved by the DNAzyme following its activation and/or synthesis, is labeled with a FAM fluorophore and quencher dye. The graph (FAM) outlines the fluorescent signal from this FAM fluorophore. For Reactions A and B containing the 'Complete' hairpined Dz molecules ('Structure A–No PR', shown as a line with square symbols) and ('Structure A–PR present' shown as a line with diamond symbols) respectively, there is an immediate increase in FAM signal which is almost identical for both. This indicates that this structure lacks specificity under these conditions as signal is produced in the absence of primer. For Reactions C and D containing the 'Fully Blocked' hairpined Dz template molecules ('Structure B–No PR' shown as a line with triangle symbols) and ('Structure B–PR present' shown as a line with circle symbols) respectively, there is an immediate and rapid increase in signal for Reaction D containing the primer, and a much slower, gradual increase in signal for Reaction C lacking the primer. This indicates that the specificity has been improved upon the 'Complete' hairpined Dz structure as the primer is required to significantly increase the signal produced, however there is still some primer-independent activity.

For Reactions E and F containing the 'Partially Blocked' hairpined Dz template molecules ('Structure C–No PR, line containing a symbol that consists of two diagonal and one vertical intersecting lines) and ('Structure C–PR present', line containing a symbol that consists of two diagonal intersecting lines) respectively, there is no increase in signal for Reaction E without the primer present, but an immediate and rapid increase in signal for Reaction F containing the primer. The 'Partially Blocked' hairpined Dz template therefore improves upon the specificity of the 'Complete' and 'Fully Blocked' hairpined Dz template molecules as there is no primer-independent signal. Finally, for Reactions G and H containing the 'Unblocked' Dz-template ('Structure D–No PR', line containing a symbol with one vertical intersecting line) and ('Structure D–PR present', line containing a symbol that consists of a filled black square) respectively, there is no increase in signal for Reaction G without the primer present, but a gradual increase in signal for Reaction H containing the primer. The 'Unblocked' Dz template contains the same specificity as the 'Partially Blocked' hairpined Dz template structure, but does not produce a signal as rapidly in the presence of the primer as does the 'Partially Blocked' hairpined Dz template structure. This is because the newly synthesized DNAzymes can re-hybridise with vacant antisense Dz templates, inevitably slowing the reaction down. This does not appear to occur with the 'Partially Blocked' hairpined Dz template because the Dz template itself is blocked within the hairpin structure and always remains double-stranded.

Example 16

Example 16 demonstrates the inactivation of a primer via its hybridization to a BL molecule, both of which are linked via a non-complementary loop to form a hairpin structure, as depicted in FIG. 23 panel i). The molecule is initially provided as a 'Partial' hairpined primer, whereby only a portion of the primer sequence is present. In the presence of a polymerase enzyme, the 3' terminus of the molecule can be extended using the BLA as a template to complete the synthesis of the primer sequence. The BLA of the hairpined primer contains a substrate for an MNAzyme, such that in the presence of its target assembly facilitator, the MNAzyme can cleave the substrate present within the BL, resulting in the release of the primer from the BL, rendering the primer active. As initially described in Example 15, a 'Partially blocked' hairpined Dz template also exists, consisting of a BLB portion consisting of a partial DNAzyme containing one substrate-binding arm and approximately half of the catalytic core sequence. This partial catalytic core also contains an inactivating mutant base. In the presence of a polymerase enzyme, the BLB is able to be extended using the Dz template (ASDz) as a template for copying, thus completing the sequence of the inactive DNAzyme at the 3' end of the hairpin molecule. Due to the mutation in the core region however, the DNAzyme is inactive even when the hairpin is open.

Once active, the primer can function to hybridize to the loop of the 'Partially blocked' hairpined Dz template and be extended at its 3' end by a strand displacing polymerase, as initially described in Example 9. Primer extension results in the synthesis of a new and complete copy of the DNAzyme, via the use of the 'Partially blocked' hairpined Dz template sequence as a template for copying. The extension of the primer also results in the completion of a double-stranded nicking enzyme recognition site. The nicking enzyme can recognize this site and selectively nick the newly synthesized strand at a region between the upstream primer and downstream DNAzyme sequence. Nicking therefore generates a new primer, which is extended by polymerase to both synthesize another DNAzyme copy and displace the pre-existing copy from the Dz template. This cycle of nicking, polymerization and displacement can then occur autonomously to generate several active DNAzyme molecules capable of cleaving their own substrates.

Oligonucleotides

The 'Partially blocked' hairpined Dz template (SEQ ID NO: 47; hp(R11b)ADz45) providing a template for Dz2 to be synthesized that is capable of cleaving Substrate 2 (Sub45, SEQ ID NO: 3) was utilized. In this example Sub45 was labeled with a 6-fluorescein ("6-FAM") moiety at the 5' end and an Iowa Black quencher moiety ("IB") at the 3' end. A partial hairpined primer (SEQ ID NO: 50; hpPR(R15h) Sub2) was employed to activate and synthesize additional copies of Dz2, once extended by polymerase and subsequently cleaved by an MNAzyme (Mz1). Mz1 consists of Partzyme A (KrasA4/2-P, SEQ ID: 51), Partzyme B (KrasB5/2-P, SEQ ID: 52) and Assembly facilitator 1 ('AF1', AF-Kras, SEQ ID: 53). The ability of the cleaved hairpin primer to prime synthesis of new Dz2 molecules was compared to that of a non-hairpined linear primer (PR(R8b) Dz45(14), SEQ ID: 49). The catalytic activity of the Dz2 synthesized from the hairpined template was also compared to that of a corresponding non-hairpined positive control Dz2, (SEQ ID NO: 4; Dz45(9:10)).

The sequences of these oligonucleotides are listed from 5' to 3' below. Bases in uppercase are deoxyribonucleotides and base in lowercase are ribonucleotides. Bases in italics refer to partial DNAzyme sequence within the 'Partially blocked' hairpined DNAzyme template structure and to primer sequence within the hairpined primer structure. Underlined bases represent regions of complementarity between the primer and the 'Partially blocked' hairpined Dz template. Highlighted bases represent the partial nicking enzyme recognition site. Boxed bases represent bases that correspond to the catalytic core of Partzymes and DNAzymes. /3Phos/indicates 3' end phosphorylation.

```
Substrate 2: Sub45-FIB
                                           SEQ ID NO: 3
ACGGGTCCCguCTCCTTTGGAA Positive Control Dz2: Dz45(9:10)
                                           SEQ ID NO: 4
CCAAAGGAGAGGCTAGCTACAACGAGGGACCCGT 'Partially blocked' hairpined Dz2 template:
hp(R11b)ADz45
                                           SEQ ID NO: 47
ACGGGTCCCTCGTTGTAGCTAGCCTCTCCTTTGGTCGCTGATCCTGTACTT
GACCAAAGGAGATGCTAGC Partial hairpined primer: hpPR(R15h)Sub2
                                           SEQ ID NO: 50
CTGATCCTGTACTTCCGAGCATCCTTTTTGGATGCTCAGGTTTCCTCguC
CCTGGGCAAGTAC Partzyme A: KrasA4/2-P
                                           SEQ ID NO: 51
TAAACTTGTGGTAGTTGGAGACAACGAGAGGAAACCTT/3Phos/

Partzyme B: KrasB5/2-P
                                           SEQ ID NO: 52
TGCCCAGGGAGGCTAGCTCTGGTGGCGTAGGCAAGAGTGCC/3Phos/

AF1: AF-Kras
                                           SEQ ID NO: 53
CAAGGCACTCTTGCCTACGCCACCAGCTCCAACTACCACAAGTTTATATT
CA Linear Primer: PR(R8b)Dz45(14)
                                           SEQ ID NO: 49
AAGTACAGGATCAG
```

Reaction Components

Reactions A, B, C, D, E, and F were set up to contain the following oligonucleotide fragments, Polymerase and nicking enzymes as listed in Table 19, with reference to oligonucleotides in the previous section and structures illustrated in FIG. 23 panel i).

TABLE 19

| Reaction A (Negative control) | Reaction B (Positive control) | Reaction C ('Partially blocked' hairpined Dz template only) | Reaction D ('Partially blocked' hairpined Dz template + linear primer) | Reaction E ('Partially blocked' hairpined Dz template + hairpined primer, No AF1) | Reaction F ('Partially blocked' hairpined Dz template + hairpined primer, AF1 present) |
|---|---|---|---|---|---|
| Sub45-FIB 200 nM | Sub45-FIB 200 nM | Sub45-FIB 200 nM | Sub45-FIB 200 nM | Sub45-FIB 200 nM | Sub45-FIB 200 nM |
|  | Dz45(9:10) 20 nM |  |  |  |  |
|  |  | hp(R11b)ADz45 100 nM | hp(R11b)ADz45 100 nM | hp(R11b)ADz45 100 nM | hp(R11b)ADz45 100 nM |
|  |  |  | PR(R8b)Dz45(14) 20 nM |  |  |

TABLE 19-continued

|  |  | Reaction C ('Partially blocked' hairpined Dz template only) | Reaction D ('Partially blocked hairpined Dz template + linear primer) | Reaction E ('Partially blocked hairpined Dz template + hairpined primer, No AF1) | Reaction F ('Partially blocked' hairpined Dz template + hairpined primer, AF1 present) |
|---|---|---|---|---|---|
| Reaction A (Negative control) | Reaction B (Positive control) |  |  |  |  |
|  |  |  |  | hpPR(15h)Sub2 30 nM | hpPR(15h)Sub2 30 nM |
|  |  | KrasA4/2-P 50 nM | KrasA4/2-P 50 nM | KrasA4/2-P 50 nM | KrasA4/2-P 50 nM |
|  |  | KrasB5/2-P 50 nM | KrasB5/2-P 50 nM | KrasB5/2-P 50 nM | KrasB5/2-P 50 nM |
|  |  |  |  |  | AF-Kras 20 nM |
|  |  | Bst 2.0 warm start (0.8 U) Nt.AlwI (2.5 U) | Bst 2.0 warm start (0.8 U) Nt.AlwI (2.5 U) | Bst 2.0 warm start (0.8 U) Nt.AlwI (2.5 U) | Bst 2.0 warm start (0.8 U) Nt.AlwI (2.5 U) |

Oligos were purchased from IDT or Biosearch technologies. The polymerase enzyme, Bst 2.0 warm start (3'→5' exo$^-$) and the nicking enzyme, Nt.AlwI were purchased from New England Biolabs. All reactions contained 1×NEB buffer 2 (New England Biolabs) and nuclease free water (Ambion). Reactions C-F also contained 200 µM dNTPs (Bioline). The total volume of all reactions was 25 µL. All reactions were performed in duplicate at 54° C. in a Bio-Rad® CFX96 thermocycler. Fluorescence signal was measured on Channel 1 (FAM) and was programmed to be read every 30 seconds (scan mode: FAM only) for a total of 105 minutes.

Results

FIG. 23 panel ii) demonstrates the fluorescent signal achieved from the strategy depicted in FIG. 23 panel i). Substrate 2, which can be cleaved by the Dz2 following its synthesis from the 'Partially blocked' hairpined Dz template, is labeled with a FAM fluorophore and quencher dye. The graph (FAM) outlines the fluorescent signal from this FAM fluorophore. For Reactions C and E where either the 'Partially blocked' hairpined Dz template exists on its own (Reaction C, "Partially blocked' hairpined template only" shown as a line with triangle symbols) or the 'Partially blocked' hairpined Dz template is present with the hairpined primer but without AF1 (Reaction E, "Partially blocked hairpined template+hairpined primer, No AF1' shown as a line with symbols consisting of one vertical and two diagonal intersecting lines), there is little increase in signal indicating little to no extension of the primer, little to no subsequent synthesis of Dz2 and therefore little to no cleavage of Substrate 2 and corresponding increase in FAM signal. This is shown in comparison to Reaction A containing the negative control ('Negative control', line containing square symbols) which contains the same fluorescently-labeled Substrate 2 only.

For Reaction D where the active linear primer is present ("Partially blocked' hairpined Dz template+linear primer', line containing circle symbols) there is a rapid increase in signal which quickly reaches a plateau within approximately 10 minutes. For Reaction F, containing the hairpined primer and AF1 ("Partially blocked' hairpined Dz template+hairpined primer, AF1 present', line containing a symbol that consists of two diagonal intersecting lines), there is a gradual increase in signal, reaching a plateau at approximately 60 minutes. For both reactions D and F, the increase in signal indicates the primer is being extended using the 'Partially blocked' hairpined Dz template as a template for copying and results in the synthesis of active DNAzymes via the synergistic action of the polymerase and nicking enzymes. The signal from the hairpined primer activation is slower due to the time required for the primer to be separated from its BL after the BL has been cleaved by the MNAzyme. The signal from Reactions D and F are shown in comparison to Reaction B containing the positive control ('Positive control', line containing diamond symbols) which consists of the same concentration of Substrate 2 and free positive control Dz2. The signal from Reaction D completes slightly faster than that of Reaction B, demonstrating the synthesis of Dz2 from 20 nM of linear primer is proceeding at a rate faster than that of the catalytic activity of the same concentration of Dz2 in the positive control.

Example 17

The following example demonstrates the inactivation of DNAzymes by hybridization to complementary BL molecules within a quasi-circular structure, as previously demonstrated in Example 1. In this current Example 17 however, three different substrate sequences are present within the BL. The cleavage of either Substrate 1, Substrate 2 or Substrate 3 by an active MNAzyme results in the release and subsequent re-activation of the previously inactive DNAzyme (depicted schematically in FIG. 20 panel i)).

Oligonucleotides

In the current example, the BL (SEQ ID NO: 54; C(R19b)) which is composed of (i) 5' and 3' ends that are complementary to a portion of Dz4 (Dz45(9:10), SEQ ID NO: 4) and (ii) a central portion connecting the 5' and 3' ends that is equivalent to the adjacent sequences of Substrate 1, Substrate 2 and Substrate 3. The BL is utilized to block the activity of Dz4 by pre-hybridizing the BL with Dz4. Mz1, consisting of partzymes (Partzyme 1A, SEQ ID NO: 56; TFRCA4/77-P and Partzyme 1B, SEQ ID NO: 57; TFRCB5/55-P), and an assembly facilitator target, AF1 (SEQ ID NO: 35 AF-TFRC), is utilized to cleave the Substrate 1 portion of the BL. Mz2, consisting of partzymes (Partzyme 2A, SEQ ID NO: 58; KrasA4/6-P and Partzyme 2B, SEQ ID NO: 59; KrasB5/6-P), and an assembly facilitator target, AF2 (SEQ ID NO: 53 AF-Kras), is utilized to cleave the Substrate 2 portion of the BL. Mz3, consisting of partzymes (Partzyme 3A, SEQ ID NO: 60; RO5A4/2-P and Partzyme 3B, SEQ ID NO: 61; RO5B5/2-P), and an assembly facilitator target, AF3 (SEQ ID NO: 62; AF-R05), is utilized to cleave the Substrate 3 portion of the BE For either Mz1, 2 or 3, the target dependent cleavage event facilitates the release of Dz4. Dz4 can then act upon Substrate 4 (SEQ ID NO: 3; Sub45), which in this example is end-labeled with a FAM moiety on the 5' end and an Iowa Black ("IB") moiety on the 3' end.

The sequences of these oligonucleotides are listed from 5' to 3' below. Bases in uppercase are deoxyribonucleotides and bases in lowercase are ribonucleotides. Underlined bases represent regions in the BL that are complementary to a portion of Dz4. Bases in italics refer to regions corresponding to a substrate sequence within the BL molecule. Boxed bases represent the catalytic core or partial catalytic core of the DNAzymes and Partzymes. Nucleotides highlighted in grey represent the bases in the Dz4 that are complementary to and blocked by, the underlined bases in the BL molecule. /3Phos/ indicates 3' end phosphorylation.

```
Substrate 4: Sub45-FIB
                                          SEQ ID NO: 3
ACGGGTCCCguCTCCTTTGGAA Partzyme 1A: TFRCA4/77-P
                                          SEQ ID NO: 56
GGAATATGGAAGAGACTGTCACAACGAGAGGGAGGAG/3Phos/

Partzyme 1B: TFRCB5/55-P
                                          SEQ ID NO: 57
GAGCTGGGGAGGCTAGCTCCTCTGACTGGAAAACAGACT/3Phos/

Assembly facilitator (AF1): AF-TFRC
                                          SEQ ID NO: 35
AGTCTGTTTTCCAGTCAGAGGGACAGTCTCCTTCCATATTCC Partzyme 2A: KrasA4/6-P
                                          SEQ ID NO: 58
TAAACTTGTGGTAGTTGGAGACAACGAGAGGCGTGAT/3Phos/

Partzyme 2B: KrasB5/6-P
                                          SEQ ID NO: 59
CTGGGAGGAAGGCTAGCTCTGGTGGCGTAGGCAAGAGTGCC/3Phos/

Assembly facilitator (AF2): AF-Kras
                                          SEQ ID NO: 53
CAAGGCACTCTTGCCTACGCCACCAGCTCCAACTACCACAAGTTTATATT
CA Partzyme 3A: RO5A4/2-P
                                          SEQ ID NO: 60
CAAACGAGTCCTGGCCTTGTCTACAACGAGAGGAAACCTT/3Phos/

Partzyme 3B: RO5B5/2-P
                                          SEQ ID NO: 61
TGCCCAGGGAGGCTAGCTGTGGAGACGGATTACACCTTC/3Phos/

Assembly facilitator (AF3): AF-RO5
                                          SEQ ID NO: 62
GAAGGTGTAATCCGTCTCCACAGACAAGGCCAGGACTCGTTTG BL: C(R19b)
                                          SEQ ID NO: 54
AGCCTCTCCTTTGTCCTCCCTCguCCCCAGCTTCACGCCTCguTCCTCCC
AAAGGTTTCCTCguCCCTGGGCGGGTCCCTCGTTG Dz4: Dz45(9:10)
                                          SEQ ID NO: 4
CCAAAGGAGAGGCTAGCTACAACGAGGGACCCGT
```

Reaction Components

Reactions A, B, C, D, E and F were set up to contain the following oligonucleotides as listed in Table 20, with reference to oligonucleotides listed in the previous section and structures illustrated in FIG. 20 panel i). For all reactions, the BL and Dz4 were initially pre-hybridized together for 30 minutes at room temperature before the addition of any further oligonucleotide components.

TABLE 20

| Reaction A (Mz1, No AF) | Reaction B (Mz1, AF1 present) | Reaction C (Mz2, No AF) | Reaction D (Mz2, AF2 present) | Reaction E (Mz3, No AF) | Reaction F (Mz3, AF3 present) |
| --- | --- | --- | --- | --- | --- |
| Sub45-FIB 200 nM | Sub45-FIB 200 nM | Sub45-FIB 200 nM | Sub45-FIB 200 nM | Sub45-FIB 200 nM | Sub45-FIB 200 nM |
| C(R19b) 200 nM | C(R19b) 200 nM | C(R19b) 200 nM | C(R19b) 200 nM | C(R19b) 200 nM | C(R19b) 200 nM |
| Dz45(9:10) 100 nM | Dz45(9:10) 100 nM | Dz45(9:10) 100 nM | Dz45(9:10) 100 nM | Dz45(9:10) 100 nM | Dz45(9:10) 100 nM |
| TFRCA4/77-P 50 nM | TFRCA4/77-P 50 nM | | | | |
| TFRCB5/55-P 50 nM | TFRCB5/55-P 50 nM | | | | |
| | | KrasA4/6-P 50 nM | KrasA4/6-P 50 nM | | |
| | | KrasB5/6-P 50 nM | KrasB5/6-P 50 nM | | |
| | | | | RO5A4/2-P 50 nM | RO5A4/2-P 50 nM |
| | | | | RO5B5/2-P 50 nM | RO5B5/2-P 50 nM |
| | AF-TFRC 10 nM | | | | |
| | | | AF-Kras 10 nM | | |
| | | | | | AF-RO5 10 nM |

Oligos were purchased from Integrated DNA Technologies (IDT) or Biosearch technologies. All reactions contained 1×PCR buffer II (Applied Biosystems), nuclease free water (Ambion) and 45 mM of MgCl$_2$ (Ambion). The total volume of all reactions was 25 µL. All reactions were performed in duplicate at 48° C. in a Bio-Rad® CFX96 thermocycler and fluorescence signal was measured in Channel 1 (FAM) and was programmed to be read every 30 seconds (scan mode: FAM only) for a total of 105 minutes.

Results

FIG. 20 panel ii) shows results comparing the fluorescent signal for the DNAzyme quasi-circle containing three different substrates within the BL. In these reactions, Substrate 4 which is labeled with a FAM fluorophore and quencher can be cleaved by Dz4 once Dz4 has been released from the BL, and hence the release and activation of the Dz4 can be monitored by changes in fluorescence for FAM. For reactions A ('Mz1, no AF' shown as a line with square symbols), Reaction C ('Mz2, no AF2' shown as a line with triangle symbols) and Reaction E ('Mz3, no AF3', shown as a line with a symbol consisting of one vertical and two diagonal intersecting lines), where the quasi-circle (Dz4 hybridized to the BL), Substrate 4 and only the partzymes of either Mz1, Mz2 or Mz3 are present respectively, there is very little cleavage of Substrate 4 and as a result, minimal increase in FAM signal over time. This indicates that Dz4 is inactive when complexed with a BL containing three separate adjacent substrate sequences. Reaction B contains the same components as Reaction A, but with the addition of MNAzyme assembly facilitator ('Mz1, AF1 present', line with diamond symbols). Reaction D contains the same components as Reaction C, but with the addition of MNAzyme assembly facilitator ('Mz2, AF2 present', line containing circle symbols). Reaction F contains the same components as Reaction E, but with the addition of MNAzyme assembly facilitator ('Mz3, AF3 present', line containing a symbol consisting of two diagonal intersecting lines). In each of Reactions B, D and F, there is an immediate increase in FAM signal indicating the BL has been cleaved and Dz4 is released and can cleave Substrate 4. The increase in signal from each of Reactions B, D and F is occurring at approximately the same rate, indicating that despite the increased length of the BL, a single cleavage event at any point in the intermediate region of the BL is all that is required for Dz4 to be released from the BL.

Example 18

The following example demonstrates the inactivation of DNAzymes by hybridization to complementary BL molecules within a quasi-circular structure, as previously demonstrated in Example 1. In this example however, one substrate sequence (Substrate 1) is present within the BL that can be cleaved by an 8:17 MNAzyme (Mz1) and another substrate (Substrate 2) is present within the BL that can be cleaved by a 10:23 MNAzyme (Mz2). Substrate 1 consists of two parts, the first 5' part is sequence that is unique to Substrate 1 and the other 3' part of substrate is sequence that also functions as the 5' part of Substrate 2. The 8:17 MNAzyme (Mz1) can recognize and cleave Substrate 1. This Mz1 can therefore be designed to recognize and cleave a sequence composed of half of an 8:17 MNAzyme substrate and half of a 10:23 MNAzyme substrate. The cleavage of either Substrate 1 by Mz1 or Substrate 2 by Mz2 respectively, results in the release and subsequent re-activation of the previously inactive Dz3 (depicted schematically in FIG. 20 panel iii)).

Oligonucleotides

In the current example, the BL (SEQ ID NO: 63; C(R14b)Sub1_2) which is composed of (i) 5' and 3' ends that are complementary to a portion of Dz3 (Dz6(8:7), SEQ ID NO: 8) and (ii) a central portion connecting the 5' and 3' ends that is equivalent to the adjacent sequences of Substrate 1 and Substrate 2. The BL is utilized to block the activity of the Dz3 by pre-hybridizing the BL with Dz3. Mz1, consisting of partzymes (Partzyme 1A, SEQ ID NO: 65; PPIAA2/1-P and Partzyme 1B, SEQ ID NO: 66; PPIAB3/2(9)), and an assembly facilitator target, AF1 (SEQ ID NO: 67; AF-PPIA), is utilized to cleave the Substrate 1 portion of the BL. Mz2, consisting of partzymes (Partzyme 2A, SEQ ID NO: 51; KrasA4/2-P and Partzyme 2B, SEQ ID NO: 52; KrasB5/2-P), and an assembly facilitator target, AF2 (SEQ ID NO: 53; AF-Kras), is utilized to cleave the Substrate 2 portion of the BL. For either Mz1, or Mz2, the target dependent cleavage event facilitates the release of Dz3. The Dz3 can then act upon Substrate 3 (SEQ ID NO: 11; Sub6), which in this example is end-labeled with a FAM moiety on the 5' end and a Black Hole Quencher ("BHQ1") moiety on the 3' end.

The sequences of these oligonucleotides are listed from 5' to 3' below. Bases in uppercase are deoxyribonucleotides and bases in lowercase are ribonucleotides. Underlined bases represent regions in the BL that are complementary to a portion of the Dz. Bases in italics refer to regions corresponding to a substrate sequence within the BL molecule. Boxed bases represent the catalytic core of the DNAzymes and Partzymes. Nucleotides highlighted in grey represent the bases in the Dz that are complementary to and blocked by, the underlined bases in the BL molecule. /3Phos/ indicates 3' end phosphorylation.

Substrate 3: Sub6-FB
SEQ ID NO: 11
ATCACGCCTCguTCCTCCCAG

Partzyme 1A: PPIAA2/1-P
SEQ ID NO: 65
TGGTTGGATGGCAAGCATGTG CGGTCGAA ATAGTGAGT/3Phos/

Partzyme 1B: PPIAB3/2(9)
SEQ ID NO: 66
GAGGAAACT CCGAGC GTGTTTGGCAAAGTGAAAGAAG

Assembly facilitator (AF1): AF-PPIA
SEQ ID NO: 67
CTTCTTTCACTTTGCCAAACACCACATGCTTGCCATCCAACCA Partzyme 2A: KrasA4/2-P
SEQ ID NO: 51
TAAACTTGTGGTAGTTGGAG ACAACGA GAGGAAACCTT/3Phos/

Partzyme 2B: KrasB5/2-P
SEQ ID NO: 52
TGCCCAGGGA GGCTAGCT CTGGTGGCGTAGGCAAGAGTGCC/3Phos/

Assembly facilitator (AF2): AF-Kras
SEQ ID NO: 53
CAAGGCACTCTTGCCTACGCCACCAGCTCCAACTACCACAAGTTTATATTCA BL: C(R14b)Sub1_2
SEQ ID NO: 63
TAGCCTTCCTCC*CTCACTATaGGTTTCCTCguCCCTGG*CACGCCTCTCGT Dz3: Dz6(8:7)
SEQ ID NO: 8
GGAGGAA GGCTAGCTACAACGA GAGGCGTG Reaction Components Reactions A, B and C were set up to contain the following oligonucleotides as listed in Table 21, with reference to oligonucleotides listed in the previous section and structures illustrated in FIG. 20 panel iii). For all reactions, the BL and Dz3 were initially pre-hybridized together for 30 minutes at room temperature before the addition of any further oligonucleotide components.

TABLE 21

| Reaction A (No AF) | Reaction B (AF1 present) | Reaction C (AF2 present) |
|---|---|---|
| Sub6-FB 200 nM | Sub6-FB 200 nM | Sub6-FB 200 nM |
| C(R14b)Sub1_2 200 nM | C(R14b)Sub1_2 200 nM | C(R14b)Sub1_2 200 nM |
| Dz6(8:7) 100 nM | Dz6(8:7) 100 nM | Dz6(8:7) 100 nM |
| PPIAA2/1 100 nM | PPIAA2/1 100 nM | PPIAA2/1 100 nM |
| PPIAB3/2(9) 100 nM | PPIAB3/2(9) 100 nM | PPIAB3/2(9) 100 nM |
|  | AF-PPIA 50 nM |  |
| KrasA4/2-P 100 nM | KrasA4/2-P 100 nM | KrasA4/2-P 100 nM |
| KrasB5/2-P 100 nM | KrasB5/2-P 100 nM | KrasB5/2-P 100 nM |
|  |  | AF-Kras 50 nM |

Oligos were purchased from Integrated DNA Technologies (IDT) or Biosearch technologies. All reactions contained 50 mM Tris (pH 9.0) buffer (In house), nuclease free water (Ambion) and 50 mM of MgCl$_2$ (Ambion). The total volume of all reactions was 25 µL. All reactions were performed in duplicate at 44° C. in a Bio-Rad® CFX96 thermocycler and fluorescence signal was measured in Channel 1 (FAM) and was programmed to be read every 10 seconds (scan mode: FAM only) for a total of 48 minutes.

Results

FIG. 20 panel iv) shows results comparing the fluorescent signal for the DNAzyme quasi-circle containing Substrate 1 and Substrate 2, which contain shared sequence such that they can be cleaved by either an 8:17 MNAzyme (Mz1) or a 10:23 MNAzyme (Mz2). In these reactions, Substrate 3 which is labeled with a FAM fluorophore and quencher can be cleaved by Dz3 and hence the release and activation of Dz3 can be monitored by changes in fluorescence for FAM. For Reaction A ('No AF' shown as a line with square symbols), there is very little cleavage of Substrate 3 and as a result, minimal increase in FAM signal over time. This indicates that the Dz3 is inactive when complexed with the BL. Reaction B contains the same components as Reaction A, but with the addition of the 8:17 MNAzyme assembly facilitator, AF1 ('AF1 present', line with diamond symbols). Reaction C also contains the same components as Reaction A, but with the addition of the 10:23 MNAzyme assembly facilitator, AF2 ('AF2 present', line containing triangle symbols). For both reactions B and C, there is an immediate increase in FAM signal indicating the BL has been cleaved and Dz3 is released and can cleave Substrate 3. The increase in signal from each of Reaction B and C is occurring at approximately the same rate, indicating that despite the increased length of the BL, a single cleavage event at any point in the intermediate region of the BL is all that is required for the Dz to be released from the BL.

Example 19

The following example demonstrates the inactivation of a DNAzyme by hybridization to a complementary BL molecule within a quasi-circular structure, as previously demonstrated in Example 1. In this current Example 19 however, auto-catalytic signal amplification is demonstrated by comparing three different circles (Circles A, B and C, depicted schematically in FIG. 21 panels i), ii) and iii) respectively). Each of the three circles comprise a DNAzyme (Dz2) capable of cleaving a separate Substrate 2 and a BL containing Substrate 1, which is capable of being cleaved by an MNAzyme (Mz1) in the presence of its target assembly facilitator (AF1). In addition, the BL of Circle A also contains an additional Substrate 2a, which is adjacent to Substrate 1 and is capable of being cleaved by Dz2 once it has been released via cleavage of Substrate 1 by Mz1. The Dz2 from Circle A therefore has the potential to feedback (i.e. cleave the same BL with which it was previously bound) in an auto-catalytic manner. The BL of Circle B contains an additional Substrate 3, which is adjacent to Substrate 1, but is not capable of being cleaved by either Mz1 or Dz2. The BL from circle C contains only the single substrate, Substrate 1. The DNAzymes from Circles B and C therefore do not have the potential to feedback in an auto-catalytic manner. When AF1 is present, the reaction containing Circle A results in a comparably faster fluorescent signal than does the reactions containing Circles B and C, indicating that the Dz2 from Circle A is feeding back in an auto-catalytic manner to cleave Substrate 2 in the BL and thus activate more Dz2.

Oligonucleotides

In the current example, the BL molecules from Circle A (BLA; SEQ ID NO: 68; C(R22h)), Circle B (BLB; SEQ ID NO: 69; C(R31c)) and Circle C (BLC; SEQ ID NO: 70; C(R31d)) are composed of 5' and 3' ends that are complementary to a portion of Dz2 (SEQ ID NO: 71; Dz77_55 (8:9)). BLA also consists of a central portion connecting the 5' and 3' ends that is the adjacent sequences of both Substrate 1 and Substrate 2a which is equivalent to the sequence of Substrate 2 (Sub77_55, SEQ ID No: 55), but lacks the 3' terminal nucleotide. BLB also consists of a central portion connecting the 5' and 3' ends that is equivalent to the adjacent sequences of both Substrate 1 and Substrate 3. BLC also consists of a central portion connecting the 5' and 3' ends that is equivalent to the sequence of Substrate 1. For each circle, the BL is utilized to block the activity of the Dz2 by pre-hybridising the BL with Dz2.

An MNAzyme (Mz1), consisting of partzymes (Partzyme A, SEQ ID NO: 74; LTFRCA4/72 and Partzyme B, SEQ ID NO: 75; LTFRCB5/72), and an assembly facilitator (AF1, SEQ ID NO: 76; AF-LTFRC), is utilized to cleave the Substrate 1 portion of either BLA, BLB or BLC. This target dependent cleavage event facilitates the release of the Dz2, allowing it to act upon Substrate 2, which is provided as a separate, independent molecule. In this example, the independent Substrate 2 was end-labeled with a FAM moiety on the 5' end and an Iowa Black quencher moiety ("IB") on the 3' end.

The sequences of these oligonucleotides are listed from 5' to 3' below. Bases in uppercase are deoxyribonucleotides and bases in lowercase are ribonucleotides. Underlined bases represent regions in the BL that are complementary to a portion of the Dz. Bases in italics refer to regions corresponding to substrate sequences within the BL molecule. Boxed bases represent the catalytic core of the DNAzymes and Partzymes. Nucleotides highlighted in grey represent the bases in Dz that are complementary to and blocked by, the underlined bases in the BL. /3Phos/ indicates 3' end phosphorylation.

```
Substrate 2: Sub77_55-FIB
                                          SEQ ID NO: 55
CTCCTCCCTCguCCCCAGCTC Partzyme A: LTFRCA4/72
                                          SEQ ID NO: 74
GCAAGGAACAATAACTCAGAACTTACAACGAGAGGCGTGAT Partzyme B: LTFRCB5/72
                                          SEQ ID NO: 75
CTGGGAGGAGAGGCTAGCTACGCCTGCTTTCTGATTCTA Assembly facilitator (AF1): AF-LTFRC
                                          SEQ ID NO: 76
AGTCTGTTTTCCAGTCAGAGGGACAGTCTCCTTCCATATTCCTAGAATCA
GAAAGCAGGCGTAAGTTCTGAGTTATTGTTCCTTGC BLA: C(R22h)
                                          SEQ ID NO: 68
AGCCTCCCCAGCTATCACGCCTCguCTCCTCCCAGCTCCTCCCTCguCCC
CAGCTTCCTCCCTCTCGTTG BLB: C(R31c)
                                          SEQ ID NO: 69
AGCCTCCCCAGCTATCACGCCTCguCTCCTCCCAGCTCGACCCCguCTCC
ACGCCTCCTCCCTCTCGTTG BLC: C(R31d)
                                          SEQ ID NO: 70
AGCCTCCCCAGCTATCACGCCTCguCTCCTCCCAGTCCTCCCTCTCGTTG Dz2: Dz77_55(8:9)
                                          SEQ ID NO: 71
AGCTGGGAGGCTAGCTACAACGAGAGGGAGG
```

Reaction Components

Reactions A, B, C, D, E and F were set up to contain the following oligonucleotides as listed in Table 22, with reference to oligonucleotides listed in the previous section and structures illustrated in FIG. 21 panels i), ii) and iii). For all reactions the BL and Dz2 were initially pre-hybridized together for 30 minutes at room temperature before the addition of any further oligonucleotide components.

TABLE 22

| Reaction A (Circle A, No AF1) | Reaction B (Circle A, AF1 present) | Reaction C (Circle B, No AF1) | Reaction D (Circle B, AF1 present) | Reaction E (Circle C, No AF1) | Reaction F (Circle C, AF1 present) |
|---|---|---|---|---|---|
| Sub77_55-FIB 200 nM | Sub77_55-FIB 200 nM | Sub77_55-FIB 200 nM | Sub77_55-FIB 200 nM | Sub77_55-FIB 200 nM | Sub77_55-FIB 200 nM |
| C(R22h) 14 nM | C(R22h) 14 nM | | | | |
| | | C(R31c) 14 nM | C(R31c) 14 nM | | |
| | | | | C(R31d) 14 nM | C(R31d) 14 nM |
| Dz77_55 (8:9) 10 nM | Dz77_55 (8:9) 10 nM | Dz77_55 (8:9) 10 nM | Dz77_55 (8:9) 10 nM | Dz77_55 (8:9) 10 nM | Dz77_55 (8:9) 10 nM |
| LTFRCA4/72 50 nM | LTFRCA4/72 50 nM | LTFRCA4/72 50 nM | LTFRCA4/72 50 nM | LTFRCA4/72 50 nM | LTFRCA4/72 50 nM |
| LTFRCB5/72 50 nM | LTFRCB5/72 50 nM | LTFRCB5/72 50 nM | LTFRCB5/72 50 nM | LTFRCB5/72 50 nM | LTFRCB5/72 50 nM |
| | AF-LTFRC 25 pM | | AF-LTFRC 25 pM | | AF-LTFRC 25 pM |

Oligos were purchased from Integrated DNA Technologies (IDT) or Biosearch technologies. All reactions contained 1×PCR buffer II (Applied Biosystems), nuclease free water (Ambion) and 45 mM of MgCl$_2$ (Ambion). The total volume of all reactions was 25 µL. All reactions were performed in duplicate at 54° C. in a Bio-Rad® CFX96 thermocycler and fluorescence signal was measured in Channel 1 (FAM) and was programmed to be read every 30 seconds (scan mode: FAM only) for a total of 154 minutes.

Results

FIG. 21 panel iv) shows results comparing the fluorescent signal from each of Circles A, B and C. Substrate 2 which is labeled with a FAM fluorophore and quencher, can be cleaved by Dz2 and hence the release and activation of Dz2 can be monitored by changes in fluorescence for FAM. For Reaction A, ('Circle A, no AF1' shown as a line with square symbols), Reaction C ('Circle B, No AF1' shown as a line with triangle symbols) and Reaction E ('Circle C, No AF1', line with symbols consisting of two diagonal and one vertical intersecting lines) there is very little cleavage of Substrate 2 and as a result, very little increase in FAM signal over time. This indicates that Dz2 is kept fairly inactive via its hybridisation to BLA, BLB and BLC for Reactions A, C and E respectively.

For Reaction B ('Circle A, AF1 present' shown as a line containing diamond symbols), there is an initial lag phase followed by an immediate increase in FAM signal which reaches a plateau quickly. This sigmoidal curve indicates that the FAM signal is accumulating exponentially, indicating that the Dz2 from Circle A is feeding back and cleaving Substrate 2a, present in additional BLA molecules, after it has been initially released from its own BLA via Mz1 cleavage of Substrate 1. In contrast, Reaction D ('Circle B, AF1 present', line containing circle symbols) and Reaction F ('Circle C, AF1 present', line containing symbols consisting of two diagonal intersecting lines) result in a comparably slower increase in FAM signal, indicating there is no feedback occurring, as Substrate 2a is not present within BLB and BLC for Reactions D and F respectively.

Example 20

The following example demonstrates the initial inactivation of a DNAzyme by hybridization to a complementary BL molecule within an auto-catalytic, quasi-circular structure, as previously demonstrated in Example 19. In this current Example 20, signal amplification is demonstrated by comparing two MNAzyme target detection reactions; the first with an auto-catalytic circle present (FIG. 22 panel ii)) and the second with the circle absent (i.e. MNAzyme only, FIG. 22 panel 1)). In both reactions, the same MNAzyme (Mz1) is designed to recognize and bind to the same target assembly facilitator (AF1) and to cleave either Substrate 1, provided as a linear sequence which has been modified with a fluorophore and quencher or Substrate 1a, which is present within the intermediate region of the BL molecule of the circle. The BL molecule consists of sequence at its 5' and 3' ends, which hybridizes to a DNAzyme (Dz2), resulting in the temporary inactivation of the Dz2. The BL also contains a second substrate sequence (Substrate 2a), adjacent to substrate 1a, which is capable of being cleaved by Dz2, once it has been released from the BL via MNAzyme cleavage of Substrate 1. In addition, Substrate 2 is provided as a linear sequence which has been modified with a fluorophore and quencher to monitor the DNAzyme cleavage reaction. When AF1 is present, the reaction containing the auto-catalytic circle results in a comparably faster fluorescent signal than does the reaction containing the MNAzyme alone, and in addition can result in the detection of a target concentration that is unable to be visualized by the signal from the MNAzyme alone.

Oligonucleotides

In the current example, the BL (SEQ ID NO: 68; C(R22h)) which is composed of (i) 5' and 3' ends that are complementary to a portion of Dz2 (SEQ ID NO: 71; Dz77_55 (8:9)) and (ii) a central portion connecting the 5' and 3' ends that is the adjacent sequences of Substrate 1a, which is equivalent to Substrate 1 (Sub72, SEQ ID NO: 72) and Substrate 2a, which is equivalent to the sequence of Substrate 2 (Sub77_55, SEQ ID No: 55) but lacks the 3' terminal 'C' nucleotide. The BL is utilized to block the activity of the Dz2 by pre-hybridizing the BL with Dz2.

An MNAzyme (Mz1), consisting of partzymes (Partzyme A, SEQ ID NO: 74; LTFRCA4/72 and Partzyme B, SEQ ID NO: 75; LTFRCB5/72), and an assembly facilitator target (AF1, SEQ ID NO: 76; AF-LTFRC), is utilized to cleave the Substrate 1a portion of the BL. This target dependent cleavage event facilitates the release of the Dz2, allowing it to act upon Substrate 2a present within the BL. The MNAzyme can also act upon a separate, independent, Substrate 1, which is not a component of a quasi-circle. In this example, this independent Substrate 1 was end-labeled with a FAM moiety on the 5' end and an Iowa Black quencher moiety ("IB") on the 3' end. Dz2 can also act upon a separate, independent, Substrate 2, which is not a component of a quasi-circle. In this example, this independent Substrate 2 was end-labeled with a FAM moiety on the 5' end and an Iowa Black quencher moiety ("IB") on the 3' end.

The sequences of these oligonucleotides are listed from 5' to 3' below. Bases in uppercase are deoxyribonucleotides and bases in lowercase are ribonucleotides. Underlined bases represent regions in the BL that are complementary to a portion of the Dz. Bases in italics refer to regions corresponding to a substrate sequence within the BL molecule. Boxed bases represent the catalytic core of the DNAzymes and Partzymes. Nucleotides highlighted in grey represent the bases in Dz that are complementary to and blocked by, the underlined bases in the BL.

```
Substrate 1: Sub72-FIB
                                            SEQ ID NO: 72
ATCACGCCTCguCTCCTCCCAG Substrate 2: Sub77_55-FIB
                                            SEQ ID NO: 55
CTCCTCCCTCguCCCCAGCTC Partzyme A: LTFRCA4/72
                                            SEQ ID NO: 74
GCAAGGAACAATAACTCAGAACTTACAACGAGAGGCGTGAT Partzyme B: LTFRCB5/72
                                            SEQ ID NO: 75
CTGGGAGGAGAGGCTAGCTACGCCTGCTTTCTGATTCTA Assembly facilitator (AF1): AF-LTFRC
                                            SEQ ID NO: 76
AGTCTGTITTCCAGTCAGAGGGACAGTCTCCTTCCATATTCCTAGAATCA
GAAAGCAGGCGTAAGTTCTGAGTTATTGTTCCTTGC BL: C(R22h)
                                            SEQ ID NO: 68
AGCCTCCCCAGCTATCACGCCTCguCTCCTCCCAGCTCCTCCCTCguCCC
CAGCTTCCTCCCTCTCGTTG Dz2: Dz77_55(8:9)
                                            SEQ ID NO: 71
AGCTGGGGAGGCTAGCTACAACGAGAGGGAGG
```

Reaction Components

Figure 22:
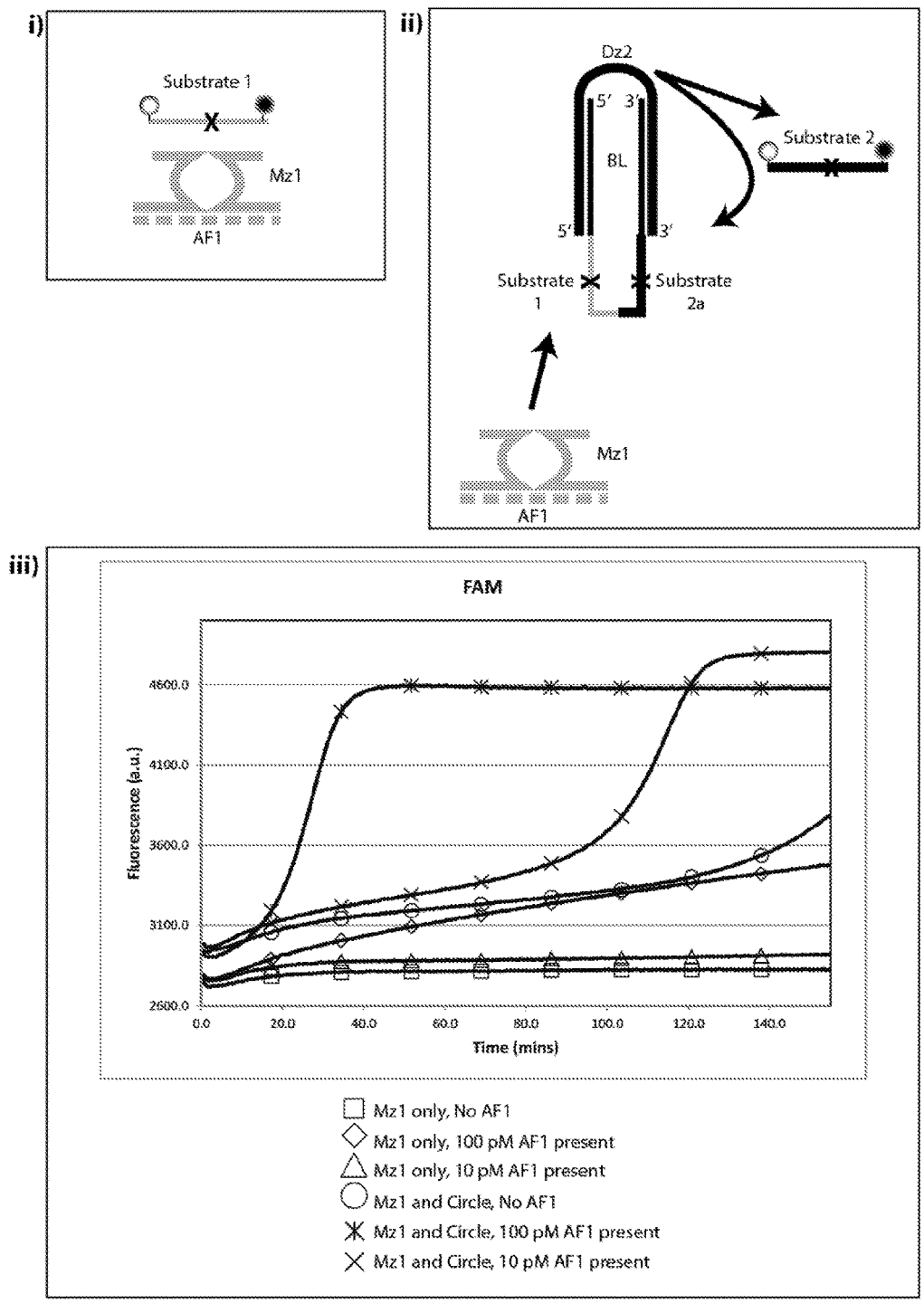
FIG. 22 panel i) depicts an MNAzyme (Mz1) cleaving its substrate (Substrate 1) which is provided as an independent entity labeled with a fluorophore and quencher dye pair. Alternatively, panel ii) depicts the same Mz1 cleaving Substrate 1 present within the BL of an auto-catalytic quasi circle (originally outlined in FIG. 21 panel i), whereby cleavage of Substrate 1 results in the release and activation of a DNAzyme (Dz2) and the subsequent initiation of an auto-catalytic cascade (via cleavage of Substrate 2 (Substrate 2a in panel ii)) within the BL by Dz2). The active Dz2 may also cleave Substrate 2 provided as a separate entity labeled with a fluorophore and quencher dye pair. Panel iii) demonstrates and compares the fluorescent signal achieved from the two strategies depicted in panels i) and ii).

Reactions A, B, C, D, E and F were set up to contain the following oligonucleotides as listed in Table 23, with reference to oligonucleotides listed in the previous section and structures illustrated in FIG. 22 panels i) and ii). For all reactions containing the BL and Dz2, these two oligos were initially pre-hybridized together for 30 minutes at room temperature before the addition of any further oligonucleotide components.

TABLE 23

| Reaction A (Mz1 only, No AF1) | Reaction B (Mz1 only, 100 pM AF1 present) | Reaction C (Mz1 only, 10 pM AF1 present) | Reaction D (Mz1 and Circle, No AF1) | Reaction E (Mz1 and Circle, 100 pM AF1 present) | Reaction F (Mz1 and Circle, 10 pM AF1 present) |
|---|---|---|---|---|---|
| Sub72-FIB 200 nM | Sub72-FIB 200 nM | Sub72-FIB 200 nM | | | |
| | | | Sub77_55-FIB 200 nM | Sub77_55-FIB 200 nM | Sub77_55-FIB 200 nM |
| | | | C(R22h) 10 nM | C(R22h) 10 nM | C(R22h) 10 nM |
| | | | Dz77_55 (8:9) 8 nM | Dz77_55 (8:9) 8 nM | Dz77_55 (8:9) 8 nM |
| LTFRCA4/72 50 nM | LTFRCA4/72 50 nM | LTFRCA4/72 50 nM | LTFRCA4/72 50 nM | LTFRCA4/72 50 nM | LTFRCA4/72 50 nM |

TABLE 23-continued

| Reaction A (Mz1 only, No AF1) | Reaction B (Mz1 only, 100 pM AF1 present) | Reaction C (Mz1 only, 10 pM AF1 present) | Reaction D (Mz1 and Circle, No AF1) | Reaction E (Mz1 and Circle, 100 pM AF1 present) | Reaction F (Mz1 and Circle, 10 pM AF1 present) |
|---|---|---|---|---|---|
| LTFRCB5/72 50 nM | LTFRCB5/72 50 nM AF-LTFRC 100 pM | LTFRCB5/72 50 nM AF-LTFRC 10 pM | LTFRCB5/72 50 nM | LTFRCB5/72 50 nM AF-LTFRC 100 pM | LTFRCB5/72 50 nM AF-LTFRC 10 pM |

Oligos were purchased from Integrated DNA Technologies (IDT) or Biosearch technologies. All reactions contained 1×PCR buffer II (Applied Biosystems), nuclease free water (Ambion) and 45 mM of $MgCl_2$ (Ambion). The total volume of all reactions was 25 μL. All reactions were performed in duplicate at 52° C. in a Bio-Rad® CFX96 thermocycler and fluorescence signal was measured in Channel 1 (FAM) and was programmed to be read every 30 seconds (scan mode: FAM only) for a total of 154 minutes.

Results

FIG. 22 panel iii) shows results comparing the fluorescent signal with an MNAzyme only versus an MNAzyme and an autocatalytic circle present. In the MNAzyme only reactions, Substrate 1 which is labeled with a FAM fluorophore and quencher can be cleaved by Mz1 which can be monitored by changes in fluorescence for FAM. For the reactions containing the Mz1 in conjunction with an auto-catalytic circle, Substrate 2 which is labeled with a FAM fluorophore and quencher, can be cleaved by Dz2 and hence the release and activation of the Dz can be monitored by changes in fluorescence for FAM.

In Reaction A, ('Mz1 only, no AF1' shown as a line with square symbols) there is no cleavage of Substrate 1 and as a result, no increase in FAM signal over time. This is because the MNAzyme is not active in the absence of target assembly facilitator. Reaction B contains the same components as Reaction A, but with the addition of 100 pM of MNAzyme assembly facilitator ('Mz1 only, 100 pM AF1 present', line with diamond symbols) and results in a slow linear increase in FAM signal over time, which does not reach a plateau during the reaction time. Reaction C contains the same components as Reaction A, but with the addition of 10 pM of MNAzyme assembly facilitator ('Mz1 only, 10 pM AF1 present', line containing triangle symbols) there is very little if any increase in FAM signal over the course of the reaction time, indicating that very little of Substrate 1 is being cleaved.

In Reaction D, ('Mz1 and Circle, no AF1' shown as a line with circle symbols) there is a gradual but only slight increase in FAM signal over time, which begins to increase within the last 30 minutes of the reaction. The background fluorescence level is higher than that of the MNAzyme only reactions, indicating there may be some hybridisation of Substrate 2 to the circle components and/or that Substrate 2 is less efficiently quenched than Substrate 1. The increase in signal towards the end of the reaction may indicate that the cascade is beginning to function in the absence of an MNAzyme trigger. Reaction E contains the same components as Reaction D, but with the addition of 100 pM of MNAzyme assembly facilitator ('Mz1 and Circle, 100 pM AF1 present', line with symbols consisting of two diagonal and one vertical intersecting lines) and results in a rapid and exponential increase in FAM signal, reaching a plateau after approximately 30 minutes. In comparison to Reaction B containing the same MNAzyme facilitator concentration but without the circle, this increase in FAM signal is considerably faster, indicating the presence of the circle results in the amplification of signal and a consequently faster detection of 100 pM of target assembly facilitator. Reaction F contains the same components as Reaction D, but with the addition of 10 pM of MNAzyme assembly facilitator ('MNAzyme and circle, 10 pM AF1 present', line containing symbols consisting of two diagonal intersecting lines) and there is an initial lag phase, followed by a rapid and exponential increase in FAM signal, reaching a plateau after approximately 120 minutes. In comparison to Reaction C containing the same MNAzyme facilitator concentration but without the circle, this increase in FAM signal is not only considerably faster, but is detectable ahead of the no target reaction (Reaction D). In this case, the presence of the circle results in the amplification of signal such that detection of 10 pM of target assembly facilitator ahead of the background signal is possible, indicating the circle increases both speed and sensitivity of MNAzyme target detection.

Example 21

The following example demonstrates the inactivation of a DNAzyme by hybridization to a complementary BL molecule, whereby the DNAzyme and BL are linked via a non-complementary hairpin loop (hairpined Dz2). In this example, the BL also contains an additional substrate sequence (Substrate 1) which can be recognized and cleaved by an MNAzyme (Mz1) in the presence of its target assembly facilitator molecule (AF1). Cleavage of Substrate 1 by Mz1 results in the release and subsequent re-activation of the previously inactive hairpined Dz2 (depicted schematically in FIG. 3 panel i)).

Oligonucleotides

In the current example, the Hairpined Dz2 (SEQ ID NO: 77; hpBL(R3a)-Dz2_Sub6), capable of cleaving Substrate 2 (SEQ ID NO: 5; Sub2) was utilized. In this example, Substrate2 is end-labeled with a FAM moiety on the 5' end and a Black Hole Quencher 1 ("BHQ1") moiety on the 3' end. Mz1 consisting of partzyme A (SEQ ID NO: 58; KrasA4/6-P), partzyme B (SEQ ID NO: 59; KrasB5/6-P) and AF1 (SEQ ID NO: 53; AF-Kras) was employed to cleave Substrate 1 within the Hairpined Dz2 molecule and thus produce Active Dz2. The catalytic activity of the Active Dz2 was compared to that of a corresponding Non-hairpined Control Dz2 (SEQ ID NO: 26; Dz2(9:8)).

The sequences of these oligonucleotides are listed from 5' to 3' below. Bases in uppercase are deoxyribonucleotides and bases in lowercase are ribonucleotides. Underlined bases represent regions in the BL that are complementary to a portion of the Dz2. Bases in italics refer to regions corresponding to a substrate sequence within the BL molecule. Boxed bases represent the catalytic core of the DNAzymes and Partzymes. Nucleotides highlighted in grey represent the bases in the Dz2 that are complementary to and blocked by, the underlined bases in the BL molecule. /3Phos/ indicates 3' end phosphorylation.

Substrate 2: Sub2
SEQ ID NO: 5
AAGGTTTCCTCguCCCTGGGCA

Partzyme A: KrasA4/6-P
SEQ ID NO: 58
TAAACTTGTGGTAGTTGGAGACAACGAGAGGCGTGAT/3Phos/

Partzyme B: KrasB5/6-P
SEQ ID NO: 59
CTGGGAGGAAGGCTAGCTCTGGTGGCGTAGGCAAGAGTGCC/3Phos/

Assembly facilitator (AF1): AF-Kras
SEQ ID NO: 53
CAAGGCACTCTTGCCTACGCCACCAGCTCCAACTACCACAAGTTTATATTCA Hairpined Dz2: hpBL(R3a)-Dz2_Sub6
SEQ ID NO: 77
CCCAGGGAGGCTAGCTACAACGAGAGGAAACCTTTTTGGTTTCCTCTCGTT
*TTCACGCCTCguTCCTCCC*ATTAGCCTCCCTGGG Non-hairpined Control Dz2: Dz2(9:8)
SEQ ID NO: 26
CCCAGGGAGGCTAGCTACAACGAGAGGAAACC Reaction Components Reactions A, B, C, D and E were set up to contain the following oligonucleotides as listed in Table 24, with reference to oligonucleotides listed in the previous section and structures illustrated in FIG. 3 panel i).

TABLE 24

| Reaction A (Negative control) | Reaction B (Positive control) | Reaction C (Hairpined Dz2 only) | Reaction D (Hairpined Dz2 + Mz1, No AF1), | Reaction E (Hairpined Dz2 + Mz1, AF1 present) |
|---|---|---|---|---|
| SubK-FB 200 nM | SubK-FB 200 nM | SubK-FB 200 nM hpBL(R3a)-Dz2_Sub6 50 nM | SubK-FB 200 nM hpBL(R3a)-Dz2_Sub6 50 nM | SubK-FB 200 nM hpBL(R3a)-Dz2_Sub6 50 nM |
|  | Dz2(9:8) 50 nM |  | KrasA4/6-P 50 nM KrasB5/6-P 50 nM | KrasA4/6-P 50 nM KrasB5/6-P 50 nM AF-Kras 50 nM |

Oligos were purchased from Integrated DNA Technologies (IDT) or Biosearch technologies. All reactions contained 1×PCR buffer II (Applied Biosystems), nuclease free water (Ambion) and 45 mM of $MgCl_2$ (Ambion). The total volume of all reactions was 25 µL. All reactions were performed in duplicate at 52° C. in a Bio-Rad® CFX96 thermocycler and fluorescence signal was measured in Channel 1 (FAM) and was programmed to be read every 30 seconds (scan mode: FAM only) for a total of 126 minutes.

Results

FIG. 3 panel ii) shows results of the fluorescent signal for the activation of Hairpined Dz2 by Mz1. In these reactions, Substrate 2 is labeled with a FAM fluorophore and quencher dye and can be cleaved by the active Dz2. The release and activation of the Hairpined Dz2 can be monitored by changes in fluorescence for FAM. For reaction C ('Hairpined Dz2 only' shown as a line with triangle symbols) and Reaction D ('Hairpined Dz2+Mz1, No AF1' shown as a line with circle symbols), there is little to no increase in FAM signal indicating that Hairpined Dz2 is unable to cleave Substrate 2. This signal is shown in comparison to Reaction A ('Negative control' shown as a line containing square symbols) which contains the same fluorescently labeled substrate sequence only.

For Reaction E ('Hairpined Dz2+Mz1, AF1 present' shown as a line with a symbol consisting of two diagonal and one vertical intersecting lines), there is a gradual increase in FAM signal over time, reaching a plateau towards the end of the reaction time. This indicates that the addition of AF1 results in an active Mz1, which is able to then cleave Substrate1 present as part of the Hairpined Dz2. The Dz2 component then becomes active and can cleave Substrate 2 resulting in the increase in fluorescent signal. The signal of Reaction E is shown in comparison to that of Reaction B ('Positive control', line containing diamond symbols), consisting of the same concentration of the corresponding, non-hairpined Dz2 as Reaction E and results in a rapid increase in signal, reaching a plateau within 30 minutes of the reaction. The signal for Reaction E is slower than Reaction B due to the time required for Mz1 to cleave Substrate 1, the subsequent activation of Dz2 and its cleavage of Substrate 2.

Example 22

The following example demonstrates the attachment of an auto-catalytic, DNAzyme quasi-circle (previously demonstrated in Example 19) to a solid surface. Here, the BL of the quasi circle is modified at its 3' terminus with a biotin moiety and along with the DNAzyme (Dz2), is incubated with silica microspheres that have been streptavidin-coated. The BL and the microsphere therefore attach to one another via a biotin-streptavidin bond and the Dz2 hybridizes with the BL via Watson-Crick base pairing (FIG. 24 panel i)). Following the incubation process, the microspheres are washed several times with buffer to remove any unbound oligonucleotides. The population of microspheres remaining contain tethered auto-catalytic quasi circles and cascades can be initiated when microspheres are placed in solution with an MNAzyme (Mz1) that can cleave Substrate 1 present in the BL, following assembly by its target molecule (AF1).

Oligonucleotides

In the current example, the BL molecule (SEQ ID NO: 78; C(R22h)-Bio), is composed 5' and 3' regions that are complementary to a portion of Dz2 (SEQ ID NO: 71; Dz77_55 (8:9)). Adjacent to the Dz2-binding region at the very 3' end, the BL contains a 5 nucleotide poly A tail which is not complementary to Dz2 and which contains a biotin moiety attached to the 3' terminus. The central portion of the BL connecting the 5' and 3' ends is comprised of the adjacent sequences of both Substrate 1 and Substrate 2a, which is equivalent to the sequence of Substrate 2 (Sub77_55, SEQ ID No: 55) but lacks the 3' terminal 'C' nucleotide. The BL is utilized to block the activity of the Dz2 by pre-hybridizing the BL with Dz2. An MNAzyme (Mz1), consisting of partzymes (Partzyme A, SEQ ID NO: 74; LTFRCA4/72 and Partzyme B, SEQ ID NO: 75; LTFRCB5/72), and an assembly facilitator (AF1, SEQ ID NO: 76; AF-LTFRC), is utilized to cleave the Substrate 1 portion of the BL. This target dependent cleavage event facilitates the release of the Dz2, allowing it to act upon Substrate 2a which is present within the BL, or Substrate 2 which is provided as a separate, independent molecule. In this example, the independent Substrate 2 was end-labeled with a FAM moiety on the 5' end and an Iowa Black quencher ("IB") moiety on the 3' end.

The sequences of these oligonucleotides are listed from 5' to 3' below. Bases in uppercase are deoxyribonucleotides and bases in lowercase are ribonucleotides. Underlined bases represent regions in the BL that are complementary to a portion of the Dz. Bases in italics refer to regions corresponding to a substrate sequence within the BL molecule. Boxed bases represent the catalytic core of the DNAzymes and Partzymes. Nucleotides highlighted in grey represent the bases in Dz that are complementary to and blocked by, the underlined bases in the BL. /3Bio/ indicates 3' end biotinylation.

```
Substrate 2: Sub77_55-FIB
                                     SEQ ID NO: 55
CTCCTCCCTCguCCCCAGCTC Partzyme A: LTFRCA4/72
                                     SEQ ID NO: 74
GCAAGGAACAATAACTCAGAACTTACAACGAGAGGCGTGAT Partzyme B: LTFRCB5/72
                                     SEQ ID NO: 75
CTGGGAGGAGAGGCTAGCTACGCCTGCTTTCTGATTCTA Assembly facilitator (AF1): AF-LTFRC
                                     SEQ ID NO: 76
AGTCTGTTTTCCAGTCAGAGGGACAGTCTCCTTCCATATTCCTAGAATCA
GAAAGCAGGCGTAAGTTCTGAGTTATTGTTCCTTGC BL: C(R22h)-Bio
                                     SEQ ID NO: 78
AGCCTCCCCAGCTATCACGCCTCguCTCCTCCCAGCTCCTCCCTCguCCC
CAGCTTCCTCCCTCTCGTTGAAAAA/3Bio/

Dz2: Dz77_55(8:9)
                                     SEQ ID NO: 71
AGCTGGGGAGGCTAGCTACAACGAGAGGGAGG
```

Reaction Components

The 3 μm silica, streptavidin-coated microspheres (Bangs Laboratories), were provided as 1% (w/v) solids in a storage buffer (100 mM Borate, pH 8.5+0.01% BSA+0.05% Tween® 20+10 mM EDTA+<0.1% NaN3). 2 μL/reaction of the microsphere suspension was removed and washed three times in 1×PBST buffer (10 mM Phosphate Buffer 017.3-7.5, 137 mM Sodium Chloride, and 2.7 mM Potassium Chloride (Amresco) and 0.05% Tween-20 (Promega)) prior to use. Briefly, this involved suspension of the microspheres in 100 μL of 1×PBST buffer, followed by centrifugation at 13000×g for 30 seconds to form a microsphere pellet. The supernatant was then removed and the microsphere pellet re-suspended in fresh 1×PBST buffer. This process was repeated an additional two times, followed by re-suspension in the original 2 μL/reaction volume of fresh 1×PBST buffer. The washed microspheres were then incubated with 100 nM of BL (C(R22h)-Bio) and 75 nM of Dz2 (Dz77_55 (8:9)). The incubation mixes were pre-hybridized together for 30 minutes at room temperature, followed by an additional three washes in 1×PBST buffer.

The microsphere incubation mixes were added to the following oligonucleotides as listed in Table 25, with reference to oligonucleotides listed in the previous section and structures illustrated in FIG. 24 panel i).

TABLE 25

| Reaction A (No AF1) | Reaction B (AF1 present) |
|---|---|
| Sub77_55-FIB 200 nM Incubation mix 5 uL LTFRCA4/72 50 nM LTFRCB5/72 50 nM | Sub77_55-FIB 200 nM Incubation mix 5 uL LTFRCA4/72 50 nM LTFRCB5/72 50 nM AF-LTFRC 100 pM |

Oligos were purchased from Integrated DNA Technologies (IDT) or Biosearch technologies. All reactions contained 1×PCR buffer II (Applied Biosystems), nuclease free water (Ambion) and 45 mM of MgCl$_2$ (Ambion). The total volume of all reactions was 25 μL. All reactions were performed in duplicate at 54° C. in a Bio-Rad® CFX96 thermocycler and fluorescence signal was measured in Channel 1 (FAM) and was programmed to be read every 30 seconds (scan mode: FAM only) for a total of 148 minutes.

Results

FIG. 24 panel ii) demonstrates the fluorescent signal from Reactions A and B. Substrate 2 which is labeled with a FAM fluorophore and quencher can be cleaved by Dz2 and hence the release and activation of Dz2 can be monitored by changes in fluorescence for FAM. For Reaction A, ('No AF1' shown as a line with square symbols), there is very little cleavage of Substrate 2 and as a result, only a slight increase in FAM signal over time. This indicates that Dz2 is kept fairly inactive via its hybridization to the BL. For Reaction B ('AF1 present' shown as a line containing diamond symbols), there is an initial lag phase followed by a gradual increase in FAM signal over time indicating that the Mz1 is cleaving Substrate 1, resulting in the release of Dz2 from the circle, where it functions to cleave Substrate 2a within the BL of the circle or the separate, fluorescently labeled Substrate 2 instead. The increase in fluorescent signal from Reaction B also indicates that the microsphere population, which was rigorously washed prior to its addition to both reactions, contains quasi circles that are tethered the microspheres and that these quasi circles can function in a similar manner to those free in solution.

Example 23

Example 23 demonstrates use of a template molecule to direct the synthesis of a primer (Primer 1), which is initiated by a different primer (Primer 2) as originally depicted in FIG. 13 panel iii). In this example however, the primer template is composed of a hairpin structure whereby one strand contains the template for synthesis of New Primer 1 adjacent to an RE recognition site, whilst the other is partially complementary to the template (FIG. 25 panel i)). This partially complementary strand contains a mis-matched base pair at the 3' end to prevent it from performing like an active Primer 1 and also has another mismatch within the center of the sequence to disrupt, potential hybridisation between it and the Primer 1 binding site present within the loop of the Partially blocked hairpined Dz1 template. This mis-matched base pair does not affect its hybridisation with the Primer, 1 binding site in the hairpined primer template as when there it is present within a more thermodynamically stable hairpin structure. The sole purpose of this partially complementary strand is therefore to help prevent the newly synthesised Primer 1 from re-hybridising to other primer templates, as those primer templates which are not in use will be kept in a closed hairpin confirmation. The loop strand of the hairpined primer template structure is complementary to Primer 2, such that when Primer 2 binds to this loop, it can be extended by a strand-displacing polymerase, resulting in the simultaneous opening of the hairpin and synthesis of both a complete RE recognition site and adjacent Primer 1. When a nicking enzyme is present, it can recognise the completed RE recognition site and selectively nick the newly synthesized strand at a region between the upstream Primer 2 and downstream Primer 1 sequence. Nicking therefore generates a new Primer 2, which is extended by polymerase to both synthesize another Primer 1 copy and displace the pre-existing copy from the template strand. This cycle of nicking, polymerization and displacement can then occur autonomously to generate several active Primer 1 molecules.

As initially described in Example 15, a 'Partially blocked' hairpined DNAzyme template also exists, consisting of a BL portion which is a partial DNAzyme containing one sub-strate-binding arm and approximately half of the catalytic core sequence. This partial catalytic core also contains an inactivating mutated base. In the presence of a polymerase enzyme, the 3' end of the BL, is able to extend this sequence using the Dz template as a template for copying, thus completing the sequence of the inactive DNAzyme at the 3' end of the hairpin molecule. Due to the mutation in the core region however, the mutant DNAzyme is inactive even when the hairpin is open. Once synthesised and displaced from the template, Primer 1 can hybridize to the loop of the 'Partially blocked' hairpined DNAzyme template structure and be extended at its 3' end by a strand displacing polymerase, as initially described in Example 9. Primer 1 extension results in the synthesis of a new and complete copy of the DNAzyme, via the use of the partially blocked hairpined DNAzyme template as a template for copying. The extension of Primer 1 also results in the completion of a double-stranded nicking enzyme recognition site. The nicking enzyme can recognize this site and selectively nick the newly synthesised strand at a region between the upstream Primer 1 and downstream DNAzyme sequence. Nicking therefore generates a new Primer 1, which is extended by polymerase to both synthesize another DNAzyme copy and displace the pre-existing copy from the Dz template. This cycle of nicking, polymerization and displacement can then occur autonomously to generate several active DNAzyme molecules capable of cleaving their own substrates (depicted in FIG. 25 panel i)).

Oligonucleotides

The hairpined primer template (SEQ ID NO: 79; hpPRF (R12b)) was employed to provide a template for the synthesis of Primer 1 (SEQ ID: 49; PR(R8b)Dz45(14)) via the extension of Primer 2 (SEQ ID NO: 80; PR(R12b)PRF). The 'Partially blocked' hairpined Dz1 template (SEQ ID NO: 47; hp(R11b)ADz45) was employed to provide a template for Dz1 to be synthesized that is capable of cleaving Substrate 1 (Sub45, SEQ ID NO: 3). In this example Sub45 was labeled with a 6-fluorescein ("6-FAM") moiety at the 5' end and an Iowa Black quencher ("IB") moiety at the 3' end. The catalytic activity of the Dz1 synthesized from the hairpined Dz1 template was also compared to that of a corresponding non-hairpined positive control Dz1, (SEQ ID NO: 45; Dz45 (9:9)).

The sequences of these oligonucleotides are listed from 5' to 3' below. Bases in uppercase are deoxyribonucleotides and base in lowercase are ribonucleotides. Bases in italics refer to DNAzyme sequence within the 'Partially hairpined' DNAzyme template structure and to Primer 1 sequence within the hairpined primer template. Underlined bases represent regions of complementarity between Primer 1 sequence and the hairpined DNAzyme template. Highlighted bases represent the partial nicking enzyme recognition site. Boxed bases represent bases corresponding to the catalytic core of a DNAzyme.

```
Substrate 1: Sub45
                                          SEQ ID NO: 3
ACGGGTCCCguCTCCTTTGGAA Positive Control Dz1: Dz45(9:9)
                                          SEQ ID NO: 45
CAAAGGAGAGGCTAGCTACAACGAGGGACCCGT 'Partially blocked' hairpined Dz template1:
hp(R11b)ADz45
                                          SEQ ID NO: 47
ACGGGTCCCTCGTTGTAGCTAGCCTCTCCTTTGGTCGCTGATCCTGTACTT
GACCAAAGGAGATGCTAGC Hairpined primer template: hpPRF(R12b)
                                          SEQ ID NO: 79
ATCCTGTACTTAGGTCCGATCCTGCAGCATAGGGACCTAAGTGCAGGAC Primer 1: PR(R8b)Dz45(14)
                                          SEQ ID NO: 49
AAGTACAGGATCAG Primer 2: PR(R12b)PRF
                                          SEQ ID NO: 80
CTATGCTGCAGGATC
```

Reaction Components

Reactions A, B, C, D, E, F, G and H were set up to contain the following oligonucleotide fragments, Polymerase and nicking enzymes as listed in Table 26, with reference to oligonucleotides in the previous section and structures illustrated in FIG. 25 panel i).

TABLE 26

| Reaction A (Negative control) | Reaction B (Positive control) | Reaction C ('Partially blocked' hairpined Dz template only – No PR) | Reaction D ('Partially blocked' hairpined Dz template – PR1 present) | Reaction E ('Partially blocked' hairpined Dz template only – PR2 present) | Reaction F ('Partially blocked' hairpined Dz template + hairpined primer template – No PR) | Reaction G ('Partially blocked' hairpined Dz template + hairpined primer template – PR1 present) | Reaction H ('Partially blocked' hairpined Dz template + hairpined primer template – PR2 present) |
|---|---|---|---|---|---|---|---|
| Sub45-FIB 200 nM | Sub45-FIB 200 nM Dz45(9:9) 10 nM | Sub45-FIB 200 nM | Sub45-FIB 200 nM | Sub45-FIB 200 nM | Sub45-FIB 200 nM | Sub45-FIB 200 nM | Sub45-FIB 200 nM |
| | | | hp(R11b)ADz45 25 nM | hp(R11b)ADz45 25 nM | hp(R11b)ADz45 25 nM | hp(R11b)ADz45 25 nM hpPRF(R12b) 25 nM | hp(R11b)ADz45 25 nM hpPRF(R12b) 25 nM |
| | | | PR(R8b)Dz45(14) 10 nM | | | PR(R8b)Dz45(14) 10 nM | |
| | | | | PR(R12b)PRF 10 nM | | | PR(R12b)PRF 10 nM |
| | | Bst 2.0 warm start (0.8 U) Nt.AlwI (2.5 U) | Bst 2.0 warm start (0.8 U) Nt.AlwI (2.5 U) | Bst 2.0 warm start (0.8 U) Nt.AlwI (2.5 U) | Bst 2.0 warm start (0.8 U) Nt.AlwI (2.5 U) | Bst 2.0 warm start (0.8 U) Nt.AlwI (2.5 U) | Bst 2.0 warm start (0.8 U) Nt.AlwI (2.5 U) |

Oligos were purchased from IDT or Biosearch technologies. The polymerase enzyme, Bst 2.0 warm start (3'→5' exo⁻) and the nicking enzyme, Nt.AlwI were purchased from New England Biolabs. All reactions contained 1×NEB buffer 2 (New England Biolabs) and nuclease free water (Ambion). Reactions C-H also contained 200 μM dNTPs (Bioline). The total volume of all reactions was 25 μL. All reactions were performed in duplicate at 52° C. in a Bio-Rad® CFX96 thermocycler. Fluorescence signal was measured on Channel 1 (FAM) and was programmed to be read every 30 seconds (scan mode: FAM only) for a total of 148 minutes.

Results

FIG. 25 panel ii) demonstrates the fluorescent signal achieved from the strategy depicted in FIG. 25 panel i). Substrate 1, which can be cleaved by the Dz1 following its synthesis from the 'Partially blocked' hairpined Dz template, is labeled with a FAM fluorophore and quencher dye. The graph (FAM) outlines the fluorescent signal from this FAM fluorophore. For Reaction C where the 'Partially blocked' hairpined Dz template exists on its own (Reaction C, "Partially blocked' hairpined Dz template only–No PR' shown as a line with triangle symbols) and Reaction E, where it is placed with Primer 2 (Reaction E "Partially blocked' hairpined Dz template only–PR2 present' shown as a line with symbols consisting of one vertical and two diagonal intersecting lines) there is little to no increase in fluorescent signal, as there is no Primer 1 present to initiate synthesis of Dz1 and hence, no cleavage of Substrate 1. When the 'Partially blocked' hairpined Dz template is provided with the hairpined primer template (Reaction F, "Partially blocked' hairpined Dz template+hairpined primer template–No PR' shown as a line with symbols consisting of two diagonal intersecting lines), there is also little to no increase in fluorescent signal, as Primer 1 is not present and cannot be synthesized. Reactions C, E and F are shown in comparison to Reaction A containing the negative control ('Negative control', line containing square symbols) which contains the same fluorescently-labeled Substrate 1 only.

Reactions D ("Partially blocked' hairpined Dz template only–PR1 present', line containing circle symbols) and G ("Partially blocked' hairpined Dz template+hp primer template–PR1 present', line containing symbols consisting of one vertical and horizontal intersecting lines) both contain the 'Partially blocked' hairpined Dz template and Primer 1, with Reaction G also comprising the hairpined primer template. Due to the presence of Primer 1 in these reactions, there is a rapid increase in signal which quickly reaches a plateau within approximately 20 minutes, indicating that Primer 1 is initiating the synthesis of Dz1, which in turn cleaves Substrate 1. The fluorescent signal is very similar between the two reactions, indicating that the presence of the hairpined primer template in Reaction G does not deter this. For Reaction H, comprising the 'Partially blocked' hairpined DNAzyme template, the hairpined primer template and Primer 2 ("Partially blocked' hairpined Dz template+hp primer template–PR2 present', line containing filled black square symbols), there is an initial lag phase, followed by gradual increase in signal, reaching a plateau at approximately 70 minutes. Since Primer 2 cannot directly prime synthesis of Dz1, this indicates that Primer 2 is binding to the hairpined primer template and initiating the synthesis of Primer 1. Primer 1 can therefore prime the synthesis of Dz1 via the 'Partially blocked' hairpined Dz template, resulting in the production of Dz1 molecules than cleave Substrate 1. The signal from Reaction H is slower than that of Reactions D and G due to the time required for Primer 1 to be synthesized before it can in turn synthesize Dz1. The signal from Reactions D, G and H are shown in comparison to Reaction B containing the positive control ('Positive control', line containing diamond symbols) which consists of the same concentration of Substrate 1 and free positive control Dz1.

Example 24

The following example demonstrates the inactivation of DNAzymes by hybridization to complementary BL molecules within auto-catalytic, quasi-circular structures as previously demonstrated in Example 19. In this current Example 24 (depicted in FIG. 26 panel i)), a multiplex detection reaction is demonstrated whereby two independent, auto-catalytic quasi circles are placed together in the same reaction tube. Each cascade reaction is initiated by the cleavage of a substrate present within the BL by a different MNAzyme, each of which can function following assembly mediated by their unique target sequences. Circle A is comprised of a DNAzyme (Dz2) and BLA. BLA consists of sequence at its 5' and 3' ends, which hybridizes to a portion of Dz2, resulting in the temporary inactivation of Dz2. BLA also contains an intermediate region consisting of the adjacent sequences Substrate 1 and Substrate 2a. Substrate 1 can be cleaved by Mz1, in the presence of its target assembly facilitator (AF1). Substrate 2a is capable of being cleaved by Dz2, once it has been released from BLA via Mz1 cleavage of Substrate 1.

Circle B is comprised of a DNAzyme (Dz4) and BLB. BLB consists of sequence at its 5' and 3' ends, which hybridizes to a portion of Dz4, resulting in the temporary inactivation of Dz4. BLB also contains an intermediate region consisting of the adjacent sequences of Substrate 3 and Substrate 4a. Substrate 3 can be cleaved by Mz3, in the presence of its target assembly facilitator (AF3). Substrate 4a is capable of being cleaved by. Dz4, once it has been released from BLB via Mz3 cleavage of Substrate 3. To monitor each cascade reaction independently, Substrate 2 and Substrate 4 are also provided as linear sequences which have been labeled with a different fluorophore and quencher pair to individually monitor cleavage by Dz2 and Dz4 respectively.

Oligonucleotides

In the current example, BLA (SEQ ID NO: 68; C(R22h)) is composed of (i) 5' and 3' ends that are complementary to a portion of Dz2 (SEQ ID NO: 71; Dz77_55 (8:9)) and (ii) a central portion connecting the 5' and 3' ends that is two adjacent substrate sequences, Substrate 1 and Substrate 2a which is equivalent to Substrate 2 (Sub77_55, SEQ ID No: 55) but lacks the 3' terminal 'C' nucleotide. BLA is utilized to block the activity of the Dz2 by pre-hybridizing BLA with Dz2. An MNAzyme (Mz1), consisting of partzymes (Partzyme 1A, SEQ ID NO: 74; LTFRCA4/72 and Partzyme 1B, SEQ ID NO: 75; LTFRCB5/72), and an assembly facilitator target (AF1, SEQ ID NO: 76; AF-LTFRC), is utilized to cleave the Substrate 1 portion of BLA. This target dependent cleavage event facilitates the release of the Dz2, allowing it to act upon Substrate 2a present within BLA.

BLB (SEQ ID NO: 81; C(R27a)) is composed of (i) 5' and 3' ends that are complementary to a portion of Dz4 (SEQ ID NO: 82; Dz3(8:9)) and (ii) a central portion connecting the 5' and 3' ends that is the adjacent sequences of Substrate 3 and Substrate 4a, which is equivalent to the sequence of Substrate 4 (Sub3, SEQ ID No: 83). BLB is utilized to block the activity of the Dz4 by pre-hybridizing BLB with Dz4. An MNAzyme (Mz3), consisting of partzymes (Partzyme 3A, SEQ ID NO: 84; RO5A4/56-P and Partzyme 3B, SEQ ID NO: 85; RO5B5/56-P), and an assembly facilitator target (AF3, SEQ ID NO: 62; AF-R05), is utilized to cleave the Substrate 3 portion of BLB. This target dependent cleavage event facilitates the release of the Dz4, allowing it to act upon Substrate 4a present within BLB.

Dz2 and Dz4 can both also act upon a separate, independent, version of Substrate 2 and Substrate 4 respectively, which are not components of a quasi-circle. In this example, the independent Substrate 2 was end-labeled with a FAM moiety on the 5' end and an Iowa Black quencher ("IB") moiety on the 3' end. The independent Substrate 4 was end-labeled with a Texas Red (TR) moiety on the 5' end and a Black Hole Quencher 2 ("BHQ2") moiety on the 3' end.

The sequences of these oligonucleotides are listed from 5' to 3' below. Bases in uppercase are deoxyribonucleotides and bases in lowercase are ribonucleotides. Underlined bases represent regions in the BL that are complementary to a portion of the Dz. Bases in italics refer to regions corresponding to a substrate sequence within the BL molecule. Boxed bases represent the catalytic core of the DNAzymes and Partzymes. Highlighted bases represent the bases in Dz that are complementary to and blocked by, the underlined bases in the BL. /3Phos/indicates 3' phosphorylation.

Substrate 2: Sub77_55-FIB
SEQ ID NO: 55
CTCCTCCCTCguCCCCAGCTC

Substrate 4: Sub3-TRB
SEQ ID NO: 83
CAGCACAACCguCACCAACCG

Partzyme 1A: LTFRCA4/72
SEQ ID NO: 74
GCAAGGAACAATAACTCAGAACTT ACAACGA GAGGCGTGAT Partzyme 1B: LTFRCB5/72
SEQ ID NO: 75
CTGGGAGGAGA GGCTAGCT ACGCCTGCTTTCTGATTCTA Assembly facilitator (AF1): AF-LTFRC
SEQ ID NO: 76
AGTCTGTTTTCCAGTCAGAGGGACAGTCTCCTTCCATATTCCTAGAATCA
GAAAGCAGGCGTAAGTTCTGAGTTATTGTTCCTTGC Partzyme 3A: RO5A4/56-P
SEQ ID NO: 84
CAAACGAGTCCTGGCCTTGTCT ACAACGA GGGGTCGAG/3Phos/

Partzyme 3B: RO5B5/56-P
SEQ ID NO: 85
TGGCGTGGAGA GGCTAGCT GTGGAGACGGATTACACCTTC/3Phos/

Assembly facilitator (AF3): AF-R05
SEQ ID NO: 62
GAAGGTGTAATCCGTCTCCACAGACAAGGCCAGGACTCGTTTG BLA: C(R22h)
SEQ ID NO: 68
AGCCTCCCCAGCTAT CACGCCTCguCTCCTCCCAGCTCCTCCCTCguCCC CAGCTT CCTCCCTCTCGTTG Dz2: Dz77_55(8:9)
SEQ ID NO: 71
AGCTGGGGA GGCTAGCTACAACGA GAGGGAGG BLB: C(R27a)
SEQ ID NO: 81
TAGCCTCACCAACCG CTCGACCCCguCTCCACGCCACAGCACAACCguCA CCAACCGC AGCACAACCTCGTTG Dz4: Dz3(8:9)
SEQ ID NO: 82
GGTTGGTGA GGCTAGCTACAACGA GGTTGTGC Reaction Components Reactions A, B, C, D, E and F were set up to contain the following oligonucleotides as listed in Table 27, with reference to oligonucleotides listed in the previous section and structures illustrated in FIG. 26 panel i). For all reactions containing BLA and Dz2 and/or BLB and Dz4, each DNAzyme and BL combination were initially pre-hybridized separately for 30 minutes at room temperature before the addition of any further oligonucleotide components.

TABLE 27

| Reaction A (Circle A only, No AF) | Reaction B (Circle A only, AF1 present) | Reaction C (Circle B only, No AF) | Reaction D (Circle B only, AF3 present) | Reaction E (Circle A + Circle B, No AF) | Reaction F (Circle A + Circle B, AF1 present) | Reaction G (Circle A + Circle B, AF3 present) |
|---|---|---|---|---|---|---|
| Sub77_55-FIB 200 nM | Sub77_55-FIB 200 nM | | | Sub77_55-FIB 200 nM | Sub77_55-F1B 200 nM | Sub77_55-FIB 200 nM |
| | | Sub3-TRB 200 nM | Sub3-TRB 200 nM | Sub3-TRB 200 nM | Sub3-TRB 200 nM | Sub3-TRB 200 nM |
| C(R22h) 14 nM | C(R22h) 14 nM | | | C(R22h) 14 nM | C(R22h) 14 nM | C(R22h) 14 nM |
| Dz77_55(8:9) 10 nM | Dz77_55(8:9) 10 nM | | | Dz77_55(8:9) 10 nM | Dz77_55(8:9) 10 nM | Dz77_55(8:9) 10 nM |
| | | C(R27a) 7 nM | C(R27a) 7 nM | C(R27a) 7 nM | C(R27a) 7 nM | C(R27a) 7 nM |
| | | Dz3(8:9) 5 nM | Dz3(8:9) 5 nM | Dz3(8:9) 5 nM | Dz3(8:9) 5 nM | Dz3(8:9) 5 nM |
| LTFRCA4/72 50 nM | LTFRCA4/72 50 nM | | | LTFRCA4/72 50 nM | LTFRCA4/72 50 nM | LTFRCA4/72 50 nM |
| LTFRCB5/72 50 nM | LTFRCB5/72 50 nM | | | LTFRCB5/72 50 nM | LTFRCB5/72 50 nM | LTFRCB5/72 50 nM |
| | AF-LTFRC 100 pM | | | | AF-LTFRC 100 pM | |
| | | RO5A4/56-P 50 nM | RO5A4/56-P 50 nM | RO5A4/56-P 50 nM | RO5A4/56-P 50 nM | RO5A4/56-P 50 nM |
| | | RO5B5/56-P 50 nM | RO5B5/56-P 50 nM | RO5B5/56-P 50 nM | RO5B5/56-P 50 nM | RO5B5/56-P 50 nM |
| | | | AF-RO5 100 pM | | | AF-RO5 100 pM |

Oligos were purchased from Integrated DNA Technologies (IDT) or Biosearch technologies. All reactions contained 1×PCR buffer II (Applied Biosystems), nuclease free water (Ambion) and 45 mM of $MgCl_2$ (Ambion). The total volume of all reactions was 25 µL. All reactions were performed in duplicate at 52° C. in a Bio-Rad® CFX96 thermocycler and fluorescence signal was measured in Channel 1 (FAM) and Channel 3 (TxR) to monitor FAM and Texas Red, respectively and was programmed to be read every 30 seconds (scan mode: all channels) for a total of 154 minutes.

Results

FIG. 26 panel ii) shows the results comparing the fluorescent signal from two independent auto-catalytic DNAzyme quasi circles, when they are placed separately or together in the reaction tube. Substrate 2 which is labeled with a FAM fluorophore and quencher, can be cleaved by Dz2 and hence the release and activation of Dz2 can be monitored by changes in fluorescence for FAM. Alternatively, Substrate 4 is labeled with a TxR fluorophore and quencher and can be cleaved by Dz4 and hence the release and activation of Dz4 can be monitored by changes in fluorescence for TxR. The graphs 'FAM' and 'TxR' outline the fluorescent signal from the FAM and TxR fluorophores respectively.

In the graph FAM, for Reaction A, ('Circle A only, no AF' shown as a line with square symbols) where Circle A is present on its own without any AF1 present, there is initially very little cleavage of Substrate 2 and as a result, only a slight increase in FAM signal during the reaction time. This indicates that Dz2 is kept inactive within the quasi circle complex. This is shown in comparison to Reaction E ('Circle A+Circle B, no AF' shown as a line with symbols consisting of two diagonal and one vertical intersecting lines) and Reaction G ('Circle A+Circle B, AF3 present', line containing symbols consisting of one vertical and one horizontal intersecting line) both containing Circle A and B together in the one reaction, with neither AF present (Reaction E) or only AF3 present (Reaction G). In Reaction B, ('Circle A only, AF1 present', line containing diamond symbols), where Circle A is present on its own and AF1 is also present, there is a slight lag followed by an immediate increase in FAM signal, which quickly reaches a plateau. This indicates that AF1 assembles Mz1, which cleaves Substrate 1 and thereby triggers a cascade of Dz2 activation and Substrate 2 (and Substrate 2a) cleavage events. This signal is shown in comparison to that of Reaction F ('Circle A+Circle B, AF1 present', line containing symbols consisting of two diagonal interesting lines) whereby both Circle A and B are together in the one reaction, with AF1 present. The FAM signal is very similar between that of Reactions A, E and G and of Reactions B and F, indicating that the presence of Circle B minimally affects the activity of Circle A and that release of Dz4 from Circle B does not generate signal in the FAM channel showing that there is no cross-talk or non-specificity in the system.

In the graph for TxR, for Reaction C, ('Circle B only, no AF' shown as a line with triangle symbols) where Circle B is present on its own without any AF3 present, there is very little cleavage of Substrate 4 and as a result, very little increase in TxR signal, which only begins to increase slightly towards the end of the reaction time. This indicates that Dz4 is kept inactive within the quasi Circle B complex. This is shown in comparison to Reactions E and F, both consisting of Circle B and A together in the one reaction, with either no AF present (Reaction E), or AF1 only present (Reaction F). In Reaction D, ('Circle B only, AF3 present', line containing circle symbols), where Circle B is present on its own and AF3 is also present, there is a slight lag followed by an increase in TxR signal. This indicates that AF3 assembles Mz3, which cleaves Substrate 3 and thereby triggers a cascade of Dz4 activation and Substrate 4 (and Substrate 4a) cleavage events. This signal is shown in comparison to that of Reaction G whereby both Circle B and A are together in the one reaction, with AF3 present. The TxR signal is also very similar between that of Reactions C, E and F and of Reactions D and G, indicating that the presence of Circle A minimally affects the activity of Circle B and that release of Dz2 from Circle A does not generate signal in the TxR channel showing that there is no cross-talk or non-specificity in the system. The signal present in the FAM channel for Reaction F and in the TxR channel for Reaction G also indicates that the two targets may be able to be detected simultaneously.

The fluorescent signal produced is comparable between reactions consisting of either Circle A or B on their own, or when Circles A and B are complexed together within the same reaction tube. This indicates that there is minimal unwanted interaction between the two circles and that they can be used to amplify the signal following the detection of two unique target sequences.

Example 25

The following example demonstrates the inactivation of a DNAzyme by hybridization to a complementary BL molecule within an auto-catalytic, quasi-circular structure, as previously demonstrated in Example 19. In this current Example 25, the cascade is initiated via the hybridization of a target sequence (Target 1) to a substrate (Substrate 1) within the BL, which recruits the activity of an RE to selectively nick the BL (FIG. 27, panel i)). Substrate 1 and Target 1 each comprise one strand of the duplex required for the RE recognition sequence, such that the binding of the two together results in the formation of the complete double-stranded recognition site. The BL molecule consists of sequence at its 5' and 3' ends, which hybridizes to a portion of a DNAzyme (Dz2), resulting in the temporary inactivation of the Dz2. The BL also contains a second substrate sequence adjacent to Substrate 1, namely Substrate 2a which is capable of being cleaved by Dz2, once Dz2 has been released from the BL via target-dependant RE-mediated nicking of Substrate 1. In addition, Substrate 2 is provided as a linear sequence which has been modified with a fluorophore and quencher to monitor the Dz2 cleavage reaction. Only when Target 1 and the RE are both present will Substrate 1 be nicked, resulting in the initiation of the auto-catalytic cascade.

Oligonucleotides

In the current example, the BL (SEQ ID NO: 86; C(R39c)) which is composed of (i) 5' and 3' ends that are complementary to a portion of Dz2 (SEQ ID NO: 71; Dz77_55 (8:9)) and (ii) a central portion connecting the 5' and 3' ends that consists of the adjacent sequences of Substrate 1 and Substrate 2a which is equivalent to Substrate 2 (Sub77_55, SEQ ID No: 55) but lacks the 3' terminal 'C' nucleotide of this sequence. The BL is utilized to block the activity of the Dz2 by pre-hybridizing the BL with Dz2.

Target 1 (SEQ ID NO: 88; AF-(R38e)) is utilized to recruit the activity of an RE to selectively cleave the Substrate 1 portion of the BL. This target dependent cleavage event facilitates the release of the Dz2, allowing it to act upon Substrate 2a present within the BL. Dz2 can also act upon a separate, independent Substrate 2, which is not a component of a quasi-circle. In this example, this independent Substrate 2 was end-labeled with a FAM moiety on the 5' end and an Iowa Black quencher ("IB") moiety on the 3' end.

The sequences of these oligonucleotides are listed from 5' to 3' below. Bases in uppercase are deoxyribonucleotides and bases in lowercase are ribonucleotides. Underlined bases represent regions in the BL that are complementary to a portion of the Dz. Bases in italics refer to regions corresponding to a substrate sequence within the BL molecule. Boxed bases represent the catalytic core of the DNAzymes. Nucleotides highlighted in grey represent both (a) the bases in Dz that are complementary to and blocked by, the underlined bases in the BL and (b) the partial RE recognition site within the BL and Target 1.

Substrate 2: Sub77_55-FIB
SEQ ID NO: 55
CTCCTCCCTCguCCCCAGCTC

Target 1: AF-(R38e)
SEQ ID NO: 88
GGGATGAGGCGAATGATCCGAT

BL: C(R39c)
SEQ ID NO: 86
AGCCTCCCCAGCTATCGGATCATTCGCCTCATCCC*CTCCTCCCTCguCCC CAGCTA*CCTCCCTCTCGTTG

Dz2: Dz77_55(8:9)
SEQ ID NO: 71
AGCTGGGGA GGCTAGCTACAACGA GAGGGAGG

Reaction Components

Reactions A, B, C and D were set up to contain the following oligonucleotides as listed in Table 28, with reference to oligonucleotides listed in the previous section and structures illustrated in FIG. 27 panel i). For all reactions containing the BL and Dz2, these two oligos were initially pre-hybridized together for 30 minutes at room temperature before the addition of any further oligonucleotide components.

TABLE 28

| Reaction A (No RE, No Target 1) | Reaction B (No RE, Target 1 present) | Reaction C (RE present, No Target 1) | Reaction D (RE present, Target 1 present) |
| --- | --- | --- | --- |
| Sub77_55-FIB 200 nM | Sub77_55-FIB 200 nM | Sub77_55-FIB 200 nM | Sub77_55-FIB 200 nM |
| C(R39c) 10 nM | C(R39c) 10 nM | C(R39c) 10 nM | C(R39c) 10 nM |
| Dz77_55(8:9) 8 nM | Dz77_55(8:9) 8 NM | Dz77_55 (8:9) 8 nM | Dz77_55 (8:9) 8 nM |
| | | Nt.AlwI (4 U) | Nt.AlwI (4 U) |
| | AF-(R38e) 500 pM | | AF-(R38e) 500 pM |

Oligos were purchased from Integrated DNA Technologies (IDT) or Biosearch technologies. All reactions contained 1×PCR buffer II (Applied Biosystems), nuclease free water (Ambion) and 25 mM of $MgCl_2$ (Ambion). The total volume of all reactions was 25 µL. All reactions were performed in duplicate at 52° C. in a Bio-Rad® CFX96 thermocycler and fluorescence signal was measured in Channel 1 (FAM) and was programmed to be read every 30 seconds (scan mode: FAM only) for a total of 126 minutes.

Results

FIG. 27 panel ii) shows results comparing the fluorescent signal in the presence or absence of both Target 1 and the RE. Substrate 2 which is labeled with a FAM fluorophore and quencher can be cleaved by Dz2 and hence the release and activation of the Dz can be monitored by changes in fluorescence for FAM.

In Reaction A, ('No RE, no Target 1' shown as a line with square symbols), Reaction B ('No RE, Target 1 present', shown as a line with diamond symbols) and Reaction C ('RE, present, No target 1', shown as a line with triangle symbols) there is very little cleavage of Substrate 2 and as a result, minimal increase in FAM signal over time. For Reactions A and B this is because there is no RE present, so regardless of whether Target 1 is present to hybridize to the BL, there is still no RE available to cleave Substrate 1 and this Dz2 is not released from the quasi-circle. For Reaction C, the RE is available, but there is no Target 1 present, so the RE recognition site has not been completed and Dz2 is not released from the quasi-circle. In contrast, for Reation D ('RE present, Target 1 present', line containing circle symbols) there is a gradual increase in FAM signal throughout the course of the reaction, indicating that Target 1 can hybridize to Substrate 1 and this can result in the formation of a duplex RE recognition site and thus ability of the RE to selectively nick Substrate 1. The nicking of Substrate 1 then results in the release and activation of Dz2, triggering an auto-catalytic cascade of Dz2 activation and Substrate 2a cleavage events. As Substrate 2 is also provided as an independent, fluorescently labeled version, the accumulation of fluorescent signal occurs. This result therefore demonstrates that an auto-catalytic cascade utilizing the DNAzyme quasi circle strategy can be initiated via RE cleavage in a target-dependent manner.

Example 26

The following example demonstrates the inactivation of a DNAzyme by hybridization to a complementary BL molecule within a quasi-circular structure, as previously demonstrated in Example 1. In this current Example 26, cleavage of the substrate within the BL (Substrate 1) occurs via an Aptazyme (FIG. 28, panel i)). The Aptazyme consists of a DNAzyme domain (Dz1) covalently linked with an Aptamer domain. In this example, the Aptamer binds the ligand deoxy-Adenosine Triphosphate (dATP). In the absence of dATP, the Dz1 is rendered inactive due to the presence of the Aptamer domain, which shares some base pair homology with Dz1. In the presence of dATP however, the Aptamer domain can bind to the dATP which leads to a change in conformation of the Aptazyme structure. This results in a change in conformation of the DNAzyme domain, restoring the catalytic activity of Dz1 such that it can now cleave Substrate 1 within the quasi-circle. Cleavage of Substrate 1 results in the release of Dz2 from the quasi circle which restores its catalytic activity and allows it to cleave its substrate (Substrate 2). Substrate 2 has been labeled with a fluorophore and a quencher such that cleavage results in the generation of a detectable fluorescent signal. There is no increase in fluorescent signal in the presence of closely related analytes such as the nucleotide triphosphates dCTP, dGTP and dTTP indicating that the Aptazyme can be activated in a target specific manner to initiate the release of catalytic nucleic acids from BL molecules in this invention.

Oligonucleotides

In the current example, the BL (SEQ ID NO: 64; C(R43e)) which is composed of (i) 5' and 3' ends that are complementary to a portion of Dz2 (SEQ ID NO: 73; Dz3(8:10)) and (ii) a central portion connecting the 5' and 3' ends that consists of Substrate 1. The BL is utilized to block the activity of the Dz2 by pre-hybridizing the BL with Dz2. The Aptazyme molecule (SEQ ID NO: 87; Dz1-(R40a)) is utilized to cleave the Substrate 1 portion of the BL when activated by the presence of dATP. This target dependent cleavage event facilitates the release of the Dz2 from the BL, allowing it to act upon Substrate 2 (SEQ ID NO: 83; Sub3). In this example, Substrate 2 was end-labeled with a FAM moiety on the 5' end and an IowaBlack ("IB") moiety on the 3' end.

The sequences of these oligonucleotides are listed from 5' to 3' below. Bases in uppercase are deoxyribonucleotides and bases in lowercase are ribonucleotides. Underlined bases represent regions in the BL that are complementary to a portion of the Dz. Bases in italics refer to regions corresponding to a substrate sequence within the BL molecule. Boxed bases represent the catalytic core of the DNAzymes. Nucleotides highlighted in grey represent both (a) the bases in Dz2 that are complementary to, and blocked by, the underlined bases in the BL and (b) the Aptamer domain within the Aptazyme.

```
Substrate 2: Sub3-FIB
                                          SEQ ID NO: 83
CAGCACAACCguCACCAACCG Aptazyme: Dz1-(R40a)
                                          SEQ ID NO: 87
ATCTCTTCT CCGAGCCGGTCGAA ATAGTGAGACCTGGGGGAGTATGTGCGG
AGGAAGGT BL: C(R43e)
                                          SEQ ID NO: 64
TAGCCTCACCAACCCCTCACTATaGGAAGAGATAGCACAACCTCGTTG Dz2: Dz3(8:10)
                                          SEQ ID NO: 73
CGGTTGGTGA GGCTAGCTACAACGA GGTTGTGC
```

Reaction Components

Reactions A, B, C, D and E were set up to contain the following oligonucleotides and ligands as listed in Table 29, with reference to oligonucleotides listed in the previous section and structures illustrated in FIG. 28 panel i). For all reactions, the BL and Dz2 were initially pre-hybridized together for 30 minutes at room temperature before the addition of any further oligonucleotide or ligand components.

TABLE 29

| Reaction A (No ligand) | Reaction B (dATP present) | Reaction C (dCTP present) | Reaction D (dGTP present) | Reaction E (dTTP present) |
|---|---|---|---|---|
| Sub3-FIB 200 nM | Sub3-FIB 200 nM | Sub3-FIB 200 nM | Sub3-FIB 200 nM | Sub3-FIB 200 nM |
| C(R43e) 20 nM | C(R43e) 20 nM | C(R43e) 20 nM | C(R43e) 20 nM | C(R43e) 20 nM |
| Dz3(8:10) 10 nM | Dz3(8:10) 10 nM | Dz3(8:10) 10 nM | Dz3(8:10) 10 nM | Dz3(8:10) 10 nM |
| Dz1-(R40a) 40 nM | Dz1-(R40a) 40 NM dATP 1 mM | Dz1-(R40a) 40 nM dCTP 1 mM | Dz1-(R40a) 40 nM dGTP 1 mM | Dz1-(R40a) 40 nM dTTP 1 mM |

Oligos were purchased from Integrated DNA Technologies (IDT) or Biosearch technologies. The dATP, dCTP, dGTP and dTTP solutions were purchased from Bioline. All reactions contained 1× Immobuffer (Bioline), nuclease free water (Ambion) and 45 mM of MgCl$_2$ (Ambion). The total volume of all reactions was 25 µL. All reactions were performed in duplicate in a Bio-Rad® CFX96 thermocycler. Reactions were run under a two-step thermal cycling profile, the first step consisted of 42° C. for 30 minutes and the second step at 52° C. for 60 minutes. Fluorescence signal was measured in Channel 1 (FAM) every 10 seconds during the second step (scan mode: FAM only).

Results

FIG. 28 panel iii) demonstrates the fluorescent signal that is specifically achieved in the presence of the dATP target analyte due to Aptazyme initiation of a quasi-circular DNAzyme structure. Substrate 2 which is labeled with a FAM fluorophore and quencher can be cleaved by Dz2 and hence the release and activation of the Dz2 can be monitored by changes in fluorescence for FAM.

In Reaction A, ('No ligand' shown as a line with square symbols), Reaction C ('dCTP present', shown as a line with triangle symbols), Reaction D ('dGTP present', shown as a line with circle symbols) and Reaction E ('dTTP present', shown as a line with symbols consisting of two vertical and one horizontal intersecting lines) there is very little cleavage of Substrate 2 and as a result, minimal increase in FAM signal over time. This because the Dz1 domain of the Aptazyme has been rendered inactive due to the presence of the Aptamer domain. In Reaction B however ('dATP present', line containing diamond symbols) there is an immediate increase in FAM fluorescent signal indicating that the dATP is binding to the Aptamer domain of the Aptazyme and resulting in a change in conformation of the Aptazyme, such that the Dz1 domain is now active. The active Dz1 can then cleave Substrate 1 present within the BL of the quasi circle. The Dz2 is then released from the BL of the quasi-circle and can cleave Substrate 2, generating the increase in fluorescent signal. The signal from the presence of dATP, but not the other closely-related nucleotide tri-phosphate molecules, indicates that the Aptazyme can be used as an enzyme to specifically initiate the release of catalytic nucleic acids from BL molecules in a target-dependent manner and may therefore be useful to initiate to cascade reactions.

The invention claimed is:

1. A method for detecting the presence or absence of a first target molecule in a sample, the method comprising:
   (a) contacting the sample with at least one molecular complex comprising a blocker oligonucleotide (BL) and a first catalytic nucleic acid enzyme, the BL comprising first and second segments hybridised to the first enzyme by complementary base pairing, and an intermediate segment between the first and second segments comprising a first substrate for a catalytic nucleic acid enzyme, wherein at least a segment of the first substrate is not hybridised to the first enzyme;
   a first initiator enzyme, and a reporter substrate; wherein,
   the first initiator enzyme has binding specificity for the first target and the first substrate of said intermediate segment and hybridisation of the target to the first initiator enzyme induces catalytic activity of the first initiator enzyme thereby facilitating cleavage of the first substrate when hybridised to the first initiator enzyme;
   the cleavage of the first substrate causes dissociation of hybridised strands of the blocker oligonucleotide and the first catalytic nucleic acid enzyme of said molecular complex; and
   the first enzyme of said molecular complex has binding specificity for the reporter substrate and, after said dissociation, is capable of hybridising to the reporter substrate and cleaving it to thereby provide a detectable signal indicative of the presence of the first target in the sample; and
   (b) determining whether a detectable signal is generated by said contacting, wherein detection of the signal indicates the first target molecule is present, and failure to detect the signal indicates the first target molecule is absent.

2. The method according to claim 1, wherein said molecular complex contacted with the sample is provided with a 5' terminus of the blocker oligonucleotide opposing a 5' terminus of the catalytic nucleic acid enzyme.

3. The method according to claim 1, wherein said molecular complex contacted with the sample is provided with a 5' terminus of the blocker oligonucleotide opposing a 3' terminus of the catalytic nucleic acid enzyme.

4. The method according to claim 1, comprising contacting the sample with first and second molecular complexes, wherein
   the first molecular complex comprises said BL and said first catalytic nucleic acid enzyme, and the intermediate segment between said first and second segments comprises the first substrate and a second substrate;
   the second molecular complex comprises a second BL and a second catalytic nucleic acid enzyme, the second BL comprising first and second segments hybridised to the second enzyme by complementary base pairing, and an intermediate segment between the first and second segments comprising a copy of said first substrate and a third substrate;
   said initiator enzyme has binding specificity for the target and the first substrate of each said intermediate segment, and hybridisation of the target to the initiator enzyme induces catalytic activity of the initiator enzyme thereby facilitating cleavage of the first substrate of each said intermediate segment when hybridised to the initiator enzyme;
   the cleavage of the first substrate of each said intermediate segment causes dissociation of hybridised strands of the blocker oligonucleotide and the catalytic nucleic acid enzyme of each said molecular complex;
   the first enzyme has binding specificity for said third substrate, and the second enzyme has binding specificity for said second substrate; and
   after the dissociation of each said molecular complex, the first enzyme is capable of hybridising and cleaving the third substrate of another second molecular complex, and the second enzyme is capable of hybridising and cleaving the second substrate of another first molecular complex, thereby amplifying said detectable signal.

5. The method according to claim 4, wherein said first, second or third substrate is identical to said reporter substrate.

6. The method according to claim 4, wherein
the substrate of the intermediate segment of said molecular complex is identical to the reporter substrate, and
upon said dissociation from the blocker oligonucleotide, the first catalytic nucleic acid enzyme of a first said molecular complex can hybridise and cleave the substrate of the intermediate segment of a second said molecular complex,
thereby facilitating amplification of the detectable signal.

7. The method according to claim 4, wherein the reporter substrate is identical to the second substrate, and said first catalytic nucleic acid enzyme of said molecular complex is capable of hybridising to and cleaving the second substrate.

8. The method according to claim 1, wherein any one or more of the first catalytic nucleic acid, the first substrate, the first initiator enzyme, and the reporter substrate is tethered to an insoluble support.

9. The method according to claim 2, wherein
any said substrate of any said molecular complex comprises a partial restriction enzyme recognition site, and any said target comprises a complementary portion of said partial restriction enzyme recognition site;
said method further comprises contacting the sample with a restriction enzyme capable of recognising and cleaving the restriction enzyme recognition site;
said target is capable of hybridising to said BL comprising the partial recognition site by complementary base pairing to thereby complete the restriction enzyme recognition site, thereby allowing said restriction enzyme to cleave the BL comprising the partial recognition site causing dissociation of hybridised strands of the blocker oligonucleotide and the catalytic nucleic acid enzyme of said molecular complex; and
the catalytic nucleic acid enzyme of said molecular complex has binding specificity for the reporter substrate and, after said dissociation, is capable of hybridising to the reporter substrate and cleaving it to thereby provide a detectable signal indicative of the presence of said target in the sample.

10. The method according to claim 1, wherein
any said initiator enzyme comprises an aptamer;
in the absence of the target the aptamer adopts a conformation that prevents catalytic activity of the initiator enzyme; and
in the presence of the target the aptamer binds to the target and adopts a conformation that allows catalytic activity of the initiator enzyme, to thereby cleave the substrate of the molecular complex.

11. A method according to claim 1 for detecting the presence or absence of a target molecule in a sample, the method comprising:

(a) contacting the sample with
first and second molecular complexes, wherein said first complex comprising a first BL and a first catalytic nucleic acid enzyme, wherein said second complex comprising a second BL and a second catalytic nucleic acid enzyme, the first and second BL each comprising first and second segments hybridised to the enzyme by complementary base pairing, and an intermediate segment between the first and second segments comprising a substrate for a catalytic nucleic acid enzyme, wherein at least a segment of the substrate is not hybridised to the first or second enzyme; and
an initiator enzyme, wherein
the initiator enzyme has binding specificity for the target and the substrate of said first molecular complex and hybridisation of the target to the initiator enzyme induces catalytic activity of the initiator enzyme thereby facilitating cleavage of the substrate when hybridised to the initiator enzyme;
the cleavage of the substrate of the first molecular complex causes dissociation of hybridised strands of the blocker oligonucleotide and the catalytic nucleic acid enzyme of said first molecular complex;
the catalytic nucleic acid enzyme of said first molecular complex, after said dissociation, is capable of hybridising to and cleaving the substrate of the second molecular complex causing dissociation of hybridised strands of the blocker oligonucleotide and the catalytic nucleic acid enzyme of the second molecular complex;
the catalytic nucleic acid enzyme of said second molecular complex, after said dissociation, is capable of hybridising to and cleaving the substrate of a further said first molecular complex causing dissociation of the blocker oligonucleotide and the catalytic nucleic acid enzyme of the further said first molecular complex; and
either or both substrates of the first and second molecular complexes is a reporter substrate capable of providing a detectable signal when cleaved; and (b) determining whether a detectable signal is generated by said contacting, wherein detection of the signal indicates the target molecule is present, and failure to detect the signal indicates the target molecule is absent.

12. The method according to claim 1, wherein the first catalytic nucleic enzyme and/or the initiator catalytic enzyme is a ribozyme, a DNAzyme, an aptazyme, an MNAzyme or an apta-MNAzyme.

13. The method according to any claim 4, wherein the second catalytic nucleic enzyme is a ribozyme, a DNAzyme, an aptazyme, an MNAzyme or an apta-MNAzyme.

14. The method according to claim 1, wherein the target molecule is a nucleic acid comprising DNA, RNA, ligand or a combination thereof.

* * * * *

SEQUENCE LISTING

```
<160> NUMBER OF SEQ ID NOS: 105

<210> SEQ ID NO 1
<211> LENGTH: 48
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: C(4)Sub45(24:24)(2)-FB
<220> FEATURE:
<221> NAME/KEY: misc_feature
<222> LOCATION: (24)..(25)
<223> OTHER INFORMATION: ribonucleotides

<400> SEQUENCE: 1
agcctccctg ggcatcgggt cccguctcct tgtaaggtt tcctctcg                 48

<210> SEQ ID NO 2
<211> LENGTH: 34
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: DzK(10:9)

<400> SEQUENCE: 2
gcccagggag gctagctaca acgagaggaa acct                              34

<210> SEQ ID NO 3
<211> LENGTH: 22
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Sub45
<220> FEATURE:
<221> NAME/KEY: misc_feature
<222> LOCATION: (9)..(10)
<223> OTHER INFORMATION: ribonucleotides

<400> SEQUENCE: 3
acgggtcccg uctcctttgg aa                                           22
```

```
<210> SEQ ID NO 4
<211> LENGTH: 34
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz45(9:10)

<400> SEQUENCE: 4
ccaaaggaga ggctagctac aacgagggac ccgt                              34

<210> SEQ ID NO 5
<211> LENGTH: 22
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Sub2
<220> FEATURE:
<221> NAME/KEY: misc_feature
<222> LOCATION: (12)..(13)
<223> OTHER INFORMATION: ribonucleotides

<400> SEQUENCE: 5
aaggtttcct cguccctggg ca                                          22

<210> SEQ ID NO 6
<211> LENGTH: 45
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: C4Sub45(22:23)
<220> FEATURE:
<221> NAME/KEY: misc_feature
<222> LOCATION: (22)..(23)
<223> OTHER INFORMATION: ribonucleotides

<400> SEQUENCE: 6
tagcctccct gggcgggtcc cguctccttt gtcacgcctc tcgtt                 45

<210> SEQ ID NO 7
<211> LENGTH: 30
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: DzK(8:7)

<400> SEQUENCE: 7
ccagggaggc tagctacaac gagaggaaac                                  30

<210> SEQ ID NO 8
<211> LENGTH: 30
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz6(8:7)
```

```
<400> SEQUENCE: 8
ggaggaaggc tagctacaac gagaggcgtg                                      30

<210> SEQ ID NO 9
<211> LENGTH: 45
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: C4Sub45T(21:24)
<220> FEATURE:
<221> NAME/KEY: misc_feature
<222> LOCATION: (21)..(22)
<223> OTHER INFORMATION: ribonucleotides

<400> SEQUENCE: 9
tagccttcct cccgggtccc guctcctttg ggtttcctct cgttg                     45

<210> SEQ ID NO 10
<211> LENGTH: 31
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz45(8:9)

<400> SEQUENCE: 10
caaaggagag gctagctaca acgagggacc c                                    31

<210> SEQ ID NO 11
<211> LENGTH: 21
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Sub6
<220> FEATURE:
<221> NAME/KEY: misc_feature
<222> LOCATION: (11)..(12)
<223> OTHER INFORMATION: ribonucleotides

<400> SEQUENCE: 11
atcacgcctc gutcctccca g                                               21

<210> SEQ ID NO 12
<211> LENGTH: 78
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: hp(R6)Dz45BUB0(4)

<400> SEQUENCE: 12
caaaggagag gctagctaca acgagggacc cgtttttac gggtccctcg ttgtagcctc      60
tcctttggtg atgacctg                                                   78

<210> SEQ ID NO 13
<211> LENGTH: 40
<212> TYPE: DNA
```

<213> ORGANISM: Artificial sequence
<220> FEATURE:
<223> OTHER INFORMATION: Synthetic
<220> FEATURE:
<221> NAME/KEY: misc_feature
<223> OTHER INFORMATION: RL-Dz45BUB0(4)

<400> SEQUENCE: 13
caggtcatca ccaaaggaga ggctacaacg agggacccgt        40

<210> SEQ ID NO 14
<211> LENGTH: 86
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: dhp6Dz2(5)M4

<400> SEQUENCE: 14
gcctcgactg cacgggtcga gctcacgagg tttcctctcg ttgtagctgc ccagggaggc        60
tagctacaac gagaggaaac ctcgtg        86

<210> SEQ ID NO 15
<211> LENGTH: 78
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: dhp5Dz6(3)

<400> SEQUENCE: 15
tgggaggaag gctagctaca acgagaggcg tgagttgtag ctagccttcc tcccactcag        60
cgtccgtgca gtcgaggc        78

<210> SEQ ID NO 16
<211> LENGTH: 63
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: RL-dhp6

<400> SEQUENCE: 16
acgctgagtg ggaggaaggc tagctacaac agctacaacg agaggaaacc tcgtgagctc        60
gac        63

<210> SEQ ID NO 17
<211> LENGTH: 36
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz2

<400> SEQUENCE: 17
tgcccaggga ggctagctac aacgagagga aacctt        36

<210> SEQ ID NO 18

```
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz6

<400> SEQUENCE: 18
ctgggaggaa ggctagctac aacgagaggc gtgat                              35

<210> SEQ ID NO 19
<211> LENGTH: 48
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: BL(MM1)-Dz2

<400> SEQUENCE: 19
aaggtttcct ctcgttgtag ctggcctccc tgggcagtgc atactcta                48

<210> SEQ ID NO 20
<211> LENGTH: 46
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz2(21:10)

<400> SEQUENCE: 20
tgcccaggga ggctagctac aacgagagga aaccttcacc tgactg                  46

<210> SEQ ID NO 21
<211> LENGTH: 27
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Sub2h-FB
<220> FEATURE:
<221> NAME/KEY: misc_feature
<222> LOCATION: (22)..(23)
<223> OTHER INFORMATION: ribonucleotides

<400> SEQUENCE: 21
aaggtttcct cguccctggg cacgagg                                       27

<210> SEQ ID NO 22
<211> LENGTH: 53
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: RL(MM1)(+5)-Dz2

<400> SEQUENCE: 22
tagagtatgc actgcccagg gaggccagct acaacgagag gaaaccttca cct          53

<210> SEQ ID NO 23
```

```
<211> LENGTH: 35
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: BL-Dz2Nic7-FB

<400> SEQUENCE: 23
aaggtttcct ctcgctcttc tagcctccct gggca                              35

<210> SEQ ID NO 24
<211> LENGTH: 27
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: RL-Dz2Nic7a

<400> SEQUENCE: 24
tgcccaggga ggctagaaga gcgagag                                       27

<210> SEQ ID NO 25
<211> LENGTH: 67
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: hpBLr-Dz2BUB0(4)-P
<220> FEATURE:
<221> NAME/KEY: misc_feature
<222> LOCATION: (67)..(67)
<223> OTHER INFORMATION: 3' end phosphorylation

<400> SEQUENCE: 25
gtgcatactc taggtttcct ctcgttgtag cctccctggg atcgaccacg ttttttacgt   60
ggtcgat                                                             67

<210> SEQ ID NO 26
<211> LENGTH: 32
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz2(9:8)
<220> FEATURE:
<221> NAME/KEY: misc_feature
<222> LOCATION: (32)..(32)
<223> OTHER INFORMATION: 3' end phosphorylation

<400> SEQUENCE: 26
cccagggagg ctagctacaa cgagaggaaa cc                                 32

<210> SEQ ID NO 27
<211> LENGTH: 49
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: RLr-Dz2BUB0(4)(-2)-P
<220> FEATURE:
```

```
<221> NAME/KEY: misc_feature
<222> LOCATION: (49)..(49)
<223> OTHER INFORMATION: 3' end phosphorylation

<400> SEQUENCE: 27
gtggtcgatc ccagggaggc tacaacgaga ggaaacctag agtatgcac          49

<210> SEQ ID NO 28
<211> LENGTH: 14
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: PR(3)-BLDz2(10)

<400> SEQUENCE: 28
gcatatcgac cacg                                                14

<210> SEQ ID NO 29
<211> LENGTH: 64
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: hp(R3a)Dz45BUB0(4)

<400> SEQUENCE: 29
caaaggagag gctagctaca acgagggacc cgttagggac gggtccttgt agctagcctc   60
tcct                                                               64

<210> SEQ ID NO 30
<211> LENGTH: 63
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: hpRLb(R4)-Sub2
<220> FEATURE:
<221> NAME/KEY: misc_feature
<222> LOCATION: (31)..(32)
<223> OTHER INFORMATION: ribonucleotides

<400> SEQUENCE: 30
ggtccttgta gcgtttcctc gucctggga gcctctcttt tgagaggct agctacaagg   60 acc                                                               63

<210> SEQ ID NO 31
<211> LENGTH: 83
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: hp(R6b)Dz45

<400> SEQUENCE: 31
acgggtccct cgttgtagct agcctctcct ttggtcgtcg atcctgagac caaaggagag   60
gctagctaca acgagggacc cgt                                         83
```

```
<210> SEQ ID NO 32
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: PR(R6)Dz45(10)

<400> SEQUENCE: 32
tcaggatcga                                                                 10

<210> SEQ ID NO 33
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: TFRCA4/45-P
<220> FEATURE:
<221> NAME/KEY: misc_feature
<222> LOCATION: (37)..(37)
<223> OTHER INFORMATION: 3' end phosphorylation

<400> SEQUENCE: 33
ggaatatgga aggagactgt cacaacgagg gacccgt                                   37

<210> SEQ ID NO 34
<211> LENGTH: 41
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: TFRCB5/45-P
<220> FEATURE:
<221> NAME/KEY: misc_feature
<222> LOCATION: (41)..(41)
<223> OTHER INFORMATION: 3' end phosphorylation

<400> SEQUENCE: 34
ttccaaagga gaggctagct cctctgactg gaaaacagac t                              41

<210> SEQ ID NO 35
<211> LENGTH: 42
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: AF-TFRC

<400> SEQUENCE: 35
agtctgtttt ccagtcagag ggacagtctc cttccatatt cc                             42

<210> SEQ ID NO 36
<211> LENGTH: 59
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: C(R15a)Sub45_2
<220> FEATURE:
<221> NAME/KEY: misc_feature
```

```
<222> LOCATION: (21)..(22)
<223> OTHER INFORMATION: riboonucleootides
<220> FEATURE:
<221> NAME/KEY: misc_feature
<222> LOCATION: (39)..(40)
<223> OTHER INFORMATION: ribonucleotides

<400> SEQUENCE: 36
tagccttcct cccgggtccc guctcctttg gtttcctcgu ccctgggcac gcctctcgt     59

<210> SEQ ID NO 37
<211> LENGTH: 33
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz6(9:9)

<400> SEQUENCE: 37
tgggaggaag gctagctaca acgagaggcg tga                                 33

<210> SEQ ID NO 38
<211> LENGTH: 64
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: C(R16d)Sub45_6
<220> FEATURE:
<221> NAME/KEY: misc_feature
<222> LOCATION: (23)..(24)
<223> OTHER INFORMATION: ribonucleotides
<220> FEATURE:
<221> NAME/KEY: misc_feature
<222> LOCATION: (42)..(43)
<223> OTHER INFORMATION: ribonucleotides

<400> SEQUENCE: 38
ctagcctccc tggtcgggtc ccguctcctt tgtcacgcct cgutcctccc agtttcctct    60
cgtt                                                                 64

<210> SEQ ID NO 39
<211> LENGTH: 32
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz2(9:8)

<400> SEQUENCE: 39
cccagggagg ctagctacaa cgagaggaaa cc                                  32

<210> SEQ ID NO 40
<211> LENGTH: 32
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz6(9:8

<400> SEQUENCE: 40
```

```
gggaggaagg ctagctacaa cgagaggcgt ga                                32
```

<210> SEQ ID NO 41
<211> LENGTH: 39
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: TFRCA4/2-P
<220> FEATURE:
<221> NAME/KEY: misc_feature
<222> LOCATION: (39)..(39)
<223> OTHER INFORMATION: 3' end phosphorylation

<400> SEQUENCE: 41

```
ggaatatgga aggagactgt cacaacgaga ggaaacctt                          39
```

<210> SEQ ID NO 42
<211> LENGTH: 39
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: TFRCB5/2-P
<220> FEATURE:
<221> NAME/KEY: misc_feature
<222> LOCATION: (39)..(39)
<223> OTHER INFORMATION: 3' end phosphorylation

<400> SEQUENCE: 42

```
tgcccaggga ggctagctcc tctgactgga aaacagact                          39
```

<210> SEQ ID NO 43
<211> LENGTH: 26
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: SubK1(14:12)-FB
<220> FEATURE:
<221> NAME/KEY: misc_feature
<222> LOCATION: (24)..(25)
<223> OTHER INFORMATION: ribonucleotides

<400> SEQUENCE: 43

```
cgaaggtttc ctcguccctg ggcacg                                        26
```

<210> SEQ ID NO 44
<211> LENGTH: 80
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: hp(R22a)ADz45

<400> SEQUENCE: 44

```
gatccgacta ggacgggtcc ctcgttgtag ctagcctctc ctttgggctg atccgaggaa   60
accttccaaa ggagaagcta                                               80
```

<210> SEQ ID NO 45
<211> LENGTH: 33

```
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz45(9:9)

<400> SEQUENCE: 45
caaaggagag gctagctaca acgagggacc cgt                                    33

<210> SEQ ID NO 46
<211> LENGTH: 83
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: hp(R8b)ADz45

<400> SEQUENCE: 46
acgggtccct cgttgtagct agcctctcct ttggtcgctg atcctgtact tgaccaaagg       60
agaggctaca acgagggacc cgt                                               83

<210> SEQ ID NO 47
<211> LENGTH: 70
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: hp(R11b)ADz45

<400> SEQUENCE: 47
acgggtccct cgttgtagct agcctctcct ttggtcgctg atcctgtact tgaccaaagg       60
agatgctagc                                                              70

<210> SEQ ID NO 48
<211> LENGTH: 53
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: (R15a)-Dz45

<400> SEQUENCE: 48
acgggtccct cgttgtagct agcctctcct ttggaatcgc tgatcctgta ctt              53

<210> SEQ ID NO 49
<211> LENGTH: 14
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: PR(R8b)Dz45(14)

<400> SEQUENCE: 49
aagtacagga tcag                                                         14

<210> SEQ ID NO 50
<211> LENGTH: 63
```

```
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: hpPR(R15h)Sub2
<220> FEATURE:
<221> NAME/KEY: misc_feature
<222> LOCATION: (48)..(49)
<223> OTHER INFORMATION: ribonucleotides

<400> SEQUENCE: 50
ctgatcctgt acttccgagc atccttttg gatgctcagg tttcctcguc cctgggcaag    60
tac                                                                  63

<210> SEQ ID NO 51
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: KrasA4/2-P
<220> FEATURE:
<221> NAME/KEY: misc_feature
<222> LOCATION: (38)..(38)
<223> OTHER INFORMATION: 3' end phosphorylation

<400> SEQUENCE: 51
taaacttgtg gtagttggag acaacgagag gaaacctt                            38

<210> SEQ ID NO 52
<211> LENGTH: 41
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: KrasB5/2-P
<220> FEATURE:
<221> NAME/KEY: misc_feature
<222> LOCATION: (41)..(41)
<223> OTHER INFORMATION: 3' end phosphorylation

<400> SEQUENCE: 52
tgcccaggga ggctagctct ggtggcgtag gcaagagtgc c                        41

<210> SEQ ID NO 53
<211> LENGTH: 52
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: AF-Kras

<400> SEQUENCE: 53
caaggcactc ttgcctacgc caccagctcc aactaccaca gtttatatt ca             52

<210> SEQ ID NO 54
<211> LENGTH: 85
<212> TYPE: DNA
<213> ORGANISM: Artificial sequence
<220> FEATURE:
<223> OTHER INFORMATION: Synthetic
<220> FEATURE:
```

```
<221> NAME/KEY: misc_feature
<223> OTHER INFORMATION: C(R19b)
<220> FEATURE:
<221> NAME/KEY: misc_feature
<222> LOCATION: (23)..(24)
<223> OTHER INFORMATION: ribonucleotides
<220> FEATURE:
<221> NAME/KEY: misc_feature
<222> LOCATION: (42)..(43)
<223> OTHER INFORMATION: ribonucleotides
<220> FEATURE:
<221> NAME/KEY: misc_feature
<222> LOCATION: (63)..(64)
<223> OTHER INFORMATION: ribonucleotides

<400> SEQUENCE: 54
agcctctcct ttgtcctccc tcgucccag cttcacgcct cgutcctccc aaaggtttcc      60
tcguccctgg gcgggtccct cgttg                                          85

<210> SEQ ID NO 55
<211> LENGTH: 21
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Sub77_55
<220> FEATURE:
<221> NAME/KEY: misc_feature
<222> LOCATION: (11)..(12)
<223> OTHER INFORMATION: ribonucleotides

<400> SEQUENCE: 55
ctcctccctc gucccagct c                                               21

<210> SEQ ID NO 56
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: TFRCA4/77-P
<220> FEATURE:
<221> NAME/KEY: misc_feature
<222> LOCATION: (38)..(38)
<223> OTHER INFORMATION: 3' end phosphorylation

<400> SEQUENCE: 56
ggaatatgga aggagactgt cacaacgaga gggaggag                            38

<210> SEQ ID NO 57
<211> LENGTH: 39
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: TFRCB5/55-P
<220> FEATURE:
<221> NAME/KEY: misc_feature
<222> LOCATION: (39)..(39)
<223> OTHER INFORMATION: 3' end phosphorylation

<400> SEQUENCE: 57
gagctgggga ggctagctcc tctgactgga aaacagact                           39
```

```
<210> SEQ ID NO 58
<211> LENGTH: 37
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: KrasA4/6-P
<220> FEATURE:
<221> NAME/KEY: misc_feature
<222> LOCATION: (37)..(37)
<223> OTHER INFORMATION: 3' end phosphorylation

<400> SEQUENCE: 58
taaacttgtg gtagttggag acaacgagag gcgtgat                              37

<210> SEQ ID NO 59
<211> LENGTH: 41
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: KrasB5/6-P
<220> FEATURE:
<221> NAME/KEY: misc_feature
<222> LOCATION: (41)..(41)
<223> OTHER INFORMATION: 3' end phosphorylation

<400> SEQUENCE: 59
ctgggaggaa ggctagctct ggtggcgtag gcaagagtgc c                         41

<210> SEQ ID NO 60
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: RO5A4/2-P
<220> FEATURE:
<221> NAME/KEY: misc_feature
<222> LOCATION: (40)..(40)
<223> OTHER INFORMATION: 3' end phosphorylation

<400> SEQUENCE: 60
caaacgagtc ctggccttgt ctacaacgag aggaaacctt                           40

<210> SEQ ID NO 61
<211> LENGTH: 39
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: RO5B5/2-P
<220> FEATURE:
<221> NAME/KEY: misc_feature
<222> LOCATION: (39)..(39)
<223> OTHER INFORMATION: 3' end phosphorylation

<400> SEQUENCE: 61
tgcccaggga ggctagctgt ggagacggat tacaccttc                            39

<210> SEQ ID NO 62
<211> LENGTH: 43
<212> TYPE: DNA
```

```
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: AF-R05

<400> SEQUENCE: 62
gaaggtgtaa tccgtctcca cagacaaggc caggactcgt ttg            43

<210> SEQ ID NO 63
<211> LENGTH: 50
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: C(R14b)Sub1_2
<220> FEATURE:
<221> NAME/KEY: misc_feature
<222> LOCATION: (21)..(21)
<223> OTHER INFORMATION: ribonucleotide
<220> FEATURE:
<221> NAME/KEY: misc_feature
<222> LOCATION: (31)..(32)
<223> OTHER INFORMATION: ribonucleotides

<400> SEQUENCE: 63
tagccttcct ccctcactat aggtttcctc guccctggca cgcctctcgt      50

<210> SEQ ID NO 64
<211> LENGTH: 48
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: C(R43e)
<220> FEATURE:
<221> NAME/KEY: misc_feature
<222> LOCATION: (24)..(24)
<223> OTHER INFORMATION: ribonucleotide

<400> SEQUENCE: 64
tagcctcacc aacccctcac tataggaaga gatagcacaa cctcgttg        48

<210> SEQ ID NO 65
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: PPIAA2/1-P
<220> FEATURE:
<221> NAME/KEY: misc_feature
<222> LOCATION: (38)..(38)
<223> OTHER INFORMATION: 3' end phosphorylation

<400> SEQUENCE: 65
tggttggatg gcaagcatgt gcggtcgaaa tagtgagt                   38

<210> SEQ ID NO 66
<211> LENGTH: 37
<212> TYPE: DNA
<213> ORGANISM: Artificial sequence
<220> FEATURE:
<223> OTHER INFORMATION: Synthetic
```

<220> FEATURE:
<221> NAME/KEY: misc_feature
<223> OTHER INFORMATION: PPIAB3/2(9)

<400> SEQUENCE: 66
gaggaaactc cgagcgtgtt tggcaaagtg aaagaag                              37

<210> SEQ ID NO 67
<211> LENGTH: 43
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: AF-PPIA

<400> SEQUENCE: 67
cttctttcac tttgccaaac accacatgct tgccatccaa cca                       43

<210> SEQ ID NO 68
<211> LENGTH: 70
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: C(R22h)
<220> FEATURE:
<221> NAME/KEY: misc_feature
<222> LOCATION: (24)..(25)
<223> OTHER INFORMATION: ribonucleotides
<220> FEATURE:
<221> NAME/KEY: misc_feature
<222> LOCATION: (46)..(47)
<223> OTHER INFORMATION: ribonucleotides

<400> SEQUENCE: 68
agcctcccca gctatcacgc ctcguctcct cccagctcct ccctcguccc cagcttcctc     60
cctctcgttg                                                            70

<210> SEQ ID NO 69
<211> LENGTH: 70
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: C(R31c)
<220> FEATURE:
<221> NAME/KEY: misc_feature
<222> LOCATION: (24)..(25)
<223> OTHER INFORMATION: ribonucleotides
<220> FEATURE:
<221> NAME/KEY: misc_feature
<222> LOCATION: (45)..(46)
<223> OTHER INFORMATION: ribonucleotides

<400> SEQUENCE: 69
agcctcccca gctatcacgc ctcguctcct cccagctcga ccccguctcc acgcctcctc     60
cctctcgttg                                                            70

<210> SEQ ID NO 70
<211> LENGTH: 50
<212> TYPE: DNA
<213> ORGANISM: Artificial sequence
<220> FEATURE:

```
<223> OTHER INFORMATION: Synthetic
<220> FEATURE:
<221> NAME/KEY: misc_feature
<223> OTHER INFORMATION: C(R31d)
<220> FEATURE:
<221> NAME/KEY: misc_feature
<222> LOCATION: (24)..(25)
<223> OTHER INFORMATION: ribonucleotides

<400> SEQUENCE: 70
agcctcccca gctatcacgc ctcguctcct cccagtcctc cctctcgttg         50

<210> SEQ ID NO 71
<211> LENGTH: 32
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz77_55(8:9)

<400> SEQUENCE: 71
agctggggag gctagctaca acgagaggga gg                            32

<210> SEQ ID NO 72
<211> LENGTH: 22
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Sub72
<220> FEATURE:
<221> NAME/KEY: misc_feature
<222> LOCATION: (11)..(12)
<223> OTHER INFORMATION: ribonucleotides

<400> SEQUENCE: 72
atcacgcctc guctcctccc ag                                       22

<210> SEQ ID NO 73
<211> LENGTH: 33
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz3(8:10)

<400> SEQUENCE: 73
cggttggtga ggctagctac aacgaggttg tgc                           33

<210> SEQ ID NO 74
<211> LENGTH: 41
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: LTFRCA4/72

<400> SEQUENCE: 74
gcaaggaaca ataactcaga acttacaacg agaggcgtga t                  41

<210> SEQ ID NO 75
```

```
<211> LENGTH: 39
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: LTFRCB5/72

<400> SEQUENCE: 75
ctgggaggag aggctagcta cgcctgcttt ctgattcta                    39

<210> SEQ ID NO 76
<211> LENGTH: 86
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: AF-LTFRC

<400> SEQUENCE: 76
agtctgtttt ccagtcagag ggacagtctc cttccatatt cctagaatca gaaagcaggc    60
gtaagttctg agttattgtt ccttgc                                        86

<210> SEQ ID NO 77
<211> LENGTH: 85
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: hpBL(R3a)-Dz2_Sub6
<220> FEATURE:
<221> NAME/KEY: misc_feature
<222> LOCATION: (62)..(63)
<223> OTHER INFORMATION: ribonucleotides

<400> SEQUENCE: 77
cccagggagg ctagctacaa cgagaggaaa ccttttggt ttcctctcgt tttcacgcct     60
cgutcctccc attagcctcc ctggg                                         85

<210> SEQ ID NO 78
<211> LENGTH: 75
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: C(R22h)-Bio
<220> FEATURE:
<221> NAME/KEY: misc_feature
<222> LOCATION: (24)..(25)
<223> OTHER INFORMATION: ribonucleotides
<220> FEATURE:
<221> NAME/KEY: misc_feature
<222> LOCATION: (46)..(47)
<223> OTHER INFORMATION: ribonucleotides
<220> FEATURE:
<221> NAME/KEY: misc_feature
<222> LOCATION: (75)..(75)
<223> OTHER INFORMATION: 3' end biotinylation

<400> SEQUENCE: 78
agcctcccca gctatcacgc ctcguctcct cccagctcct ccctcguccc cagcttcctc    60
cctctcgttg aaaaa                                                    75
```

```
<210> SEQ ID NO 79
<211> LENGTH: 49
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: hpPRF(R12b)

<400> SEQUENCE: 79
atcctgtact taggtccgat cctgcagcat agggacctaa gtgcaggac          49

<210> SEQ ID NO 80
<211> LENGTH: 15
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: PR(R12b)PRF

<400> SEQUENCE: 80
ctatgctgca ggatc                                               15

<210> SEQ ID NO 81
<211> LENGTH: 73
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: C(R27a)
<220> FEATURE:
<221> NAME/KEY: misc_feature
<222> LOCATION: (25)..(26)
<223> OTHER INFORMATION: ribonucleotides
<220> FEATURE:
<221> NAME/KEY: misc_feature
<222> LOCATION: (47)..(48)
<223> OTHER INFORMATION: ribonucleotides

<400> SEQUENCE: 81
tagcctcacc aaccgctcga ccccguctcc acgccacagc acaaccguca ccaaccgcag    60
cacaacctcg ttg                                                      73

<210> SEQ ID NO 82
<211> LENGTH: 32
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Dz3(8:9)

<400> SEQUENCE: 82
ggttggtgag gctagctaca acgaggttgt gc                            32

<210> SEQ ID NO 83
<211> LENGTH: 21
<212> TYPE: DNA
<213> ORGANISM: Artificial sequence
<220> FEATURE:
<223> OTHER INFORMATION: Synthetic
<220> FEATURE:
```

```
<221> NAME/KEY: misc_feature
<223> OTHER INFORMATION: Sub3
<220> FEATURE:
<221> NAME/KEY: misc_feature
<222> LOCATION: (11)..(12)
<223> OTHER INFORMATION: ribonucleotides

<400> SEQUENCE: 83
cagcacaacc gucaccaacc g                                           21

<210> SEQ ID NO 84
<211> LENGTH: 38
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: R05A4/56-P
<220> FEATURE:
<221> NAME/KEY: misc_feature
<222> LOCATION: (38)..(38)
<223> OTHER INFORMATION: 3' end phosphorylation

<400> SEQUENCE: 84
caaacgagtc ctggccttgt ctacaacgag gggtcgag                         38

<210> SEQ ID NO 85
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: R05B5/56-P
<220> FEATURE:
<221> NAME/KEY: misc_feature
<222> LOCATION: (40)..(40)
<223> OTHER INFORMATION: 3' end phosphorylation

<400> SEQUENCE: 85
tggcgtggag aggctagctg tggagacgga ttacaccttc                       40

<210> SEQ ID NO 86
<211> LENGTH: 70
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: C(R39c)
<220> FEATURE:
<221> NAME/KEY: misc_feature
<222> LOCATION: (46)..(47)
<223> OTHER INFORMATION: ribonucleotides

<400> SEQUENCE: 86
agcctcccca gctatcggat cattcgcctc atccctcct ccctcguccc cagctacctc  60
cctctcgttg                                                        70

<210> SEQ ID NO 87
<211> LENGTH: 59
<212> TYPE: DNA
<213> ORGANISM: Artificial sequence
<220> FEATURE:
<223> OTHER INFORMATION: Synthetic
<220> FEATURE:
<221> NAME/KEY: misc_feature
```

<223> OTHER INFORMATION: Dz1-(R40a)

<400> SEQUENCE: 87
atctcttctc cgagccggtc gaaatagtga gacctggggg agtatgtgcg gaggaaggt    59

<210> SEQ ID NO 88
<211> LENGTH: 22
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: AF-(R38e)

<400> SEQUENCE: 88
gggatgaggc gaatgatccg at    22

<210> SEQ ID NO 89
<211> LENGTH: 15
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Eco606ORF4215P recognition sequence
<220> FEATURE:
<221> NAME/KEY: misc_feature
<222> LOCATION: (4)..(11)
<223> OTHER INFORMATION: n is a, c, g, or t

<400> SEQUENCE: 89
tgannnnnnn ntgct    15

<210> SEQ ID NO 90
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Bgl I recognition sequence
<220> FEATURE:
<221> NAME/KEY: misc_feature
<222> LOCATION: (4)..(8)
<223> OTHER INFORMATION: n is a, c, g, or t

<400> SEQUENCE: 90
gccnnnnngg c    11

<210> SEQ ID NO 91
<211> LENGTH: 12
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: BcgI recognition sequence
<220> FEATURE:
<221> NAME/KEY: misc_feature
<222> LOCATION: (4)..(9)
<223> OTHER INFORMATION: n is a, c, g, or t

<400> SEQUENCE: 91
cgannnnnnt gc    12

```
<210> SEQ ID NO 92
<211> LENGTH: 15
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: CfrAI, M.CfrAI, S.CfrAI recognition sequence
<220> FEATURE:
<221> NAME/KEY: misc_feature
<222> LOCATION: (4)..(11)
<223> OTHER INFORMATION: n is a, c, g, or t

<400> SEQUENCE: 92
gcannnnnnn ngtgg                                                    15

<210> SEQ ID NO 93
<211> LENGTH: 15
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Eco37I, M.Eco37I, S.Eco37I, Eco377I, M.Eco377I,
      S.Eco377I recognition sequence
<220> FEATURE:
<221> NAME/KEY: misc_feature
<222> LOCATION: (4)..(11)
<223> OTHER INFORMATION: n is a, c, g, or t

<400> SEQUENCE: 93
ggannnnnnn natgc                                                    15

<210> SEQ ID NO 94
<211> LENGTH: 14
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: EcoprrI, M.EcoprrI, S.EcoprrI recognition
      sequence
<220> FEATURE:
<221> NAME/KEY: misc_feature
<222> LOCATION: (4)..(10)
<223> OTHER INFORMATION: n is a, c, g, or t

<400> SEQUENCE: 94
ccannnnnnn rtgc                                                     14

<210> SEQ ID NO 95
<211> LENGTH: 14
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: KpnBI, M.KpnBI, S.KpnBI recognition sequence
<220> FEATURE:
<221> NAME/KEY: misc_feature
<222> LOCATION: (5)..(10)
<223> OTHER INFORMATION: n is a, c, g, or t

<400> SEQUENCE: 95
caaannnnnn rtca                                                     14

<210> SEQ ID NO 96
```

-continued

<210> SEQ ID NO 96
<211> LENGTH: 13
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: StySBLI, M.StySBLI, S.StySBL recognition
      sequence
<220> FEATURE:
<221> NAME/KEY: misc_feature
<222> LOCATION: (4)..(9)
<223> OTHER INFORMATION: n is a, c, g, or t

<400> SEQUENCE: 96
cgannnnnnt acc                                                          13

<210> SEQ ID NO 97
<211> LENGTH: 14
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: StySQI, M.StySQI, S.StySQI recognition sequence
<220> FEATURE:
<221> NAME/KEY: misc_feature
<222> LOCATION: (4)..(9)
<223> OTHER INFORMATION: n is a, c, g, or t

<400> SEQUENCE: 97
aacnnnnnnr tayg                                                         14

<210> SEQ ID NO 98
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: BglI recognition sequence
<220> FEATURE:
<221> NAME/KEY: misc_feature
<222> LOCATION: (4)..(8)
<223> OTHER INFORMATION: n is a, c, g, or t

<400> SEQUENCE: 98 gccnnnnnggg c                                                           11

<210> SEQ ID NO 99
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: BsmDI recognition sequence
<220> FEATURE:
<221> NAME/KEY: misc_feature
<222> LOCATION: (3)..(7)
<223> OTHER INFORMATION: n is a, c, g, or t

<400> SEQUENCE: 99
acnnnnnctc c                                                            11

<210> SEQ ID NO 100
<211> LENGTH: 10
<212> TYPE: DNA

<213> ORGANISM: Artificial sequence
<220> FEATURE:
<223> OTHER INFORMATION: Synthetic
<220> FEATURE:
<221> NAME/KEY: misc_feature
<223> OTHER INFORMATION: BmuSORF1564P recognition sequence
<220> FEATURE:
<221> NAME/KEY: misc_feature
<222> LOCATION: (4)..(8)
<223> OTHER INFORMATION: n is a, c, g, or t

<400> SEQUENCE: 100 gagnnnnngt                                                           10

<210> SEQ ID NO 101
<211> LENGTH: 14
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: AjuI recognition sequence
<220> FEATURE:
<221> NAME/KEY: misc_feature
<222> LOCATION: (4)..(10)
<223> OTHER INFORMATION: n is a, c, g, or t

<400> SEQUENCE: 101
gaannnnnnn ttgg                                                      14

<210> SEQ ID NO 102
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: BsaXI recognition sequence
<220> FEATURE:
<221> NAME/KEY: misc_feature
<222> LOCATION: (3)..(7)
<223> OTHER INFORMATION: n is a, c, g, or t

<400> SEQUENCE: 102
acnnnnnctc c                                                         11

<210> SEQ ID NO 103
<211> LENGTH: 12
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: TstI recognition sequence
<220> FEATURE:
<221> NAME/KEY: misc_feature
<222> LOCATION: (4)..(9)
<223> OTHER INFORMATION: n is a, c, g, or t

<400> SEQUENCE: 103
cacnnnnnnt cc                                                        12

<210> SEQ ID NO 104
<211> LENGTH: 11
<212> TYPE: DNA
<213> ORGANISM: Artificial sequence
<220> FEATURE:
<223> OTHER INFORMATION: Synthetic

```
<220> FEATURE:
<221> NAME/KEY: misc_feature
<223> OTHER INFORMATION: Bsl I (55oC) recognition sequence
<220> FEATURE:
<221> NAME/KEY: misc_feature
<222> LOCATION: (3)..(9)
<223> OTHER INFORMATION: n is a, c, g, or t

<400> SEQUENCE: 104
ccnnnnnnng g                                                            11

<210> SEQ ID NO 105
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<223> OTHER INFORMATION: Mwo I (60oC) recognition sequence
<220> FEATURE:
<221> NAME/KEY: misc_feature
<222> LOCATION: (3)..(9)
<223> OTHER INFORMATION: n is a, c, g, or t

<400> SEQUENCE: 105
gcnnnnnnng c                                                            11
```